(12) United States Patent
Dunn et al.

(10) Patent No.: US 6,451,804 B1
(45) Date of Patent: Sep. 17, 2002

(54) HETEROALKYLAMINO-SUBSTITUTED BICYCLIC NITROGEN HETEROCYCLES

(75) Inventors: James Patrick Dunn, Los Altos; Lawrence Emerson Fisher, Mountain View; David Michael Goldstein, San Jose, all of CA (US); William Harris, Bedfordshire (GB); Christopher Huw Hill, Hertfordshire (GB); Ian Edward David Smith, Bedfordshire (GB); Teresa Rosanne Welch, Sunnyvale, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 09/693,337

(22) Filed: Oct. 20, 2000

Related U.S. Application Data

(60) Provisional application No. 60/213,743, filed on Jun. 22, 2000, and provisional application No. 60/160,803, filed on Oct. 21, 1999.

(51) Int. Cl.[7] ............... A61K 31/505; C07D 295/00; C07D 487/00; C07D 237/00
(52) U.S. Cl. .............. 514/262.1; 544/6; 544/256; 544/230
(58) Field of Search .............. 514/262.1; 544/256, 544/6, 230

(56) References Cited

U.S. PATENT DOCUMENTS 5,162,316 A    11/1992  Coates ............... 514/212
6,150,373 A    11/2000  Harris et al. ............... 514/258

FOREIGN PATENT DOCUMENTS

| EP | 0 351 058 B1 | 6/1993 |
| WO | WO 96/34867 | 11/1996 |
| WO | WO 99/61444 | 12/1999 |

*Primary Examiner*—Mukund J. Shah
*Assistant Examiner*—Tamthom N. Truong
(74) *Attorney, Agent, or Firm*—Rohan Peries

(57) ABSTRACT

The invention provides compounds represented by the formula:

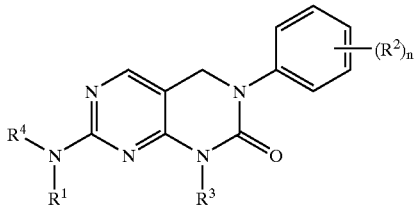

(I)

wherein $R^1$, $R^2$, $R^3$, $R^4$, and n are as defined in the Summary of the Invention; and individual isomers, racemic or non-racemic mixtures of isomers, and pharmaceutically acceptable salts thereof. The invention further relates to pharmaceutical compositions containing such compounds, methods for their use as therapeutic agents, and methods of preparation thereof.

31 Claims, No Drawings

HETEROALKYLAMINO-SUBSTITUTED BICYCLIC NITROGEN HETEROCYCLES

CROSS-REFERENCE TO RELATED APPLICATION

This application claims the benefit under 35 U.S.C. 119(e) of U.S. Provisional Application Serial No. 60/213,743, filed Jun. 22, 2000, and U.S. Provisional Application Serial No. 60/160,803, filed Oct. 21, 1999, each incorporated herein by reference in its entirety.

FIELD OF THE INVENTION

The present invention relates to bicyclic nitrogen heterocycles. More particularly, the invention is concerned with certain heteroalkylamino-substituted dihydropyrimido[4,5-d]pyrimidinone derivatives, pharmaceutical preparations containing them, methods for their use as therapeutic agents, and methods for their manufacture.

BACKGROUND OF THE INVENTION

Mitogen-activated protein kinases (MAP) are a family of proline-directed serine/threonine kinases that activate their substrates by dual phosphorylation. The kinases are activated by a variety of signals including nutritional and osmotic stress, UV light, growth factors, endotoxin and inflammatory cytokines. One group of MAP kinases is the p38 kinase group which includes various isoforms (e.g., p38α, p38β and p38γ). The p38 kinases are responsible for phosphorylating and activating transcription factors as well as other kinases, and are themselves activated by physical and chemical stress, pro-inflammatory cytokines and bacterial lipopolysaccharide.

More importantly, the products of the p38 phosphorylation have been shown to mediate the production of inflammatory cytokines, including TNF and IL-1, and cyclooxygenase-2. Each of these cytokines has been implicated in numerous disease states and conditions. For example, TNF-α is a cytokine produced primarily by activated monocytes and macrophages. Its excessive or unregulated production has been implicated as playing a causative role in the pathogenesis of rheumatoid arthritis. More recently, inhibition of TNF production has been shown to have broad application in the treatment of inflammation, inflammatory bowel disease, multiple sclerosis and asthma.

TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpesvirus-6 (HHV-6), human herpesvirus-7 (HHV-7), human herpesvirus-8 (HHV-8), pseudorabies and rhinotracheitis, among others.

Similarly, IL-1 is produced by activated monocytes and macrophages, and plays a role in many pathophysiological responses including rheumatoid arthritis, fever and reduction of bone resorption.

The inhibition of these cytokines by inhibition of the p38 kinase is of benefit in controlling, reducing and alleviating many of these disease states.

SUMMARY OF THE INVENTION

In one aspect, the present invention provides compounds represented by the formula:

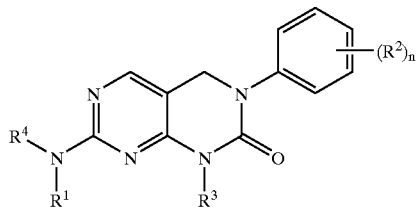

wherein
the subscript n is an integer of from 0 to 3;
$R^1$ is acyl, heteroalkyl, arylheteroalkyl, heteroalkenyl, heteroalkynyl, heteroalkylcarbonyl, heterosubstituted cycloalkyl, heterosubstituted cycloalkylalkyl, heterosubstituted cycloalkylalkenyl, heterosubstituted cycloalkylalkynyl, heteroalkylsubstituted cycloalkyl, heterocyclyl, heterocyclylalkyl, heterocyclyl spiro cycloalkyl, -(alkylene)—C(O)—$R^{11}$ or -(heteroalkylene)—C(O)—$R^1$;
wherein:
$R^{11}$ is alkyl, haloalkyl, amino, monosubstituted amino, disubstituted amino, cycloalkyl, cycloalkylalkyl, aryl, aralkyl, heteroaryl, heteroaralkyl, hydroxy, or alkoxy;
$R^2$ is each independently in each occurrence alkyl, halo, heteroalkyl or vinyl;
$R^3$ is hydrogen, alkyl, heteroalkyl, aryl, aralkyl, heteroaryl, heteroaralkyl, cycloalkyl, cycloalkenyl, cycloalkylalkyl, haloalkyl, cyanoalkyl, heterosubstituted cycloalkyl, heterosubstituted cycloalkylalkyl, heteroalkylsubstituted cycloalkyl, heterocyclyl, heterocyclylalkyl, -(alkylene)—C(O)$R^{31}$, or -(heteroalkylene)—C(O)$R^{31}$; and
$R^4$ is hydrogen, alkyl, or -(alkylene)—C(O)$R^{31}$;
wherein:
$R^{31}$ is alkyl haloalkyl, hydroxy, alkoxy, amino, monsubstituted amino, disubstituted amino, cycloalkyl, cycloalkylalkyl, aryl, aralkyl, heteroaryl, or heteroaralkyl; and their individual isomers, racemic or nonracemic mixture of isomers, and their pharmaceutically acceptable salts thereof.

In another aspect, the present invention provides methods of preparing the compounds described above.

The compounds of formula I and their aforementioned salts are inhibitors of protein kinases, and exhibit surprisingly effective activity against p38 in vivo. Interestingly, the compounds of formula I do not exhibit activity against the T-cell tyrosine kinase $p_{56}^{lck}$ at levels below about 10 μM. The compounds can be used for the treatment of diseases mediated by the pro-inflammatory cytokines such as TNF and IL-1.

Accordingly, the present invention provides methods for the treatment of p38 mediated diseases or conditions in which a therapeutically effective amount of a compound of formula I is administered to a subject in need of such treatment.

In still another aspect, the present invention provides methods of preparing medicaments useful for the treatment of the p38 mediated diseases and conditions.

DESCRIPTION OF THE INVENTION

Abbreviations and Definitions

As used herein:
"Alkyl" means a linear saturated monovalent hydrocarbon radical of one to six carbon atoms or a branched saturated monovalent hydrocarbon radical of three to six carbon atoms, e.g., methyl, ethyl, n-propyl, 2-propyl, tert-butyl, pentyl, and the like.

"Alkylene" means a linear saturated divalent hydrocarbon radical of one to six carbon atoms or a branched saturated divalent hydrocarbon radical of three to six carbon atoms, e.g., methylene, ethylene, propylene, 2-methyl-propylene, pentylene, and the like.

"Alkenylene" means a linear or branched divalent hydrocarbon radical containing from two to ten carbon atoms and also containing at least one carbon-carbon double bond, e.g., —CH=CH—, —CH$_2$CH=CH—, —C(CH$_3$)=CH—, CH$_2$CH=CHCH$_2$—, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Cycloalkyl" refers to a saturated monovalent cyclic hydrocarbon radical of three to seven ring carbons. The cycloalkyl may be optionally substituted independently with one, two, or three substituents selected from alkyl, optionally substituted phenyl, or —C(O)R (where R is hydrogen, alkyl, haloalkyl, amino, monosubstituted amino, disubstituted amino, hydroxy, alkoxy, or optionally substituted phenyl). More specifically, the term cycloalkyl includes, but is not limited to, for example, cyclopropyl, cyclohexyl, phenylcyclohexyl, 4-carboxycyclohexyl, 2-carboxamidocyclohexyl, 2-dimethylaminocarbonylcyclohexyl, and the like.

"Cycloalkylalkyl" means a radical —R$^a$R$^b$ where R$^a$ is an alkylene group and R$^b$ is a cycloalkyl group as defined herein, e.g., cyclopropylmethyl, cyclohexylpropyl, 3-cyclohexyl-2-methylpropyl, and the like.

"Acyl" means the group —C(O)R', where R' is hydrogen, alkyl, haloalkyl, heteroalkyl, aryl, heteroaryl, aralkyl or heteroaralkyl.

"Alkoxy", "aryloxy", "aralkyloxy", or "heteroaralkyloxy" means a radical —OR where R is an alkyl, aryl, aralkyl, or heteroaralkyl respectively, as defined herein, e.g., methoxy, phenoxy, pyridin-2-ylmethyloxy, benzyloxy, and the like.

"Halo" or "halogen," means fluoro, chloro, bromo, or iodo, preferably fluoro or chloro.

"Haloalkyl" means alkyl substituted with one or more same or different halo atoms, e.g., —CH$_2$Cl, —CF$_3$, —CH$_2$CF$_3$, —CH$_2$CCl$_3$, and the like, and further includes those alkyl groups such as perfluoroalkyl in which all hydrogen atoms are replaced by fluorine atoms.

"Hydroxyalkyl" means an alkyl radical as defined herein, substituted with one or more, preferably one, two or three hydroxy groups, provided that the same carbon atom does not carry more than one hydroxy group. Examples include, but are not limited to, 2-hydroxyethyl, 2-hydroxypropyl, 3-hydroxypropyl, 1-(hydroxymethyl)-2-methyl-propyl, 2-hydroxybutyl, 3-hydroxybutyl, 4-hydroxy-butyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl and 1-(hydroxymethyl)-2-hydroxyethyl.

"Monosubstituted amino" means a radical —NHR' where R is alkyl, heteroalkyl, haloalkyl, cycloalkyl, cycloalkylalkyl, aryl, aralkyl, aralkenyl, heteroaryl, heteroaralkyl, heteroaralkenyl, heterocyclyl, or heterocyclylalkyl, e.g., methylamino, ethylamino, phenylamino, benzylamino, and the like.

"Disubstituted amino" means a radical —NRR' where R and R' are, independently of each other, alkyl, heteroalkyl, haloalkyl, cycloalkyl, cycloalkylalkyl, aryl, aralkyl, aralkenyl, heteroaryl, heteroaralkyl, heteroaralkenyl, heterocyclyl, or heterocyclylalkyl, or R and R' together with the nitrogen atom to which they are attached form a heterocyclyl ring. Examples include, but are not limited to, dimethylamino, methylethylamino, di(1-methylethyl)amino, piperazin-1-yl, and the like.

"Aryl" means a monovalent monocyclic or bicyclic aromatic hydrocarbon radical of 6 to 10 ring atoms which is substituted independently with one or more substituents, preferably one, two, or three substituents selected from alkyl, haloalkyl, heteroalkyl, halo, nitro, cyano, methylenedioxy, ethylenedioxy, cycloalkyl, optionally substituted phenyl, heteroaryl, haloalkoxy, optionally substituted phenoxy, heteroaryloxy, —COR (where R is alkyl or optionally substituted phenyl), —(CR'R")$_n$—COOR (where n is an integer from 0 to 5, R' and R" are independently hydrogen or alkyl, and R is hydrogen, alkyl, cycloalkyl or cycloalkylalkyl) or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl or cycloalkylalkyl, or R$^a$ and R$^b$ together with the nitrogen atom to which they are attached form a heterocyclyl ring). Examples include, but are not limited to, phenyl, 1-naphthyl, and 2-naphthyl, and the derivatives thereof.

"Aralkyl" means a radical —R$^a$R$^b$ where R$^a$ is an alkylene group and R$^b$ is an aryl group as defined herein, e.g., benzyl, phenylethyl, 3-(3-chlorophenyl)-2-methylpentyl, and the like.

"Aralkenyl" means a radical —R$^a$R$^b$ where R$^a$ is an alkenylene group and R$^b$ is an aryl group as defined herein, e.g., 3-phenyl-2-propenyl, and the like.

"Arylheteroalkyl" means a radical —R$^a$R$^b$ where R$^a$ is an heteroalkylene group and R$^b$ is an aryl group as defined herein, e.g., 2-hydroxy-2-phenylethyl, 2-hydroxy-1-hydroxymethyl-2-phenylethyl, and the like.

"Optionally substituted phenyl" means a phenyl ring which is optionally substituted independently with one or more substituents, preferably one or two substituents selected from alkyl, alkoxy, hydroxy, haloalkyl, heteroalkyl, halo, nitro, cyano, methylenedioxy, ethylenedioxy, cycloalkyl, cycloalkylalkyl, —COR (where R is alkyl or optionally substituted phenyl), —(CR' R")$_n$—COOR (where n is an integer from 0 to 5, R' and R" are independently hydrogen or alkyl, and R is hydrogen, alkyl, cycloalkyl or cycloalkylalkyl), or —(CR' R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl or cycloalkylalkyl, or R$^a$ and R$^b$ together with the nitrogen atom to which they are attached form a heterocyclyl ring).

"Heteroaryl" means a monovalent monocyclic or bicyclic radical of 5 to 12 ring atoms having at least one aromatic ring containing one, two, or three ring heteroatoms selected from N, O, or S, and the remaining ring atoms being C, with the understanding that the attachment point of the heteroaryl radical will be on an aromatic ring. The heteroaryl ring is optionally substituted independently with one or more substituents, preferably one or two substituents, selected from alkyl, haloalkyl, heteroalkyl, halo, nitro, cyano, cycloalkyl, cycloalkylalkyl, —COR (where R is alkyl or optionally substituted phenyl, —(CR' R")$_n$—COOR (where n is an integer from 0 to 5, R' and R" are independently hydrogen or alkyl, and R is hydrogen, alkyl, cycloalkyl or cycloalkylalkyl), —NR$^a$R$^b$ (where R$^a$ and R$^b$ are independently of each other, hydrogen, alkyl, cycloalkyl or cycloalkylalkyl), or —(CR' R")$_n$—CONR$^c$R$^d$ (where n is an integer from 0 to 5, R' and R" are independently hydrogen or alkyl, and R$^c$ and R$^d$ are, independently of each other, hydrogen, alkyl, cycloalkyl or cycloalkylalkyl, or R$^c$ and R$^d$ together with the nitrogen atom to which they are attached form a heterocyclyl ring). Examples include, but are not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, and the derivatives thereof.

"Heteroaralkyl" means a radical —R$^a$R$^b$ where R$^a$ is an alkylene group and R$^b$ is a heteroaryl group as defined herein, e.g., pyridin-3-ylmethyl, 3-(benzofuran-2-yl)-propyl, and the like.

"Heteroaralkenyl" means a radical —R$^a$R$^b$ where R$^a$ is an alkenylene group and R$^b$ is a heteroaryl group as defined herein, e.g., 3-(pyridin-3-yl)propen-2-yl, and the like.

"Heterocyclyl" means a saturated or unsaturated non-aromatic cyclic radical of 3 to 8 ring atoms in which one or two ring atoms are heteroatoms selected from N, O, or S(O)$_n$ (where n is an integer from 0 to 2), the remaining ring atoms being C, where one or two C atoms may optionally be replaced by a carbonyl group. The heterocyclyl ring may be optionally substituted independently with one, two, or three substituents selected from alkyl, haloalkyl, heteroalkyl, halo, nitro, cyanoalkyl, hydroxy, alkoxy, amino, monosubstituted amino, disubstituted amino, aralkyl, —(CR'R")$_n$—COR (where n is an integer from 0 to 5, and R is alkyl or optionally substituted phenyl), —(CR'R")$_n$—COOR (where n is an integer from 0 to 5, R' and R" are independently hydrogen or alkyl, and R is hydrogen, alkyl, cycloalkyl or cycloalkylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl or cycloalkylalkyl, or R$^a$ and R$^b$ together with the nitrogen atom to which they are attached form a heterocyclyl ring), or —S(O)$_n$R$^d$ (where n is an integer from 0 to 2, and R$^d$ is hydrogen (provided that n is 0), alkyl, haloalkyl, cycloalkyl, cycloalkylalkyl, amino, monsubstituted amino, disubstituted amino, or hydroxyalkyl). More specifically the term heterocyclyl includes, but is not limited to, tetrahydropyranyl, piperidino, N-methylpiperidin-3-yl, 1-(2-hydroxyethyl)piperidin-4-yl, piperazino, N-methylpyrrolidin-3-yl, 3-pyrrolidino, morpholino, thiomorpholino, thiomorpholino-1-oxide, thiomorpholino-1,1 -dioxide, pyrrolinyl, imidazolinyl, and the derivatives thereof.

"Heterocyclylalkyl" means a radical —R$^a$R$^b$ where R$^a$ is an alkylene group and R$^b$ is a heterocyclyl group as defined herein, e.g., tetrahydropyran-2-ylmethyl, 4-methylpiperazin-1-ylethyl, 3-piperidinylmethyl, and the like.

"Heteroalkyl" means an alkyl radical as defined herein with one, two or three substituents independently selected from —OR$^a$, —NR$^b$R$^c$, and —S(O)$_n$R$^d$ (where n is an integer from 0 to 2). R$^a$ is hydrogen, alkyl, haloalkyl, cycloalkyl, cycloalkylalkyl, heterocyclyl, heterocyclylalkyl, aryl, aralkyl, heteroaryl, heteroaralkyl, alkoxycarbonyl, aryloxycarbonyl, carboxamido, or mono- or di-alkylcarbamoyl. R$^b$ is hydrogen, alkyl, haloalkyl, cycloalkyl, cycloalkylalkyl, heterocyclyl, heterocyclylalkyl, aryl, aralkyl, heteroaryl or heteroaralkyl. R$^c$ is hydrogen, alkyl, haloalkyl, cycloalkyl, cycloalkylalkyl, heterocyclyl, heterocyclylalkyl, aryl, aralkyl, alkylsulfonyl, alkylcarbonyl, alkoxycarbonyl, aryloxycarbonyl, carboxamido or mono- or di-alkylcarbamoyl. R$^d$ is hydrogen (provided that n is 0), alkyl, haloalkyl, cycloalkyl, cycloalkylalkyl, heterocyclyl, heterocyclylalkyl, aryl, aralkyl, heteroaryl, heteroaralkyl, amino, monsubstituted amino, disubstituted amino, or hydroxyalkyl. Examples include, but are not limited to, for example, 2-methoxyethyl, benzyloxymethyl, thiophen-2-ylthiomethyl, 2-hydroxyethyl, and 2,3-dihydroxypropyl.

"Heteroalkylene" means a linear saturated divalent hydrocarbon radical of one to six carbons or a branched saturated hydrocarbon radical of three to six carbon atoms with one, two or three substituents independently selected from —OR$^a$, —NR$^b$R$^c$, and —S(O)$_n$R$^d$ (where n is an integer from 0 to 2) where, R$^a$, R$^b$, R$^c$, and R$^d$ are as defined herein for a heteroalkyl radical. Examples include, but are not limited to, 2-hydroxyethan-1,1-diyl, 2-hydroxypropan-1,1-diyl and the like.

"Heterosubstituted cycloalkyl" means a cycloalkyl radical which is optionally independently substituted with one, two, or three substituents selected from hydroxy, hydroxyimino (=NOH), alkoxy, amino, monosubstituted amino, disubstituted amino, oxo (=O), —OC(O)R$^a$ (where R$^a$ is hydrogen, alkyl, haloalkyl, amino, monosubstituted amino, disubstituted amino, hydroxy, alkoxy, or optionally substituted phenyl), —OR$^b$ (where R$^b$ is hydroxyalkyl, haloalkyl, alkenyl, or alkoxyalkyl), —S(O)$_n$R$^c$ (where n is an integer from 0 to 2, and R$^c$ is hydrogen (provided that n is 0), alkyl, haloalkyl, cycloalkyl, cycloalkylalkyl, amino, monosubstituted amino, disubstituted amino, or hydroxyalkyl) or —NS(O)$_2$R$^d$ (where R$^d$ is alkyl, haloalkyl, cycloalkyl, cycloalkylalkyl, amino, monosubstituted amino, disubstituted amino, or hydroxyalkyl). Examples include, but are not limited to, for example, 4-hydroxycyclohexyl (including cis- or trans-4-hydroxycyclohexyl), 4-methoxycyclohexyl, 2-aminocyclohexyl, (2-methoxyethoxy)cyclohexyl, 4-oxocyclohexyl, 4-(methanesulfonylamino)cyclohexyl, allyloxycyclohexyl, and the like.

"Heteroalkylsubstituted cycloalkyl" means a cycloalkyl radical which may be optionally substituted with one, two, or three heteroalkyl groups as defined herein. Examples include, but are not limited to, 1-hydroxymethyl-cyclopent-1-yl, 2-hydroxymethyl-cyclohex-2-yl and the like.

"Heterocyclyl spiro cycloalkyl" means a spiro radical consisting of a cycloalkyl ring and a heterocyclic ring with each ring having 5 to 8 ring atoms and the two rings having only one carbon atom in common, with the understanding that the point of attachment of the heterocyclyl spiro cycloalkyl radical is via the cycloalkyl ring. The spiro radical is formed when two hydrogen atoms from the same carbon atom of the cycloalkyl radical are replaced with a heterocyclyl group as defined herein, and may be optionally substituted with alkyl, hydroxy, hydroxyalkyl, or oxo. Examples include, but are not limited to, for example, 1,4-dioxaspiro[4.5]decan-8-yl, 1,3-diazaspiro[4.5]decan-8-yl, 2,4-dione-1,3-diaza-spiro[4.5]decan-8-yl, 1,5-dioxa-spiro[5.5]undecan-9-yl, (3-hydroxymethyl-3-methyl)-1,5-dioxa-spiro[5.5]undecan-9-yl, and the like.

"Leaving group" has the meaning conventionally associated with it in synthetic organic chemistry, i.e., an atom or group capable of being displaced by a nucleophile and includes halo (such as chloro, bromo, iodo), alkanesulfonyloxy, arenesulfonyloxy, alkylcarbonyloxy (e.g. acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al. *Angew. Chem. Inter.* Edit. 1966, 5, 385; errata 511; Cahn et al. *Angew. Chem.* 1966, 78, 413; Cahn and Ingold *J. Chem. Soc.* (London) 1951, 612; Cahn et al. *Experientia* 1956, 12, 81; Cahn, *J. Chem.Educ.* 1964, 41, 116).

"Geometric Isomers" means the diastereomers that owe their existence to hindered rotation about double bonds. These configurations are differentiated in their names by the prefixes cis- and trans- or Z and E, which indicate that the groups are on the same or opposite side of a reference plane identifiable as common among stereoisomers, for example, a double bond in the molecule or to designate positions of substituents on rings relative to one another according to the Cahn-Ingold-Prelog rules.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Pro-drugs" means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy, amino, or sulfhydryl group in a compound of Formula (V) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of Formula (I), and the like.

"Protecting group" refers to a grouping of atoms that when attached to a reactive group in a molecule masks, reduces or prevents that reactivity. Examples of protecting groups can be found in T. W. Greene and P. G. Futs, *Protective Groups in Organic Chemistry*, (Wiley, 2nd ed. 1991) and Harrison and Harrison et al., *Compendium of Synthetic Organic Methods*, Vols. 1–8 (John Wiley and Sons. 1971–1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitroveratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers and allyl ethers.

"Treating" or "treatment" of a disorder includes:

(1) preventing the disorder, i.e., causing the clinical symptoms of the disease not to develop in a mammal that may be exposed to or predisposed to the disease but does not yet experience or display symptoms of the disease, (2) inhibiting the disorder, i.e., arresting or reducing the development of the disease or its clinical symptoms, or (3) relieving the disorder, i.e., causing regression of the disease or its clinical symptoms.

"A therapeutically effective amount" means the amount of a compound that, when administered to a mammal for treating a disorder, is sufficient to effect such treatment for the disorder. The "therapeutically effective amount" will vary depending on the compound, the disorder state being treated, the severity of the disorder treated, the age and relative health of the subject, the route of administration, the judgement of the attending medical practitioner, and other factors.

Compounds

In one aspect, the present invention provides compounds represented by the formula:

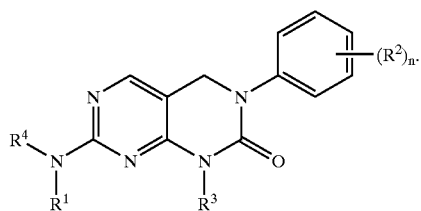

(I)

In formula (I), $R^1$ represents an acyl, heteroalkyl, arylheteroalkyl, heteroalkenyl, heteroalkynyl, heteroalkylcarbonyl, heterosubstituted cycloalkyl, heterosubstituted cycloalkylalkyl, heterosubstituted cycloalkylalkenyl, heterosubstituted cycloalkylalkynyl, heteroalkylsubstituted cycloalkyl, heterocyclyl, heterocyclylalkyl, heterocyclyl spiro, -(alkylene)—C(O)—$R^{11}$ group or (heteroalkylene)—C(O)—$R^{11}$; wherein $R^{11}$ represents an alkyl, haloalkyl, hydroxy, alkoxy, amino, monosubstituted amino, disubstituted amino, cycloalkyl, cycloalkylalkyl, aryl, aralkyl, heteroaryl or heteroaralkyl group.

In preferred embodiments, $R^1$ is heteroalkyl, arylheteroalkyl, heterosubstituted cycloalkyl, heterosubstituted cycloalkylalkyl, heteroalkylsubstituted cycloalkyl, heterocyclyl or heterocyclylalkyl, more preferably heteroalkyl or heterosubstituted cycloalkyl. In certain preferred embodiments, $R^1$ is hydroxyalkyl. In still other preferred embodiments, $R^1$ is a group having a tetrahedral carbon atom attached to the nitrogen atom, more preferably having lower alkyl groups attached to that carbon atom. For example, $R^1$ will preferably be 1-hydroxy-2-methyl-2-propyl, 1-hydroxy-2-propyl, 4-hydroxy-1-cyclohexyl, 4-hydroxycycloalkyl, 4-hydroxycycloalkyl (including cis- or trans-4-hydroxycycloalkyl), 4-oxocycloalkyl, or 4-methoxycycloalkyl and the like.

Returning to formula I, $R^2$ represents alkyl, halo, heteroalkyl or vinyl and can be attached to the phenyl ring at any of the remaining five valences otherwise occupied by hydrogen. The subscript n is an integer of from 0 to 3, indicating that the phenyl ring is substituted by from zero to three $R^2$ groups. For those embodiments in which two or three $R^2$ groups are present, each can be independent of the other(s). In preferred embodiments, n is 1 or 2 and each $R^2$ is halo or alkyl, more preferably halo. Still further preferred are those embodiments in which —$(R^2)_n$ represents 2-halo or 2,6-dihalo, more preferably 2-chloro or 2,6-dichloro.

$R^3$ represents hydrogen, alkyl, heteroalkyl, aryl, aralkyl, heteroaryl, heteroaralkyl, cycloalkyl, cycloalkenyl, cycloalkylalkyl, haloalkyl, cyanoalkyl, heterosubstituted cycloalkyl, heterosubstituted cycloalkylalkyl, heteroalkyl-substituted cycloalkyl, heterocyclyl, heterocyclylalkyl, -(alkylene)—C(O)$R^{31}$ or -(heteroalkylene)—C(O)$R^{31}$; wherein $R^{31}$ represents alkyl, haloalkyl, hydroxy, alkoxy, amino, monsubstituted amino, disubstituted amino, cycloalkyl, cycloalkylalkyl, aryl, aralkyl, heteroaryl and heteroaralkyl.

In preferred embodiments, $R^3$ is selected from hydrogen, alkyl, cycloalkyl, haloalkyl, heteroalkyl, heterocyclyl and heterosubstituted cycloalkyl. In one group of particularly preferred embodiments, $R^3$ is hydrogen. In another group of particularly preferred embodiments, $R^3$ is methyl. In yet another group of particularly preferred embodiments, $R^3$ is haloalkyl or heteroalkyl.

$R^4$ represents hydrogen, alkyl, and acyl. In preferred embodiments, $R^4$ represents hydrogen and alkyl, more preferably hydrogen.

In addition to the compounds described above, the present invention includes all pharmaceutically acceptable salts of those compounds along with prodrug forms of the compounds and all isomers whether in a pure chiral form or a racemic mixture or other form of mixture.

Still further, combinations of the preferred groups described above will form other preferred embodiments. For example, in one group of particularly preferred embodiments $R^1$ is heteroalkyl or heterosubstituted cycloalkyl, $R^2$ is halo, $R^3$ is methyl, and n is 1 or 2.

Processes for Preparing the Compounds

The compounds of the present invention can be prepared by a variety of methods, using procedures well-known to those of skill in the art. For example, in one embodiment, the compounds are prepared using methods similar to those provided in copending applications U.S. Ser. No. 60/160,803, filed Oct. 21, 1999, and U.S. Ser. No. 60/213,743, filed Jun. 22, 2000 (Bicyclic Nitrogen Heterocycles,); and U.S. Ser. No. 60/16,804, filed Oct. 21, 1999, and U.S. Ser. No. 60/213,718, filed Jun. 22, 2000 (Alkylamino-Substituted Bicyclic Nitrogen Heterocycles,) and outlined in Scheme 1.

Alternatively, the compounds of the present invention can be prepared by methods outlined in Scheme 4.

Scheme 1

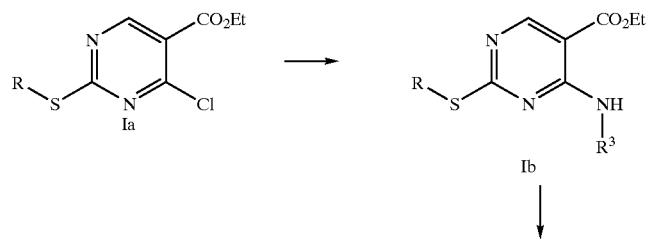

-continued

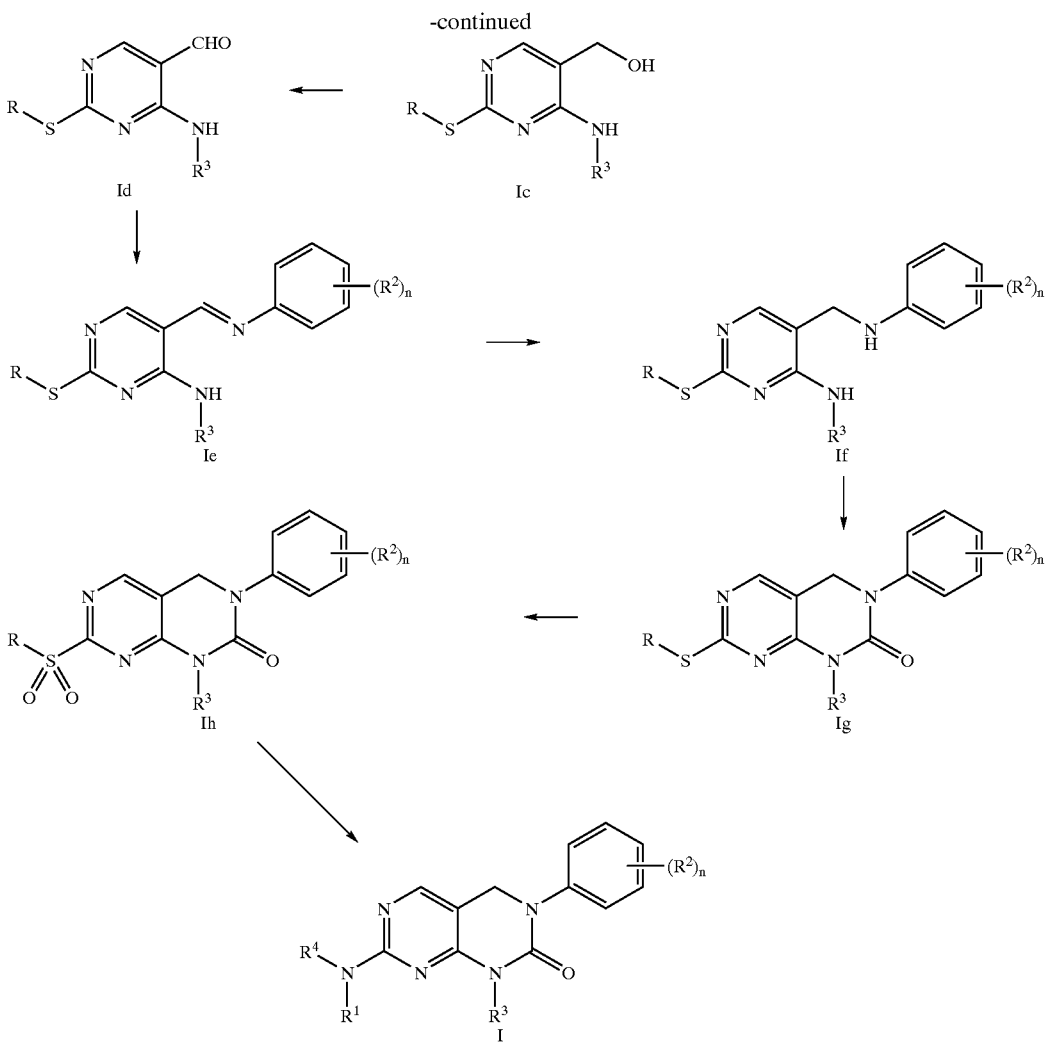

Treatment of a compound of formula Ia (where R is an alkyl, aryl or aralkyl group) with a primary amine ($R^3$—$NH_2$) provides a compound of formula Ib. This reaction is conveniently carried out in a solvent which is inert under the reaction conditions, preferably an open-chain or cyclic ether (such as tetrahydrofuran), a halogenated aliphatic hydrocarbon, especially dichloromethane, an optionally halogenated aromatic hydrocarbon, a formamide, a lower alkanol, or water. Suitably, the reaction is carried out at about −20° C. to about 120° C.

Reduction of a compound of formula Ib provides an alcohol of formula Ic. This reduction is typically carried out using lithium aluminium hydride in a manner well known to those of skill in the art (e.g. in a solvent which is inert under the conditions of the reduction, preferably an open-chain or cyclic ether, especially tetrahydrofuran, at about −20° C. to about 70° C., preferably at about 0° C. to about room temperature).

Oxidation of an alcohol of formula Ic in the next step provides a carboxaldehyde of formula Id. The oxidation is typically carried out with manganese dioxide, although numerous other methods can also be employed (see, for example, ADVANCED ORGANIC CHEMISTRY, $4^{TH}$ ED., March, John Wiley & Sons, New York (1992)). Depending on the oxidating agent employed, the reaction is carried out conveniently in a solvent which is inert under the specific oxidation conditions, preferably a halogenated aliphatic hydrocarbon, especially dichloromethane, or an optionally halogenated aromatic hydrocarbon. Suitably, the oxidation is carried out at about 0° C. to about 60° C.

Reaction of a carboxaldehyde of formula Id with a substituted aniline $(R^2)_n$—$C_6H_{5-n}NH_2$ provides a compound of formula Ie. This reaction may be carried out in the presence of an acid, e.g. an aromatic sulfonic acid, preferably 4-toluenesulfonic acid, with azeotropic removal of the water formed during the reaction. Conveniently, the reaction is carried out in a solvent which is inert under the reaction conditions, preferably an aromatic hydrocarbon, especially toluene or xylene, or an optionally halogenated aromatic hydrocarbon, and at a temperature of about 70° C. to about 150° C., especially at the reflux temperature of the solvent to assist in the noted azeotropic removal of water.

Reduction of a compound of formula Ie to give a compound of formula If can be carried out using, for example, hyride reducing agents such as sodium borohydride, lithium aluminium hydride or sodium triacetoxyborohydride under conditions well known to those of skill in the art. Preferably, the compound of formula Ie is not purified, but rather the reaction mixture in which it is prepared is concentrated and the concentrate obtained is taken up in a solvent which is inert under the conditions of the reduction, preferably an open-chain or cyclic ether, especially tetrahydrofuran or an optionally halogenated aromatic hydrocarbon or a lower alkanol, and then treated with an aforementioned reducing agents. The reduction is suitably carried out at about −10° C. to about 100° C., preferably at about 0° C.

Cyclization of a compound of formula If provides a bicyclic nitrogen heterocycle of formula Ig. The cyclization can be effected by reaction of If with a carbonylating agent such as phosgene or trichloromethyl chloroformate (or another phosgene equivalent), conveniently in the presence of a tertiary organic base, preferably a tri(lower alkyl)amine, especially triethylamine. More particularly, the cyclization is carried out in a solvent which is inert under the conditions of the reaction, preferably an open-chain or cyclic ether, especially tetrahydrofuran, an optionally halogenated aromatic hydrocarbon or a halogenated aliphatic hydrocarbon. Conveniently, the reaction is carried out at about −20° C. to about 50° C., preferably at about −20 to 0° C.

Oxidation of Ig with a peroxy acid such as 3-chloroperbenzoic acid or with Oxone® (potassium monopersulphate triple salt) in an aqueous aprotic solvent such as tetrahydrofuran, provides a sulfone (Ih) (or, if desired, its corresponding sulfoxide by controlling the oxidation conditions) which can be converted to a variety of target compounds. Typically the oxidation of Ig is carried out in a solvent which is inert under the conditions of the oxidation, preferably a halogenated aliphatic hydrocarbon, especially chloroform or dichloromethane, and at about −20° C. to about 50° C., preferably about 0° C. to about room temperature.

Finally, treatment of Ih with an amine ($R^1R^4$—NH) provides the target compounds for formula I. The reaction can be carried out in the presence or absence of solvent. Solvents that may be used include polar aprotic solvents including ethers such as dimethoxyethane, dimethoxyethyl ether and tetrahydrofuran and dipolar aprotic solvents such as dimethyl formamide and N,N-dimethylpyrrolidinone. Conveniently, the reaction is carried out at temperatures of from about 0° C. to about 200° C., more preferably about room temperature to about 150° C.

Accordingly, the present invention provides a method of preparing compounds of formula I, by treating a compound of general formula Ii with an amine ($R^1R^4$—NH).

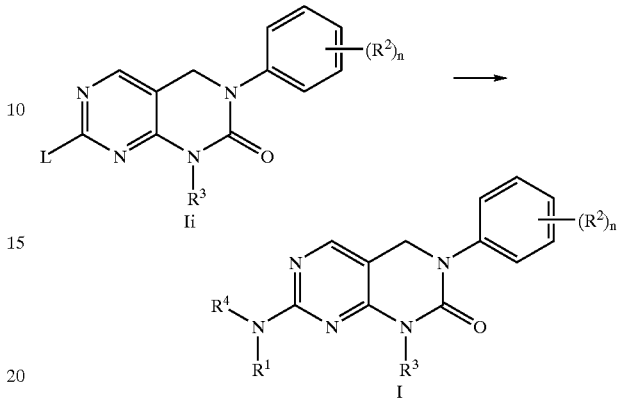

In compound Ii, the symbols $R^2$, $R^3$, $R^4$ and the subscript n have the meanings provided above with reference to formula I. The letter L represents a leaving group which can be a halogen, a lower alkanesulfonyl or alkanesulfinyl group (e.g., methanesulfonyl, methanesulfinyl or trifluoromethanesulfonyl) or an aromatic sulfonyl or sulfinyl group (e.g., benzenesulfonyl, benzenesulfinyl or 4-toluenesulfonyl). Other suitable leaving groups are known to those of skill in the art and can be found in, for example, ADVANCED ORGANIC CHEMISTRY, $4^{TH}$ ED., March, John Wiley & Sons, New York (1992). Suitable amines ($R^1$—$NH_2$) are those in which $R^1$ represents any of the $R^1$ groups noted for formula I.

In another embodiment, the bicyclic nitrogen heterocycle can be constructed first and $R^3$ can be introduced at a later stage of synthesis as shown in Scheme 2.

Scheme 2

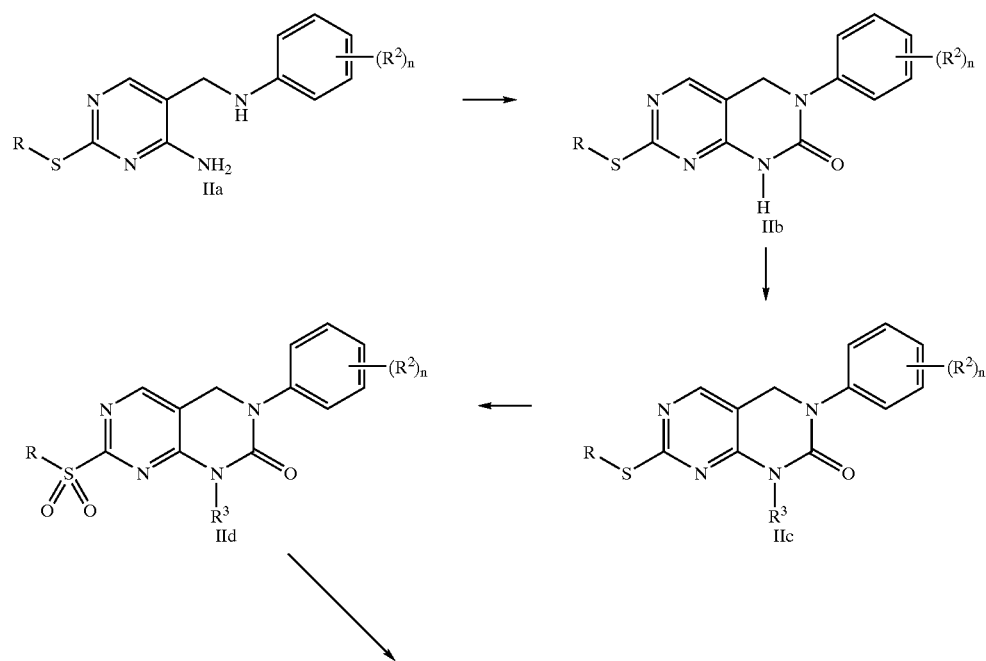

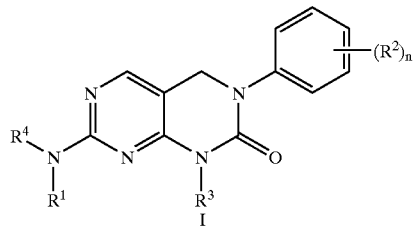

I

Compound IIa, the starting material in Scheme 2, can be prepared by the displacement reaction of commercially available compounds of formula Ia to provide compounds of formula Ib as previously described in Scheme 1. Briefly, treatment of the mercapto compound with a suitable amine provides a compound of formula Ib ($R^3$=H). Conversion of Ib ($R^3$=H) to IIa can follow the steps provided in Scheme 1.

Cyclization of IIa provides a bicyclic nitrogen heterocycle of formula IIb. The cyclization can be effected by reaction of IIa with phosgene or trichloromethyl chloroformate (or phosgene equivalent), typically in the presence of a tertiary organic base, preferably a tri(lower alkyl)amine, especially triethylamine. More particularly, the cyclization is carried out in a solvent which is inert under the conditions of the reaction, preferably an open-chain or cyclic ether, especially tetrahydrofuran, an optionally halogenated aromatic hydrocarbon or a halogenated aliphatic hydrocarbon. Conveniently, the reaction is carried out at about −20° C. to about 50° C., preferably at about 0° C. to about room temperature.

Introduction of an $R^3$ group to provide a compound of formula IIc can be accomplished under a variety of conditions. For example, IIb can be treated with alkali metal hydride, especially sodium hydride, and subsequent reaction with a compound of the general formula $R^3$—L, wherein $R^3$ has any of the values accorded to $R^3$ hereinbefore except hydrogen, aryl or heteroaryl and L represents a leaving group (e.g., halo, methanesulfonate, trifluoromethanesulfonate, and the like). The N-substitution is conveniently carried out in a solvent which is inert under the reaction conditions, preferably a formamide, especially N-methylpyrrolidinone or dimethylformamide, an open-chain or cyclic ether or an optionally halogenated aromatic hydrocarbon. Suitably, the reaction is carried out at about 50° C. to about 200° C., preferably at about 50° C. to about 150° C. Alternatively, the alkylation may be carried out with an inorganic base such as potassium carbonate in a formamide solvent such as N-methylpyrrolidinone temperatures from about 0° C. to about 25° C.

An alternative, and preferable method for the introduction of $R^3$ involves a alkylation of the pyrimidinone nitrogen via the Mitsunobu reaction. In this method, an alcohol of the general formula $R^3$—OH is combined with a compound of general formula IIb in the presence of, for example, triphenylphosphine and diethyl azodicarboxylate or diphenylpyridyl phosphine and tert-butylazodicarboxylate (See, *Tetrahedron Lett.*, 40: 4497–4500 (1999). The alkylation is conveniently carried out in a solvent which is inert under the reaction conditions, preferably an open-chain or cyclic ether, at temperatures of about −20° C. to about 100° C., preferable at about 0° C. to about 30° C. (or room temperature). As with other alkylation methods, primary and secondary alcohols are the most suitable for reaction under these conditions.

Following the introduction of $R^3$, the oxidation and displacement steps (to introduce $R^1R^4N$—) can be accomplished as outlined in Scheme 1 above to provide target compounds of formula I.

In still other embodiments, the compounds can be prepared by reversing the order of alkylation and displacement steps, thereby reversing the order of —$R^3$ and —$NR^1R^4$ introduction, shown in Scheme 3.

Scheme 3

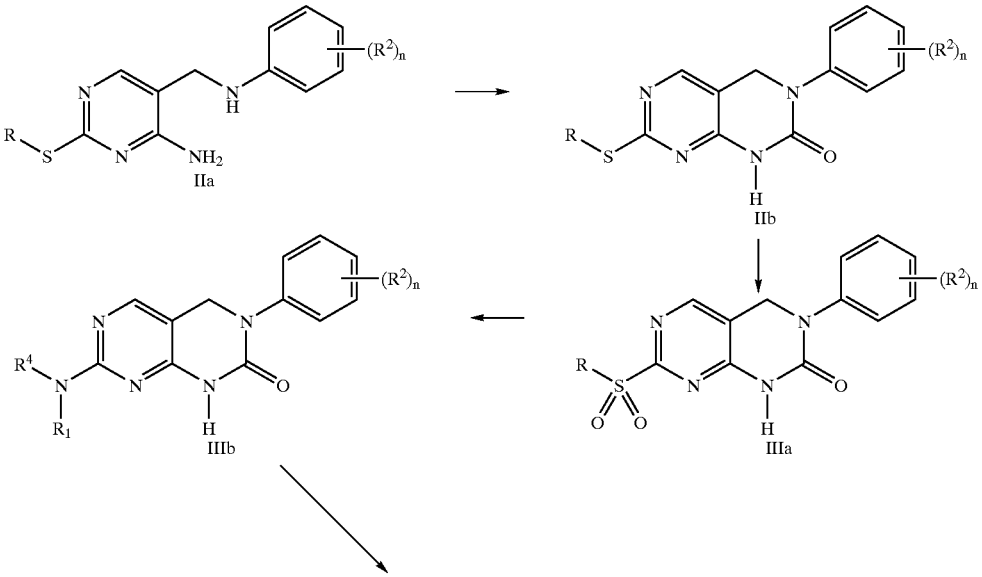

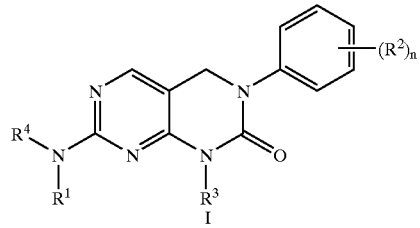

Accordingly, a compound of formula IIa can be cyclized to IIb (as earlier shown in Scheme 2). Oxidation of IIb to IIa provides the template for the subsequent displacement and alkylation steps. Thus, treatment of IIIa with $R^1$—$NH_2$ under the conditions described above, provides IIIb, which can be alkylated using $R^3$—L (wherein L has the meaning noted above) or $R^3$—OH using a Mitsunobu reaction as described earlier to provide the target compounds of formula I.

Scheme 4

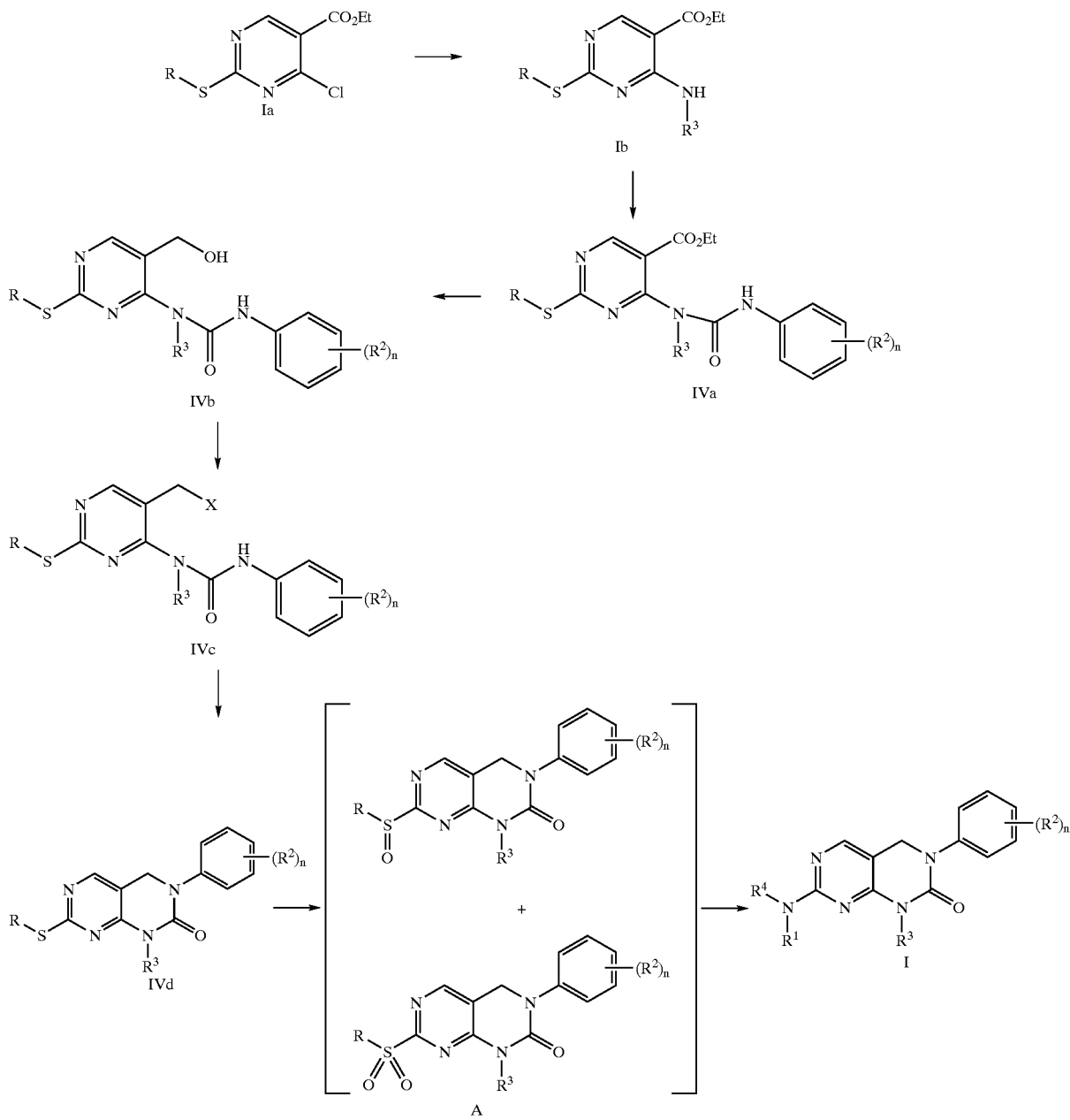

Scheme 4 provides an alternative method of preparing the compounds of Formula I.

Compound Ia, the starting material in Schemes 1 and 4, is commercially available. The treatment of a compound of formula Ia with a suitable aminating agent or nucleophile as described in Scheme 1, provides a compound of formula Ib.

Treatment of a compound of formula Ib with a substituted or unsubstituted phenylisocyanate provides an amide compound of formula IVa. This reaction is carried out in an inert organic solvent, preferably an aromatic hydrocarbon such as toluene or xylenes, and at a temperature of about 0° C. to about 150° C.

Reduction of a compound of formula IVa provides an alcohol of formula IVb. This reduction is carried out using lithium aluminium hydride in a manner well known to those skilled in the art (e.g., in an inert organic solvent such as an open-chain or cyclic ether, especially tetrahydrofuran, at about −60° C. to about 90° C., preferably at about −20° C. to about room temperature.

Reaction of an alcohol of formula IVb with a halogenating agent provides a compound of formula IVc wherein X is bromo, chloro, or iodo, preferably bromo. Although numerous halogenating methods can be employed (see, for example, ADVANCED ORGANIC CHEMISTRY, $4^{TH}$ ED., March, John Wiley & Sons, New York (1992)), this reaction can be carried out using phosphorus tribromide or phosphorous pentachloride to obtain the corresponding bromo or chloro compound, respectively. Conveniently, the reaction is carried out in a solvent which is inert under reaction conditions, preferably an open-chain or cyclic ether, especially tetrahydrofuran, or a halogenated aliphatic hydrocarbon, and at about 0° C. to about 60° C.

Cyclization of a compound of formula IVc provides a bicyclic nitrogen heterocycle of formula IVd. The cyclization can be effected in the presence of a base, preferably hexamethyldisilazane. Typically the cyclization is carried out in the presence of a solvent which is inert under the conditions of the reaction, preferably a dipolar organic solvent, such as 1-methyl-2-pyrrolidinone, N,N-dimethylformamide, or N,N-dimethylacetamide, or dimethyl sulphoxide, and at about 10° C. to about 200° C. for about 1 to 50 hours. Preferably the reaction is heated for about 1 to 10 hours at about 60° C. to about 150° C.

Finally, treatment of Id with a oxidizing agent such as N-chloro-succinimide or chlorine and water, and an amine ($R^1R^4$—NH) provides the target compounds of formula I via a sulfoxide intermediate compound of formula A. The in situ oxidation/displacement reaction is carried out in the presence of solvent which is inert under conditions of the reaction, preferably dipolar aprotic solvents 1-methyl-2-pyrrolidinone, N,N-dimethyl formamide or tetrahydrofuran. Conveniently, the reaction is carried out at about 0° C. to about 120° C., more preferably about room temperature.

One of skill in the art will understand that certain modifications to the above schemes are contemplated and within the scope of the present invention. For example, certain steps will involve the protection and deprotection of reactive functional groups that are not compatible with particular reaction conditions.

Pharmaceutical Compositions Containing the Compounds

The compounds of formula I and the pharmaceutically acceptable salts of basic compounds of formula I with acids can be used as medicaments, e.g. in the form of pharmaceutical preparations. The pharmaceutical preparations can be administered enterally, e.g. orally in the form of tablets, coated tablets, dragées, hard and soft gelatine capsules, solutions, emulsions or suspensions, nasally, e.g. in the form of nasal sprays, or rectally, e.g. in the form of suppositories. However, they may also be administered parenterally, e.g. in the form of injection solutions.

The compounds of formula I and their aforementioned pharmaceutically acceptable salts can be processed with pharmaceutically inert, organic or inorganic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active ingredient no carriers are, however, usually required in the case of soft gelatine capsules. Suitable carriers for the production of solutions and syrups are, for example, water, polyols, sucrose, invert sugar, glucose and the like. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, masking agents or antioxidants. They can also contain therapeutically valuable substances other than the compounds of formula I and their aforementioned pharmaceutically acceptable salts.

Medicaments which contain a compound of formula I or a pharmaceutically acceptable salt of a basic compound of formula I with an acid in association with a compatible pharmaceutical carrier material are also an object of the present invention, as is a process for the production of such medicaments which comprises bringing one or more of these compounds or salts and, if desired, one or more other therapeutically valuable substances into a galenical administration form together with a compatible pharmaceutical carrier.

As mentioned earlier, the compounds of formula I and their aforementioned pharmaceutically acceptable salts can be used in accordance with the invention as therapeutically active substances, especially as antiinflammatory agents or for the prevention of graft rejection following transplant surgery. The dosage can vary within wide limits and will, of course, be fitted to the individual requirements in each particular case. In general, in the case of administration to adults a convenient daily dosage should be about 0.1 mg/kg to about 100 mg/kg, preferably about 0.5 mg/kg to about 5 mg/kg. The daily dosage may be administered as a single dose or in divided doses and, in addition, the upper dosage limit referred to earlier may be exceeded when this is found to be indicated.

Finally, the use of compounds of formula I and their aforementioned pharmaceutically acceptable salts for the production of medicaments, especially in the treatment or prophylaxis of inflammatory, immunological, oncological, bronchopulmonary, dermatological and cardiovascular disorders, in the treatment of asthma, central nervous system disorders or diabetic complications or for the prevention of graft rejection following transplant surgery, is also an object o[0086] the invention.

Methods of Using the Compounds and Compositions

Compounds of Formula I would be useful for, but not limited to, the treatment of any disorder or disease state in a human, or other mammal, which is excacerbated or caused by excessive or unregulated TNF and/or IL-1 or p38 kinase production by such mammal. Accordingly, the present invention provides a method of treating a cytokine-mediated disease which comprises administering an effective cytokine-interfering amount of a compound of Formula I, or a pharmaceutically acceptable salt or tautomer thereof.

Compounds of Formula I would be useful for, but not limited to, the treatment of inflammation in a subject, and for use as antipyretics for the treatment of fever. Compounds of the invention would be useful to treat arthritis, including but not limited to, rheumatoid arthritis, spondyloarthropathies, gouty arthritis, osteoarthritis, systemic lupus erythematosus and juvenile arthritis, arthritis and other arthritic conditions. Such compounds would be useful for the treatment of pulmonary disorders or lung inflammation, including adult respiratory distress syndrome, pulmonary sarcoidosis, asthma, silicosis, and chronic pulmonary inflammatory disease. The compounds are also useful for the treatment of viral and bacterial infections, including sepsis, septic shock, gram negative sepsis, malaria, meningitis, cachexia secondary to infection or malignancy, cachexia secondary to acquired immune deficiency syndrome (AIDS), AIDS, AR$^c$ (AIDS related complex), pneumonia, and herpesvirus. The compounds are also useful for the treatment of bone resorption diseases, such as osteoporosis, endotoxic shock, toxic shock syndrome, reperfusion injury, autoimmune disease including graft vs. host reaction and allograft rejections, cardiovascular diseases including atherosclerosis, thrombosis, congestive heart failure, and cardiac reperfusion injury, renal reperfusion injury, liver disease and nephritis, and myalgias due to infection.

The compounds are also useful for the treatment of influenza, multiple sclerosis, cancer, diabetes, systemic lupus erthrematosis (SLE), skin-related conditions such as psoriasis, eczema, burns, dermatitis, keloid formation, and scar tissue formation. Compounds of the invention also would be useful to treat gastrointestinal conditions such as inflammatory bowel disease, Crohn's disease, gastritis, irritable bowel syndrome and ulcerative colitis. The compounds would also be useful in the treatment of ophthalmic diseases, such as retinitis, retinopathies, uveitis, ocular photophobia, and of acute injury to the eye tissue. Compounds of the invention also would be useful for treatment of angiogenesis, including neoplasia; metastasis; ophthalmological conditions such as corneal graft rejection, ocular neovascularization, retinal neovascularization including neovascularization following injury or infection, diabetic retinopathy, retrolental fibroplasia and neovascular glaucoma; ulcerative diseases such as gastric ulcer; pathological, but non-malignant, conditions such as hemaginomas, including invantile hemaginomas, angiofibroma of the nasopharynx and avascular necrosis of bone; diabetic nephropathy and cardiomyopathy; and disorders of the female reproductive system such as endometriosis. The compounds of the invention may also be useful for preventing the production of cyclooxygenase-2 and the compounds of this invention are also expected to be useful in the prevention and treatment of cancer, in particular colon cancer. The compounds of this invention are also expected to be useful in the prevention and treatment of Alzheimer's disease.

Besides being useful for human treatment, these compounds are also useful for veterinary treatment of companion animals, exotic animals and farm animals, including got mammals, rodents, and the like. More preferred animals include horses, dogs, and cats.

The present compounds may also be used in co-therapies, partially or completely, in place of other conventional antiinflammatories, such as together with steroids, cyclooxygenase-2 inhibitors, NSAIDs, DMARDS, immunosuppressive agents, 5-lipoxygenase inhibitors, LTB$_4$ antagonists and LTA$_4$ hydrolase inhibitors.

As used herein, the term "TNF mediated disorder" refers to any and all disorders and disease states in which TNF plays a role, either by control of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disorder mediated by TNF.

As used herein, the term "p38 mediated disorder" refers to any and all disorders and disease states in which p38 plays a role, either by control of p38 itself, or by p38 causing another factor to be released, such as but not limited to IL-1, IL-6 or IL-8. A disease state in which, for instance, IL-1 is a major component, and whose production or action, is exacerbated or secreted in response to p38, would therefore be considered a disorder mediated by p38.

As TNF-β has close structural homology with TNF-α (also known as cachectin), and since each induces similar biologic responses and binds to the same cellular receptor, the synthesis of both TNF-α and TNF-β are inhibited by the compounds of the present invention and thus are herein referred to collectively as "TNF" unless specifically delineated otherwise.

EXAMPLES

The following examples are offered to illustrate, but not to limit the claimed invention.

In the examples below, unless otherwise stated, temperatures are given in degrees Celsius (° C.); operations were carried out at room or ambient temperature (typically a range of from about 18–25° C.; evaporation of solvent was carried out using a rotary evaporator under reduced pressure (typically, 4.5–30 mmHg) with a bath temperature of up to 60° C.; the course of reactions was typically followed by TLC and reaction times are provided for illustration only; melting points are uncorrected; products exhibited satisfactory $^1$H-NMR and/or microanalytical data; yields are provided for illustration only; and the following conventional abbreviations are also used: mp (melting point), L (liter(s)), mL (milliliters), mmol (millimoles), g (grams), mg (milligrams), min (minutes), and h (hours).

DEAD stands for diethyl azodicarboxylate

DIAD stands for diisopropyl azodicarboxylate

DMPU stands for 1,3-dimethyl-3,4,5,6-tetrahydro-2(1H)-pyrimidinone

Example 1

This example illustrates the preparation of 3-(2,6-dichlorophenyl)-7-methanesulfonyl-1-methyl-3,4-dihydropyrimido[4,5-d]pyrimidin-2(1H)-one beginning with ethyl 4-chloro-2-methylthiopyrimidine-5-carboxylate.

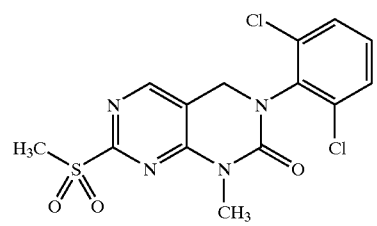

1.1 Preparation of ethyl 4-methylamino-2-methyliopyrimidine-5-carboxylate

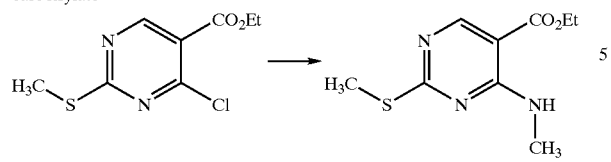

A solution of ethyl 4-chloro-2-methylthiopyrimidine-5-carboxylate (20 g, 86 mmol) (Aldrich Chemical Co., Milwaukee, Wis., USA) in 250 mL of dichloromethane was cooled to 0° C. and treated slowly with a 33% solution of methylamine in ethanol (35 mL, 281 mmol). After stirring for 30 minutes, 150 mL of water were added and the phases were separated. The organic phase was dried over magnesium sulfate and filtered. The filtrate was evaporated under reduced pressure to give 19 g (97%) of ethyl 4-methylamino-2-methylthiopyrimidine-5-carboxylate as a white solid.

1.2 Preparation of 4-methylamino-2-methylthiopyrimidine-5-methanol

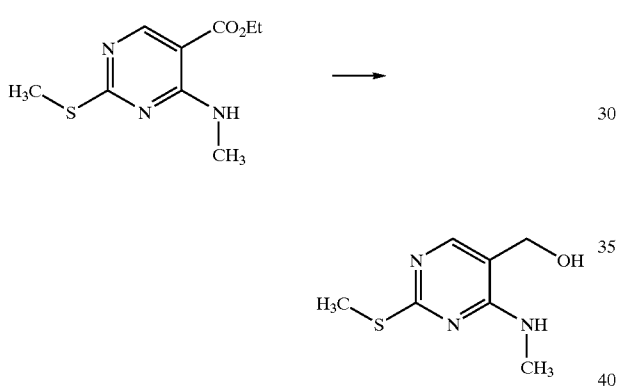

Lithium aluminium hydride (9 g, 237 mmol) was stirred in 300 mL of dry tetrahydrofuran and treated dropwise with a solution of ethyl 4-methylamino-2-methylthiopyrimidine-5-carboxylate (34 g, 143 mmol) in 300 mL of dry tetrahydrofuran and left to stand for 15 minutes. The mixture was cooled in ice and cautiously treated dropwise with 18 mL of water. Thirty six mL of 2M sodium hydroxide solution were added dropwise, followed by 48 mL of water. The resulting suspension was stirred for 17 hours at room temperature and then filtered. The filter residue was washed twice with 100 mL of ethyl acetate each time and the combined filtrate and washings were evaporated under reduced pressure. The residue was suspended in 200 mL of dichloromethane/hexane (2:1) and the solid was off and dried to give 23.5 g (86%) of 4-methylamino-2-methylthiopyrimidine-5-methanol as a yellow solid.

1.3 Preparation of 4-methylamino-2-methylthiopyrimidine-5-carboxaldehyde

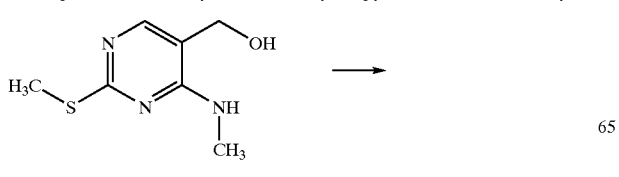

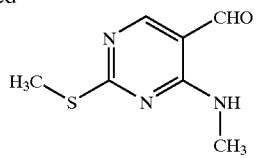

4-Methylamino-2-methylthiopyrimidine-5-methanol (20 g, 108 mmol) and 1 L of dichloromethane were combined with stirring and treated with manganese dioxide (87 g, 1 mol). The resulting suspension was stirred for 24 hours and then filtered through a filter aid. The filter residue was washed with 100 mL of dichloromethane and the combined filtrate and washings were evaporated under reduced pressure to give 15.8 g (80%) of 4-methylamino-2-methylthiopyrimidine-5-carboxaldehyde as a white solid.

1.4 Preparation of 5-(2,6-dichlorophenyl)aminomethyl-4-methylamino-2-methylthio-pyrimidine

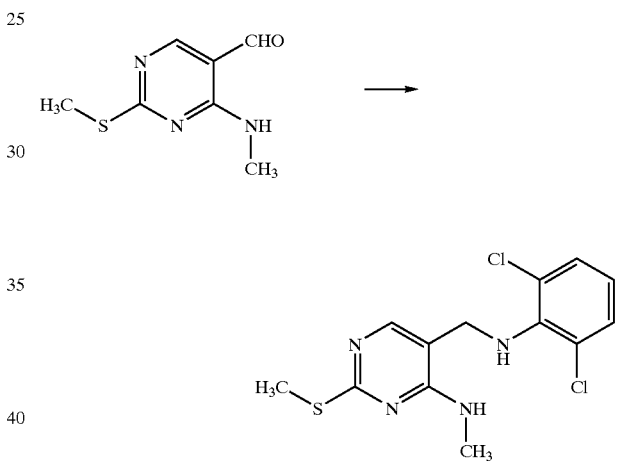

A mixture of 4-methylamino-2-methylthiopyrimidine-5-carboxaldehyde (6 g, 32.8 mmol), 2,6-dichloroaniline (5.5 g, 33.9 mmol) and 4-toluene-sulfonic acid (1 g, 5.3 mmol) in 70 mL of toluene was heated under reflux with azeotropic removal of water for 17 hours. The mixture was concentrated to a volume of about 10 mL under reduced pressure and then treated with 120 mL of ethanol. The suspension obtained was heated to 75° C. and treated over a period of 15 minutes with 6.2 g (160 mmol) of sodium borohydride pellets. The mixture was stirred for a further 15 minutes and cooled to room temperature. The solvent was evaporated under reduced pressure and the residue was stirred in a mixture of 200 mL of 2M sodium hydroxide solution and 200 mL of ethyl acetate for 1 hour. The phases were separated and the organic phase was dried over magnesium sulfate and filtered. Evaporation of the filtrate under reduced pressure and flash chromatography of the residue using 3:7 diethyl ether/hexane for the elution gave 5.2 g (48%) of 5-(2,6-dichlorophenyl)aminomethyl-4-methylamino-2-methylthio-pyrimidine as a white solid.

1.5 Preparation of 3-(2,6-dichlorophenyl)-7-methylthio-1-methyl-3,4-dihydro-pyrimidol[4,5-d]pyrimidin-2(1H)-one

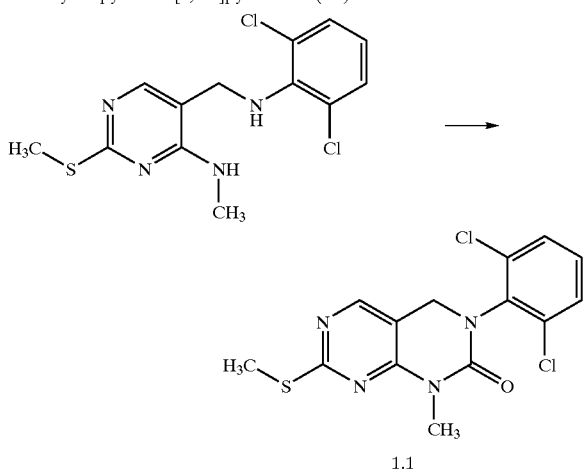

1.1

A stirred solution, cooled in ice, of 12 mL of phosgene (20% solution in toluene; 23 mmol) in 100 mL of tetrahydrofuran was treated dropwise with a solution of 5-(2,6-dichlorophenyl)aminomethyl-4-methylamino-2-methylthio-pyrimidine (5 g, 15.2 mmol) and triethylamine (4 mL, 29 mmol) in 80 mL of tetrahydrofuran. After stirring for 1 hour the mixture was treated with 100 mL of saturated aqueous ammonium chloride solution and the phases were separated. The aqueous phase was extracted with 100 mL of tetrahydrofuran and the combined organic solutions were dried over magnesium sulfate and filtered. The filtrate was concentrated under reduced pressure to give 4.8 g (89%) of 3-(2,6-dichlorophenyl)-7-methylthio-1-methyl-3,4-dihydropyrimido[4,5-d]pyrimidin-2(1H)-one (sulfide 1.1) as a white solid.

1.6 Preparation of 3-(2,6-dichlorophenyl)-7-methanesulfonyl-1-methyl-3,4-dihydropyrimidol[4,5-d]pyrimidin-2(1H)-one

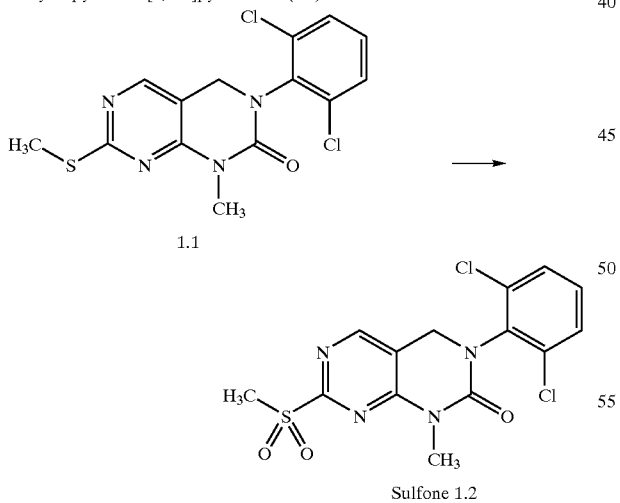

Sulfone 1.2

A solution of 3-(2,6-dichlorophenyl)-7-methylthio-1-methyl-3,4-dihydropyrimido[4,5-d]pyrimidin-2(1H)-one (1.1) (5 g, 14.1 mmol) in 200 mL of dichloromethane was cooled in ice and treated with 3-chloroperbenzoic acid (10 g, 28.9 mmol). The mixture was stirred at room temperature for 17 hours, then treated with 2 mL of dimethyl sulfoxide and left to stand for 10 minutes. Saturated aqueous sodium bicarbonate solution (100 mL) was then added and the phases were separated. The organic phase was dried over magnesium sulfate and filtered. Concentration of the filtrate under reduced pressure gave 5 g (92%) of 3-(2,6-dichlorophenyl)-7-methanesulfonyl-1-methyl-3,4-dihydropyrimido[4,5-d]pyrimidin-2(1H)-one (sulfone 1.2) as a white solid.

A related compound, 3-(2-chlorophenyl)-7-methanesulfonyl-1-methyl-3,4-dihydropyrimidin-2(1H)-one (sulfone 1.3) was prepared using 2-chloroaniline in place of 2,6-dichloroaniline in step 1.4, above.

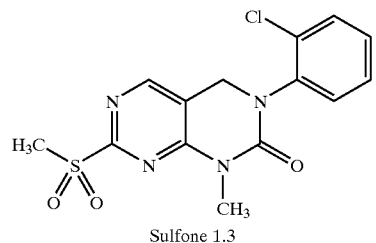

Sulfone 1.3

Similarly, 7-methanesulfonyl-3-ortho-tolyl-1-methyl-3,4-dihydropyrimidin-2(1H)-one (sulfone 1.4) was prepared using o-toluidine in place of 2,6-dichloroaniline in step 1.4, above.

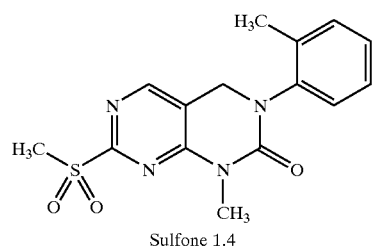

Sulfone 1.4

Example 2

Compound 1-7

This example illustrates the preparation of 3-(2-chlorophenyl)-7-(2-hydroxy-1,1-dimethylethylamino)-1-methyl-3,4-dihydropyrimido[4,5-d]pyrimidin-2(1H)-one, in which the displacement reaction is carried out in the absence of solvent.

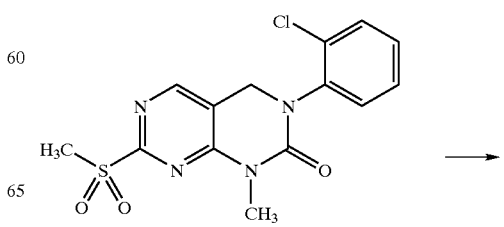

-continued

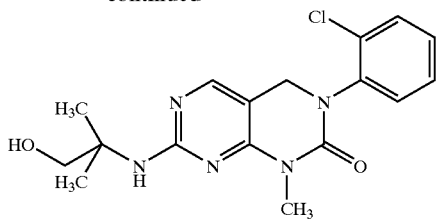

Sulfone 1.3 (0.200 g, 0.57 mmol) was combined with 2-amino-2-methyl-1-propanol (0.11 mL, 1.2 mmol). The mixture was heated to 100–110 ° C. for 1 hour at which time it was cooled to room temperature. The residue was purified by column chromatography on silica gel using 25:15 hexane/acetone. The column fractions containing product were combined and concentrated in vacuo to an oil which was redissolved in ethyl acetate. Addition of hydrochloric acid (1.0M/Et$_2$O, 1.0 equivalent) gave the salt which was filtered and dried to give 0.150 g of the hydrochloride salt of 3-(2-chlorophenyl)-7-(2-hydroxy-1,1-dimethylethylamino)-1-methyl-3,4-dihydropyrimido-[4,5-d]pyrimidin-2(1H)-one.

Replacement of 2-amino-2-methyl-1-propanol with the requisite amine R$^1$R$^4$NH gave additional compounds of the invention as listed on Tables 1–3.

Example 3

Compound 1-13

This example illustrates the preparation of 3-(2-chlorophenyl)-7-((1S,2R)-2-hydroxy-1-hydroxymethyl-propylamino)-1-methyl-3,4-dihydropyrimido-[4,5-d]pyrimidin-2(1H)-one.

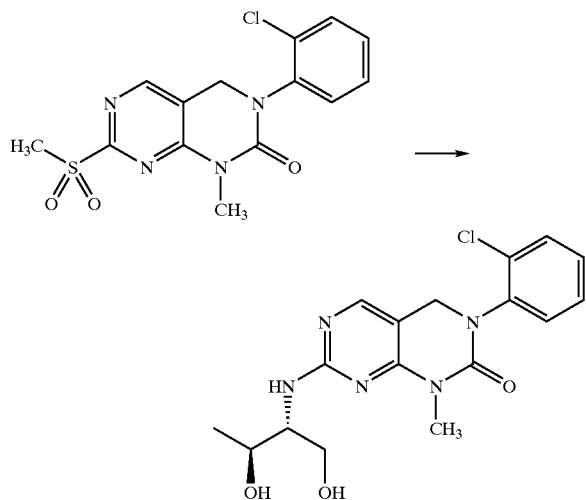

Sulfone 1.3 (0.800 g, 2.27 mmol) was combined with 2-methoxyethyl ether (3 mL) and D-allothreoninol ((2R,3S)-2-amino-3-hydroxybutanol) (0.480 g, 4.56 mmol). The mixture was heated at 100° C. for one hour at which time the temperature was raised to 130° C. since the reaction was not complete. After 30 minutes, the reaction was complete and the mixture was cooled to room temperature. The mixture was concentrated in vacuo and the residue was purified by column chromatography on silica gel using 70:5:1 dichloromethane/methanol/isopropylamine. The column fractions containing product were combined and concentrated to an oil which was redissolved in ethyl acetate. Addition of hydrochloric acid (1.0M/Et$_2$O, 1.0 equivalent) gave the salt which was filtered and dried to give 0.448 g of the hydrochloride salt of 3-(2-chloro-phenyl)-7-((1S,2R)-2-hydroxy-1-hydroxymethylpropylamino)-1-methyl-3,4-dihydropyrimido-[4,5-d]pyrimidin-2(1H)-one.

Replacement of D-allothreoninol with the requisite amine R$^1$R$^4$NH gave additional compounds of the invention as listed on Tables 1–3.

Example 4

Compound 1-2

This example illustrates the preparation of 3-(2-chlorophenyl)-7-(2-hydroxy-1-methylethylamino)-1-methyl-3,4-dihydropyrimido[4,5-d]pyrimidin-2(1H)-one.

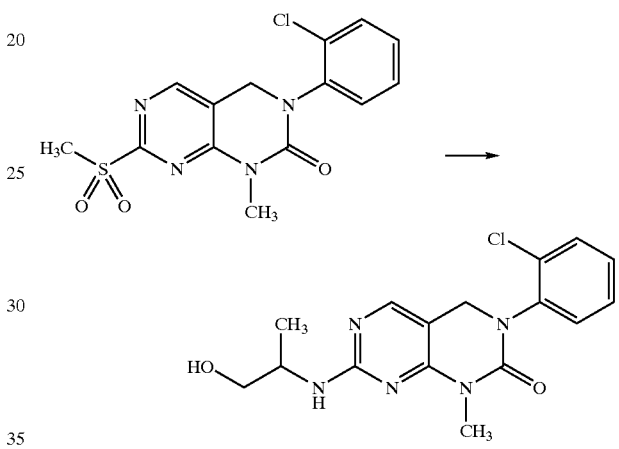

Sulfone 1.3 (0.200 g, 0.57 mmol) was combined with D,L-2-amino-1-propanol (0.09 mL, 1.13 mmol) and heated at 100–110° C. for 30 minutes. The reaction was then cooled to room temperature and the mixture was purified by column chromatography on silica gel using 9:1 dichloromethane/methanol as eluant. The column fractions containing product were combined and concentrated in vacuo to an oil which was redissolved in ethyl acetate. Addition of hydrochloric acid (1.0M/Et$_2$O, 1.0 equivalent) gave the salt which was filtered and dried to give 0.142 g of the hydrochloride salt of 3-(2-chlorophenyl)-7-(2-hydroxy-1-methylethylamino)-1-methyl-3,4-dihydropyrimido[4,5-d]pyrimidin-2(1H)-one.

Example 5

Compound 1-3

This example illustrates the preparation of 3-(2-chlorophenyl)-7-(2-hydroxypropylamino)-1-methyl-3,4-dihydropyrimido[4,5-d]pyrimidin-2(1H)-one.

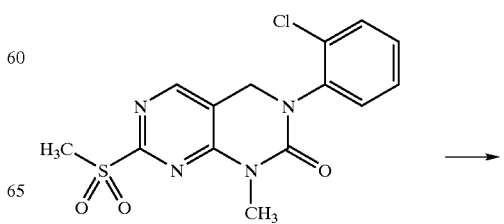

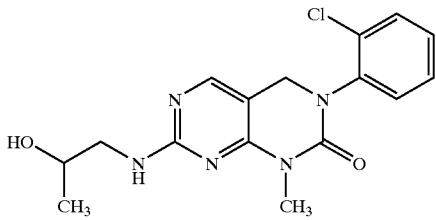

Sulfone 1.3 (0.200 g, 0.57 mmol) was combined with 1-amino-2-propanol (0.09 mL, 1.17 mmol) and heated at 100–110° C. for 30 minutes. The reaction was then cooled to room temperature and the mixture was purified by column chromatography on silica gel using 9:1 dichloromethane/methanol as eluant. The column fractions containing product were combined and concentrated in vacuo to an oil which was redissolved in ethyl acetate. Addition of hydrochloric acid (1.0M/Et$_2$O, 1.0 equivalent) gave the salt which was filtered and dried to give 0.165 g of the hydrochloride salt of 3-(2-chlorophenyl)-7-(2-hydroxypropylamino)-1-methyl-3,4-dihydropyrimido-[4,5-d]pyrimidin-2(1H)-one.

Example 6

Compound 3-28

This example illustrates the preparation of 3-(2-chlorophenyl)-7-(2,3-dihydroxy-1,1-dimethylpropylamino)-1-methyl-3,4-dihydropyrimido[4,5-d]pyrimidin-2(1H)-one.

chloride and extracted with dichloromethane. The layers were separated, and the organic layer was dried over potassium carbonate, and concentrated in vacuo. The residue was purified by flash chromatography using 2:1 hexane/ethyl acetate as eluant to give 10.02 g of (3,3-dimethyloxiranyl)methanol as an oil.

A solution of (3,3-dimethyloxiranyl)methanol (10 g, 98 mmol) in dichloromethane (735 mL) was combined with a solution of titanium isopropoxide (50mL, 169.4mmol) in dichloromethane (100 mL) and a solution of aminodiphenylmethane (40.6 mL, 235 mmol) in dichloromethane (100 mL), and the reaction mixture was stirred at room temperature for 48 hours. A solution of 10% sodium hydroxide in brine was added and the suspension stirred for an additional 12 hours, filtered and washed with 0.2M hydrochloric acid. The layers were separated, and the organic layer was dried over magnesium sulfate, filtered, concentrated. The residue was purified by column chromatography using 4:1 hexane/ethyl acetate as eluant to give 5.1 g of 3-(benzhydrylamino)-3-methylbutane-1,2-diol.

3-(Benzhydrylamino)-3-methylbutane-1,2-diol (5.1 g, 17.9 mmol) and palladium hydroxide (1.2 g) in methanol (25 mL) were shaken under hydrogen in a par apparatus at 49 psi for 18 hours. The suspension was filtered, and the filtrate was concentrated in vacuo. The residue was suspended in hexane, stirred for 2 minutes, and the hexane layer was decanted. The residue was concentrated in vacuo to give 1.74 g of 3-amino-3-methyl-1,2-butanediol.

Preparation of 3-(2-Chlorophenyl)-7-(2,3-dihydroxy-1,1-dimethylpropylamino)-1-methyl-3,4-dihydropyrimido[4,5-d]pyrimidin-2(1H)-one Sulfone 1.3 (700 mg, 1.7 mmol) was combined with 3-amino-3-methyl-1,2-butanediol (500 mg, 2.1 mmol) and Preparation of 3-amino-3-methylbutane-1,2-diol

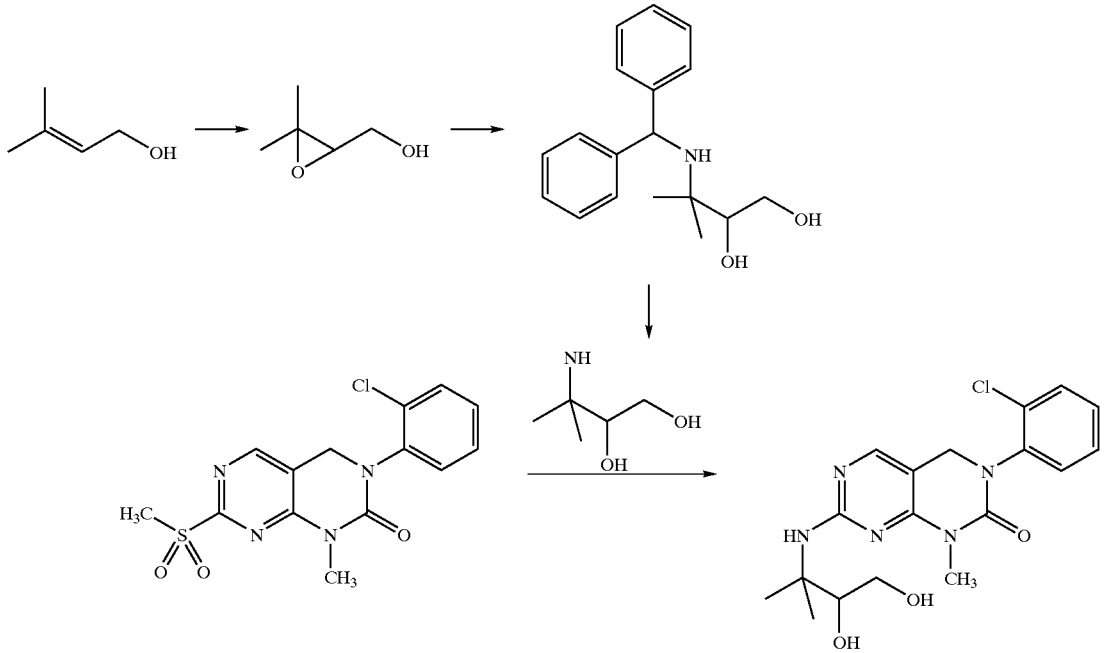

To a solution of 3-methyl-2-buten-1-ol (20 mL, 0.2 mol) in 800 mL of water was added sodium bicarbonate (42.5 g, 0.5 mol). The solution was cooled to 5° C. and 3-chloroperbenzoic acid (54 g, 0.22 mol) was added in portions over a 1 hour period. The mixture was stirred at room temperature for 12 hours, then saturated with sodium 2-methoxyethyl ether (2 mL). The mixture was heated to 100° C. for 6 hours at which time it was cooled to room temperature and concentrated in vacuo. The residue was purified by column chromatography on silica gel using 99:1 dichloromethane/methanol as eluant. The column fractions containing product were combined and concentrated in vacuo to the title compound as an oil, which was re-dissolved in ethyl acetate. Addition of hydrochloric acid (1.0M/Et$_2$O, 2.0 equivalents) gave the salt which was filtered and dried to give 256 mg of the hydrochloride salt of 3-(2-chlorophenyl)-7-(2,3-dihydroxy-1,1-dimethylpropyl-amino)-1-methyl-3,4-dihydropyrimido [4,5-d]-pyrimidin-2(1H)-one.

Example 7

Compound 3-43

This example illustrates the preparation of 3-(2-chlorophenyl)-7-[(1-hydroxymethylcyclohexyl)amino]-1-methyl-3,4-dihydropyrimido[4,5-d]pyrimidin-2(1H)-one.

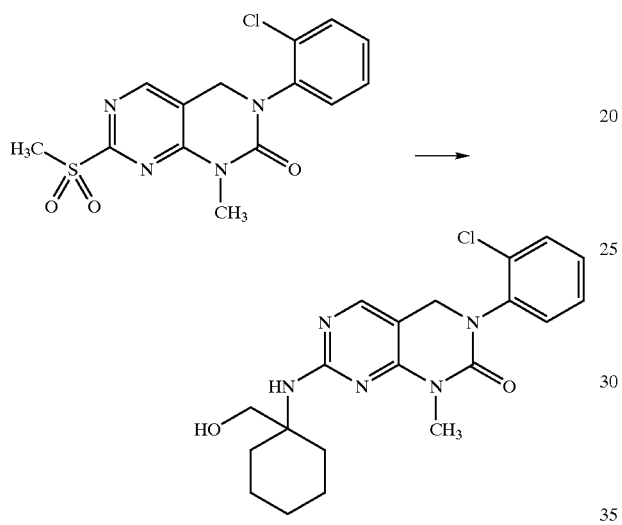

Sulfone 1.3 (500 mg, 1.2mmol) was combined with 1-amino-1-cyclohexanemethanol (602 mg, 4.6mmol) (prepared as described in *J. Med. Chem.*, 1966, 9(6), 911–920) and 1-methyl-2-pyrrolidinone (1 mL). The mixture was heated to 120° C. for 3 hours at which time it was cooled to room temperature. The residue was purified by column chromatography on silica gel using 98:2 dichloromethane/methanol as eluant. The column fractions containing product were combined and concentrated in vacuo to a solid which was triturated with water, filtered, dried and suspended in ethyl acetate. Addition of hydrochloric acid (1.0M/Et$_2$O, 2.0 equivalents) gave the salt which was filtered and dried to give 328 mg of the hydrochloride salt of 3-(2-chlorophenyl)-7-[(1-hydroxymethylcyclohexyl)amino]-1-methyl-3,4-dihydropyrimido[4,5-d]pyrimidin-2(1 H)-one.

Example 8

Compound 3-45

This example illustrates the preparation of 3-(2-chlorophenyl)-7-(1,4-dioxaspiro[4.5]dec-8-ylamino)-1-methyl-3,4-dihydropyrimido[4,5-d]pyrimidin-2(1H)-one.

Preparation of 1,4-dioxaspiro[4,5]dec-8-ylamine

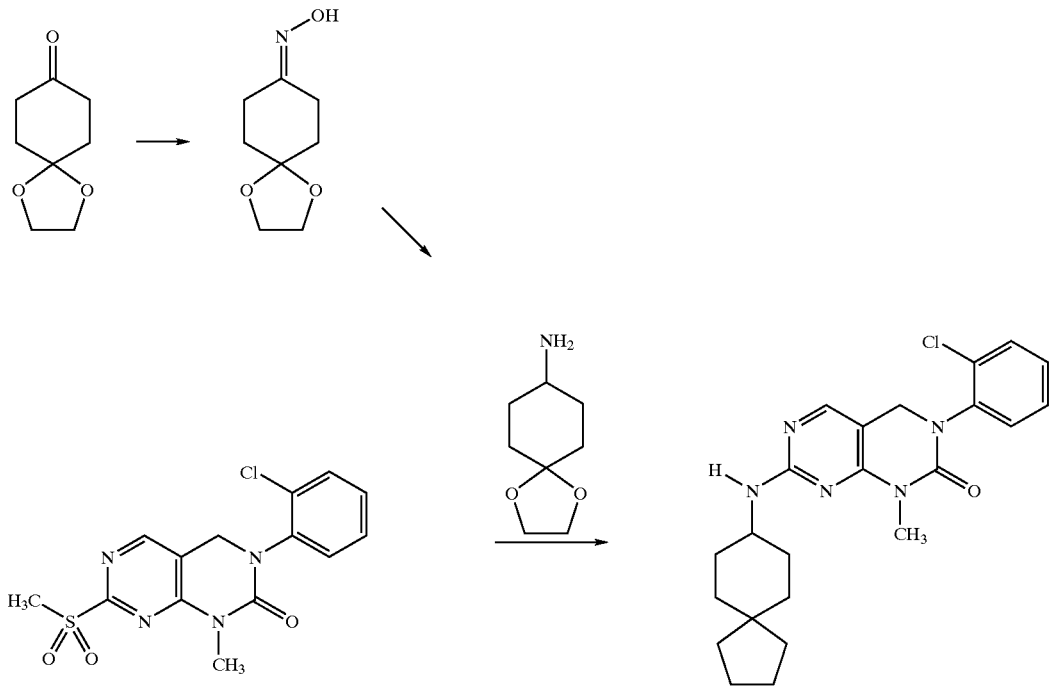

33

To a mixture of 1,4-dioxaspiro[4.5]decan-8-one (50.3 g, 322.1 mmol) and hydroxylamine hydrochloride (89.5 g, 100.3 mmol) in water (450 mL) was added portionwise sodium carbonate (102.4 g, 966.2 mmol). The reaction mixture was stirred for 40 minutes at room temperature then extracted with ethyl acetate. The organic layer was washed with brine, dried over magnesium sulfate, filtered and concentrated in vacuo to give 68.2 g of crude 1,4-dioxaspiro [4.5]decan-8-one oxime.

To a solution of 1,4-dioxaspiro[4.5]decan-8-one oxime (68 g, 400 mmol) in ethanol (200 mL) was added Raney Nickel as a suspension in ethanol (52 mL). The resulting mixture was shaken at 50 psi of hydrogen for 18 hours. The reaction was filtered and concentrated in vacuo to give 57.5g of 1,4-dioxaspiro[4.5]dec-8-ylamine.

Preparation of 3-(2-Chlorophenyl)-7-(1,4-dioxaspiro [4.5]dec-8-ylamino)-1-methyl-3,4-dihydropyrimido [4,5-d]pyrimidin-2(1H)-one Sulfone 1.3 (3.6 g, 10 mmol) was combined with 1,4-dioxaspiro[4.5]dec-8-ylamine (6.4 g, 41 mmol) in 20 mL of 1-methyl-2-pyrrolidinone and heated at 100° C. for 5 hours. The reaction mixture was then cooled to room temperature and was diluted with ethyl acetate and water. The layers were separated, and the organic layer was washed with water and brine, dried with sodium sulfate, concentrated in vacuo, and purified by column chromatography on silica gel using 0.5% ammonium hydroxide in ethyl acetate as eluant. The column fractions containing the product were combined and concentrated under reduced pressure to give 1.3 g of 3-(2-chlorophenyl)-7-(1,4-dioxaspiro[4.5]dec-8-ylamino)-1-methyl-3,4-dihydropyrimido[4,5-d]pyrimidin-2(1H)-one as an off-white solid.

Example 9

Compound 3-47

This example illustrates the preparation of 3-(2-chlorophenyl)-7-(3-hydroxymethyl-3-methyl-1,5-dioxaspiro[5.5]undec-9-ylamino)-1-methyl-3,4-dihydropyrimido[4,5-d]pyrimidin-2(1H)-one.

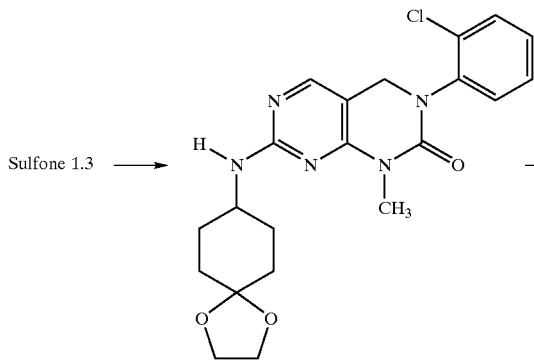

-continued

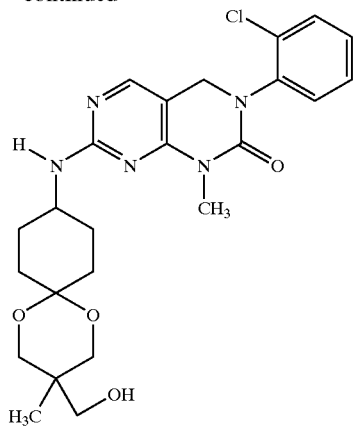

A mixture of the 3-(2-chlorophenyl)-7-(1,4-dioxaspiro [4.5]dec-8-ylamino)-1-methyl-3,4-dihydropyrimido[4,5-d] pyrimidin-2(1H)-one (0.30 g, 0.70 mmol) (prepared as described in Example 8), p-toluenesulphonic acid monohydrate (0.17 g, 0.91 mmol), and 1,1,1-tris(hydroxymethyl) ethane (0.84 g, 7.0 mmol) in 40 mL toluene was heated to reflux and allowed to stir at reflux overnight. The reaction mixture was cooled to room temperature, then diluted with ethyl acetate and saturated aqueous sodium bicarbonate. The layers were separated, and the aqueous layer was extracted with ethyl acetate. The organic layer was washed with brine, dried, concentrated under reduced pressure, and purified by flash chromatography on silica gel using 50–60% acetone in hexane as eluant. The column fractions containing product were combined and concentrated to give 0.32 g of the title compound as a white foam. Addition of 1M hydrochloric acid in diethyl ether gave the salt, which was filtered to give 160 mg of the hydrochloride salt of 3-(2-chlorophenyl)-7-(3-hydroxymethyl-3-methyl-1,5-dioxaspiro[5.5]undec-9-ylamino)-1-methyl-3,4-dihydropyrimido[4,5-d]pyrimidin-2 (1H)-one.

Example 10

Compound 3-46

This example illustrates the preparation of 3-(2-chlorophenyl)-7-(4-oxo-cyclohexylamino)-1-methyl-3,4-dihydropyrimido[4,5-d]pyrimidin-2(1H)-one.

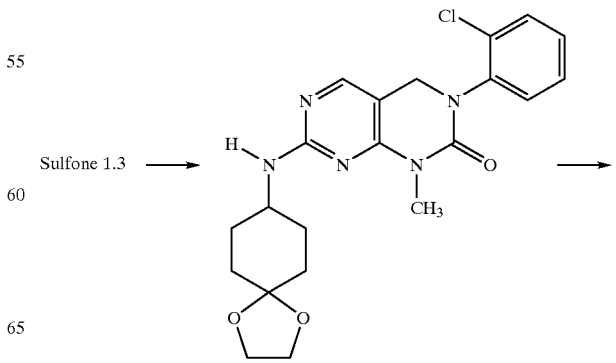

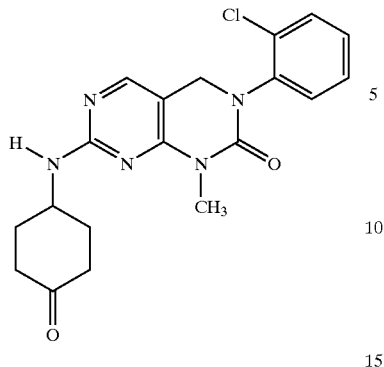

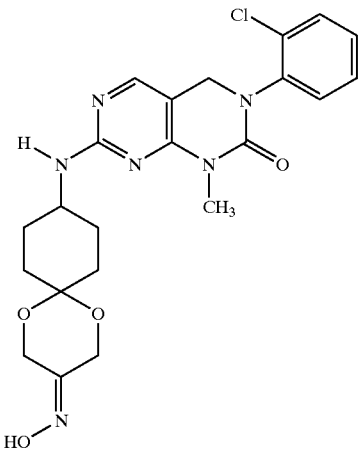

A solution of 3-(2-chlorophenyl)-7-(1,4-dioxaspiro[4.5]dec-8-ylamino)-1-methyl-3,4-dihydropyrimido[4,5-d]pyrimidin-2(1H)-one (6.0 g, 14 mmol) (prepared as described in Example 8) in 60 mL of 80% acetic acid was heated to 65° C. overnight. The reaction was then cooled to room temperature and diluted with water, ethyl acetate, and brine. The layers were separated, and the aqueous layer extracted with ethyl acetate. The organic layer was washed with saturated aqueous sodium bicarbonate and brine, dried, and concentrated under reduced pressure. The residue was taken up in chloroform and purified by flash chromatography on silica gel using 4% methanol/dichloromethane as eluant to give 2.2 g of the title compound as a white foam. A portion of the title compound (0.30 g, 0.78 mmol) was dissolved in ethyl acetate, then treated with 1M hydrochloric acid in diethyl ether to give 150 mg of the hydrochloride salt of 3-(2-chlorophenyl)-7-(4-oxo-cyclohexylamino)-1-methyl-3,4-dihydropyrimido[4,5-d]-pyrimidin-2(1H)-one as a white precipitate, which was filtered, washed with ethyl acetate, and concentrated under reduced pressure.

A mixture of 3-(2-chlorophenyl)-7-(4-oxo-cyclohexyl-amino-1-methyl-3,4-dihydropyrimido[4,5-d]pyrimidin-2-one (0.31 g, 0.80 mmol) (prepared as described in Example 10) and hydroxylamine hydrochloride (0.22 g, 3.2 mmol) in 5 mL pyridine was heated at 65° C. for 90 minutes. The reaction mixture was then cooled to room temperature, diluted with water and ethyl acetate, and the phases were separated. The organic phase was filtered, dried under reduced pressure, and suspended in methanol. Addition of 1M hydrochloric acid in diethyl ether gave the hydrochloride salt of 3-(2-chlorophenyl)-7-(4-hydroxyimino-cyclohexylamino)-1-methyl-3,4-dihydropyrimido[4,5-d]pyrimidin-2(1H)-one as a yellow foam which was concentrated under reduced pressure.

Example 11

Compound 3-50

This example illustrates the preparation of 3-(2-chlorophenyl)-7-(4-hydroxyiminocyclohexylamino)-1-methyl-3,4-dihydropyrimido[4,5-d]pyrimidin-2(1H)-one.

Example 12

Compound 3-54

This example illustrates the preparation of 8-[6-(2-chlorophenyl)-8-methyl-7-oxo-5,6,7,8-tetrahydropyrimido[4,5-d]pyrimidin-2-ylamino]-1,3-diazaspiro[4.5]decane-2,4-dione.

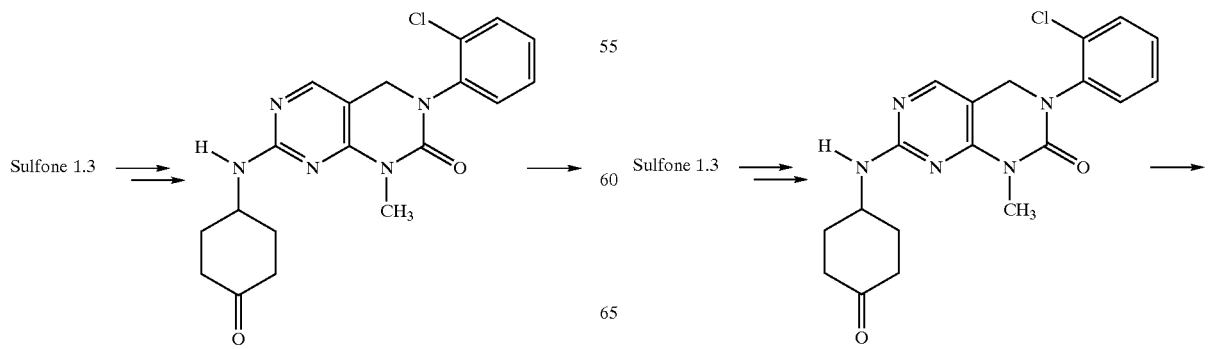

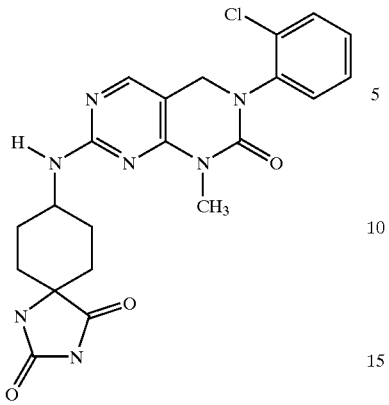

A mixture of 3-(2-chlorophenyl)-7-(4-oxo-cyclohexyl-amino)-1-methyl-3,4-dihydropyrimido[4,5-d]pyrimidin-2 (1H)-one (0.33 g, 0.86 mmol) (prepared as described in Example 10), potassium cyanide (0.084 g, 1.3 mmol), and ammonium carbonate (0.25 g, 2.6 mmol) in 25 mL of 1:1 water/ethanol was stirred at 65° C overnight. The reaction mixture was diluted with 40 mL of water and allowed to boil for 15 minutes, then cooled to room temperature and poured into 100 mL of ice-cold water. This mixture was filtered and the residue was made into a slurry in methanol. Addition of 1M hydrochloric acid in diethyl ether gave the salt which was concentrated under a stream of nitrogen to give 39 mg of the hydrochloride salt of 8-[6-(2-chlorophenyl)-8-methyl-7-oxo-5,6,7,8-tetrahydropyrimido[4,5-d]pyrimidin-2-ylamino]-1,3-diazaspiro[4.5]decane-2,4-dione as a yellow powder.

Example 13

Compound 3-42

This example illustrates the preparation of 7-(trans-4-allyloxycyclohexylamino)-3-(2-chlorophenyl)-1-methyl-3,4-dihydropyrimido[4,5-d]pyrimidin-2(1H)-one.

Sulfone 1.3 ⟶ 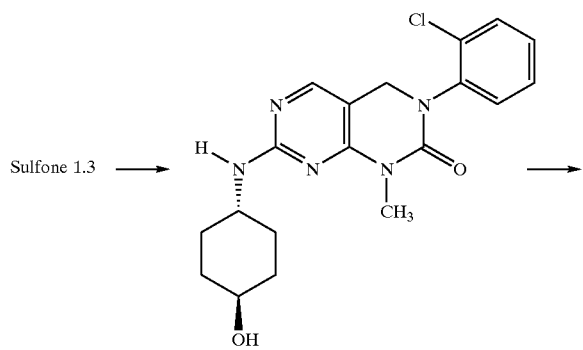

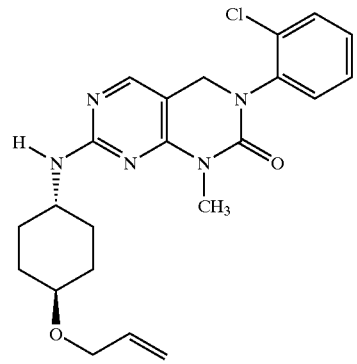

Sulfone 1.3 (2.6 g, 7.48 mmol) was combined with trans-4-aminocyclohexanol (1.63 g, 14.2 mmol) in 10 mL 1-methyl-2-pyrrolidinone and stirred at 120° C. for 4 hours, then poured into water, extracted with ethyl acetate, dried over magnesium sulfate, and evaporated in vacuo. The residue was purified by flash chromatography on silica gel using 2–4% methanol/dichloromethane as eluant to give a yellow 1-methyl-2-pyrrolidinone-based oil. This oil was redissolved in ethyl acetate, washed with water, dried over magnesium sulfate, and evaporated in vacuo to yield 3-(2-chlorophenyl)-7-(trans-4-hydroxycyclohexylamino)-1-methyl-3,4-dihydropyrimido[4,5-d]pyrimidin-2(1H)-one as an off-white foam (2.80 g, 7.21 mmol).

A portion of the 7-(trans-4-hydroxycyclohexylamino)-3-(2-chlorophenyl)-1-methyl-3,4-dihydropyrimido[4,5-d]pyrimidin-2(1H)-one (0.274 g, 0.706 mmol) was taken up with potassium tert-butoxide (0.119 g, 1.06 mmol) in 5 mL tetrahydrofuran. Allyl bromide (0.061 mL, 0.706 mmol) was added to this solution, which was heated at 50° C. overnight, then cooled to room temperature and purified by flash chromatography on silica gel using 10–25% acetone/hexanes as eluant. The column fractions containing product were combined and concentrated in vacuo. The concentrate was taken up in methanol, treated with hydrochloric acid (1.0M/Et$_2$O, 1.0 equivalent), re-evaporated to dryness, then washed with ethyl ether, filtered, and dried to give 0.102 g of the hydrochloride salt of 7-(trans-4-allyloxycyclohexylamino)-3-(2-chlorophenyl)-1-methyl-3,4-dihydropyrimido[4,5-d]pyrimidin-2(1H)-one.

Example 14

Compounds 3-38 and 3-39

This example illustrates the preparation of 3-(2-chlorophenyl)-7-(trans-4-methoxycyclohexylamino)-1-methyl-3,4-dihydropyrimido[4,5-d]pyrimidin-2(1H)-one and 3-(2-chlorophenyl)-7-[(trans-4-methoxycyclohexyl) methylamino]-1-methyl-3,4-dihydropyrimido[4,5-d]pyrimidin-2(1H)-one.

Sulfone 1.3

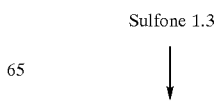

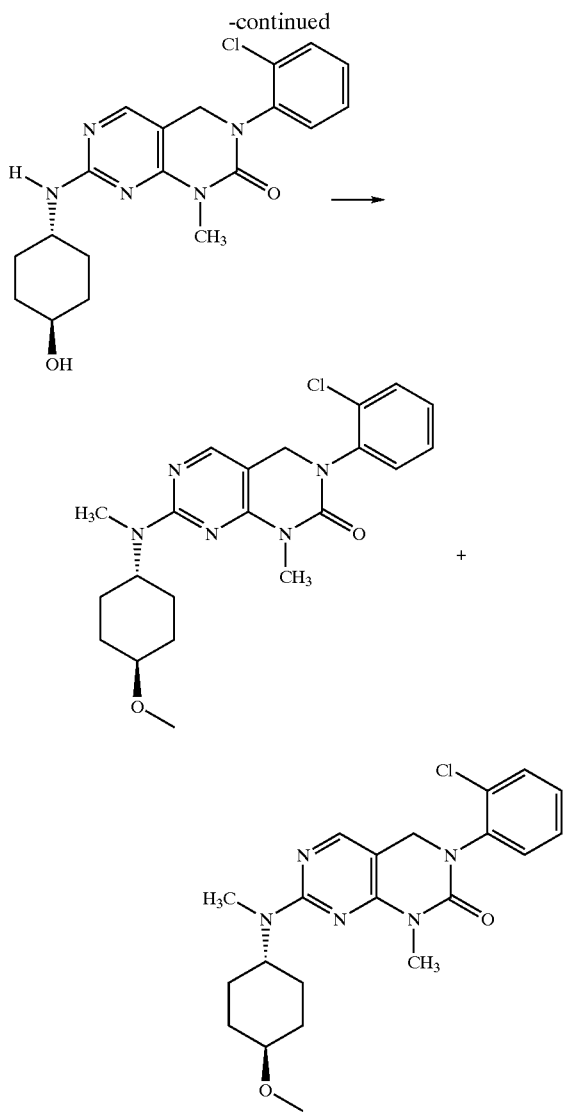

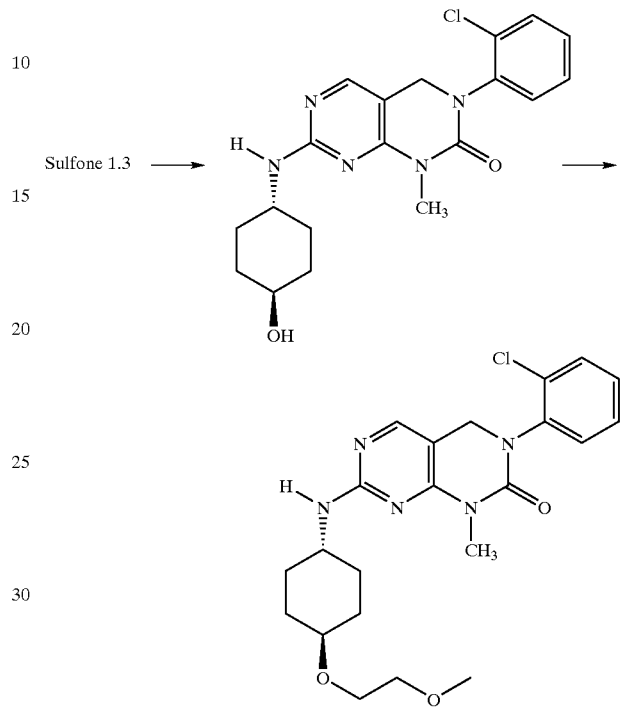

Example 15

Compound 3-40

This example illustrates the preparation of 3-(2-chlorophenyl)-7-[trans-4-(2-methoxyethoxy)cyclohexylamino]-1-methyl-3,4-dihydropyrimido[4,5-d]pyrimidin-2(1H)-one.

3-(2-Chlorophenyl)-7-(trans-4-hydroxycyclohexylamino)-1-methyl-3,4-dihydropyrimido[4,5-d]pyrimidin-2(1H)-one (0.300 g, 0.773 mmol) (prepared as described in Example 13) was combined with potassium tert-butoxide (0.174 g, 1.55 mmol) in 2 mL tetrahydrofuran. 2-Bromoethyl methyl ether (0.15 mL, 1.55 mmol) was added to this solution, which was heated at room temperature for 3 days. Additional potassium tert-butoxide was added (0.174 g, 1.55 mmol) and the temperature was gradually raised to 80° C. The reaction residue was redissolved in 2 mL N,N-dimethyl-formamide, additional potassium tert-butoxide (0.348 g, 3.10 mmol) was added, and the reaction mixture was stirred overnight at 80° C. Sodium hydride (60% in oil; 0.031 g, 0.773 mmol) was added, and the reaction stirred for one day at 100° C. and the following day at 140° C and then cooled to room temperature. The reaction was poured into water, extracted with ethyl acetate, dried over magnesium sulfate, and evaporated in vacuo. The residue was purified by flash chromatography on silica gel using 25–50% acetone/hexanes as eluant. The column fractions containing product were combined and concentrated in vacuo, and the concentrate was taken up in methanol, treated with hydrochloric acid (1.0M/Et₂O, 1.0 equivalent), re-evaporated to dryness, washed with ethyl ether, filtered, and dried to give 0.040 g of the hydrochloride salt of 3-(2-chlorophenyl)-7-[trans-4-(2-methoxyethoxy)cyclohexylamino]-1-methyl-3,4-dihydropyrimido[4,5-d]pyrimidin-2(1H)-one.

Example 16

Compound 3-41

This example illustrates the preparation of 3-(2-chlorophenyl)-7-[(trans-4-methylcarbonyloxy)

3-(2-Chlorophenyl)-7-(trans-4-hydroxycyclohexylamino)-1-methyl-3,4-dihydropyrimido[4,5-d]pyrimidin-2(1H)-one (0.300 g, 0.773 mmol) (prepared as described in Example 13) was combined with potassium tert-butoxide (0.174 g, 1.55 mmol) in 5 mL tetrahydrofuran. Methyl iodide (0.053 mL, 0.851 mmol) was added to this solution, which was stirred at room temperature for 3 days. Additional methyl iodide (0.053 mL, 0.851 mmol) and potassium tert-butoxide (0.174 g, 1.55 mmol) were added, followed after 4 hours by further potassium tert-butoxide (0.350 g, 3.12 mmol). The reaction was stirred at 60° C. overnight, then cooled to room temperature and purified by flash chromatography on silica gel using 25–35% acetone/hexanes as eluant to yield a mixture two products. The separate column fractions were each separated and concentrated in vacuo. The separate concentrates were each taken up in methanol, treated with hydrochloric acid (1.0M/Et₂O 1.0 equivalent), re-evaporated to dryness, washed with ethyl ether, filtered, and dried to give 0.049 g of 3-(2-chlorophenyl)-7-(trans-4-methoxycyclohexylamino)-1-methyl-3,4-dihydropyrimido[4,5-d]pyrimidin-2(1H)-one and 0.217 g of 3-(2-chlorophenyl)-7-[(trans-4-methoxycyclohexyl)methylamino]-3,4-dihydropyrimido[4,5-d]pyrimidin-2(1H)-one.

cyclohexylamino]-1-methyl-3,4-dihydropyrimido[4,5-d]pyrimidin-2(1H)-one.

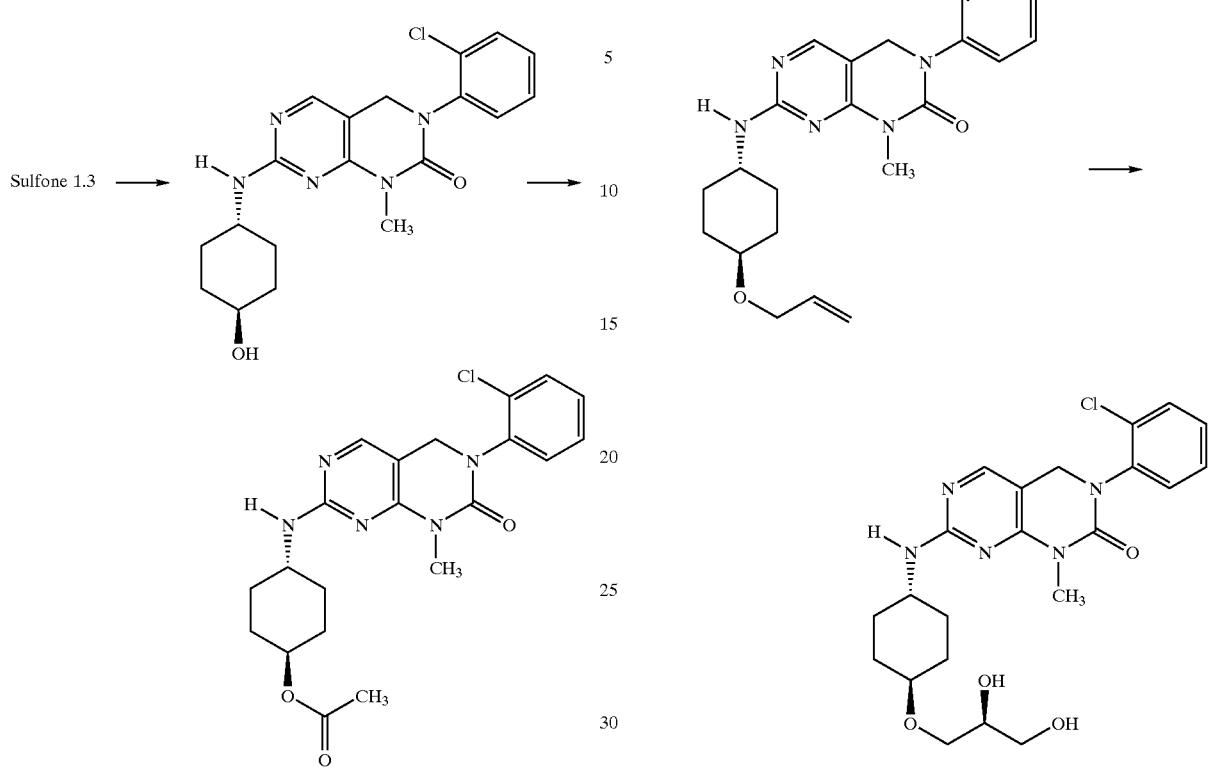

3-(2-Chlorophenyl)-7-(trans-4-hydroxycyclohexylamino)-1-methyl-3,4-dihydropyrimido[4,5-d]pyrimidin-2 (1H)-one (0.200 g, 0.516 mmol) (prepared as described in Example 13) was taken up in 2 mL dichloromethane, and combined with acetyl chloride (0.074 mL, 1.03 mmol). The reaction was stirred at room temperature overnight, then purified by flash chromatography on silica gel using 1–5% methanol/dichloromethane as eluant. The column fractions containing product were combined and concentrated in vacuo. The concentrate was taken up in methanol, treated with hydrochloric acid (1.0M/Et$_2$O, 1.0 equivalent), and re-evaporated to dryness, washed with ethyl ether, filtered, and dried to give 0.200 g of the hydrochloride salt of 3-(2-chlorophenyl)-7-[(trans-4-methylcarbonyloxy)cyclohexylamino]-1-methyl-3,4-dihydropyrimido-[4,5-d]pyrimidin-2(1H)-one.

Example 17

Compound 3-44

This example illustrates the preparation of 3-(2-chlorophenyl)-7-[trans4-(2,3-dihydroxypropoxy)cyclohexylamino]-1-methyl-3,4-dihydropyrimido[4,5-d]pyrimidin-2(1H)-one.

Sulfone 1.3 →

The free base of 7-(trans-4-allyloxycyclohexylamino)-3-(2-chlorophenyl)-1-methyl-3,4-dihydropyrimido[4,5-d]pyrimidin-2(1H)-one (0.40 g, 0.935 mmol) (prepared as described above in Example 13) was taken up in 4.9 mL tert-butanol, to which an aqueous solution of AD-mix β (Adrich Chemicals) was added (2.91 g in 4.9 mL) before heating to 100° C. for 2 days, and then 80° C. for 3 days. The reaction mixture was poured into saturated brine, extracted with ethyl acetate, dried with magnesium sulfate, and evaporated in vacuo. The crude residue was purified by flash chromatography on silica gel using 3–5% methanol/dichloromethane as eluant. The column fractions containing product were combined and concentrated in vacuo. The concentrate was taken up in methanol, treated with hydrochloric acid (1.0M/Et$_2$O, 1.0 equivalent), and re-evaporated to dryness, then washed with ethyl ether, filtered, and dried to give 0.019 g of the hydrochloride salt of 3-(2-chlorophenyl)-7-[trans-4-(2,3-dihydroxypropoxy)cyclohexylamino]-1-methyl-3,4-dihydropyrimido[4,5-d]pyrimidin-2(1H)-one.

Example 18

Compound 3-59

This example illustrates the preparation of 7-(trans-4-aminocyclohexylamino)-3-(2-chlorophenyl)-1-methyl-3,4-dihydropyrimido[4,5-d]pyrimidin-2(1H)-one.

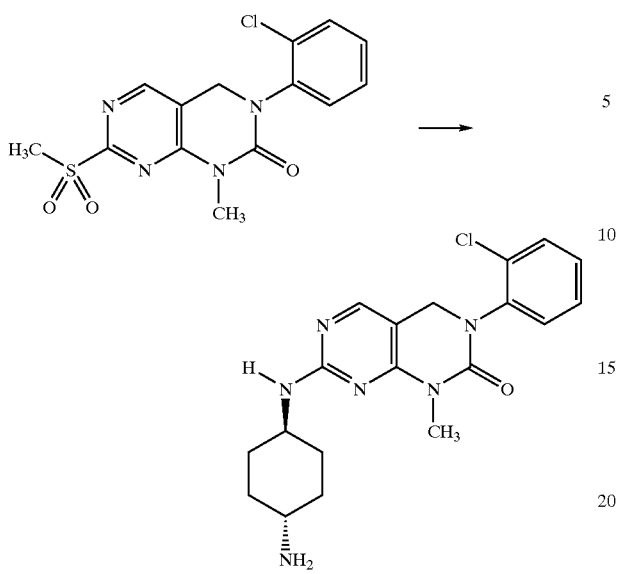

Sulfone 1.3 (605 mg, 1.71 mmol) was combined with trans-1,4-diaminocyclohexane (1.61 g, 14.1 mmol) and 5 mL of 1-methyl-2-pyrrolidinone. The reaction mixture was stirred at 85° C. for 4 hours. After cooling, the reaction mixture was diluted with 50 mL of ethyl acetate. The organic layer was sequentially washed with water and brine, dried, and concentrated in vacuo to give 654 mg (99%) of the free base of the product as a pale yellow foam. The free base was taken up in ethyl acetate and treated with a 1M solution of HCl/Et$_2$O to form the dihydrochloride salt of 7-(trans-4-aminocyclohexylamino)-3-(2-chlorophenyl)-1-methyl-3,4-dihydropyrimido-[4,5-d]pyrimidin-2(1H)-one as a white powder.

Example 19

Compound 3-57

This example illustrates the preparation of 7-(trans-4-methylsulfonylamidocyclohexylamino)-3-(2-chlorophenyl)-1-methyl-3,4-dihydropyrimido[4,5-d]pyrimidin-2(1H)-one.

Sulfone 1.3 ⟶

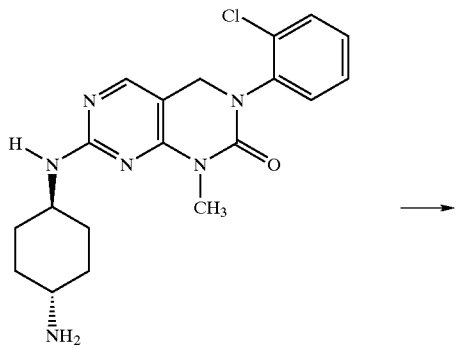

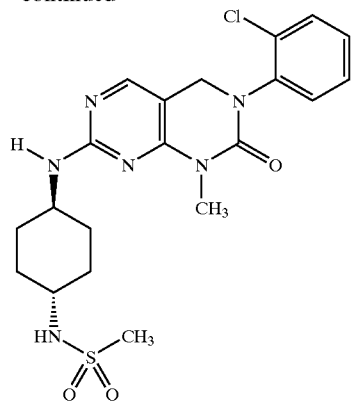

To a solution of 7-(trans-4-aminocyclohexylamino)-3-(2-chlorophenyl)-1-methyl-3,4-dihydropyrimido[4,5-d]pyrimidin-2(1H)-one (88 mg, 0.227 mmol) (prepared as described above in Example 18) in 8 mL of dichloromethane were added triethylamine (0.40 mL, 0.29 mmol) and methanesulfonic anhydride (60 mg, 0.34 mmol). The reaction mixture was stirred at ambient temperature for 3 hours. The reaction mixture was concentrated in vacuo and purification by chromatography using 5% methanol/dichloromethane as eluant gave 86 mg (81%) of the free base of the product as a white powder. The free base was taken up in ethyl acetate and treated with a 1M solution of HCl/Et$_2$O to form the hydrochloride salt of 7-(trans-4-methylsulfonylamidocyclohexylamino)-3-(2-chlorophenyl)-1-methyl-3,4-dihydropyrimido[4,5-d]pyrimidin-2(1H)-one as a white powder.

Example 20

Compound 3-58

This example illustrates the preparation of 7-[trans-4-(N,N-dimethylsulfamoylamido)cyclohexylamino]-3-(2-chlorophenyl)-1-methyl-3,4-dihydropyrimido[4,5-d]-pyrimidin-2(1H)-one.

Sulfone 1.3 ⟶

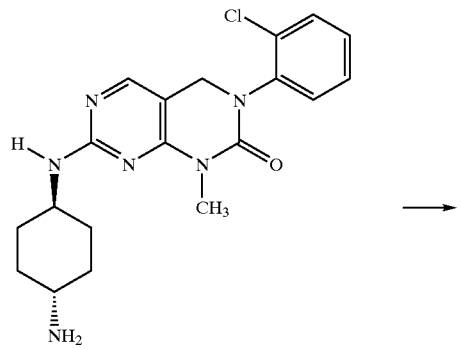

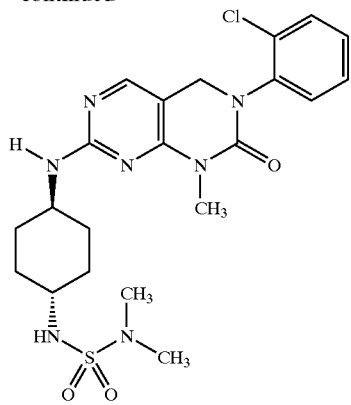

To a solution of 7-(trans-4-aminocyclohexylamino)-3-(2-chlorophenyl)-1-methyl-3,4-dihydropyrimido[4,5-d]pyrimidin-2(1H)-one (171 mg, 0.442 mmol) (prepared as described above in Example 18) in 15 mL of dichloromethane were added triethylamine (0.11 mL, 0.79 mmol) and a solution of dimethylsulfamoyl chloride (0.31 g, 0.21 mmol) in 5 mL of dichloromethane. The reaction mixture was stirred at ambient temperature for 19 hours and concentrated in vacuo. Purification by chromatography using 5% methanol/dichloromethane as eluant gave 143 mg (65%) of the free base of the product as a white powder. The free base was taken up in ethyl acetate and treated with HCl/Et$_2$O to form the hydrochloride salt of 7-[trans-4-(N,N-dimethylsulfamoylamido)cyclohexylamino]-3-(2-chlorophenyl)-1-methyl-3,4-dihydropyrimido-[4,5-d]pyrimidin-2(1H)-one as a white powder.

Example 21

Compound 3-9

This example illustrates the preparation of 7-(trans-4-hydroxycyclohexylamino)-1-methyl-3-ortho-tolyl-3,4-dihydropyrimido[4,5-d]pyrimidin-2(1H)-one.

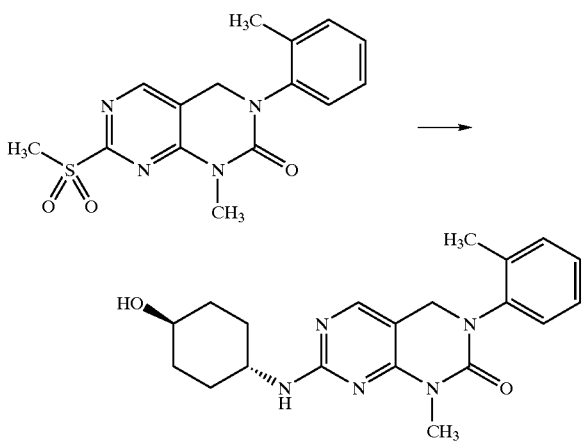

Sulfone 1.4 (300 mg, 0.903 mmol) was combined with trans-4-aminocyclohexanol (312 mg, 2.71 mmol), stirred at 120° C., and monitored by TLC (5% methanol/dichloromethane). When complete, the reaction mixture was concentrated under vacuum and purified by chromatography with 5–10% methanol/dichloromethane to provide the title compound (263 mg, 0.716 mmol, 79% yield) which was taken up in ethyl acetate and treated with 1 equivalent HCl/Et$_2$O to precipitate the HCl salt of 7-(trans-4-hydroxycyclohexylamino)-1-methyl-3-ortho-tolyl-3,4-dihydropyrimido[4,5-d]pyrimidin-2(1H)-one.

Example 22

Compound 3-23

This example illustrates the preparation of 7-((R,R)-2,3-dihydroxy-1-methylpropylamino)-3-ortho-tolyl-1-methyl-3,4-dihydropyrimido[4,5-d]pyrimidin-2(1H)-one.

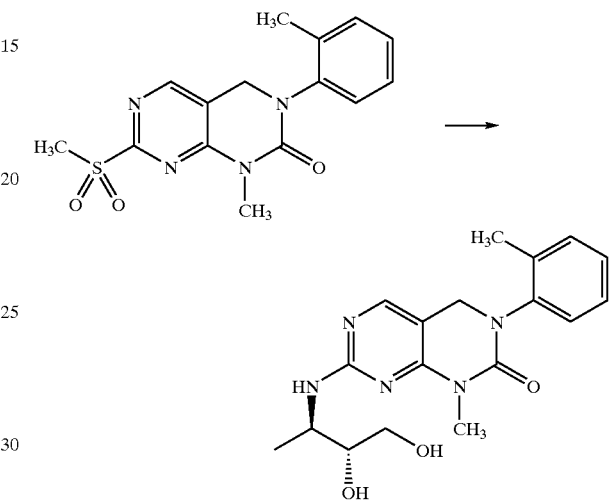

Sulfone 1.4 (455 mg, 1.37 mmol) and (R,R)-3-amino-1,2-butanediol (180 mg, 1.71 mmol) in 1,2-dimethoxyethane (1 mL) was heated to 100° C. for 2 hours under argon. The reaction was cooled to room temperature and diluted with 9:1 dichloromethane/methanol and purified by chromatography on silica gel using 96:4 dichloromethane/methanol and 9:1 dichloromethane/methanol as eluants to give 175 mg of the title compound as a colorless oil, which was dissolved in ethyl acetate and treated with 1 equivalent of hydrochloric acid (1.0M in ether). The precipitate was collected by vacuum filtration, washed with ethyl acetate and dried in vacuo to give 190 mg of 7-((R,R)-2,3-dihydroxy-1-methylpropylamino]-3-ortho-tolyl-1-methyl-3,4-dihydropyrimido[4,5-d]pyrimidin-2(1H)-one as a white solid.

Example 23

Compound 3-33

This example illustrates the preparation of 7-(2,3-dihydroxy-1,1-dimethylpropylamino]-3-ortho-tolyl-1-methyl-3,4-dihydropyrimido[4,5-d]pyrimidin-2(1H)-one.

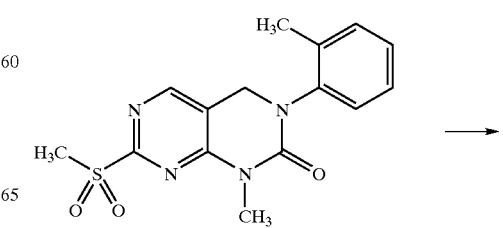

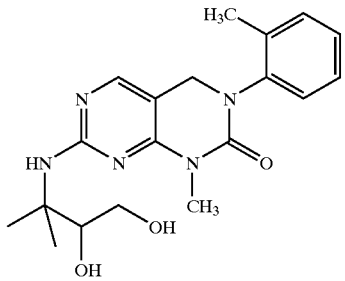

Sulfone 1.4 (400 mg, 1.2 mmol) was combined with 3-amino-3-methyl-1,2-butanediol (305 mg, 2.1 mmol) and 1-methyl-2-pyrrolidinone (1 mL). The reaction mixture was heated to 100° C. for 4 hours at which time it was cooled to room temperature and concentrated in vacuo. The residue was purified by column chromatography on silica gel using 99:1 dichloromethane/methanol as eluant. The column fractions containing product were combined and concentrated in vacuo to give the title compound as an oil, which was re-dissolved in ethyl acetate. Addition of hydrochloric acid (1.0M/Et$_2$O, 2.0 equivalents) gave the salt which was filtered and dried to give 71 mg of of the hydrochloride salt of 7-(2,3-dihydroxy-1,1-dimethylpropylamino]-3-ortho-tolyl-1-methyl-3,4-dihydropyrimido[4,5-d]pyrimidin-2(1H)-one.

Example 24

Compound 2-9

This example illustrates the preparation of 7-(1-benzylpiperidin-4-ylamino)-1-methyl-3-ortho-tolyl-3,4-dihydropyrimido[4,5-d]pyrimidin-2(1H)-one.

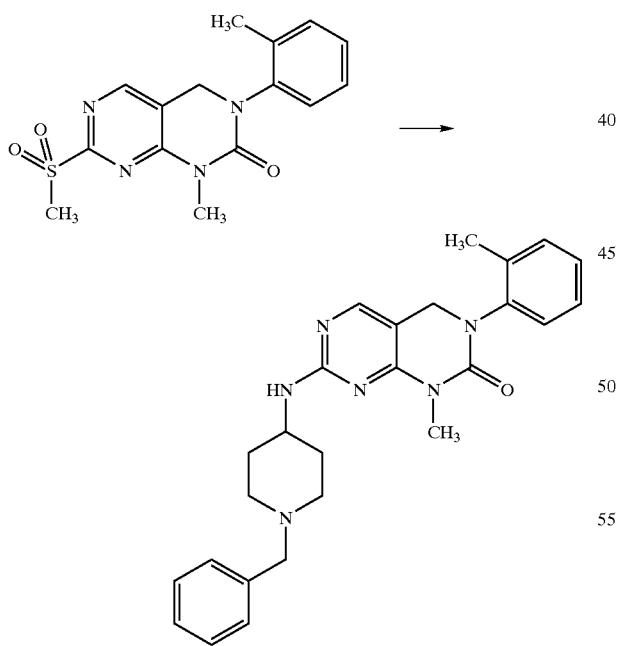

Sulfone 1.4 (1 g, 3 mmol) was combined with 4-amino-1-benzylpiperidine (687 mg, 3.6 mmol) and 2-methoxyethyl ether (1 mL). The mixture was heated to 120° C. for 4 hours at which time it was cooled to room temperature and concentrated in vacuo. The residue was purified by column chromatography on silica gel using 97:3 dichloromethane/methanol as eluant. The column fractions containing product were combined and concentrated in vacuo to an oil that was re-dissolved in ethyl acetate. Addition of hydrochloric acid (1.0M/Et$_2$O, 2.0 equivalents) gave the salt which was filtered and dried to give 198 mg of the hydrochloride salt of 7-(1-benzylpiperidin-4-ylamino)-1-methyl-3-ortho-tolyl-3,4-dihydropyrimido[4,5-d]pyrimidin-2(1H)-one.

Example 25

Compound 2-8

This example illustrates the preparation of 7-(piperidin-4-ylamino)-1-methyl-3-ortho-tolyl-3,4-dihydropyrimido[4,5-d]pyrimidin-2(1H)-one.

Sulfone 1.4 ⟶

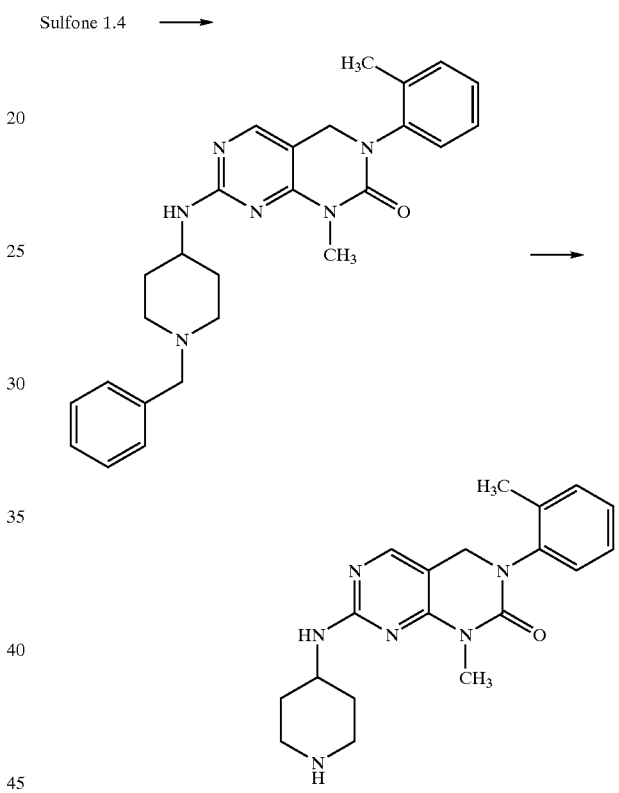

In a three-necked flask under nitrogen was charged with 10% palladium on carbon (3.0 g), and 7-(1-benzylpiperidin-4-ylamino)-1-methyl-3-ortho-tolyl-3,4-dihydropyrimido[4,5-d]pyrimidin-2(1H)-one (3.0 g, 6.78 mmol) (prepared as described in Example 24) in 60 mL of methanol was added under nitrogen through a syringe. Ammonium formate (2.1 g, 34 mmol) was then added in one batch. The mixture was heated to reflux for 30 minutes until the reaction was completed. The catalyst was filtered off through Celite and washed with methanol. The filtrate was concentrated under reduced pressure to give1.937 g (81%) of 7-(piperidin-4-ylamino)-1-methyl-3-ortho-tolyl-3,4-dihydropyrimido[4,5-d]pyrimidin-2(1H)-one as a white solid.

Example 26

Compound 2-14

This example illustrates the preparation of (R)-7-[1-(2,3-dihydroxypropyl)piperidin-4-ylamino]-1-methyl-3-ortho-tolyl-3,4-dihydropyrimido[4,5-d]pyrimidin-2(1H)-one.

Sulfone 1.4 →

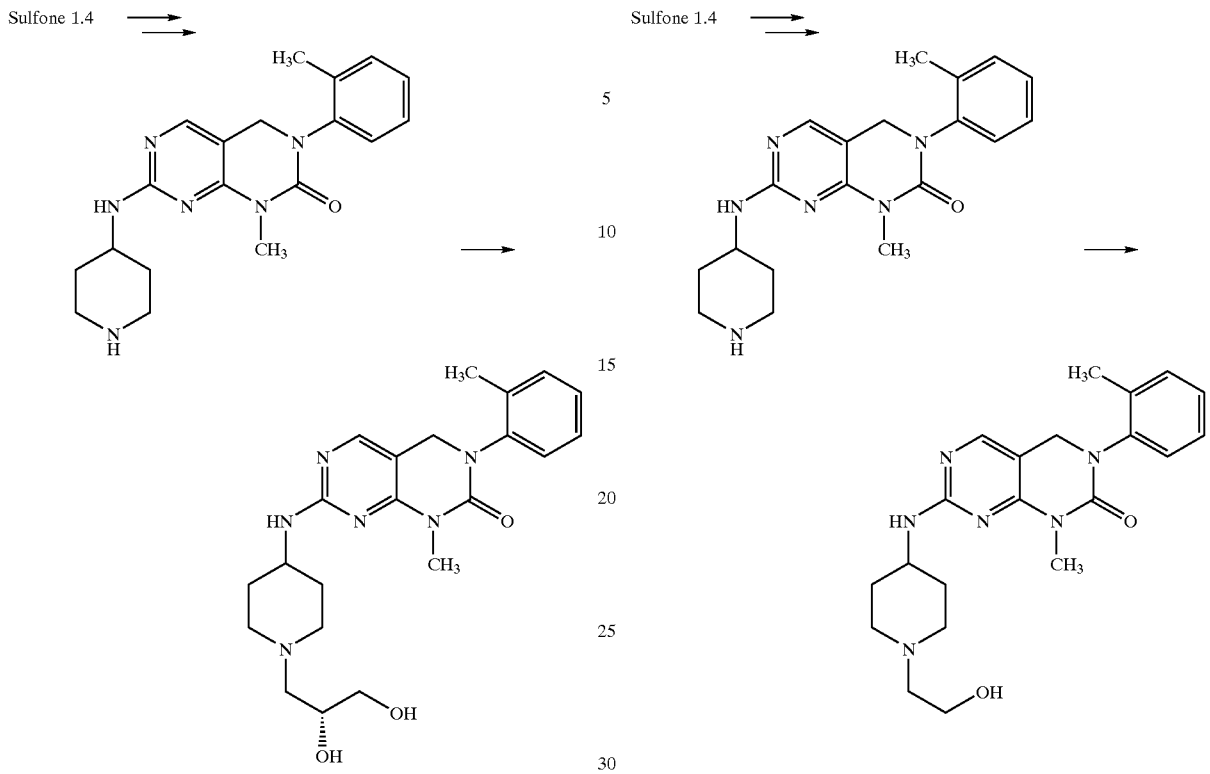

A mixture of 7-(piperidin-4-ylamino)-1-methyl-3-ortho-tolyl-3,4-dihydropyrimido[4,5-d]pyrimidin-2(1H)-one (0.2 g, 0.568 mmol) (prepared as described in Example 25), piperidine L-isopropylideneglycerol-γ-tosylate (0.264 g, 0.92 mmol), and potassium carbonate (0.12 g, 1.1 mmol) in 5mL of N,N-dimethylformamide was heated at 100° C. for 17 hours. The reaction mixture was diluted with 75 mL of water and extracted with 1:1 toluene/ethyl acetate, and the layers separated. The organic layer was washed with water and brine, dried, filtered, concentrated under reduced pressure, and purified by column chromatography on silica gel using 95:5:0.2 ethyl acetate/methanol/isopropyl amine as eluant. The column fractions containing the product (0.157 g, 0.34 mmol) was then dissolved in 10 mL of isopropanol, 1 mL of water and 0.2 mL of concentrated hydrochloric acid, and was refluxed for 1 hour until hydrolysis was completed. The mixture was concentrated under reduced pressure, and the residue was taken up in methanol and was again concentrated. The residue was purified by chromatography on silica gel using 18:2:0.5 dichloromethane/methanol/isopropyl amine as eluant to give 90 mg of the product, is each was dissolved in 1.5 mL of ethyl acetate and 1.5 mL of methanol. Addition of 1M hydrochloric acid in ether gave 113 mg (72.5%) of the hydrochloride salt of (R)-7-[1-(2,3-dihydroxypropyl)piperidin-4-ylamino]-1-methyl-3-ortho-tolyl-3,4-dihydropyrimido[4,5-d]pyrimidin-2(1H)-one.

Example 27

Compound 2-13

This example illustrates the preparation of 7-[1-(2-hydroxyethyl)-piperidin-4-ylamino]-1-methyl-3-ortho-tolyl-3,4-dihydropyrimido[4,5-d]pyrimidin-2(1H)-one.

A mixture of 7-(piperidin-4-ylamino)-1-methyl-3-ortho-tolyl-3,4-dihydropyrimido[4,5-d]pyrimidin-2(1H)-one (0.1 g, 0.284 mmol) (prepared as described in Example 25), 2-bromoethanol (0.024 mL, 0.34 mmol), and triethylamine (0.047 mL, 0.34 mmol) in 10 mL of toluene and 1.5 mL of DMPU was heated at 100° C. for 17 hours. The solvent was evaporated under reduced pressure and the residue was purified by chromatography on silica gel using 40:10:2 ethyl acetate/methanol/isopropylamine as eluant to give 70 mg (52%) of 7-[1-(2-hydroxyethyl)piperidin-4-ylamino]-1-methyl-3-ortho-tolyl-3,4-dihydropyrimido[4,5-d]pyrimidin-2(1H)-one.

Example 28

Compound 2-15

This example illustrates the preparation of 7-[1-(2-cyanoethyl)-piperidin-4-ylamino]-1-methyl-3-ortho-tolyl-3,4-dihydropyrimido[4,5-d]pyrimidin-2(1H)-one.

Sulfone 1.4 →

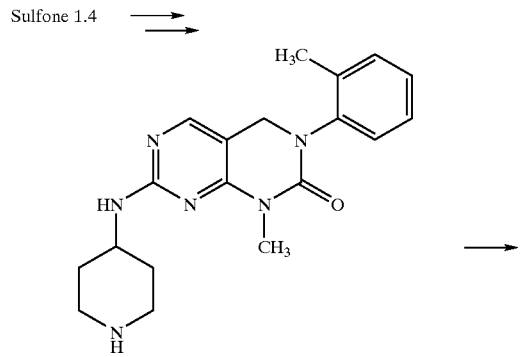

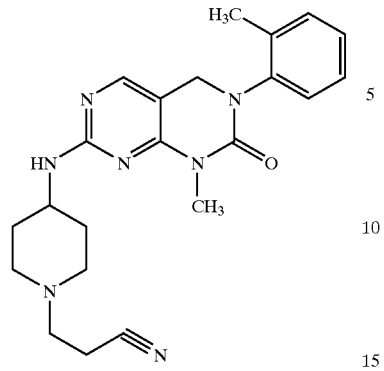

A mixture of 7-(piperidin-4-ylamino)-1-methyl-3-o-tolyl-3,4-dihydropyrimido[4,5-d]pyrimidin-2(1H)-one (0.184 g, 0.52 mmol) (prepared as described in Example 25), 1.5 mL of acrylonitrile, 0.5 mL of triethylamine, 0.5 mL of 1-methyl-2-pyrrolidinone, and 5 mL of tetrahydrofuran was heated to 75° C. for 1.5 hours until the reaction was completed. The reaction mixture was concentrated under reduced pressure and was purified by chromatography on silica gel using 10% methanol in ethyl acetate as eluant to give 0.157 g (75%) of the product. 1M Hydrochloric acid was added to 75 mg of the product dissolved in ethyl acetate, and the mixture stirred at room temperature for 1 hour, and the residue filtered under nitrogen to give the hydrochloride salt of 7-[1-(2-cyanoethyl)piperidin-4-ylamino]-1-methyl-3-ortho-tolyl-3,4-dihydropyrimido[4,5-d]pyrimidin-2(1H)-one.

Example 29

Compound 2-16

This example illustrates the preparation of 7-[1-(2-cyanoethyl)piperidin-4-ylamino]-1 methyl-3-ortho-tolyl-3,4-dihydropyrimido[4,5-d]pyrimidin-2(1H)-one.

Sulfone 1.4

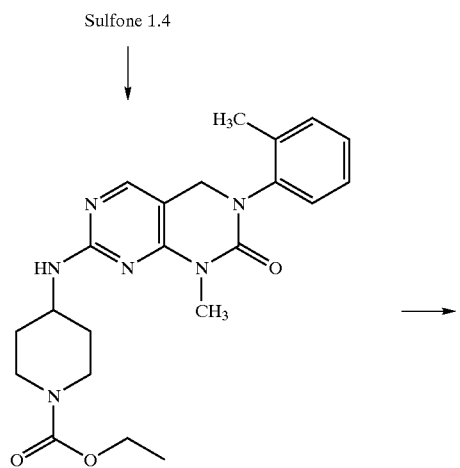

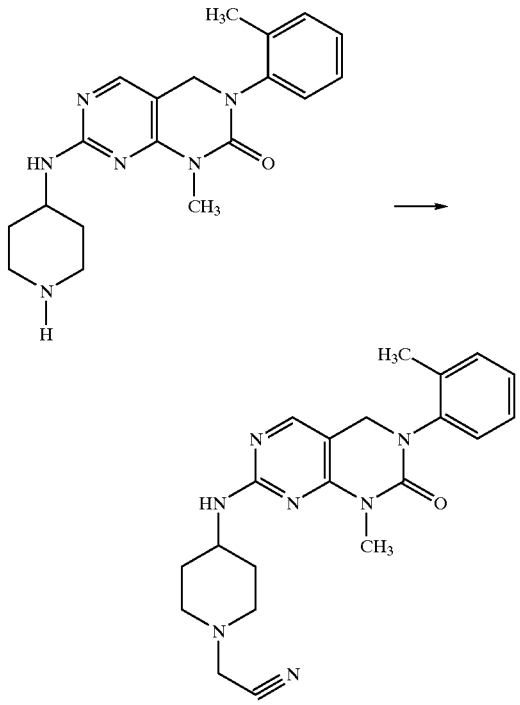

The 7-[(1-ethoxycarbonylpiperidin-4-yl)amino]-1-methyl-3-ortho-tolyl-3,4-dihydropyrimido[4,5-d]pyrimidin-2(1H)-one (52 mg, 1.28 mmol) was taken up in 5 mL dichloromethane with iodotrimethylsilane (0.88 mL, 6.18 mmol) and refluxed overnight, then quenched with 1 mL methanol and evaporated in vacuo. The dry residue was redissolved in methanol, to which 1.28 mL of 0.5M sodium methoxide/methanol was added before again evaporating in vacuo and purifying by flash chromatography on silica gel using 10–40% methanol/dichloromethane with 1% ammonium hydroxide as eluant. The column fractions containing 7-piperidin-4-ylamino-1-methyl-3-ortho-tolyl-3,4-dihydropyrimido[4,5-d]pyrimidin-2(1H)-one were combined and concentrated in vacuo.

7-(Piperidin-4-ylamino)-1-methyl-3-ortho-tolyl-3,4-dihydropyrimido[4,5-d]pyrimidin-2(1H)-one (0.035 g, 0.099 mmol) in 1 mL N,N-dimethylformamide was combined with bromoacetonitrile (0.014 mL, 0.199 mmol) and stirred at 40° C. overnight, then purified by flash chromatography on silica gel using 3–10% (1:9 ammonium hydroxide/methanol)/dichloromethane as eluant. The column fractions containing product were combined and concentrated in vacuo. The product was taken up in methanol, treated with hydrochloric acid (1.0M/Et$_2$O, 1.0 equivalent), re-evaporated to dryness, then washed with ethyl ether, filtered, and dried to give 0.007 g of the hydrochloride salt of 7-[1-(2-cyanomethyl)piperidin-4-ylamino]-1-methyl-3-ortho-tolyl-3,4-dihydropyrimido[4,5-d]pyrimidin-2(1H)-one.

Example 30

Compound 2-20

This example illustrates the preparation of 7-[1-(2-methoxycarbonylethyl)piperidin-4-ylamino]-1-methyl-3-ortho-tolyl-3,4-dihydropyrimido[4,5-d]pyrimidin-2(1H)-one.

Sulfone 1.4 ⟶

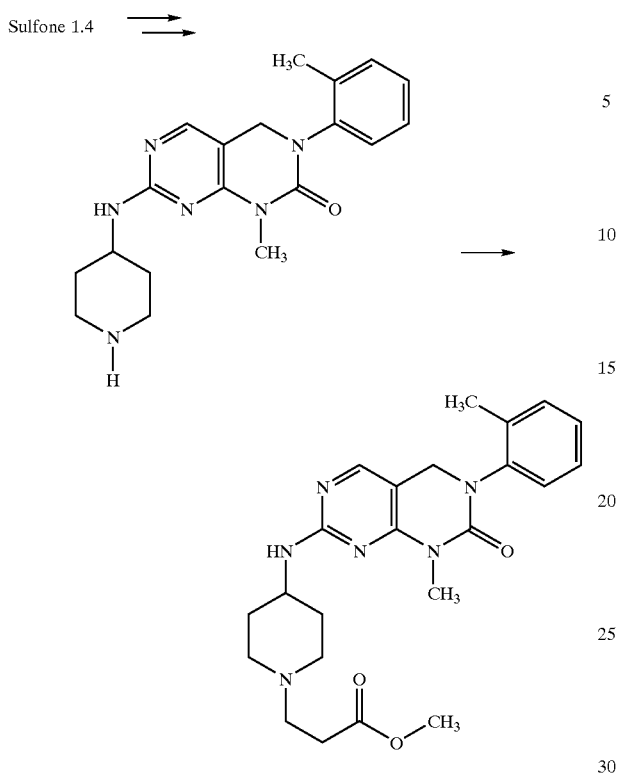

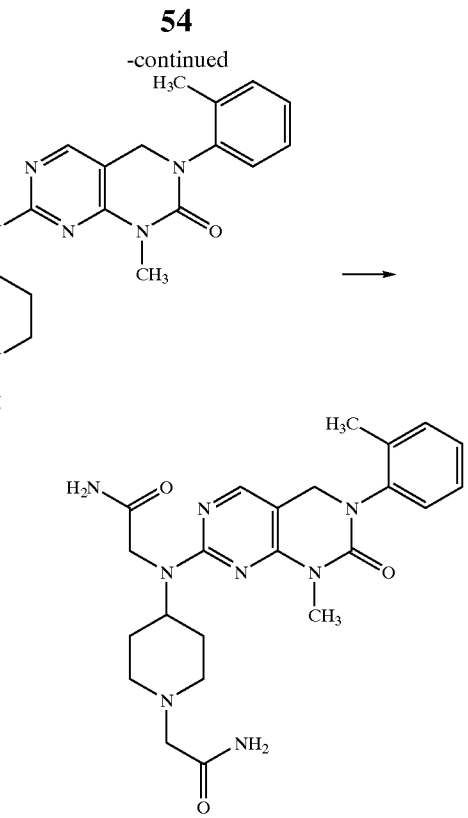

A mixture of 7-(piperidin-4-ylamino)-1-methyl-3-ortho-tolyl-3,4-dihydropyrimido[4,5-d]pyrimidin-2(1H)-one (0.19 g, 0.54 mmol) (prepared as described in Example 25), 1.0 mL of methyl acrylate, 0.5 mL of triethylamine, 0.5 mL of 1-methyl-2-pyrrolidinone, and 5 mL of tetrahydrofuran was heated at 75° C. for 17 hours. The reaction mixture was evaporated under reduced pressure, and the residue was purified by chromatography on silica gel using 5% methanol in dichloromethane as eluant to give 132 mg (56%yield) of the product. 1M Hydrochloric acid in ether was added to a solution of the product in ethyl acetate, and the suspension stirred at room temperature for 1 hour. The mixture was evaporated under reduced pressure to give the hydrochloride salt of 7-[1-(2-methoxy-carbonylethyl)piperidin-4-ylamino]-1-methyl-3-ortho-tolyl-3,4-dihydropyrimido[4,5-d]pyrimidin-2(1H)-one.

7-(Piperidin-4-ylamino)-1-methyl-3-ortho-tolyl-3,4-dihydropyrimido[4,5-d]pyrimidin-2(1H)-one (0.030 g, 0.080 mmol) (prepared as described in Example 25) was taken up in 1 mL N,N-dimethylformamide with bromoacetamide (0.022 g, 0.161 mmol) and stirred at 50° C. overnight. Another portion of bromoacetamide (0.022 g) was added before returning the reaction to 50° C. for a second night. The reaction mixture was purified by flash chromatography on silica gel using 6–20% (1:9 ammonium hydroxide/methanol)/dichloromethane as eluant. The column fractions containing product were combined and concentrated in vacuo. The final product was taken up in methanol, treated with hydrochloric acid (1.0M/Et$_2$O, 1.0 equivalent), re-evaporated to dryness, then washed with ethyl ether, filtered, and dried to give 0.001 g of the hydrochloride salt of 7-[(1-carbamoylmethylpiperidin-4-yl)carbamoylmethyl-amino]-1-methyl-3-ortho-tolyl-3,4-dihydropyrimido[4,5-d]pyrimidin-2(1H)-one.

Example 31

Compound 2-18

This example illustrates the preparation of 7-[(1-carbamoylmethyl-piperidin-4-yl)carbamoylmethylamino]-1-methyl-3-ortho-tolyl-3,4-dihydropyrimido-[4,5-d]pyrimidin-2(1H)-one.

Sulfone 1.4 ⟶

Example 32

Compound 2-12

This example illustrates the preparation of 7-(1-methanesulfonylpiperidin-4-yl)-1-methyl-3-ortho-tolyl-3,4-dihydropyrimido[4,5-d]pyrimidin-2(1H)-one.

Sulfone 1.4 ⟶

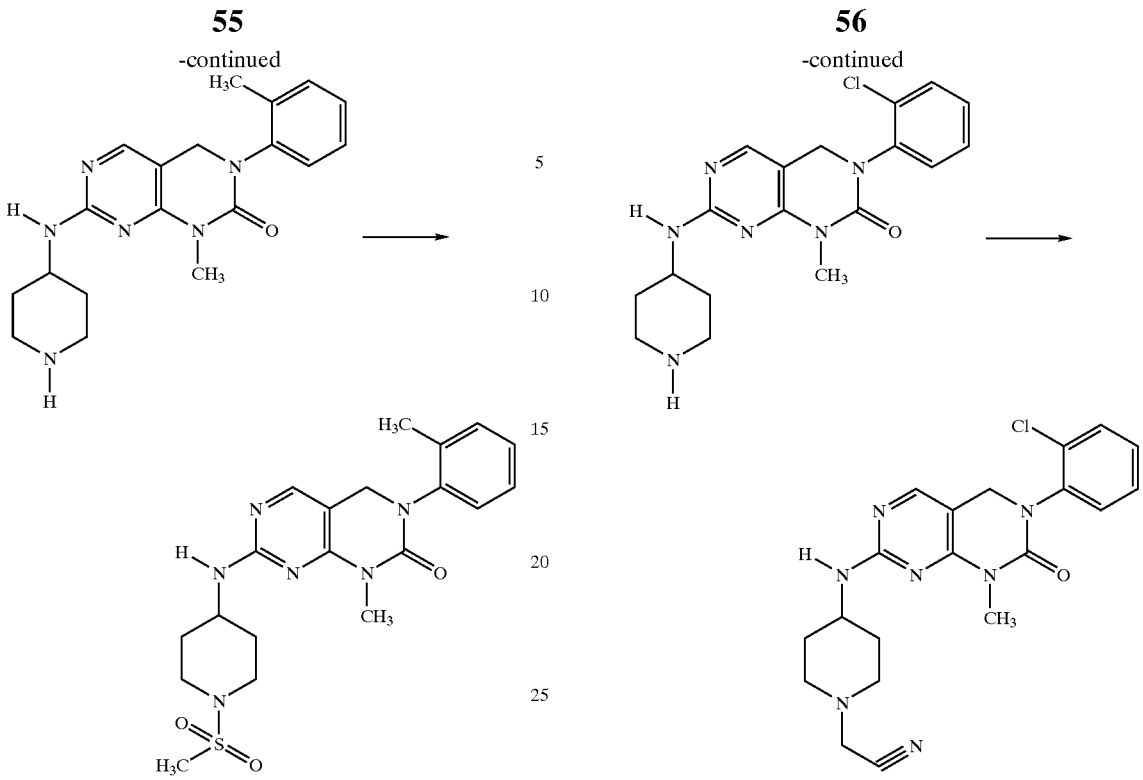

7-(Piperidin-4-ylamino)-1-methyl-3-ortho-tolyl-3,4-dihydropyrimido[4,5-d]pyrimidin-2(1H)-one (0.200 g, 0.567 mmol) (prepared as described in Example 25) was taken up in 5 mL pyridine, and the solution cooled to 0° C. before adding methanesulfonyl chloride (0.046 mL, 0.596 mmol). The reaction was stirred at 0° C. for 2 hours then quenched with ice water and extracted with ethyl acetate. The organic extracts were washed with water and saturated aqueous sodium bicarbonate, then rewashed with water and evaporated in vacuo. The residue was purified by column chromatography on silica gel using 1:15 methanol/dichloromethane as eluant. The column fractions containing product were combined and concentrated in vacuo, and the final product redissolved in a minimum volume of ethyl acetate and methanol. Addition of hydrochloric acid (1.0M/Et$_2$O, 1.0 equivalent) gave the salt which was filtered and dried to give 0.124 g of the hydrochloride salt of 7-(1-methanesulfonylpiperidin-4-yl)-1-methyl-3-ortho-tolyl-3,4-dihydropyrimido[4,5-d]pyrimidin-2(1H)-one.

Example 33

Compound 2-17

This example illustrates the preparation of 3-(2-chlorophenyl)-7-(1-cyanomethylpiperidin-4-ylamino)-1-methyl-3,4-dihydropyrimido[4,5-d]pyrimidin-2(1H)-one.

Sulfone 1.3 ⟶

3-(2-Chlorophenyl)-7-(piperidin-4-ylamino)-1-methyl-3,4-dihydropyrimido[4,5-d]pyrimidin-2(1H)-one (0.030 g, 0.080 mmol) (prepared similarly as described in Example 29) was taken up in 1 mL N,N-dimethylformamide with bromoacetonitrile (0.011 mL, 0.161 mmol) and stirred at 50° C. overnight. Another 0.011 mL bromoacetonitrile was added before returning the reaction to 50° C. for a second night. The reaction mixture was purified by flash chromatography on silica gel using 1–20% (1:9 ammonium hydroxide/methanol)/dichloromethane as eluant. The column fractions containing product were combined and concentrated in vacuo, which was taken up in methanol, treated with hydrochloric acid (1.0M/Et$_2$O, 1.0 equivalent), re-evaporated to dryness, then washed with ethyl ether, filtered, and dried to give 0.002 g of the hydrochloride salt of -3-(2-chlorophenyl)-7-(1-cyanomethylpiperidin-4-ylamino)-1-methyl-3,4-dihydropyrimido[4,5-d]pyrimidin-2(1H)-one.

Example 34

4-Amino-2-benzylthiopyrimidine-5-carboxaldehyde 34.1 Preparation of 4-amino-5-carbethoxy-pyrimidine-2-thiol

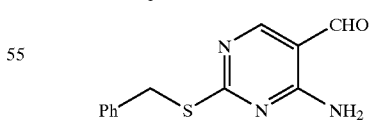

Sodium ethoxide (272 g, 4.0 mol) (Lancaster) was stirred in 1 L of ethanol and treated with thiourea (304 g, 4.0 mol) (Avocado). Ethyl ethoxymethylene cyanoacetate (676 g, 4.0 mol) (Avocado) was added and the mixture heated at reflux for 8 hours. After cooling to room temperature overnight, the reaction mixture was treated sequentially with 2 L of water and 400 mL of acetic acid. The reaction mixture was heated at reflux for 30 minutes, cooled to room temperature, and the suspension filtered. The solid was washed three 500 mL portions of water, two 500 mL portions of acetone, and 500 mL of diethyl ether. The product was dried to give 473.3 g (60%) of 4-amino-5-carbethoxy-pyrimidine-2-thiol as a cream solid of melting point >250° C.

34.2 Preparation of 4-Amino-2-benzylthiopyrimidine-5-carboxylate

A stirred suspension of 4-amino-5-carbethoxy-pyrimidine-2-thiol (473 g, 2.377 mol) in 3.5 L of ethanol was treated with potassium carbonate (180.4 g, 1.307 mol) and benzyl bromide (447.1 g, 2.615 mol). The mixture was heated at reflux for 2 hours then allowed to cool to room temperature overnight. The suspension was filtered and the solid washed with two 500 mL portions of ethanol, 2 L of water and two 500 mL portions of water. The product was dried in vacuo over phosphorus pentoxide at 50° C. to give 416 g (61%) of ethyl 4-amino-2-benzylthiopyrimidine-5-carboxylate as a cream solid of melting point 117–118° C.

34.3 Preparation of 4-Amino-2-benzylthiopyrimidine-5-methanol

A solution of ethyl 4-amino-2-benzylthiopyrimidine-5-carboxylate (462.4 g, 1.6 mol) of in 2.3 L of sieve-dried tetrahydrofuran was added slowly with stirring to a 1 M solution of lithium aluminium hydride (1.6 L, 1.6 mol) in tetrahydrofuran under a nitrogen atmosphere with ice-cooling. The solution was added at a rate to maintain a temperature of 18–20° C. On completion of the addition, the mixture was heated to 60° C. and treated cautiously with 60.8 mL of water during 1.5 hours. 15% aqueous sodium hydroxide (60.8 mL)was added during 30 minutes, followed by 182.5 mL of water during 30 minutes. The suspension was stirred at 60° C. overnight then filtered through Hyflo filter aid while still hot, and the solid washed with two 1 L portions of tetrahydrofuran. Evaporation of the filtrate to dryness gave 392.5 g (99%) of 4-amino-2-benzylthiopyrimidine-5-methanol as an off-white solid which was used in the next step without further purification.

34.4 Preparation of 4-Amino-2-benzylthiopyrimidine-5-carboxaldehyde

A suspension of 4-amino-2-benzylthiopyrimidine-5-methanol (392.5 g, 1.59 mol) in 7.75 L of dichloromethane under a nitrogen atmosphere was treated with activated manganese dioxide (1.382 Kg, 15.9 mol) (Acros). The reaction mixture was stirred at ambient temperature overnight then filtered through Hyflo filter aid. The solid was washed with three 1 L portions of dichloromethane and the combined filtrates evaporated to give 340.5 g (88%) of 4-amino-2-benzylthiopyrimidine-5-carboxaldehyde as a pale yellow solid of melting point 136–139° C.

Example 35

3-(2-Chlorophenyl)-7-benzylthio-3,4-dihydropyrimido[4,5-d]pyrimidin-2(1H)-one

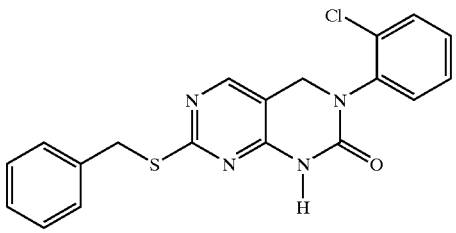

35.1 Preparation of 5-(2-chlorophenyl)aminomethyl-4-amino-2-benzylthiopyrimidine

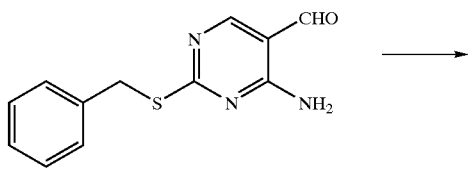

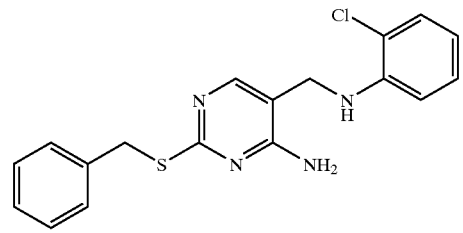

A mixture of 4-amino-2-benzylthiopyrimidine-5-carboxaldehyde (5 g, 20.4 mmol), 2-chloroaniline (2.25 mL, 21.4 mmol) and 4-toluene-sulfonic acid monohydrate (0.1 g, 0.5 mmol) in 60 mL of toluene was heated under reflux with azeotropic removal of water for 3 hours. The mixture was cooled to 0° C. and the precipitate was collected by vacuum filtration and was washed with hexanes and air dried. This solid was then dissolved in 100 mL tetrahydrofuran and the solution cooled to 0° C. Lithium aluminium hydride (0.735 g, 18.8 mmol) was added in small portions over 45 minutes. Once the addition was complete, the mixture was stirred for a further 15 minutes and carefully treated sequentially with 0.8 mL water, 0.8 mL of 15% aqueous sodium hydroxide and then 2.4 mL of water. The mixture was stirred for 30 minutes, filtered through celite, and the filtrate concentrated in vacuo. The solid was stirred with diethyl ether, filtered and air dried to give 6.1 g of 5-(2-chlorophenyl) aminomethyl-4-amino-2-benzylthiopyrimidine as a white solid.

35.2 Preparation of 3-(2-chlorophenyl)-7-benzylthio-3,4-dihydropyrimido-[4,5-d]pyrimidin-2(1H)-one

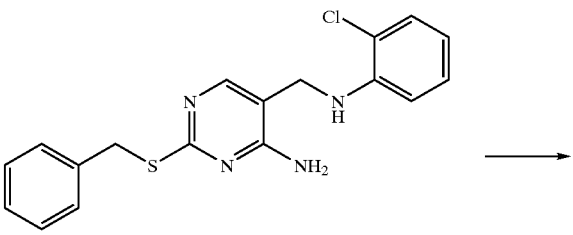

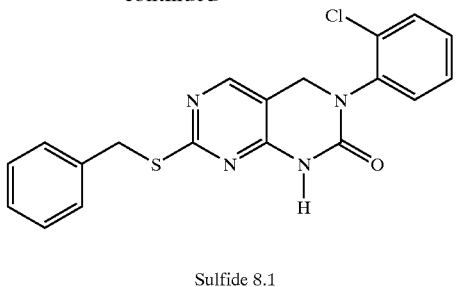

Sulfide 8.1

To a stirred solution, cooled to −10° C., of 5-(2-chlorophenyl) aminomethyl-4-amino-2-benzylthiopyrimidine (4.3 g, 12.1 mmol) in 100 mL of tetrahydrofuran was added triethylamine (3.1 mL, 22.2 mmol). This solution was then treated dropwise with a solution of phosgene (6.15 mL of 20% solution in toluene; 11.8 mmol). After stirring for 30 minutes, additional triethylamine (1.0 mL, 7.1 mmol) was added followed by phosgene (2.0 mL of 20% solution in toluene; 3.8 mmol). The reaction was warmed to room temperature, treated with 0.5 mL water and stirred for 30 minutes. The reaction was then filtered and the mother liquor was concentrated and stirred with dichloromethane. The product was then collected by vacuum filtration and dried in vacuo to give 3.83 g of 3-(2-chlorophenyl)-7-benzylthio-3,4-dihydropyrimido-[4,5-d]pyrimidin-2(1H)-one as a white solid (sulfide 8.1).

Example 36

3-(2-Chlorophenyl)-7-benzylsulfonyl-3,4-dihydropyrimido[4,5-d]pyrimidin-2(1H)-one

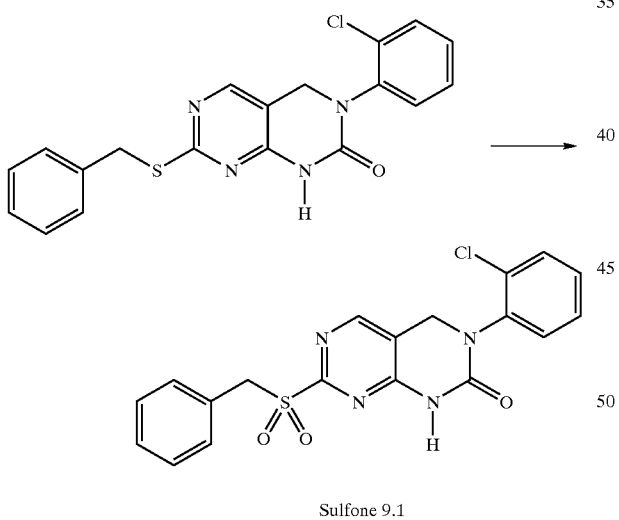

Sulfone 9.1

A suspension of sulfide 8.1 (1 g, 2.61 mmol) in 10 mL of dichloromethane was cooled in ice and treated with 70% 3-chloroperbenzoic acid (1.29 g, 5.23 mmol). The mixture was stirred at room temperature for 2 hours, then treated with 25 mL of 10% aqueous sodium thiosulphate and left to stir for 30 minutes. The resulting mixture was diluted with 100 mL dichloromethane and the phases were separated. The organic phase was washed with 10% aqueous potassium carbonate, then brine, and then dried over magnesium sulfate and filtered. Concentration of the filtrate under reduced pressure gave 0.73 g of 3-(2-chlorophenyl)-7-benzylsulfonyl-3,4-dihydropyrimido[4,5-d]-pyrimidin-2(1H)-one (sulfone 9.1) as a white solid.

A related compound, 7-benzylsulfonyl-3-ortho-tolyl-3,4-dihydropyrimido-[4,5-d]pyrimidin-2(1H)-one (sulfone 9.2) was prepared using ortho-toluidine in place of 2-chloroaniline in Example 35.

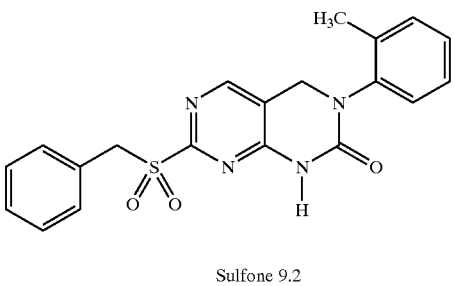

Sulfone 9.2

Example 37

Compound 3-26

This example illustrates the preparation of 3-(2-chlorophenyl)-7-(trans-4-hydroxycyclohexylamino)-1-(2-pyrrolidin-1-yl-ethyl)-3,4-dihydropyrimido[4,5-d]pyrimidin-2(1H)-one.

37.1 Preparation of 7-benzylthio-3-(2-chlorophenyl)-1-(2-pyrrolidin-1-yl-ethyl)-3,4-dihydropyrimido[4,5-d]pyrimidin-2(1H)-one.

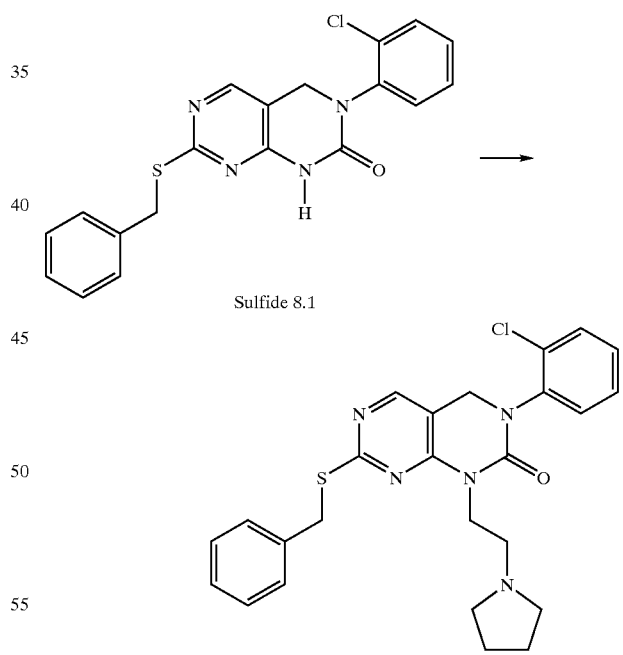

Sulfide 8.1 (500 mg, 1.31 mmol) was taken up in 2 mL tetrahydrofuran and combined with 1-(2-hydroxyethyl) pyrrolidine (0.23 mL, 1.96 mmol), triphenylphosphine (514 mg, 1.96 mmol), and DEAD (0.31 mL, 1.96 mmol). The reaction mixture was stirred at room temperature for 3 hours, when additional quantities of 1-(2-hydroxyethyl) pyrrolidine, triphenylphosphine, and DEAD were added (another 1.96 mmol each). The mixture was stirred at room temperature overnight and semipurified by chromatography on silica gel using 2.5–10% methanol/dichloromethane as eluant, to provide >1 g mixture of product 7-benzylthio-3-(2-chlorophenyl)-1-(2-pyrrolidin-1-ylethyl)-3,4-dihydropyrimido[4,5-d]pyrimidin-2(1H)-one and residual starting materials.

37.2 Preparation of 7-benzylthio-3-(2-chlorophenyl)-1-(2-pyrrolidin-1-yl-ethyl)-3,4-dihydropyrimido[4,5-d]pyrimidin-2(1H)-one.

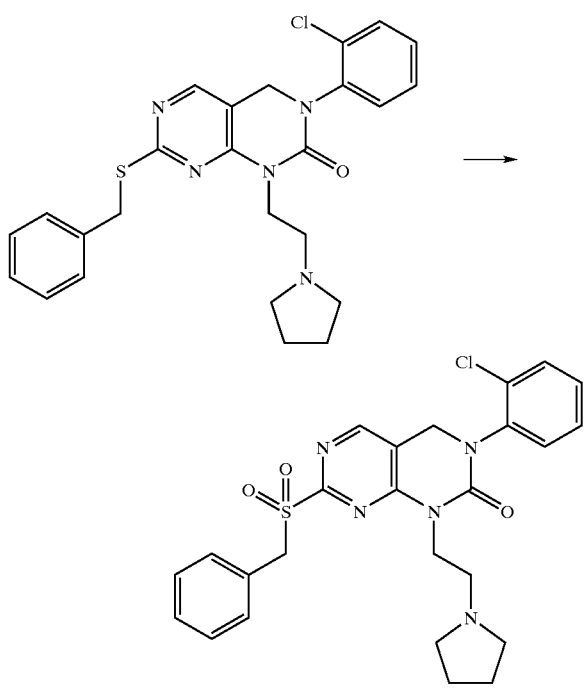

Oxidation of 7-benzylthio-3-(2-chlorophenyl)-1-(2-pyrrolidin-1-ylethyl)-3,4-dihydropyrimido[4,5-d]pyrimidin-2(1H)-one was accomplished using 3-chloroperoxybenzoic acid (0.94 g, 3.92 mmol) in dichloromethane with stirring at room temperature for 1 hour. The reaction was quenched with saturated sodium sulfite (aqueous, 1 mL) and extracted with dichloromethane. The combined extracts were dried, and concentrated in vacuo to provide 7-benzylsulfonyl-3-(2-chlorophenyl)-1-(2-pyrrolidin-1-ylethyl)-3,4-dihydropyrimido[4,5-d]pyrimidin-2(1H)-one, which was used without purification.

37.3 Preparation of 3-(2-chlorophenyl)-7-(trans-4-hydroxycychlo-hexylamino)-1-(2-pyrrolidin-1-ylethyl)-3,4-dihydropyrimido[4,5-d]pyrimidin-2(1H)-one.

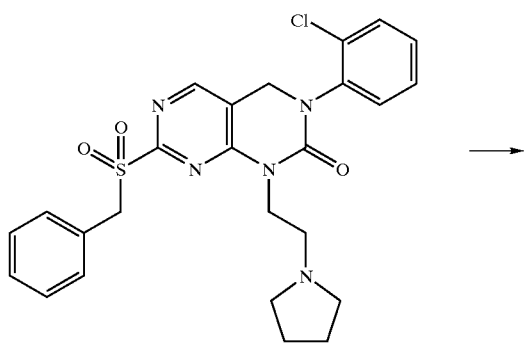

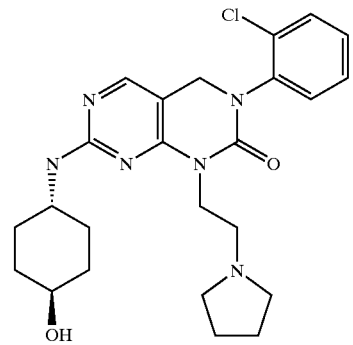

The crude 7-benzylsulfonyl-3-(2-chlorophenyl)-1-(2-pyrrolidin-1-ylethyl)-3,4-dihydropyrimido[4,5-d]pyrimidin-2(1H)-one was taken up in 6 mL diglyme with trans-4-aminocyclohexanol (165 mg, 1.44 mmol) and stirred at 120° C. for 3 hours. The mixture was purified by chromatography on silica gel using 3–30% methanol/dichloromethane as eluant to provide the title compound (45 mg, 0.096 mmol). The purified product was taken up in ethyl acetate and treated with 1 equivalent HCl/Et$_2$O to precipitate the hydrochloride salt of 3-(2-chlorophenyl)-7-(trans-4-hydroxycyclohexyl-amino)-1-(2-pyrrolidin-1-ylethyl)-3,4-dihydropyrimido[4,5-d]pyrimidin-2(1H)-one.

Example 38

Compound 3-27

This example illustrates the preparation of 3-(2-chlorophenyl)-7-(trans-4-hydroxycyclohexylamino)-1-(2-diethylaminoethyl)-3,4-dihydropyrimido[4,5-d]-pyrimidin-2(1H)-one.

38.1 Preparation of 7-benzylthio-3-(2-chlorophenyl)-1-(2-diethyl-amino-ethyl)-3,4-dihydropyrimido[4,5-d]pyrimidin-2(1H)-one.

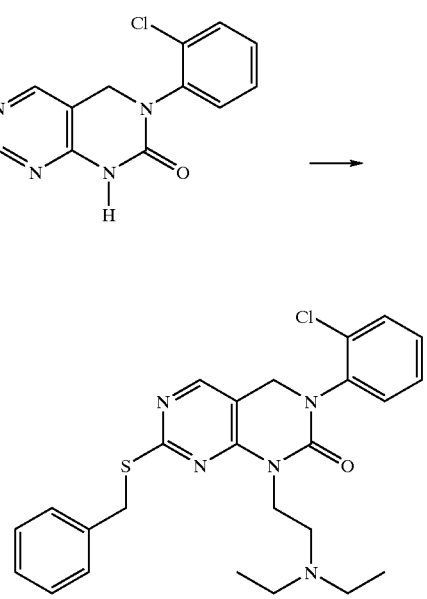

Sulfide 8.1 (500 mg, 1.31 mmol) was taken up in 2 mL tetrahydrofuran with N,N-diethylethanolamine (0.26 mL, 1.96 mmol), triphenylphosphine (514 mg, 1.96 mmol), and DEAD (0.31 mL, 1.96 mmol), and stirred at room temperature for 3 hours, when additional quantities of diethylethanolamine, triphenylphosphine, and DEAD were added (another 1.96 mmol each). The mixture was stirred at room temperature overnight and semipurified by chromatography on silica gel using 1–3.5% methanol/dichloromethane as eluant, to provide >1 g mixture of 7-benzylthio-3-(2-chlorophenyl)-1-(2-diethylaminoethyl)-3,4-dihydropyrimido[4,5-d]pyrimidin-2(1H)-one and residual starting materials. 38.2 Preparation of 7-benzylsulfonyl-3-(2-chlorophenyl)-1-(2-diethylaminoethyl)-3,4-dihydropyrimido[4,5-d]pyrimidin-2(1H)-one.

38.2 Preparation of 7-benzylsulfinyl-3-(2-chlorophenyl)-1-(2-diethylamino-ethyl)-3,4-dihydropyrimido[4,5-d]pyrimidin-2(1H)-one .

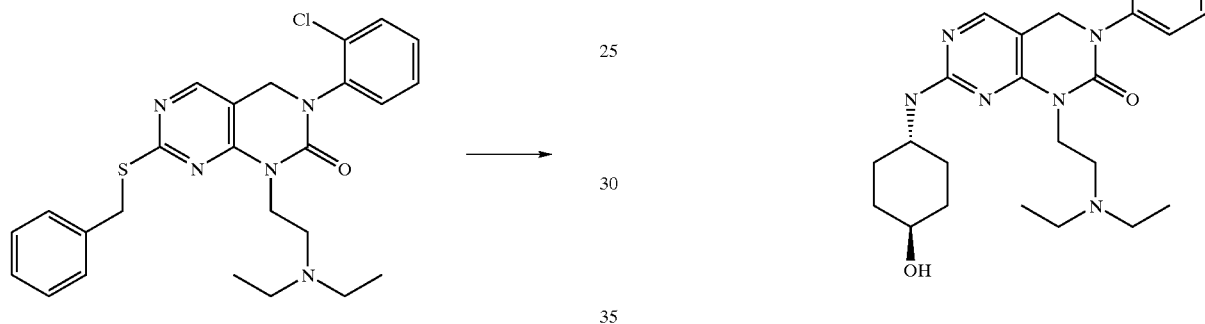

Oxidation of the 7-benzylthio-3-(2-chlorophenyl)-1-(2-diethylaminoethyl)-3,4-dihydropyrimido[4,5-d]pyrimidin-2(1H)-one was accomplished using 3-chloroperoxybenzoic acid (0.339 g, 1.96 mmol) in dichloromethane with stirring at room temperature for 1 hour. The reaction was quenched with 10% sodium sulfite solution (aq, 5 mL), poured into saturated aqueous sodium bicarbonate, and extracted with dichloromethane. The combined extracts were dried with magnesium sulfate and concentrated in vacuo to provide 7-benzylsulfinyl-3-(2-chlorophenyl)-1-(2-diethylaminoethyl)-3,4-dihydropyrimido[4,5-d]pyrimidin-2(1H)-one, which was used without purification.

38.3 Preparation of 3-(2-chlorophenyl)-1-(2-diethylaminoethyl)-7-(trans-4-hydroxy-cyclohexylamino)-3,4-dihydropyrimido[4,5-d]pyrimidin-2(1H)-one.

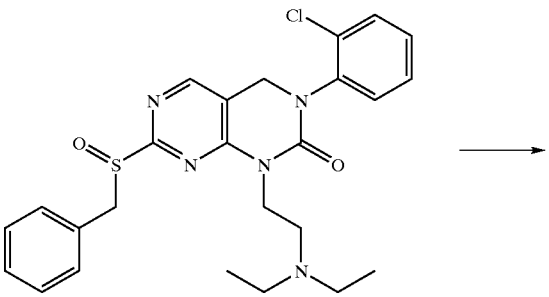

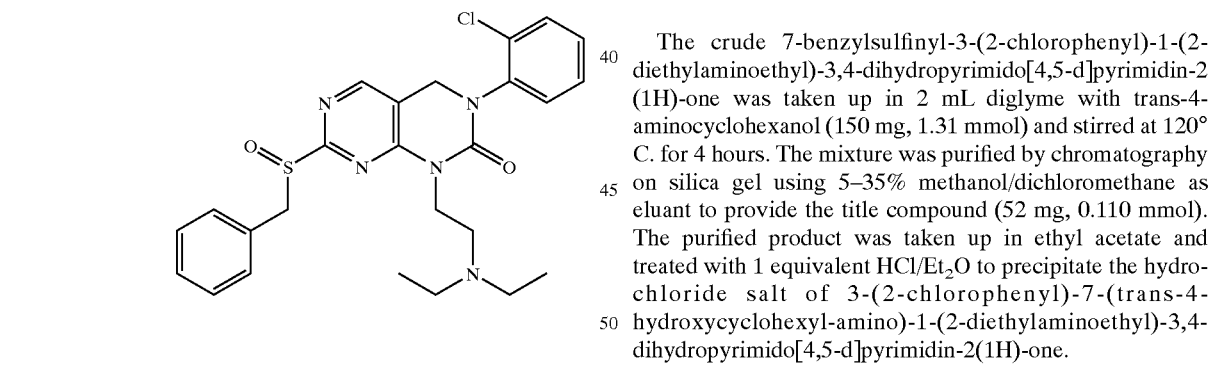

The crude 7-benzylsulfinyl-3-(2-chlorophenyl)-1-(2-diethylaminoethyl)-3,4-dihydropyrimido[4,5-d]pyrimidin-2(1H)-one was taken up in 2 mL diglyme with trans-4-aminocyclohexanol (150 mg, 1.31 mmol) and stirred at 120° C. for 4 hours. The mixture was purified by chromatography on silica gel using 5–35% methanol/dichloromethane as eluant to provide the title compound (52 mg, 0.110 mmol). The purified product was taken up in ethyl acetate and treated with 1 equivalent HCl/Et$_2$O to precipitate the hydrochloride salt of 3-(2-chlorophenyl)-7-(trans-4-hydroxycyclohexyl-amino)-1-(2-diethylaminoethyl)-3,4-dihydropyrimido[4,5-d]pyrimidin-2(1H)-one.

Example 39

Compound 3-30

This example illustrates the preparation of 3-(2-chlorophenyl)-1-(2-dimethylaminoethyl)-7-(trans-4-hydroxycyclohexylamino)-3,4-dihydropyrimido[4,5-d]pyrimidin-2(1H)-one.

39.1 Preparation of 7-benzylthio-3-(2-chlorophenyl)-1-(2-dimethyl-aminoethyl)-3,4-dihydropyrimido[4,5-d]pyrimidin-2(1H)-one.

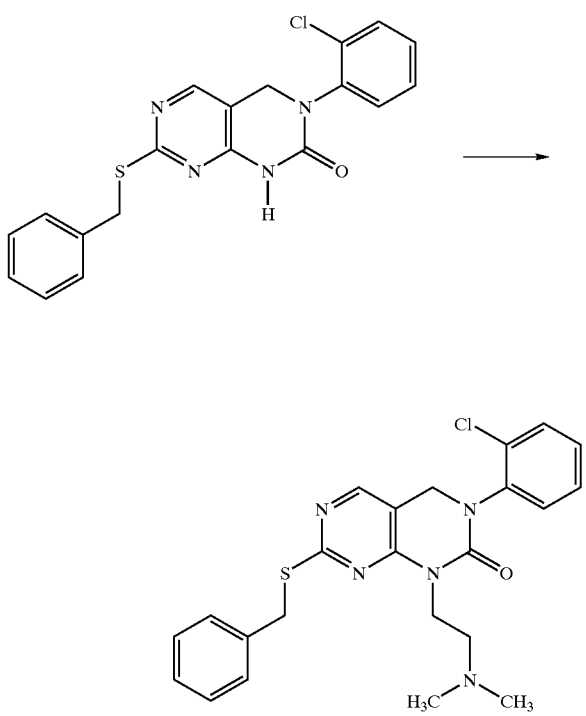

Sulfide 8.1 in 5 mL tetrahydrofuranwas combined with N,N-dimethylethanolamine (0.39 mL, 3.92 mmol), triphenylphosphine (1.04 g, 3.92 mmol), and DEAD (0.62 mL, 3.92 mmol), and stirred at room temperature for 1 hour. The mixture was semipurified by chromatography on silica gel with 1–3% methanol/dichloromethane as eluant, to provide >1 g mixture of 7-benzylthio-3-(2-chlorophenyl)-1-(2-dimethylaminoethyl)-3,4-dihydropyrimido[4,5-d]pyrimidin-2(1H)-one and residual triphenylphosphine oxide.

39.2 Preparation of 7-benzylsulfonyl-3-(2-chlorophenyl)-1-(2-dimethylamino-ethyl)-3,4-dihydropyrimido[4,5-d]pyrimidin-2-(1H)-one.

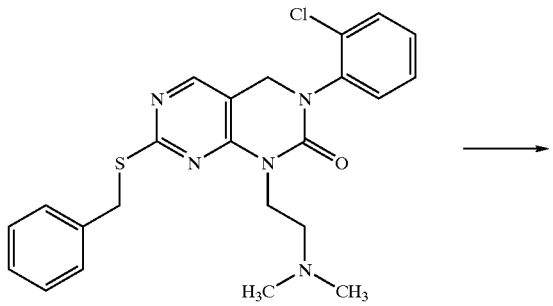

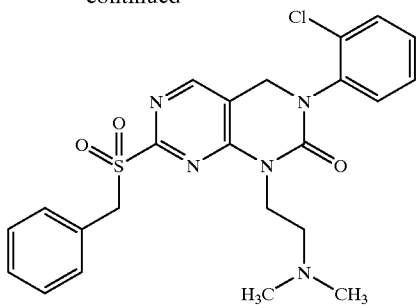

Oxidation of the sulfide was accomplished using 3-chloroperoxybenzoic acid (1.35 g, 7.84 mmol) in dichloromethane with stirring at room temperature for 1 hour. The reaction was quenched with saturated sodium sulfite (aqueous, 1 mL) and extracted with dichloromethane. The organic extracts were washed with saturated aqueous sodium bicarbonate, dried with magnesium sulfate, and concentrated in vacuo to provide 7-benzylsulfonyl-3-(2-chlorophenyl)-1-(2-dimethylaminoethyl)-3,4-dihydropyrimido[4,5-d]pyrimidin-2(1H)-one, which was used without purification.

39.3 Preparation of 3-(2-chlorophenyl)-1-(2-dimethylaminoethyl)-7-(trans-4-hydroxycyclohexylamino)-3,4-dihydropyrimido[4,5-d]pyrimidin-2(1H)-one.

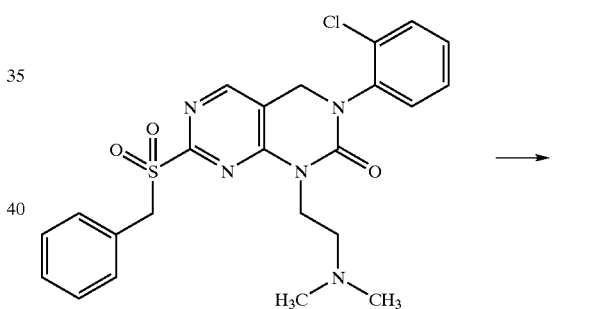

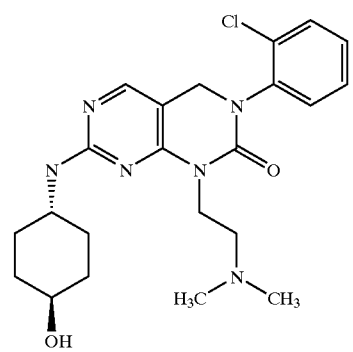

The crude 7-benzylsulfonyl-3-(2-chlorophenyl)-1-(2-dimethylaminoethyl)-3,4-dihydropyrimido[4,5-d]pyrimidin-2(1H)-one was taken up in 2 mL diglyme with trans-4-aminocyclohexanol (331 mg, 2.87 mmol) and stirred at 120° C. for 4 hours. The mixture was purified by chromatography on silica gel using 10–30% methanol/dichloromethane as eluant to provide the title compound (180 mg, 0.405 mmol). The purified product was taken up in ethyl acetate and treated with 1 equivalent HCl/Et$_2$O to precipitate the hydrochloride salt of 3-(2-chlorophenyl)-1-(2-dimethylaminoethyl)-7-(trans-4-hydroxycyclohexyl-amino)-3,4-dihydropyrimido[4,5-d]pyrimidin-2(1H)-one.

Example 40

Compound 3-22

This example illustrates the preparation of (S)-3-(2-chlorophenyl)-7-(2-hydroxy-1-methyl-ethylamino)-1-(piperidin-4-yl)-3,4-dihydropyrimido[4,5-d]pyrimidin-2(1H)-one.

40.1 Preparation of 7-benzylthio-3-(2-chlorophenyl)-1-(piperidin-4-yl)-3,4-dihydropyrimido[4,5-d]pyrimidin-2(1H)-one.

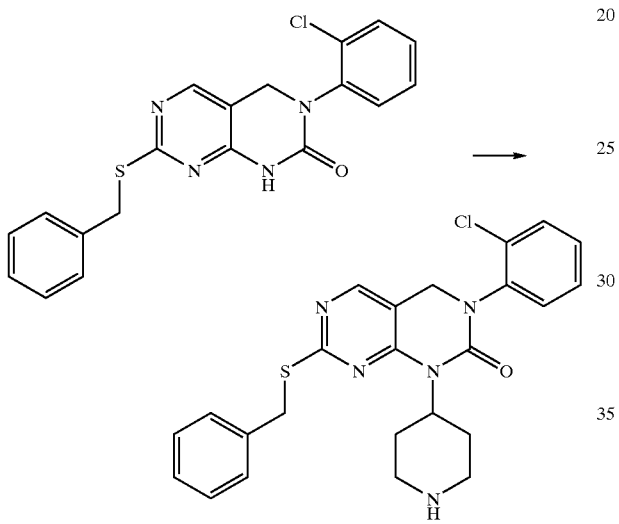

To a suspension of sulfide 8.1 (850 mg, 2.22 mmol) in tetrahydrofuran (10 mL) was added tert-butyl-4-hydroxy-1-piperidine carboxylate (411 mg, 2.22 mmol) and diphenyl-2-pyridylphosphine (878 mg, 3.3 mmol). After 5 minutes di-tert-butyl-azodicarboxylate (768 mg, 3.33 mmol) was added and the reaction was stirred at room temperature over the weekend. The reaction was placed directly on a flash silica column using 3:1–2:1 hexane ethyl acetate and 1:1 hexane/ethyl acetate as eluants to give 930 mg of 7-benzylthio-3-(2-chlorophenyl)-1-(piperidin-4-yl)-3,4-dihydropyrimido[4,5-d]-pyrimidin-2(1H)-one.

40.2 Preparation of 7-benzylsulfinyl-3-(2-chlorophenyl)-1-(piperidin-4-yl)-3,4-dihydropyrimido[4,5-d]pyrimidin-2(1H)-one.

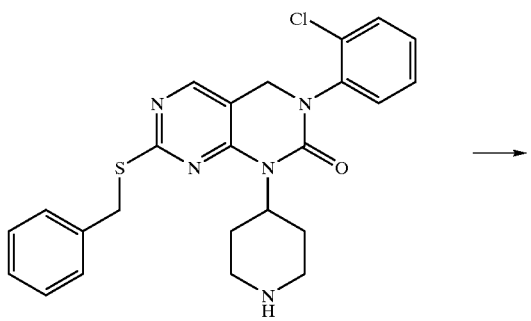

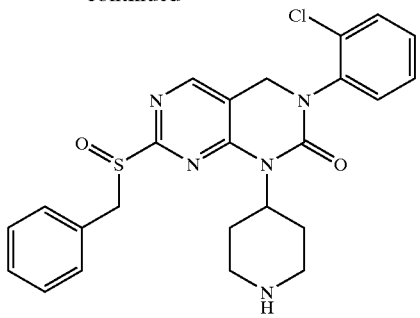

To a solution of 7-benzylthio-3-(2-chlorophenyl)-1-(piperidin-4-yl)-3,4-dihydropyrimido[4,5-d]pyrimidin-2(1H)-one (920 mg, 1.62 mmol) in dichloromethane (16 mL) cooled to 0° C. was added 3-chloroperbenzoic acid (403 mg, 1.64 mmol). After an hour at room temperature 5 mL of 10% sodium thiosulphate was added. After 10 minutes, the dichloromethane layer was separated and washed with 10% potassium carbonate and brine, dried over magnesium sulfate, concentrated in vacuo to give 650 mg of 3-(2-chlorophenyl)-7-benzylsulfinyl-1-(piperidin-4-yl)-3,4-dihydropyrimido[4,5-d]pyrimidin-2(1H)-one as a white foam.

40.3 Preparation of (S)-3-(2-chlorophenyl)-7-(2-hydroxy-1-methylethylamino)-1-(piperidin-4-yl)-3,4-dihydropyrimido[4,5-d]pyrimidin-2(1H)-one.

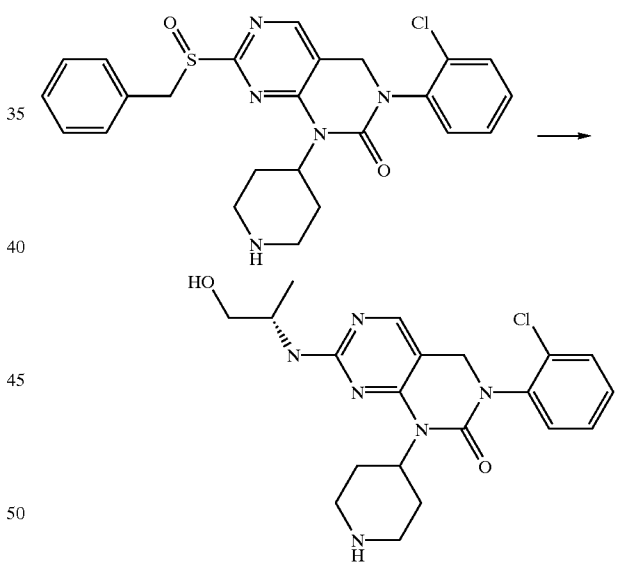

To a suspension of 7-benzylsulfinyl-3-(2-chlorophenyl)-1-(piperidin-4-yl)-3,4-dihydropyrimido[4,5-d]pyrimidin-2(1H)-one (650 mg, 1.136 mmol) in 1,2-dimethoxyethane (0.5mL) was added (S)-(+)-2-amino-1-propanol (250 mg, 3.33 mmol). The reaction was warmed to 100° C. under argon for 2 hours. The reaction was placed directly on a flash silica column using 92:8–90:10 dichloromethane/methanol as eluant to give 300 mg of the (S)-3-(2-chlorophenyl)-7-(2-hydroxy-1-methylethylamino)-1-(piperidin-4-yl)-3,4-dihydropyrimido[4,5-d]pyrimidin-2(1H)-one, which was redissolved in 5 mL of dichloromethane and 5 mL trifluoroacetic acid. After 5 hours the solvents were removed in vacuo and 5 mL of ethyl acetate and 5 mL of 10% sodium bicarbonate were added. The organic layer was separated, washed with brine, dried over magnesium sulfate and concentrated in vacuo to give 130 mg of the title compound as a white foam that was dissolved in ethyl acetate and treated with 1 equivalent of hydrochloric acid in 1.0M ether. The precipitate was collected, washed with ether and dried in vacuo to give 115 mg of the hydrochloride salt of (S)-3-(2-chloro-phenyl)-7-(2-hydroxy-1-methylethylamino)-1-(piperidin-4-yl)-3,4-dihydropyrimido[4,5-d]pyrimidin-2(1H)-one.

Example 41

Compound 3-21

This example illustrates the preparation of (R)-3-(2-chlorophenyl)-7-[(2-hydroxy-1-methylethyl)amino]-1-(2-ethoxy-1-ethoxymethylethyl)-3,4-dihydropyrimido[4,5-d]pyrimidin-2(1H)-one.

41.1 Preparation of 7-benzylthio-3-(2-chlorophenyl)-1-(2-ethoxy-1-ethoxy-methylethyl)-3,4-dihydropyrimido[4,5-d]pyrimidin-2(1H)-one.

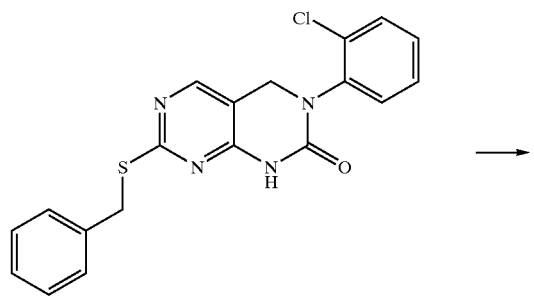

A mixture of sulfide 8.1 (600 mg, 2.4 mmol), diphenyl-2-pyridylphosphine (619 mg, 2.4 mmol) and 1,3-diethoxy-2-propanol (232 mg, 0.6 mmol) was dissolved in tetrahydrofuran under nitrogen. To this solution was added di-tert-butylazodicarboxylate (542 mg, 2.4 mmol) in one portion, and the resulting mixture was stirred at room temperature for one day. 1M hydrochloric acid in ether was added and the excess solvent was evaporated after stirring the mixture for 1 hour. The residue was dissolved in ether and washed with aqueous hydrochloric acid. The organic layer was dried over sodium sulfate, concentrated and the residue was purified by column chromatography on silica gel using 30% ethyl acetate in hexane as eluant. The column fractions containing product were combined and concentrated in vacuo to give 566 mg of 7-benzylthio-3-(2-chlorophenyl)-1-(2-ethoxy-1-ethoxymethylethyl)-3,4-dihydropyrimido[4,5-d]pyrimidin-2(1H)-one.

41.2 Preparation of 7-benzylsulfinyl-3-(2-chlorophenyl)-1-(2-ethoxy-1-ethoxy-methylethyl)-3,4-dihydropyrimido[4,5-d]pyrimidin-2(1H)-one.

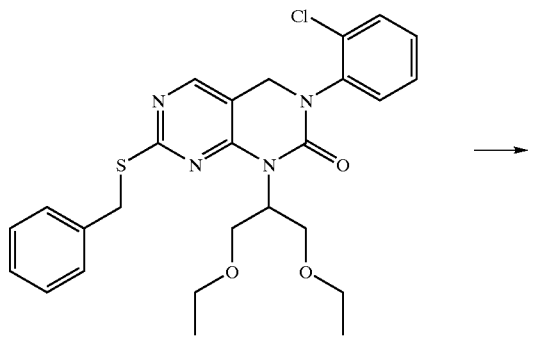

A suspension of 7-benzylthio-3-(2-chlorophenyl)-1-(2-ethoxy-1-ethoxymethylethyl)-3,4-dihydropyrimido[4,5-d]pyrimidin-2(1H)-one (566 mg, 1.1 mmol) in dichloromethane (5 mL) was cooled in an ice bath and 3-chloroperbenzoic acid was added. The reaction mixture was stirred for 1 hour, concentrated in vacuo, and the residue was purified by column chromatography on silica gel using 98:2 dichloromethane/methanol. The column fractions containing product were combined and concentrated in vacuo to yield 425 mg of 7-benzylsulfinyl-3-(2-chlorophenyl)-1-(2-ethoxy-1-ethoxymethylethyl)-3,4-dihydropyrimido[4,5-d]pyrimidin-2(1H)-one.

41.3 Preparation of (R)-3-(2-chlorophenyl)-7-[(2-hydroxy-1-methyl-e thyl)amino]-1-(2-ethoxy-1-ethoxymethylethyl)-3,4-dihydropyrimido[4,5-d]pyrimidin-2(1H)-one

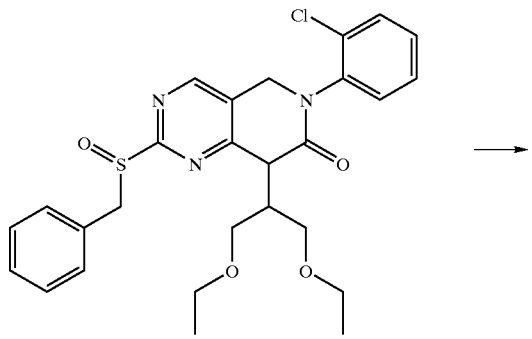

-continued

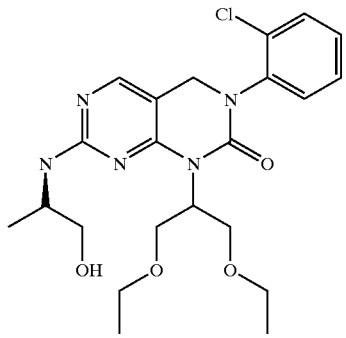

7-Benzylsulfinyl-3-(2-chlorophenyl)-1-(2-ethoxy-1-ethoxymethylethyl)-3,4-dihydropyrimido[4,5-d]pyrimidin-2(1H)-one (425 mg, 0.8 mmol) in (R)-2-amino-1-propanol (1 mL) was heated to 140° C. for 18 hours at which time it was cooled to room temperature and concentrated in vacuo. The residue was purified by column chromatography on silica gel using 98:2 dichloromethane/methanol. The column fractions containing product were combined and concentrated in vacuo to give an oil, which was re-dissolved in ethyl acetate. Addition of hydrochloric acid (1.0M/Et₂O, 2.0 equivalents) gave the salt which was filtered and dried to 156 mg of the hydrochloride salt of (R)-3-(2-chlorophenyl)-7-(2-hydroxy-1-methylethylamino)-1-(2-ethoxy-1-ethoxymethylethyl)-3,4-dihydropyrimido[4,5-d]pyrimidin-2(1H)-one.

Example 42

Compound 3-60

This example illustrates the preparation of 3-(2-chlorophenyl)-7-(trans-4-hydroxycyclohexylamino)-1-(2,2,2-trifluoroethyl)-3,4-dihydropyrimido[4,5-d]pyrimidin-2(1H)-one.

42.1 Preparation of 7-benzylthio-3-(2-chlorophenyl)-1-(2,2,2-trifluoroethyl)-3,4-dihydropyrimido[4,5-d]pyrimidin-2(1H)-one

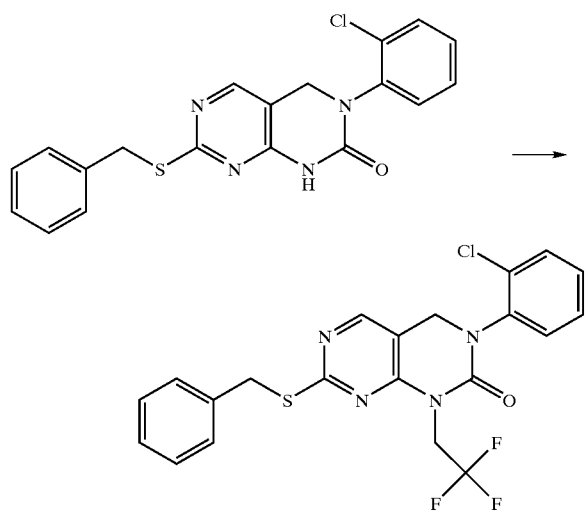

To sulfide 8.1 (0.563 g, 1.47 mmol) in dry N,N-dimethylformamide (3 mL) was added sodium hydride (60%, 0.1 g, 2.5 mmol) at 0° C. After stirring the mixture at room temperature for 30 minutes, 2,2,2-trifluoromethane sulfonate (1 mL) was added and the mixture was stirred overnight. Ethyl acetate was added to the reaction mixture, and the solution was washed with brine, dried over sodium sulfate, filtered, and evaporated. The resulting oil residue was trituated with hexanes to give 0.65 g of crude 7-benzylthio-3-(2-chlorophenyl)-1-(2,2,2-trifluoroethyl)-3,4-dihydropyrimido[4,5-d]pyrimidin-2(1H)-one, which was used directly in the next step without purification.

42.2 Preparation of 7-benzylsulfonyl-3-(2-chlorophenyl)-1-(2,2,2-trifluoro-ethyl)-3,4-dihydropyrimido[4,5-d]pyrimidin-2(1H)-one.

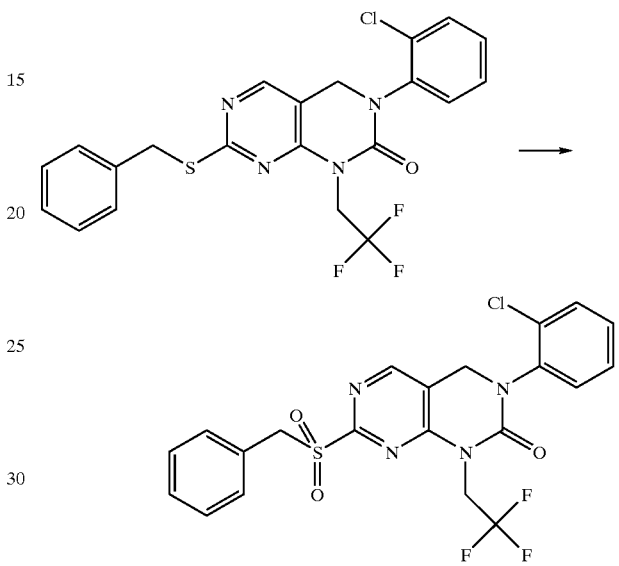

To 7-benzylthio-3-(2-chlorophenyl)-1-(2,2,2-trifluoroethyl)-3,4-dihydropyrimido[4,5-d]pyrimidin-2 (1H)-one (0.67 mg) in tetrahydrofuran (7 mL) at 0° C. was added a solution of Oxone® (2.27 g) in water (7 mL). The mixture was then stirred at room temperature for one hour. Additional Oxone® (0.8 g) in 2 mL of water was added and the mixture was stirred for another 1 hour. The mixture was diluted with ethyl acetate, washed with brine, dried over sodium sulfate, filtered and evaporated to give 0.65 g of crude 7 benzylsulfonyl-3-(2-chlorophenyl)-1-(2,2,2-trifluoroethyl)-3,4-dihydropyrimido[4,5-d]pyrimidin-2 (1H)-one as a white solid, which was used directly in the next step without purification.

42.3 Preparation of 3-(2-chlorophenyl-7-(trans-4-hydroxycyclohexyl-amino)-1-(2,2,2-trifluoroethyl)-3,4-dihydropyrimido[4,5-d]pyrimidin-2(1H)-one

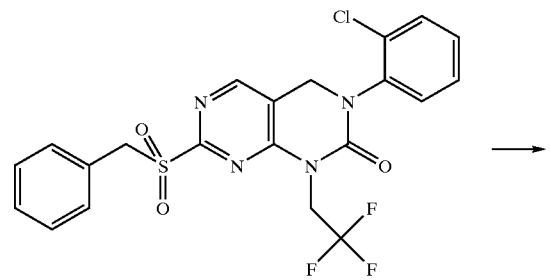

-continued

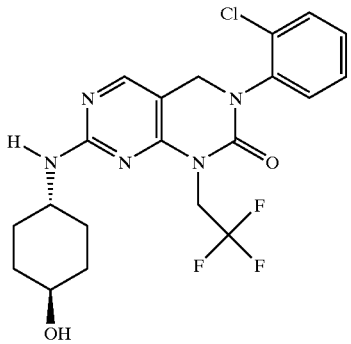

7-Benzylsulfonyl-3-(2-chlorophenyl)-1-(2,2,2-trifluoroethyl)-3,4-dihydropyrimido[4,5-d]pyrimidin-2(1H)-one (300 mg, 0.604 mmol), trans-4-aminocyclohexanol (208 mg, 3 equivalents) and 1-methyl-2-pyrrolidinone (0.3 mL) were heated with stirring at 110° C. for 20 minutes, at which time it was cooled to room temperature. The residue was purified using preparative thin layer chromatography using ethyl acetate as eluant, to give 155 mg of 3-(2-chlorophenyl)-7-(trans4-hydroxycyclohexylamino)-1-(2,2,2-trifluoroethyl)-3,4-dihydropyrimido[4,5-d]pyrimidin-2(1H)-one as an off-white powder.

Example 43

Compound 3-32

This example illustrates the preparation of 3-(2-chlorophenyl)-7-(trans-4-hydroxycyclohexylamino)-1-(dimethylaminocarbonylmethyl)-3,4-dihydropyrimido[4,5-d]pyrimidin-2(1H)-one.

43.1 Preparation of 7-benzylthio-3-(2-chlorophenyl)-1-(ethoxycarbonyl-methyl)-3,4-dihydropyrimido[4,5-d]pyrimidin-2(1H)-one

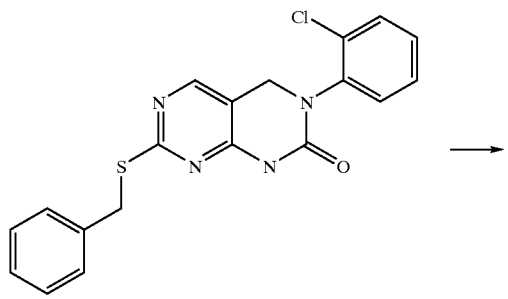

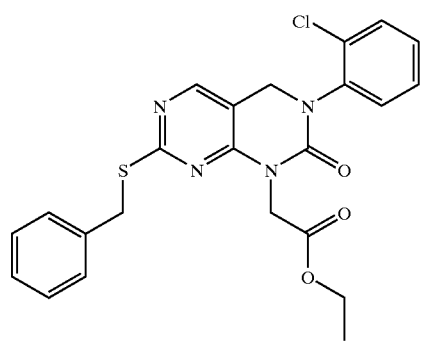

Sulfide 8.1 (2.0 g, 5.22 mmol) in N,N-dimethylformamide (10 mL) was combined with sodium hydride (230 mg, 5.75 mmol), and the reaction mixture was stirred for 20 minutes, then ethylbromoacetate (1.16 mL, 10.45 mmol) was added. After 3 hours the reaction was quenched with water and extracted into ethyl acetate. The combined organic extracts were washed with water, dried, filtered, concentrated in vacuo, and the residue was purified by column chromatography on silica gel using 30% acetone/hexane as eluant. The column fractions containing product were combined and concentrated in vacuo to give 1.438 g 7-benzylthio-3-(2-chlorophenyl)-1-(ethoxycarbonylmethyl)-3,4-dihydropyrimido[4,5-d]pyrimidin-2(1H)-one.

43.2 Preparation of 7-benzylthio-3-(2-chlorophenyl)-1-(hydroxycarbonyl-methyl)-3,4-dihydropyrimido[4,5-d]pyrimidin-2(1H)-one.

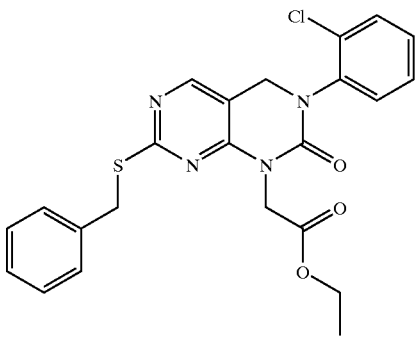

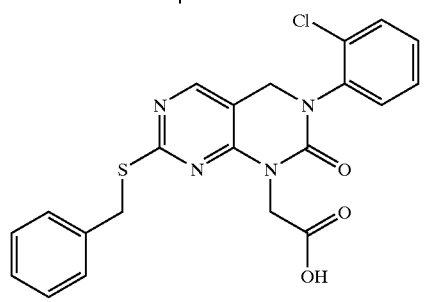

A mixture of 7-benzylthio-3-(2-chlorophenyl)-1-(ethoxycarbonylmethyl)-3,4-dihydropyrimido[4,5-d]pyrimidin-2(1H)-one (1.435 g, 3.36 mmol) and lithium hydroxide monohydrate (481 mg, 11.5 mmol) in methanol (10 mL) and water (30 mL) were refluxed for 48 hours. The reaction mixture was cooled to room temperature and diluted with ethyl acetate/water. The aqueous layer was adjusted to pH 4 and extracted with ethyl acetate. The combined organic extracts were dried, filtered and concentrated in vacuo to give 1.2 g of 7-benzylthio-3-(2-chlorophenyl)-1-(hydroxycarbonylmethyl)-3,4-dihydropyrimido[4,5-d]pyrimidin-2(1H)-one.

43.3 Preparation of 7-benzylthio-3-(2-chlorophenyl)-1-(dimethyl-amino-carbonylmethyl)-3,4-dihydropyrimido[4,5-d]pyrimidin-2(1H)-one

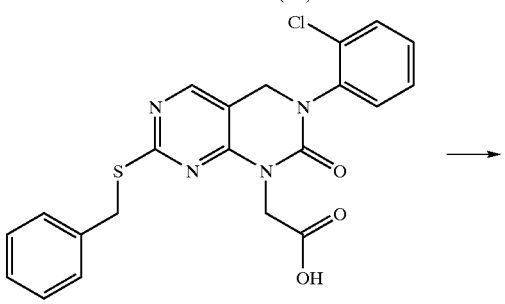

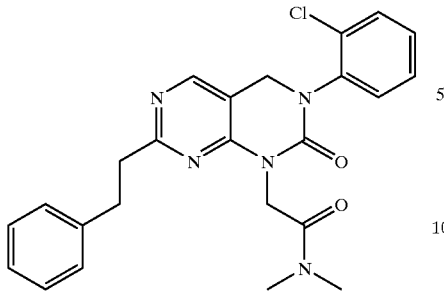

To a solution of 7-benzylthio-3-(2-chlorophenyl)-1-(hydroxycarbonylmethyl)-3,4-dihydropyrimido[4,5-d]pyrimidin-2(1H)-one (500 mg, 1.13 mmol) and benzotriazol-1-yloxytris(pyrrolidino)phosphonium hexafluorophosphate) (885 mg, 1.70 mmol) in N,N-dimethylformamide (15 mL) was bubbled dimethylamine gas into the solution for two minutes, then stirred in a sealed tube for 2 hours. The reaction mixture was quenched with water and extracted into ethyl acetate. The combined organic extracts were washed with water, dried, filtered, concentrated in vacuo, and the residue was purified by column chromatography on silica gel using 36:1 dicloromethane/methanol as eluant. The column fractions containing product were combined and concentrated in vacuo to give 490 mg of 7-benzylthio-3-(2-chlorophenyl)-1-(dimethylaminocarbonyl-methyl)-3,4-dihydropyrimido[4,5-d]pyrimidin-2(1H)-one.

43.4 Preparation of 7-benzylsulfonyl-3-(2-chlorophenyl)-1-(dimethyl-amino-carbonylmethyl)-3,4-dihydropyrimido[4,5-d]pyrimidin-2(1H)-one

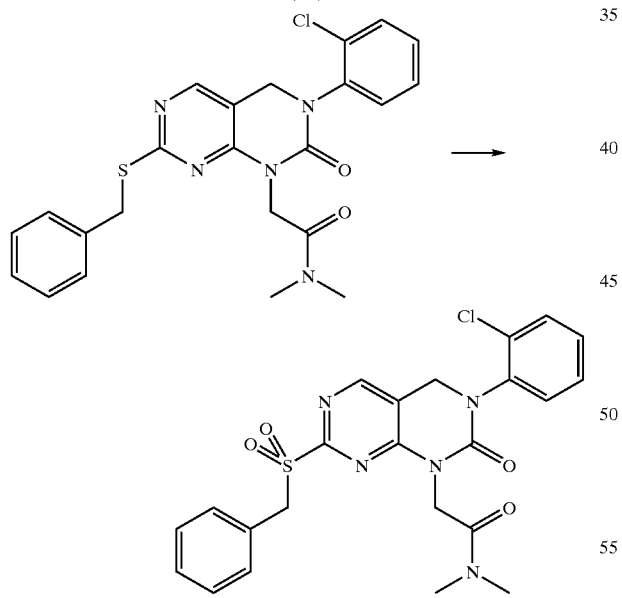

To a solution of 7-benzylthio-3-(2-chlorophenyl)-1-(dimethylaminocarbonylmethyl)-3,4-dihydropyrimido[4,5-d]pyrimidin-2(1H)-one (490 mg, 1.13 mmol) in chloroform was added 3-chloroperoxybenzoic acid (780 mg, 4.52 mmol). The mixture was stirred for 2 hours then washed with 10% solution of sodium sulfite in water and sodium bicarbonate aqueous solution, dried, filtered and concentrated to give 550 mg of 7-benzylsulfonyl-3-(2-chlorophenyl)-1-(dimethylaminocarbonylmethyl)-3,4-dihydropyrimido[4,5-d]pyrimidin-2(1H)-one.

43.5 Preparation of 3-(2-chlorophenyl)-7-(trans-4-hydroxycycloxyl-amino)-1-(dimethylaminocarbonylmethyl-3,4-dihydropyrimido[4,5-d]pyrimidin-2(1H)-one

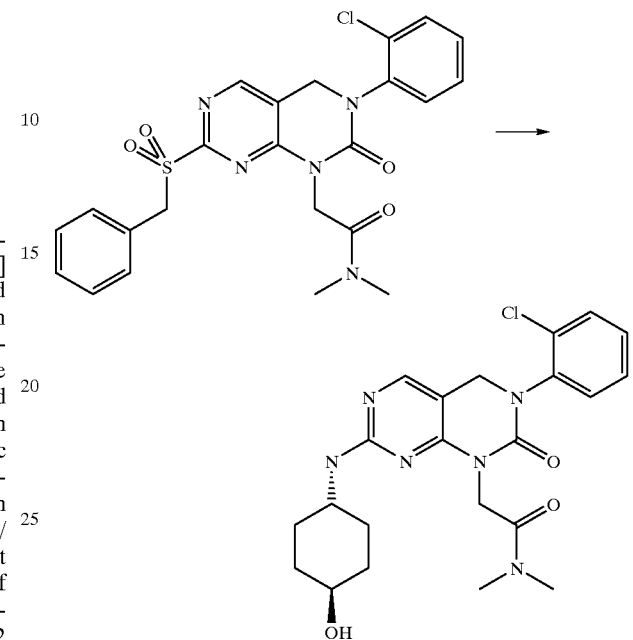

7-Benzylsulfonyl-3-(2-chlorophenyl)-1-(dimethyl-aminocarbonylmethyl)-3,4-dihydropyrimido[4,5-d]pyrimidin-2(1H)-one (550 mg, 1.1 mmol) was combined with trans-4-aminocyclohexanol (253 mg, 2.2 mmol). The mixture was heated to 100–105° C. for 3 hours, at which time it was cooled to room temperature. The residue was purified by column chromatography on silica gel using 9:1 dicloromethane/methanol as eluant. The column fractions containing product were combined and concentrated in vacuo to a solid that was triturated with methanol, filtered, dried and suspended in ethyl acetate. Addition of hydrochloric acid (1.0M/Et$_2$O, 2.0 equivalents) gave the salt which was filtered and dried to give 90 mg of the hydrochloride salt of 3-(2-chlorophenyl)-7-(trans-4-hydroxycycloxylamino)-1-(dimethylaminocarbonylmethyl)-3,4-dihydropyrimido-[4,5-d]pyrimidin-2(1H)-one.

Example 44

Compound 4-1

This example illustrates the preparation of 3-(2-chlorophenyl)-7-(2-hydroxy-1-hydroxymethyl-1-methylethylamino)-3,4-dihydropyrimido[4,5-d]pyrimidin-2(1H)-one.

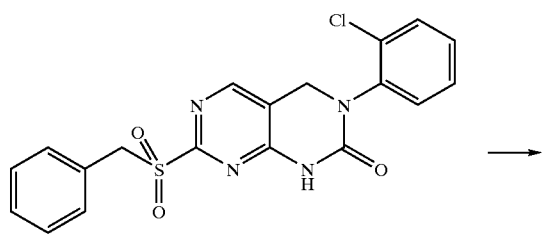

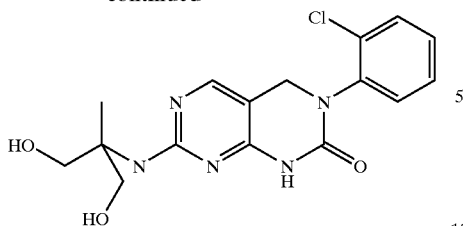

Sulfone 9.1 (0.500 g, 1.21 mmol) was combined with 2-amino-2-methyl-1,3-propanediol (0.253 g, 2.41 mmol). The mixture was heated to 120–130° C. for 2 hours at which time it was cooled to room temperature. The residue was triturated in dicloromethane/methanol. The slurry was filtered to give the free amine of the title compound, which was then slurried in methanol. Addition of hydrochloric acid (1.0 M/Et$_2$O, 1.0 equivalent) gave the salt which dissolved in methanol. The solution was filtered and the filtrate concentrated in vacuo to yield a hygroscopic solid which was triturated in ether, filtered and dried to give 0.195 g of 3-(2-chlorophenyl)-7-(2-hydroxy-1-hydroxymethyl-1-methylethylamino)-3,4-dihydropyrimido[4,5-d]pyrimidin-2(1H)-one.

Example 45

Compound 4-6

This example illustrates the preparation of 3-(2-chlorophenyl)-7-((R,R)-2-hydroxy-1-hydroxymethylpropylamino)-3,4-dihydropyrimido[4,5-d]-pyrimidin-2(1H)-one.

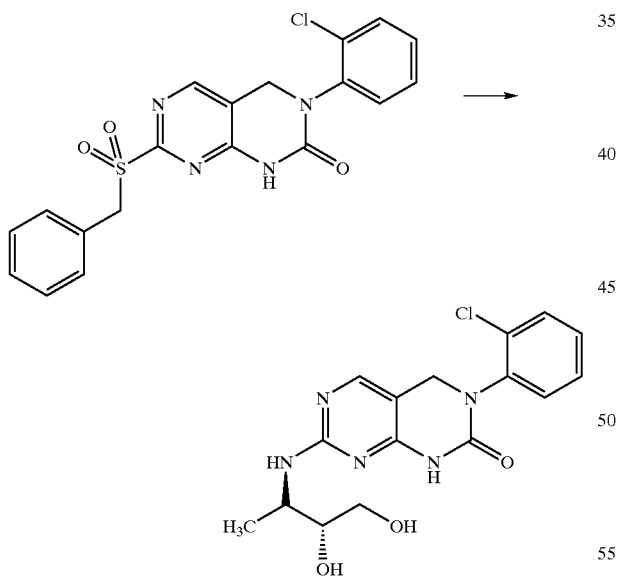

Sulfone 9.1 (776 mg, 1.9 mmol) was combined with (R,R)-3-amino-1,2-butanediol (238 mg, 2.3 mmol) and 2-methoxyethyl ether (5 mL). The mixture was heated to 120° C. for 3 hours, at which time it was cooled to room temperature and concentrated in vacuo. The residue was purified by column chromatography on silica gel using 97:3 dichloromethane/methanol as eluant. The column fractions containing product were combined and concentrated in vacuo to give an oil, which was re-dissolved in ethyl acetate. Addition of hydrochloric acid (1.0M/Et$_2$O, 2.0 equivalents) gave the salt which was filtered and dried to give 159 mg of the hydrochloride salt of 3-(2-chlorophenyl)-7-((R,R)-2-hydroxy-1-hydroxymethylpropylamino)-3,4-dihydropyrimido[4,5-d]-pyrimidin-2(1H)-one.

Example 46

Compound 4-8

This example illustrates the preparation of 3-(2-chlorophenyl)-7-[(4-hydroxycyclohexylamino)-3,4-dihydropyrimido[4,5-d]pyrimidin-2(1H)-one.

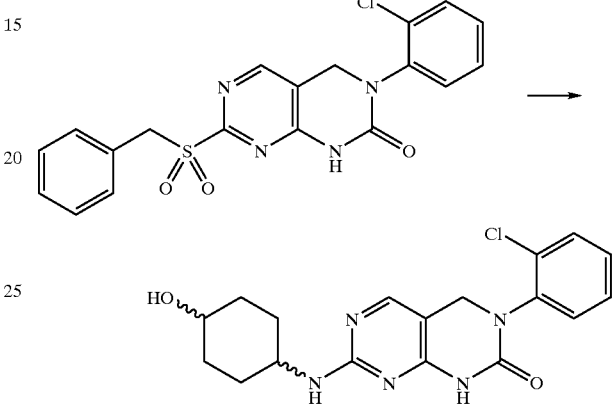

Sulfone 9.1 (0.500 g, 1.21 mmol) was combined with a racemic mixture of 4-aminocyclohexanol (0.70 g, 6.0 mmol; lyophilized from 50% aqueous solution (ICN)) in N-methylpyrrolidinone (2 mL). The mixture was heated to 120° C. for 1.5 hours at which time it was cooled to room temperature. The residue was purified by column chromatography on silica gel using 1–5% methanol/dichloromethane as eluant. The column fractions containing product were combined and concentrated in vacuo to give the title compound as yellow granules which were redissolved in ethyl acetate. Addition of hydrochloric acid (1.0M/Et$_2$O, 1.0 equivalent) gave the salt which was filtered and dried to give 0.258 g of the hydrochloride salt of 3-(2-chlorophenyl)-7-[(4-hydroxycyclohexylamino)-3,4-dihydropyrimido[4,5-d]pyrimidin-2(1H)-one.

Example 47

Compound 2-10

This example illustrates the preparation of 3-(2-chlorophenyl)-7-(tetrahydropyran-4-ylamino)-3,4-dihydropyrimido[4,5-d]pyrimidin-2(1H)-one.

Preparation of 4-aminotetrahydropyran

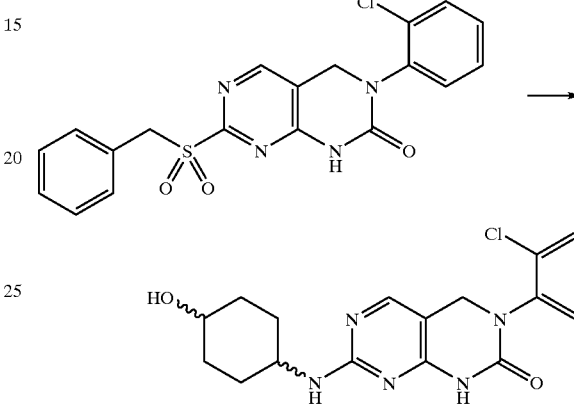

-continued

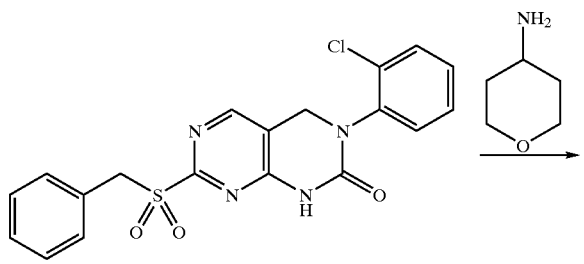

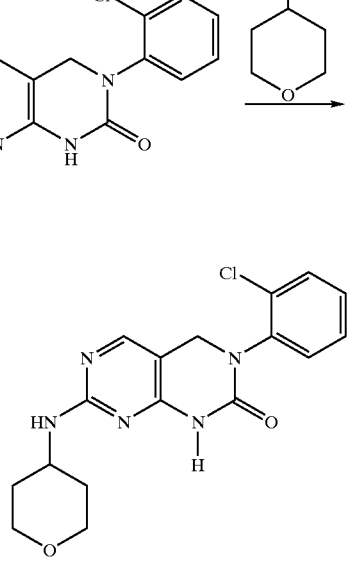

Hydroxylamine hydrochloride (4.19 g, 59.9 mmol) was taken up in 13 mL ethanol at room temperature and the resulting slurry was washed with another 15 mL ethanol into a solution of tetrahyropyran-4-one (5 g, 49.9 mmol) in 30 mL pyridine. The reaction was stirred overnight at room temperature then evaporated in vacuo to a thick pyridine-based syrup, which was poured into saturated aqueous copper sulfate and extracted with ethyl acetate. The combined extracts were dried with sodium sulfate, evaporated in vacuo, and Fluted with ethyl acetate. The filtrate was evaporated in vacuo to yield tetrahydropyran-4-one oxime as a greenish solid (5.05 g, 0.44 mmol).

A portion of the tetrahydropyran-4-one oxime (2.8 g, 24.3 mmol) was taken up in 50 mL tetrahydrofuran and chilled to 0° C. before slowly adding lithium aluminium hydride (4.6 g, 122 mmol) in portions. When the addition was complete, the reaction was removed from the ice bath, stirred at reflux overnight, and then quenched with careful addition of water and 10% aqueous sodium hydroxide. The reaction mixture was stirred at room temperature for 1 hour before filtering off the aluminum salts and rinsing with dichloromethane. The filtrate was evaporated in vacuo to yield 4-aminotetrahydropyran as a dark brown liquid (1.74 g, 0.17 mmol).

Preparation of 3-(2-chlorophenyl)-7-(tetrahydropyran-4-ylamino)-3,4-dihydropyrimido[4,5-d]pyrimidin-2(1H)-one.

Sulfone 9.1 (0.205 g, 0.494 mmol) in 5 mL 1-methyl-2-pyrrolidinone was combined with 4-aminotetrahydropyran (0.100 g, 0.988 mmol). The reaction was stirred at 100° C. for 24 hours and purified by column chromatography on silica gel using 3–7% methanol/dichloromethane as eluant. The column fractions containing product were combined and concentrated in vacuo to a give the title compound as a brown gum which was redissolved in methanol. Addition of hydrochloric acid (1.0M/Et$_2$O, 1.0 equivalent) gave 0.026 g of the hydrochloride salt 3-(2-chlorophenyl)-7-(tetrahydropyran-4-ylamino)-3,4-dihydropyrimido[4,5-d]pyrimidin-2(1H)-one.

Example 48

Compound 4-14

This example illustrates the preparation of 3-(2-chlorophenyl)-7-[(1-hydroxymethylcycylopentyl)amino]-3,4-dihydropyrimido[4,5-d]pyrimidin-2(1H)-one.

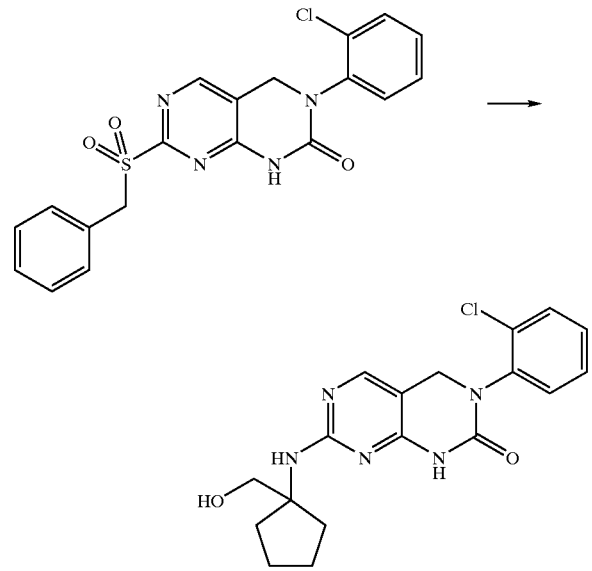

Sulfone 9.1 (500 mg, 1.2 mmol) was combined with 1-amino-1-cyclopentylmethanol (550 mg, 4.8 mmol) and 1-methyl-2-pyrrolidinone (1 mL). The mixture was heated to 120° C. for 3 hours, at which time it was cooled to room temperature. Methanol (3 mL) was added and the suspension was stirred for 10 minutes, filtered, and the residue was washed with methanol, dried and suspended in ethyl acetate. Addition of hydrochloric acid (1.0M/Et$_2$O, 2.0 equivalents) gave the salt which was filtered and dried to give 260 mg of hydrochloride salt of 3-(2-chlorophenyl)-7-[(1-hydroxymethylcycylopentyl)-amino]-3,4-dihydropyrimido[4,5-d]pyrimidin-2(1H)-one.

Example 49

Compound 4-16

This example illustrates the preparation of 3-(2-chlorophenyl)-7-[(1-hydroxymethylcyclohexyl)amino]-3,4-dihydropyrimido[4,5-d]pyrimidin-2(1H)-one.

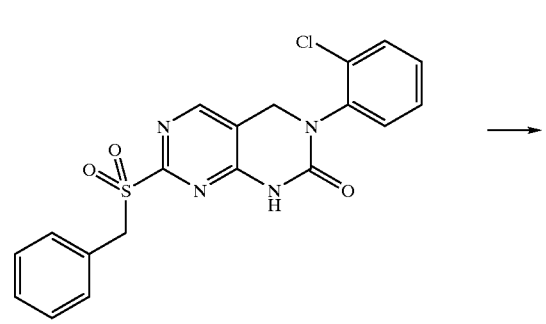

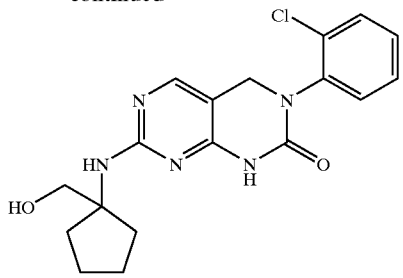

Sulfone 9.1 (500 mg, 1.2 mmol) was combined with 1-amino-1-cyclohexanemethanol (623 mg, 4.8 mmol) (prepared as described in *J. Med. Chem.*, 1966, 9(6), 911–920) and 1-methyl-2-pyrrolidinone (1 mL). The mixture was heated to 120° C. for 3 hours at which time it was cooled to room temperature. Methanol (3 mL) was added, the suspension was stirred for 10 minutes, filtered. The precipitate was washed thoroughly with methanol, dried and suspended in ethyl acetate. Addition of hydrochloric acid (1.0M/Et$_2$O, 2.0 equivalents) gave the salt which was filtered and dried to give 328 mg of the hydrochloride salt of 3-(2-chlorophenyl)-7-[(1-hydroxymethylcyclohexyl)amino]-3,4-dihydropyrimido[4,5-d]-pyrimidin-2(1H)-one.

Example 50

Compound 2-25

This example illustrates the preparation of 3-(2-chlorophenyl)-7-[(1-methylpiperidin-4-yl)methylamino]-3,4-dihydropyrimido[4,5-d]pyrimidin-2(1H)-one.

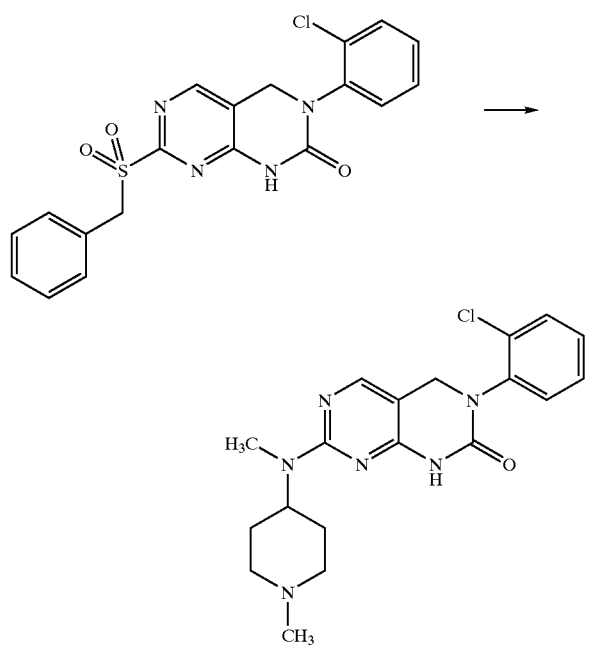

Sulfone 9.1 (0.512 g, 1.2 mmol) was combined with 1-methyl-4-(methylamino)piperidine (2 mL) (Aldrich Chemicals) in 0.3 mL of 1-methyl-2-pyrrolidinone. The mixture was heated at 100° C. for 3 hours, at which time it was cooled to room temperature, diluted with ethyl acetate and washed with brine. The organic phase was dried over sodium sulfate, filtered and evaporated. The crude product was purified by column chromatography on silica gel using 2%–10% methanol in dichloromethane as eluant, and finally 1% triethylamine/10% methanol in dichloromethane. The solids obtained were suspended in 5 mL methanol, bubbled with hydrogen chloride for 30 seconds, and the solvents were evaporated. The solids were then stirred in ethyl acetate and filtered to give 190 mg of the dichloride salt of 3 (2-chlorophenyl)-7-[(1-methylpiperidin-4-yl) methylamino]-3,4-dihydropyrimido[4,5-d]-pyrimidin-2 (1H)-one.

Example 51

Compound 4-18

This example illustrates the preparation of 3-(2-chlorophenyl)-7-(cis-4-hydroxycyclohexylamino)-3,4-dihydropyrimido[4,5-d]pyrimidin-2(1H)-one.

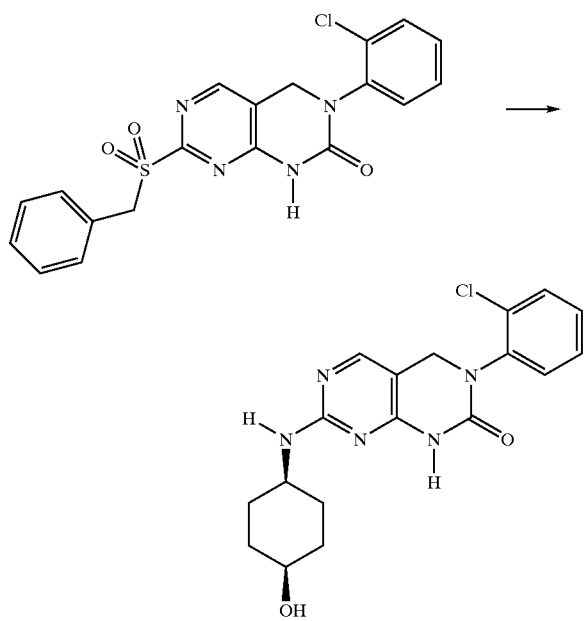

Sulfone 9.1 (0.81 g, 1.95 mmol) was combined with cis-4-aminocyclohexanol (0.45 g, 3.9 mmol) (prepared as described in *Aust. J. Chem.*, 1961, 14, 610) in 2.0 mL of 1 methyl-2-pyrrolidinone. The reaction mixture was stirred at 120° C. for 24 hours, at which time the reaction mixture was cooled to room temperature and filtered. The filtrate was suspended in anhydrous methanol, collected and dried precipitate to give 0.400 g of the title compound as a white solid (m.p. 263.7–264.6° C. ). White solid was dissolved in a 10:1 chloroform/methanol and 1M hydrochloric acid in ether was added. The reaction mixture stirred for 1 hour, concentrated and dried in vacuo, and the residue crystallized from methanol/ether to give 0.285 g of the hydrochloride salt of 3-(2-chlorophenyl)-7-(cis4-hydroxycyclohexylamino)-3,4-dihydropyrimido[4,5-d]pyrimidin-2(1H)-one as a white solid.

Example 52

Compound 2-26

This example illustrates the preparation of 3-(2-chlorophenyl)-7-[(1-carbamoylmethylpiperidin-4-yl) amino]-3,4-dihydropyrimido[4,5-d]pyrimidin-2(1H)-one.

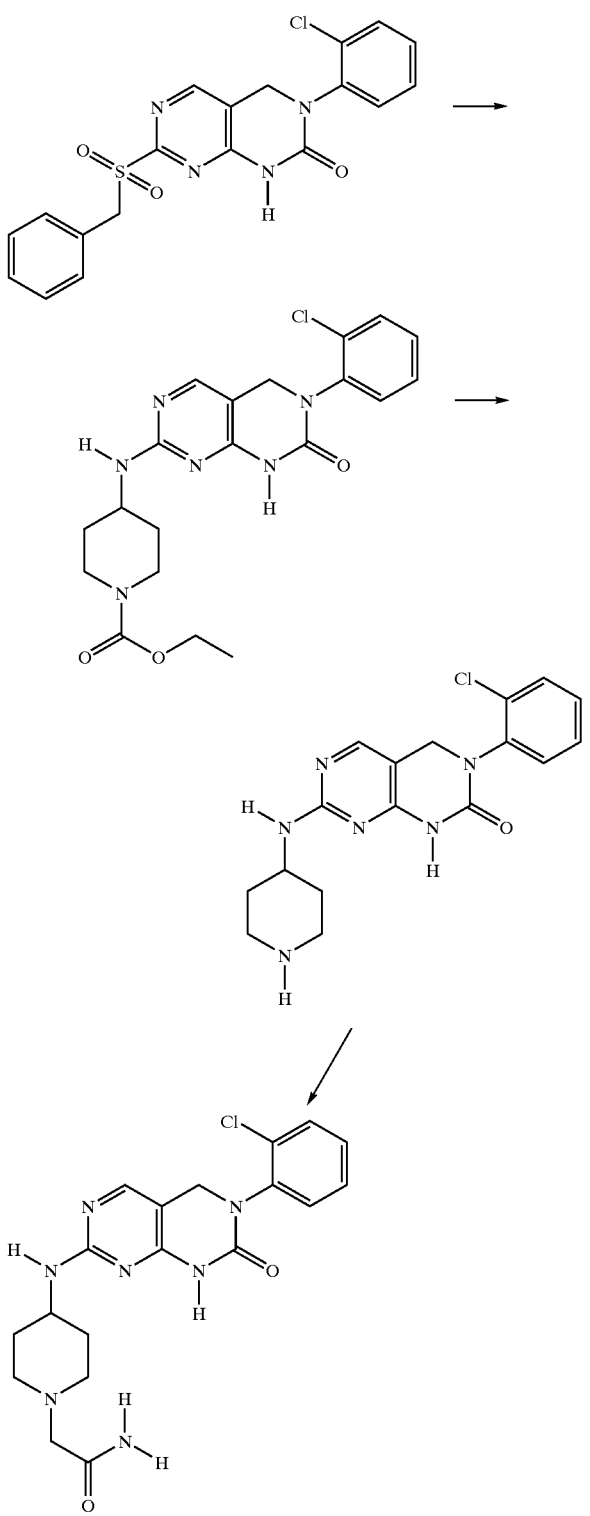

Sulfone 9.1 (1.0 g, 2.41 mmol) was taken up in 5 mL ethyl 4-amino-1-piperidinecarboxylate (29 mmol) and stirred at 150° C. After 1 hour, the reaction slurry was cooled to room temperature, poured into 50 mL methanol, and filtered to collect a white solid. The solid was washed with an additional 50 mL methanol and dried in vacuo to yield 0.569 g of 3-(2-chlorophenyl)-7-(1-ethoxycarbonylpiperidin-4-ylamino)-3,4-dihydropyrimido[4,5-d]pyrimidin-2(1H)-one.

3-(2—Chlorophenyl)-7-(1-ethoxycarbonylpiperidin-4-ylamino)-3,4-dihydropyrimido[4,5-d]pyrimidin-2(1H)-one was taken up in 2 mL dichloromethane with iodotrimethylsilane (0.94 mL, 6.60 mmol) and heated to 60° C. for 2 hours, quenched with methanol, and evaporated in vacuo. The dry residue was taken up again in minimum methanol, treated with sodium methoxide (0.5 equivalent, commercial solution of 0.5M methanol), and re-evaporated. The dry residue was purified by flash chromatography using 5,10% (1:9 ammonium hydroxide/methanol)/dichloromethane as eluant. The column fractions containing product were combined and concentrated in vacuo to yield 0.280 g (7.80 mmol) of the cleaved piperidine intermediate, 3-(2-chlorophenyl)-7-(piperidin-4-ylamino)-3,4-dihydropyrimido[4,5-d]pyrimidin-2(1H)-one.

3-(2—Chlorophenyl)-7-(piperidin-4-ylamino)-3,4-dihydropyrimido[4,5-d]pyrimidin-2(1H)-one (0.050 g, 0.139 mmol) was taken up in 1 mL N,N-dimethylformamide with bromoacetamide (0.029 g, 0.209 mmol) and stirred at room temperature for 2.5 hours, then raised to 40° C. for one hour and 80° C. overnight. The reaction was purified by flash chromatography using 5–40% methanol/dichloromethane+ 1% ammonium hydroxide as eluant. The column fractions containing product were combined and concentrated in vacuo, and the final product redissolved in a minimum volume of methanol. Addition of hydrochloric acid (1.0M/ Et$_2$O, 1.0 equivalent) gave the salt which was filtered and dried to give 0.007 g of the hydrochloride salt of 3-(2-chlorophenyl)-7-[(1-carbamoylmethylpiperidin-4-yl)amino]-3,4-dihydropyrimido[4,5-d]pyrimidin-2(1H)-one.

Example 53

Compound 2-27

This example illustrates the preparation of 3-(2-chlorophenyl)-7-[1-(2,2,2-trifloroethyl)piperidin-4-ylamino]-3,4-dihydropyrimido[4,5-d]pyrimidin-2(1H)-one.

Preparation of 1-(2,2,2-trifluoroethyl)piperidin-4-ylamine

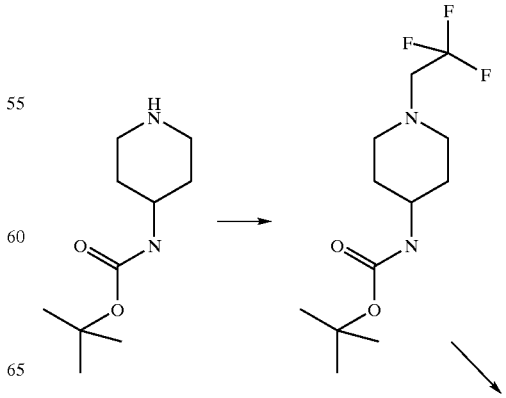

85
-continued

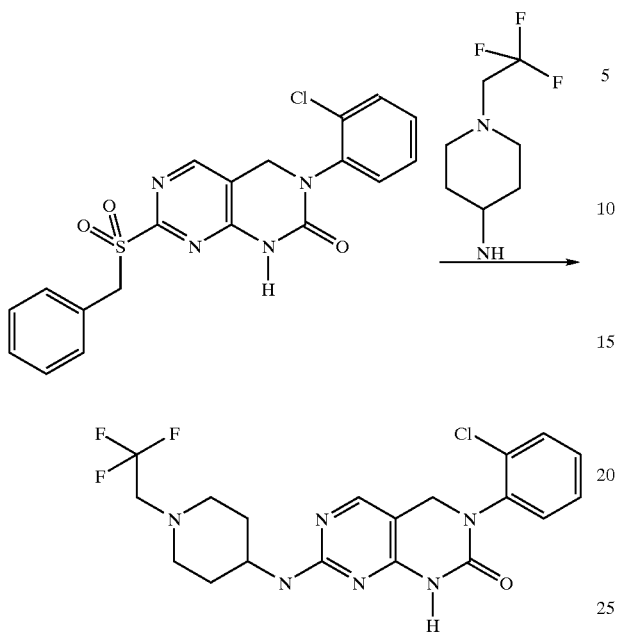

Piperidin-4-yl-carbamic acid tert-butyl ester (commercially available from ASTATECH) (5 g, 24.96 mmol), 2,2,2-trifluoroethyl trichloromethane sulfonate (7.03 g, 1 equivalent), and potassium carbonate (4.1 g, 1.2 eq) were taken up in acetone (80 mL) and heated at reflux with stirring for 17 hours. The solvent was removed under reduced pressure at 40° C. and ethyl acetate and water were added to the residue. The layers were partitioned and then separated. The organic layer was washed with water and brine, dried over magnesium sulfate, filtered, and concentrated to give a dark colored solid. Purification by chromatography on silica gel using 15% ethyl acetate in hexanes as the eluant gave [1-(2,2,2-trifluoroethyl)piperidin-4-yl]-carbamic acid tert-butyl ester (4.45 g) as an off-white powder, m.p. 99.2–99.8° C., (M+H)+=283.

[1-(2,2,2-Trifluoroethyl)piperidin-4-yl]-carbamic acid tert-butyl ester was then taken up in dioxane (80 mL) and hydrogen chloride gas was bubbled through the solution for 10 minutes. The reaction vessel was capped tightly and stirred for 1.5 hours. The solvent was removed under reduced pressure at 40° C. The residue was taken up in 42 mL of 0.5M sodium methoxide in methanol, stirred at room temperature for 3 hours, and filtered. The filtrate was concentrated, taken up in ethyl acetate, filtered, and concentrated to give 1.0 g of 1-(2,2,2-trifluoroethyl)piperidin-4-ylamine as a dark colored oil, (M+H)+=183.

Preparation of 3-(2-Chlorophenyl)-7-[1-(2,2,2-trifluoroethyl)-piperidinyl-4-yl-amino]-3,4-dihydropyrimido[4, 5-d]pyrimidin-2(1H)-one Sulfone 9.1 (200 mg, 0.482 mmol), 1-(2,2,2-trifluoroethyl)piperidin-4-ylamine (263 mg, 3 equivalents) was combined with 1-methyl-2-pyrolidinone(0.3 mL), and the reaction mixture was heated with stirring at 110° C. for 2 hours, at which time it was cooled to room temperature. Purification by preparative thin layer chromatography using 60%ethyl acetate in hexanes as eluant gave 12 mg of 3-(2-chlorophenyl)-7-[1-(2,2,2-trifluoroethyl)piperidinyl-4-ylamino]-3,4-dihydropyrimido[4,5-d]pyrimidin-2(1H)-one as an off-white powder.

86

Example 54

Compound 4-17

This example illustrates the preparation of 3-(2-chlorophenyl)-7-[(4-hydroxycyclohexylmethyl)amino]-3,4-dihydropyrimido[4,5-d]pyrimidin-2(1H)-one.

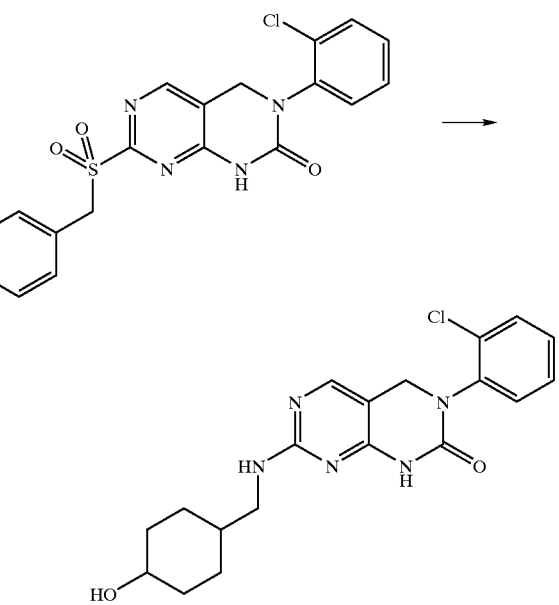

Sulfone 9.1 (400 mg, 0.96 mmol) was combined with 4-aminomethylcyclohexanol (470 mg, 3.6 mmol) and 0.4 mL of 1-methyl-2-pyrrolidinone. The mixture was heated to 120° C. for 3 hours, at which time it was cooled to room temperature. Methanol (3 mL) was added, the suspension was stirred for 10 minutes, filtered, and the precipitate was washed with methanol, dried and suspended in ethyl acetate. Addition of hydrochloric acid (1.0M/Et₂O, 2.0 equivalents) gave the salt which was filtered and dried to give 198 mg of the hydrochloride salt of 3-(2-chlorophenyl)-7-[(4-hydroxycycylohexylmethyl)amino]-3,4-dihydropyrimido[4,5-d]pyrimidin-2(1H)-one.

Example 55

Compound 2-21

This example illustrates the preparation of 3-(2-chlorophenyl)-7-[1-(2,2,2-trifluoroethyl)piperidin4-ylamino]-3,4-dihydropyrimido[4,5-d]pyrimidin-2(1H)-one.

Preparation of 4-aminomethyl-N-(2,2,2-trifluoroethyl)piperidine

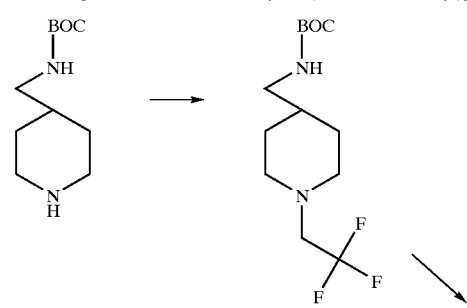

-continued

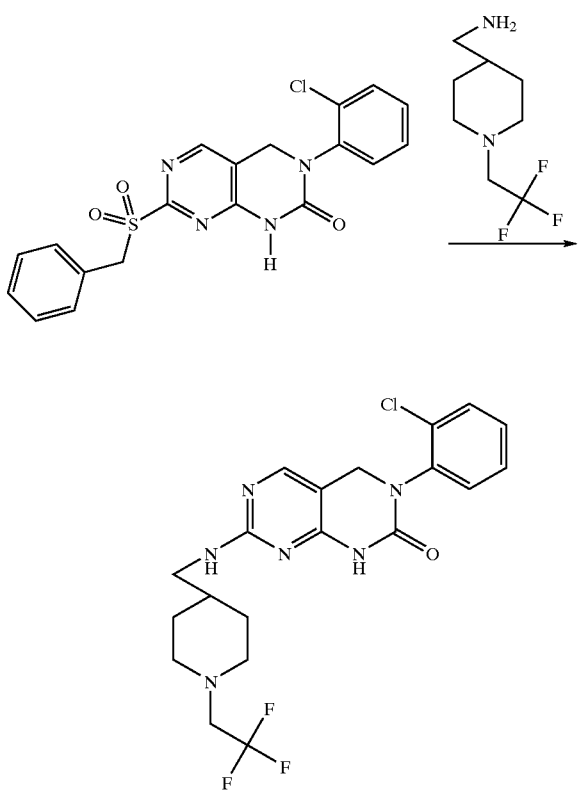

A mixture of (4-benzyloxycarbonylaminomethyl) piperidine (4 g, 16.1 mmol), 2,2,2-trifluoroethyl trichloromethanesulfonate (5.58 g, 20 mmol), and potassium carbonate (2.67 g, 19 mmol) in 40 mL of acetone was reflux d for 17 hours. The mixture was evaporated and treated with ethyl acetate and brine. The organic phase was separated, washed with brine, dried over sodium sulfate, filtered, and evaporated. The crude solids were purified by column chromatography on silica gel using 10%–20% ethyl acetate in hexanes as eluant to give 2.25 g of 4-benzyloxyaminomethyl-1-(2,2,2-trifluoroethyl)piperidine, m.p. 93.8–95.1° C.

4-Benzyloxyaminomethyl-1-(2,2,2-trifluoroethyl) piperidine was dissolved in ethanol (50 mL) and hydrogenated over 10% palladium on carbon (0.5 g) for 10 hours. The mixture was filtered through a pad of celite and washed with methanol. The filtrate was evaporated to give 1.17 g of 4-aminomethyl-1-(2,2,2-trifluoroethyl)piperidine as a semisolid.

Preparation of 3-(2-Chlorophenyl)-7-[1-(2,2,2-trifluoroethyl)piperidin-4-yl-amino]-3,4-dihydropyrimido[4,5-d]pyrimidin-2(1H)-one.

Sulfone 9.1 (0.389 g, 1 mmol) was combined with 4-aminomethyl-1-(2,2,2-trifluoroethyl)piperidine (0.50 g, 2.5 mmol) in 0.4 mL of l-methyl-2-pyrrolidinone, and was heated at 100° C. for 4 hours. The mixture was then cooled to room temperature, and treated with methanol, ethyl acetate, and ether. The solids formed were filtered and washed with ethyl acetate. The resulting solids (0.22 g) were dissolved in 5 mL methanol, and hydrogen chloride was bubbled through the solution for one minute. The solvents were removed, and the residue was titurated with 2 mL of methanol and 40 mL of ether to give 210 mg of the dihydrochloride salt of 3-(2-chlorophenyl)-7-[1-(2,2,2-trifluoroethyl)piperidin-4-ylamino]-3,4-dihydropyrimido[4,5-d]pyrimidin-2(1H)-one.

Example 56

Compound 2-22

This example illustrates the preparation of 3-(2-chlorophenyl)-7-[(1-cyanomethylpiperidin-4-ylmethyl)amino]-3,4-dihydropyrimido[4,5-d]pyrimidin-2(1H)-one.

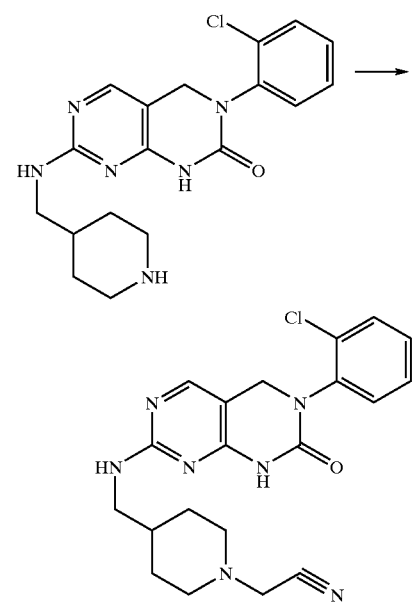

Sulfone 9.1 (2.24 g, 5.4 mmol) was combined with N-tert-butoxycarbonyl-4-aminomethylpiperidine (5.6 g, 16.2 mmol) and 1-methyl-2-pyrrolidinone (9 mL). The mixture was heated to 100–110° C. for 2 hours at which time it was cooled to room temperature and ethyl acetate was added. The resultant white solid was filtered and washed with ethyl acetate to give 2.3 g of 3-(2-chlorophenyl)-7-[(1-tert-butoxycarbony-piperidin-4-ylmethyl)amino]-3,4-dihydropyrimido[4,5-d]pyrimidin-2(1H)-one (MH$^+$=473). Hydrogen chloride gas was bubbled into 2.1 g of the protected amine which was suspended in 1,4-dioxane (22 mL), and the suspension stirred for 1 hour, concentrated in vacuo and dried to give the intermediate 3-(2-chlorophenyl)-7-[(piperidin-4-ylmethyl)amino]-3,4-dihydropyrimido[4,5-d]pyrimidin-2(1H)-one as a white solid.

3-(2—Chlorophenyl)-7-[(piperidin-4-ylmethyl)amino]-3,4-dihydropyrimido[4,5-d]pyrimidin-2(1H)-one (0.23 g, 0.52 mmol) was dissolved in N,N-dimethylformamide (8 mL). Anhydrous sodium carbonate (0.175 g, 1.6 mmol) and chloroacetonitrile (0.036 mL, 0.57 mmol) were added. The mixture was stirred for 17 hours at room temperature, and was partitioned into ethyl acetate and water. The layers were separated and the aqueous layer was extracted with ethyl acetate. The organic layer was washed with water, dried, and concentrated in vacuo, and the residue was purified by chromatography on silica gel using 10% methanol/dichloromethane as eluant. The fractions containing product were concentrated in vacuo and dissolved in 40 mL of 1,4-dioxane. Hydrogen chloride gas was bubbled in and the mixture was concentrated in vacuo. The resultant residue was triturated in ether, filtered and dried to give 0.107 g of the hydrochloride salt of 3-(2-chlorophenyl)-7-[(1-cyanomethylpiperidin-4-ylmethyl)amino]-3,4-dihydropyrimido[4,5-d]pyrimidin-2(1H)-one.

Example 57

Compound 2-19

This example illustrates the preparation of 3-(2-chlorophenyl)-7-[(1-dimethylaminocarbonylmethylpiperidin-4-ylmethyl)amino]-3,4-dihydropyrimido[4,5-d]pyrimidin-2(1H)-one.

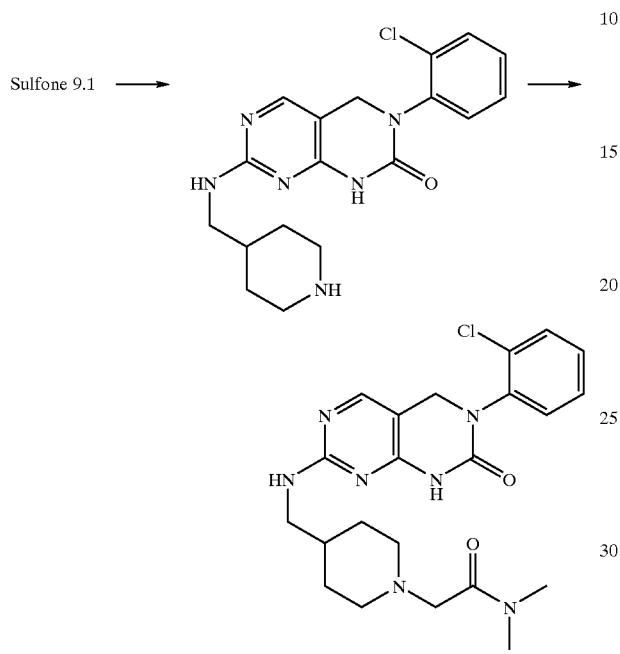

3-(2—Chlorophenyl)-7-[(piperidin-4-ylmethyl)amino]-3,4-dihydropyrimido[4,5-d]pyrimidin-2(1H)-one (prepared as described in Example 56) (0.3 g, 0.67 mmol) was dissolved in N,N-dimethylformamide (7 mL). Anhydrous sodium carbonate (0.26 g, 2.4 mmol) and 2-chloro-N,N-dimethylacetamide (0.098 g, 0.81 mmol) were added. The mixture was stirred for 17 hours at room temperature. The reaction mixture was partitioned into ethyl acetate and water. The layers were separated and the aqueous layer was extracted with ethyl acetate, and 10% isopropanol/chloroform. The organic layers were washed with saturated sodium chloride solution and then dried over anhydrous sodium sulfate. After evaporation in vacuo, the white solid was dissolved in 50% methanol/1,2-dichloroethane. Hydrogen chloride gas was bubbled in, and the solution was evaporated in vacuo. The resulting residue was triturated in ether, filtered and dried to give 0.182 g of the hydrochloride salt of 3-(2-chlorophenyl)-7-[(1-dimethylaminocarbonylmethylpiperidin-4-ylmethyl)amino]-3,4-dihydropyrimido[4,5-d]pyrimidin-2(1H)-one.

Example 58

Compound 2-23

This example illustrates the preparation of 3-(2-chlorophenyl)-7-[(1-aminocarbonylmethylpiperidin-4-ylmethyl)amino]-3,4-dihydropyrimido[4,5-d]pyrimidin-2(1H)-one.

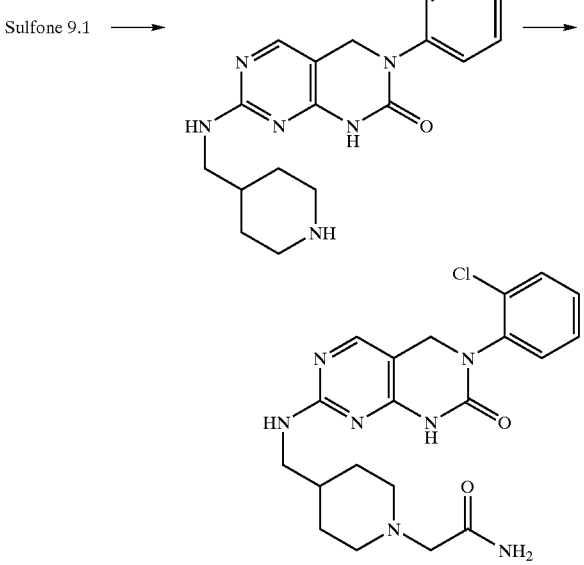

3-(2—Chlorophenyl)-7-[(piperidin-4-ylmethyl)amino]-3,4-dihydropyrimido[4,5-d]pyrimidin-2(1H)-one (prepared as described in Example 56) (0.3 g, 0.67 mmol) was dissolved in N,N-dimethylformamide (7 mL). Anhydrous sodium carbonate (0.26 g, 2.4 mmol) and 2-bromoacetamide (0.111 g, 0.81 mmol) were added. The mixture was stirred for 17 hours at room temperature. The reaction mixture was partitioned into ethyl acetate and water. The layers were separated and the aqueous layer was extracted with ethyl acetate and 10% isopropanol/chloroform. The combined organic layers were washed with saturated sodium chloride solution and then dried over anhydrous sodium sulfate. After evaporation in vacuo, the white solid was suspended in 1,4-dioxane. Hydrogen chloride gas was bubbled in, and the solution was evaporated in vacuo. The resulting residue was triturated in ether, filtered and dried to give 0.185 g of the hydrochloride salt of 3-(2-chlorophenyl)-7-[(1-aminocarbonylmethylpiperidin-4-ylmethyl)amino]-3,4-dihydropyrimido[4,5-d]pyrimidin-2(1H)-one.

Example 59

Compound 2-24

This example illustrates the preparation of 3-(2-chlorophenyl)-7-[(1-hydroxycarbonylmethylpiperidin-4-ylmethyl)amino]-3,4-dihydropyrimido[4,5-d]pyrimidin-2(1H)-one.

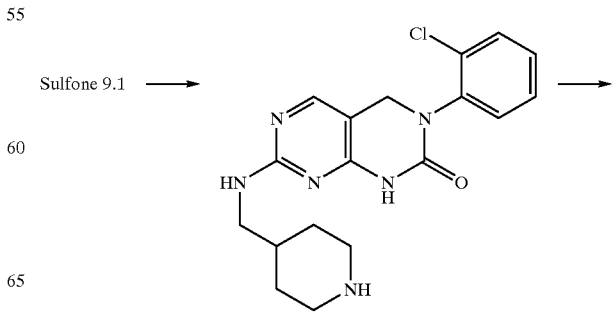

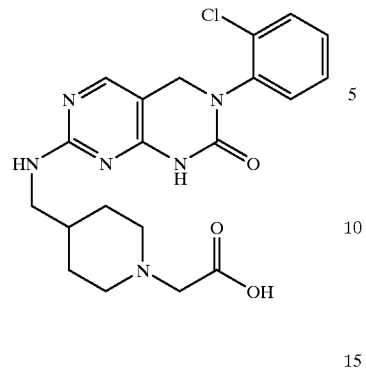

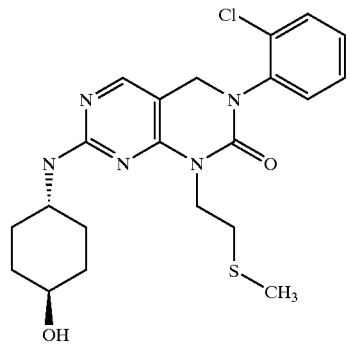

3-(2—Chlorophenyl)-7-[(piperidin-4-ylmethyl)amino]-3,4-dihydropyrimido[4,5-d]pyrimidin-2(1H)-one (prepared as described in Example 56) (0.3 g, 0.67 mol) was dissolved in N,N-dimethylformamide (7 mL). Anhydrous sodium carbonate (0.26 g, 2.4 mmol) and tert-butyl 2-bromoacetate (0.12 mL, 0.81 mmol) were added. The mixture was stirred for 17 hours at room temperature. The reaction mixture was partitioned into ethyl acetate and water. The layers were separated and the aqueous layer was extracted with ethyl acetate and 10% isopropanol/chloroform. The combined organic layers were washed with saturated sodium chloride solution and then dried over anhydrous sodium sulfate. After evaporation in vacuo, the combined white solids were suspended in 1,4-dioxane. Hydrogen chloride gas was bubbled in, and the solution was stirred for 10 hours at room temperature and evaporated in vacuo. The resulting residue was triturated in ether, filtered and dried to give 0.195 g of the hydrochloride salt of 3-(2-chlorophenyl)-7-[(1-hydroxycarbonylmethylpiperidin-4-ylmethyl)amino]-3,4-dihydropyrimido[4,5-d]pyrimidin-2(1H)-one.

Sulfone 9.1 (500 mg, 1.21 mmol) was taken up in 2 mL tetrahydrofuran with 1-(2-methylthio)ethanol (0.16 mL, 1.81 mmol), triphenylphosphine (474 mg, 1.81 mmol), and DEAD (0.28 mL, 1.81 mmol), and stirred at room temperature for 2 days. The crude product, 3-(2-chlorophenyl)-7-benzylsulfonyl-1-(2-methylthioethyl)-3,4-dihydropyrimido[4,5-d]pyrimidin-2(1H)-one, was evaporated in vacuo and used without further purification.

The crude 3-(2-chlorophenyl)-7-benzylsulfonyl-1-(2-methylthioethyl)-3,4-dihydropyrimido[4,5-d]pyrimidin-2(1H)-one was taken up in 2 mL diglyme with trans-4-aminocyclohexanol (139 mg, 1.21 mmol) and stirred at 120° C. for 4 hours. The mixture was purified by chromatography on silica gel using 2.5–4.5% methanol/dichloromethane as eluant to provide the title compound (226 mg, 0.511 mmol). The purified product was taken up in ethyl acetate and treated with 1 equivalent HCl/Et$_2$O to precipitate the hydrochloride salt of 3-(2-chlorophenyl)-7-(trans-4-hydroxycyclohexylamino)-1-(2-methylthioethyl)-3,4-dihydropyrimido[4,5-d]-pyrimidin-2(1H)-one.

Example 60

Compound 3-29

This example illustrates the preparation of 3-(2-chlorophenyl)-7-(trans-4-hydroxycyclohexylamino)-1-(2-methylthioethyl)-3,4-dihydropyrimido[4,5-d]pyrimidin-2(1H)-one.

Example 61

Compound 3-31

This example illustrates the preparation of 3-(2-chlorophenyl)-7-(trans-4-hydroxycyclohexylamino)-1-(3-dimethylamino-2,2-dimethylpropyl)-3,4-dihydropyrimido[4,5-d]pyrimidin-2(1H)-one.

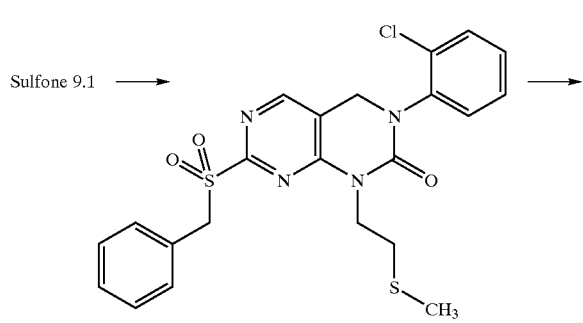

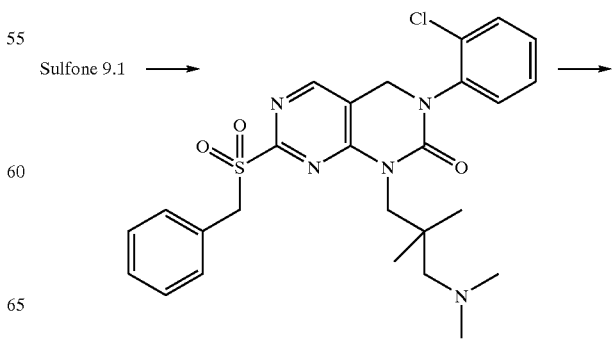

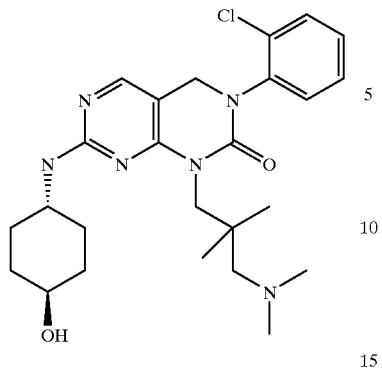
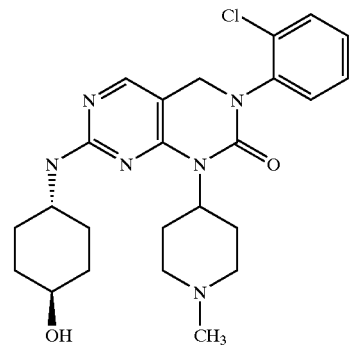

Sulfone 9.1 (500 mg, 1.21 mmol) was taken up in 2 mL tetrahydrofuran with 3-dimethylamino-2,2-dimethyl-1-propanol (0.28 mL, 1.81 mmol), triphenylphosphine (474 mg, 1.81 mmol), and DEAD (0.28 mL, 1.81 mmol), and stirred at room temperature overnight. The mixture was semipurified by chromatography on silica gel with 3–15% methanol/dichloromethane as eluant, to provide >1 g mixture of 3-(2-chlorophenyl)-7-benzylsulfonyl-1-(3-dimethylamino-2,2-dimethylpropyl)-3,4-dihydropyrimido[4,5-d]pyrimidin-2(1H)-one and residual triphenylphosphine oxide.

3-(2—Chlorophenyl)-7-benzylsulfonyl-1-(3-dimethylamino-2,2-dimethylpropyl)-3,4-dihydropyrimido[4,5-d]pyrimidin-2(1H)-one was taken up in 3 mL diglyme with trans-4-aminocyclohexanol (139 mg, 1.21 mmol) and stirred at 120° C. for 4 hours. The mixture was purified by chromatography on silica gel using 4–25% methanol/dichloromethane as eluant to provide the title compound (52 mg, 0.107 mmol). The purified product was taken up in ethyl acetate and treated with 1 equivalent HCl/Et$_2$O to precipitate the hydrochloride salt of 3-(2-chlorophenyl)-7-(trans-4-hydroxycyclohexyl-amino)-1-(3-dimethylamino-2,2-dimethylpropyl)-3,4-dihydropyrimido[4,5-d]pyrimidin-2(1H)-one.

Example 62

Compound 3-36

This example illustrates the preparation of 3-(2-chlorophenyl)-7-(trans-4-hydroxycyclohexylamino)-1-(1-methylpiperidin4-yl)-3,4-dihydropyrimido[4,5-d]pyrimidin-2(1H)-one.

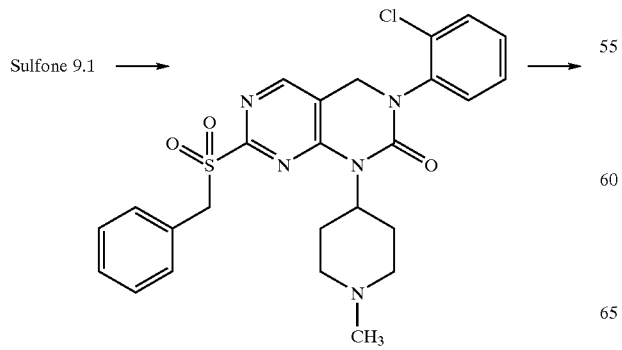

A mixture of sulfone 9.1 (1.0 g, 2.4 mmol), diphenyl-2-pyridylphosphine (1.9 g, 7.23 mmol) and 4-hydroxy-1-methylpiperidine (0.555 g, 4.8 mmol) was dissolved in anhydrous tetrahydrofuran under an atmosphere of nitrogen. To this solution was added di-tert-butylazodicarboxylate (1.67 g, 7.23 mmol) and the resulting mixture was stirred at room temperature for 2 hours, then concentrated in vacuo. The residue was purified by column chromatography on silica gel using 9:1 dichloromethane/methanol as eluant. The column fractions containing product were combined and concentrated in vacuo to give 354 mg of 7-benzylsulfonyl-3-(2-chlorophenyl)-1-(1-methylpiperidin-4-yl)-3,4-dihydropyrimido[4,5-d]pyrimidin-2(1H)-one.

7-Benzylsulfonyl-3-(2-chlorophenyl)-1-(1-methylpiperidin-4-yl)-3,4-dihydropyrimido[4,5-d]pyrimidin-2(1H)-one (354 mg, 0.69 mmol) was combined with trans-4-aminocyclohexanol (160 mg, 1.38 mmol) and 1 mL 1-methyl-2-pyrrolidinone. The mixture was heated to 1 10° C. for 1 hour at which time it was cooled to room temperature. The residue was purified by column chromatography on silica gel using 9:1:0.5 dichloromethane/methanol/diisopropylamine as eluant. The column fractions containing product were combined, concentrated in vacuo and suspended in ethyl acetate. Addition of hydrochloric acid (1.0M/Et$_2$O, 1.0 equivalents) gave the salt which was filtered and dried to give 135 mg of the hydrochloride salt of 3-(2-chlorophenyl)-7-(trans-4-hydroxycyclohexylamino)-1-(1-methylpiperidin-4-yl)-3,4-dihydropyrimido[4,5-d]-pyrimidin-2(1H)-one.

Example 63

Compound 4-4

This example illustrates the preparation of (R,R)-7-(2,3-dihydroxy-1-methylpropylamino)-3-ortho-tolyl-3,4-dihydropyrimido[4,5-d]pyrimidin-2(1H)-one.

Preparation of (R,R)-3-aminobutane-1,2-diol.

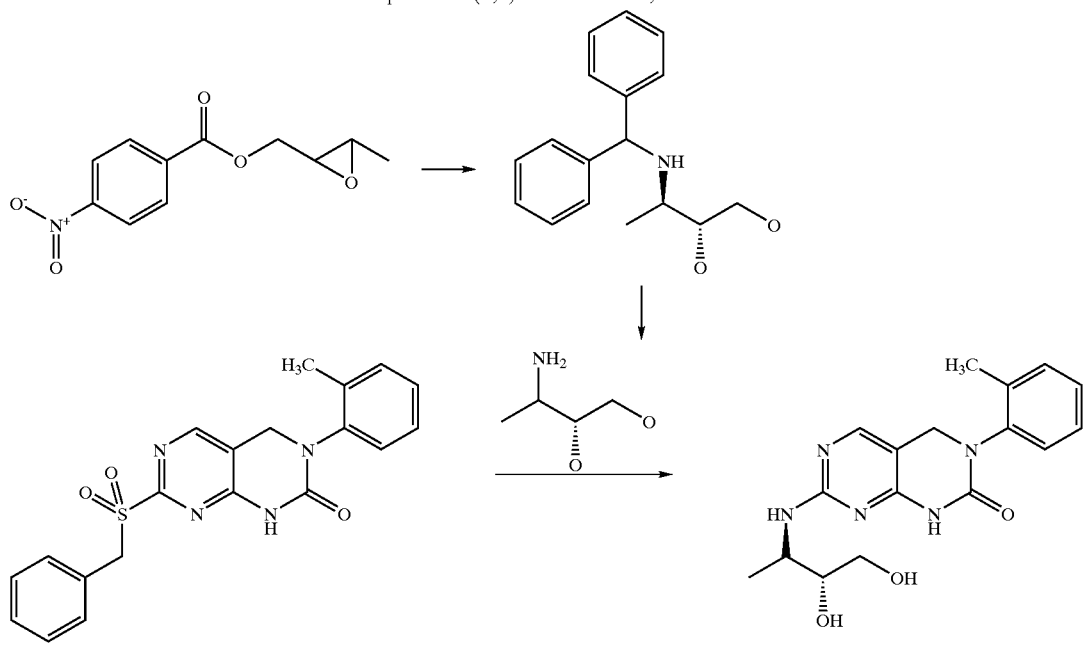

3-Aminobutane-1,2-diol was similarly prepared as described in *Tetrahedron: Asymmetry*, 1995, 6(9), 2329–2342. Briefly, to a solution of (2S,3S)-trans-3-methyloxirane-2-methyl-4-nitrobenzoate (10.0 g, 42.2 mmol) (Fluka) in dichloromethane (150 mL) under argon, was combined with titanium isopropoxide (25 mL, 84.3 mmol), and stirred for minutes at room temperature. Aminodiphenyl-methane (14.5 mL, 84.4 mmol) was added, and the reaction was stirred at room temperature overnight. A solution of 10% sodium hydroxide in saturated brine was added and the suspension was stirred for 2 hours. The mixture was filtered and extracted with 0.2M hydrochloric acid. The acidic layers were extracted with dichloromethane and discarded. The acidic layer was basified with sodium hydroxide pellets until pH 9, and then extracted into dichloromethane. The layers were separated, and the organic layer was dried over magnesium sulfate, and concentrated in vacuo to give an oil that was purified by flash column chromatography using 2:1 to 1:1 hexanes:ethyl acetate and 2:1 ethyl acetate:hexane as eluants to give 2.6 g of (R,R)-3-(benzhydrylamino)butane-1,2-diol.

To a degassed solution of (R,R)-3-(benzhydrylamino) butane-1,2-diol (2.6 g, 9.59 mmol) in methanol (20 mL) was added palladium hydroxide on carbon (260 mg). The reaction was evacuated and charged three times with hydrogen and then charged with hydrogen at 50 psi and shaken on the hydrogenator overnight at room temperature. The reaction mixture was filtered and concentrated to give 922 mg of (R,R)-3-aminobutane-1,2-diol as an oil, which was washed with hexane and then dried in vacuo. Preparation of (R,R)-7-(2,3-dihydroxy-1-methylpropylamino)-3-ortho-tolyl-3,4-dihydropyrimido[4,5-d]pyrimidin-2(1H)-one.

Sulfone 9.2 (622 mg, 1.58 mmol) was combined with (RR)-3-amino-butane-1,2-diol (250 mg, 1.9 mmol) in 1,2-dimethoxyethane (1 mL) was heated at 100° C. for 2 hours under argon. The reaction was cooled to room temperature and diluted with 9:1 dichloromethane/methanol and placed directly on a flash silica column using 96:4 dichloromethane/methanol and 9:1 dichloromethane/methanol as eluant to give 120 mg of a colorless oil, which was dissolved in ethyl acetate (10 mL) and treated with 1 equivalent of hydrochloric acid (1.0M in ether). The precipitate was collected by vacuum filtration, washed with ethyl acetate and dried in vacuo to give 118 mg of (R,R)-7-(2,3-dihydroxy-1-methylpropylamino)-3-ortho-tolyl-3,4-dihydropyrimido[4,5-d]pyrimidin-2(1H)-one as a white solid.

Example 64

3-(2-Chlorophenyl)-7-methylthio-3,4-dihydropyrimido[4,5-d]pyrimidin-2(1H)-one

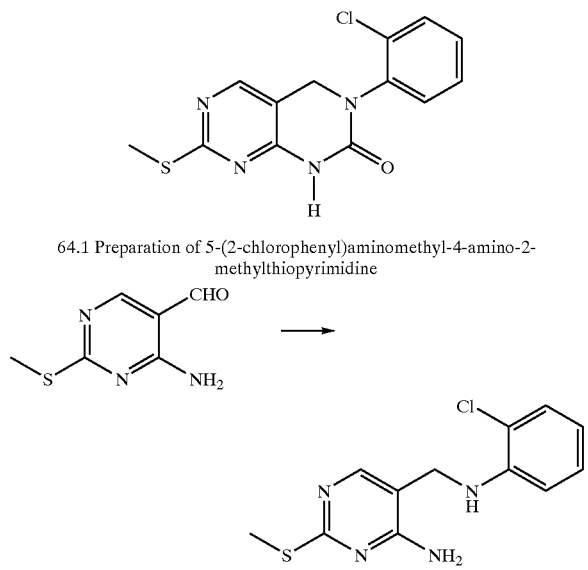

64.1 Preparation of 5-(2-chlorophenyl)aminomethyl-4-amino-2-methylthiopyrimidine A mixture of 4-amino-2-methylthiopyrimidine-5-carboxaldehyde (9.5 g, 56.1 mmol), 2-chloroaniline (6.7 mL, 63.7 mmol) and 4-toluene-sulfonic acid monohydrate (0.85 g, 4.5 mmol) in 350 mL of xylene was heated under reflux with azeotropic removal of water for 6 hours. The mixture was cooled to 25° C. and the precipitate was collected by vacuum filtration and was washed with hexanes and air dried. This solid was then dissolved in 300 mL tetrahydrofuran. and the reaction cooled to 0° C. Lithium aluminium hydride (2.3 g, 60.6 mmol) was added in small portions over 45 minutes. Once the addition was complete, the mixture was stirred for a further 15 minutes and carefully treated sequentially with 4.5 mL water, 4.5 mL of 15% aqueous sodium hydroxide and then 20 mL of water. The mixture was stirred for 30 minutes, filtered through celite, and the filtrate concentrated in vacuo. The solid was purified with column chromatography on silica gel using 25% acetone/hexane. The fractions containing product were concentrated under reduced pressure to a solid which was recrystallized from ethyl to give 7.0 g of 5-(2-chlorophenyl) aminomethyl-4-amino-2-methylthiopyrimidine as a white solid.

64.2 Preparation of 3-(2-chlorophenyl)-7-methylthio-3,4-dihydropyrimido-[4,5-d]pyrimidin-2(1H)-one

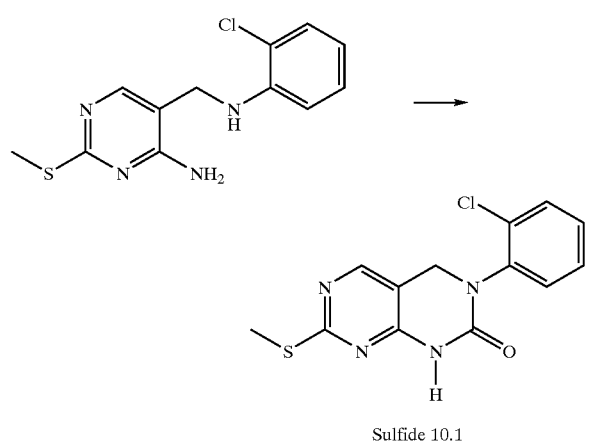

Sulfide 10.1

To a stirred solution, cooled to 0° C., of 5-(2-chlorophenyl) aminomethyl-4-amino-2-methylthiopyrimidine (7.0 g, 24.9 mmol) in 200 mL of tetrahydrofuran was added triethylamine (10 mL, 71.7 mmol). This solution was then treated dropwise with a solution of phosgene (14.2 mL of 20% solution in toluene, 27.2 mmol). After stirring for 2 hours, an additional 5.0 mL of triethylamine (35.9 mmol) was added followed by phosgene (6.5 mL of 20% solution in toluene; 12.5 mmol). After stirring for an additional 2 hours, additional triethylamine (21n, 14.3 mmol) was added followed by phosgene (3 mL of 20% solution in toluene; 5.8 mmol). The reaction was stirred for one additional hour then warmed to room temperature, poured onto a heterogeneous solution of 75 mL water and 150 mL ethyl acetate. The mixture was then filtered and the phases separated. The aqueous phase was re-extracted twice with 150 mL ethyl acetate. The combined ethyl acetate extracts were concentrated under reduced pressure. The residue was stirred with ethyl acetate. The product was then collected by vacuum filtration and dried in vacuo to give 3.2 g of 3-(2-chlorophenyl)-7-methylthio-3,4-dihydropyrimido[4,5-d]pyrimidin-2(1H)-one (sulfide 10.1)as a white solid.

Example 65

An Alternative Preparation of 3-(2-Chlorophenyl)-7-methylthio-3,4-dihydropyrimido-[4,5-d]pyrimidin-2(1H)-one 65.1 Preparation of ethyl 4-amino-2-methylthiopyrimidne-5-carboxylate

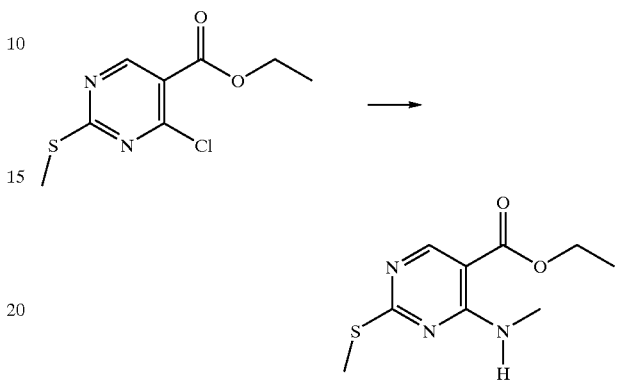

A solution of ethyl 4-chloro-2-methylthiopyrimidine-5-carboxylate (1450 g, 6.23 mole) (Aldrich Chemical Co., Milwaukee, Wis., USA) in 2987 mL of tetrahydrofuran was cooled to 5–10° C. and treated slowly with a mixture of 2407 mL of a 37% solution of ammonium hydroxide in 2978 mL triethylamine. After stirring for 16 hours, the reaction mixture was concentrated in vacuo to approximately 5L and filtered. The filter cake was washed with hexanes and dried in a vacuum oven at 60–65° C. The filtrate was evaporated under reduced pressure to give 1314 g (94%) of ethyl 4-amino-2-methylthiopyrimidine-5-carboxylate as a white solid. m.p. 130.1–130.7° C.

65.2 Preparation of ethyl 4-{[(2-chlorophenyl)amino]carbonylamino}-2 methylthiopyrimidine-5-carboxylate

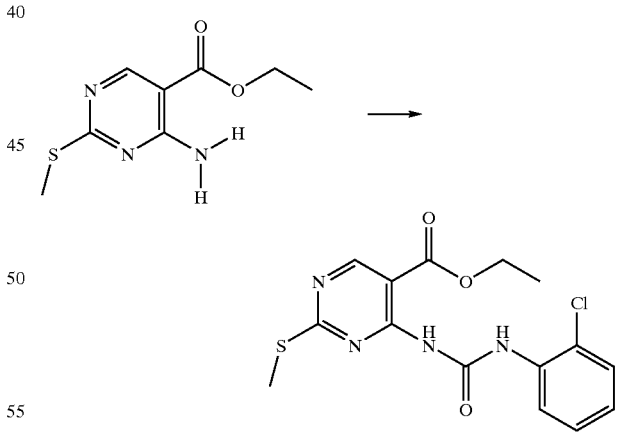

To a suspension of ethyl 4-amino-2-methylthiopyrimidine-5-carboxylate (1215 g, 5.7 moles) in 2600 mL xylenes heated at 100–105° C. was added (956.5 g, 6.23 moles 2-chlorophenylisocyanate so as to maintain the temperature at 100° C. The temperature of the reaction mixture was raised to 120° C. and stirred for 14 hours. Heating was stopped and slow cooling to 110° C. was begun. When crystallization began, slow addition of 5256 mL ethyl acetate completed the crystallization. The mixture was cooled to 20° C. and filtered. The cake was washed with ethyl acetate and was placed in a vacuum oven and dried for 10–12 hours at 60° to 80° C. to give 1895 g (90.7%) of ethyl 4-{[(2-chlorophenyl)amino]carbonylamino}-2-methylthiopyrimidine-5-carboxylate, m.p.172.3–172.6° C.

65.3 Preparation of [(2-chlorophenyl)amino]-N-[5-(hydroxymethyl)-2-methylthio-pyrimidine-4yl]carbonxamide

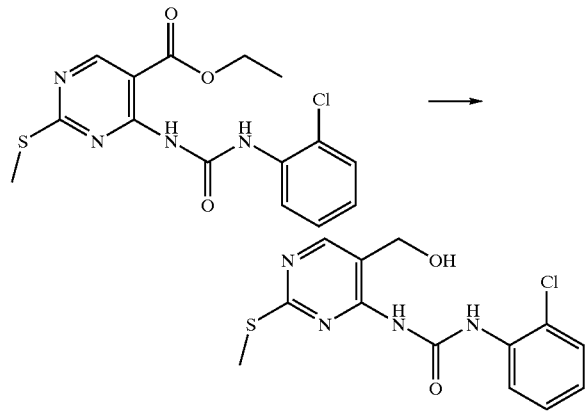

To a stirred suspension of ethyl 4-{[(2-chlorophenyl)amino]carbonylamino}-2-methylthiopyrimidine-5-carboxylate (1,000 g, 2.73 mole) in 4.7 L anhydrous tetrahydrofuran, at −25° C. under nitrogen, was added a 1.0 M solution of lithium aluminium hydride in tetrahydrofuran (2,730 mL, 3.19 mole) over a 3 hour period. The resulting yellow homogeneous solution was held at −25° C. for an additional 45 minutes, then allowed to warm to 0° C. over the next 90 minutes. HPLC analysis showed absence of starting ester. The solution was then quenched into a stirred 1.0 M Rochelle's salt solution (8.0 L) and extracted with ethyl acetate. The pooled extracts, containing suspended insoluble yellow product, were concentrated and filtered. The yellow solid was washed with hexanes then dried in vacuo at 60° C. to give 69.3% (617 g) of [(2-chlorophenyl)amino]-N-[5-(hydroxymethyl)-2-methylthiopyrimidin-4-yl]-carboxamide as yellow crystals; m.p. 182.5° C. to 182.9° C. This run was repeated on 1,168 g substrate to give 717.8 g of the title compound.

65.4 Preparation of [(2-chlorophenyl)amino]-N-[5-(bromoxymethyl)-2-methylthio-pyrimidine-4yl]carbonxamide

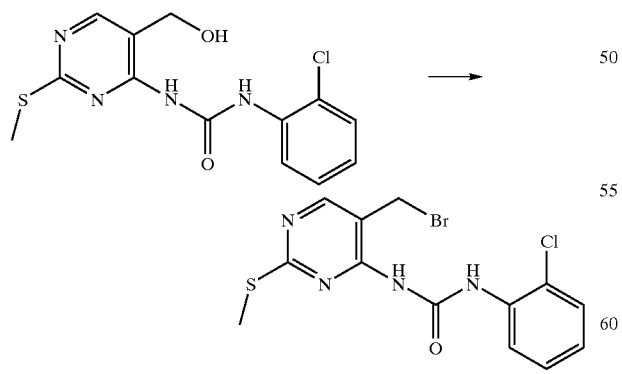

[(2—Chlorophenyl)amino]-N-[5-(hydroxymethyl)-2-methylthiopyrimidin-4-yl]carboxamide (1363 g) was mixed with 8L of tetrahydrofuran and mechanical stirring begun under nitrogen. Then phosphorus tribromide (135 mL) in 800 mL tetrahydrofuran were added to the mixture over 15 minutes. Stirring was continued for 4 hours, at which time the reaction was stopped and filtered. The filter cake was washed once with tetrahydrofuran and dried overnight at 55° C. in vacuum oven to give 1360 g (71%) of [(2-chlorophenyl)amino]-N-[5-(bromomethyl)-2-methylthio-pyrimidin-4-yl]carboxamide (M+1 377).

65.5 Preparation of 3-(2-chlorophenyl)-7-methylthio-3, 4-dihydropyrimido[4,5-d]-pyrimidin-2(1H)-one

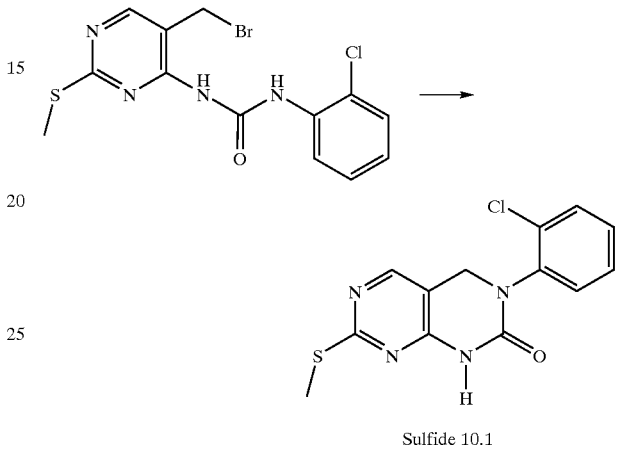

Sulfide 10.1

To a suspension of [(2-chlorophenyl)amino]-N-[5-(bromomethyl)-2-methylthiopyrimidin-4-yl]carboxamide (1360 g, 3.62 mole) of in 10 L 1-methyl-2-pyrrolidinone was added 136 mL hexamethyldisilazane. The mixture was heated to an internal temperature of 105–115° C. for 1.5 hours. The mixture was then cooled to 30° C. and treated with 20L water. The mixture was then stirred at 5–8° C. for 2 hours and filtered. The filters were collected and washed sequentially with water and hexanes. The product was placed in a drying oven and heated under vacuum for 16 hours to give 780 g (70.1%) of 3-(2-chlorophenyl)-7-methylthio-3,4-dihydropyrimido[4,5-d] pyrimidin-2(1H)-one (sulfide 10.1) as an off-white solid. (M+1 308)

A related compound, 7-methylthio-3-ortho-tolyl-3,4-dihydropyrimido[4,5-d]pyrimidin-2(1H)-one (sulfide 10.2) (M+1=287) was prepared using ortho-tolyl isocyanate in place of 2-chlorophenyl isocyanate in step 65.2 above.

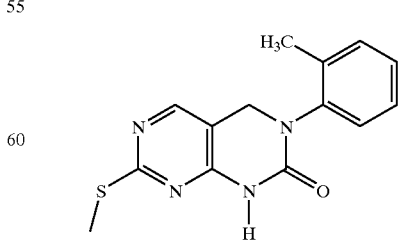

Sulfide 10.2

Example 66

3-(2-Chlorophenyl)-7-methylsulfonyl-3,4-dihydropyrimido[4,5-d]pyrimidin-2(1H)-one

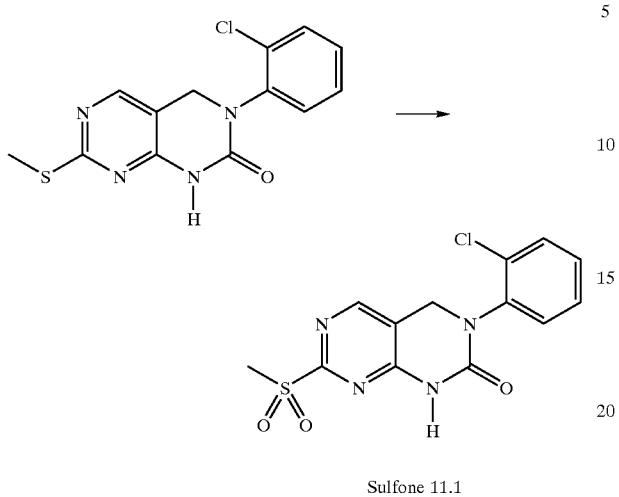

Sulfone 11.1

A suspension of 3-(2-chlorophenyl)-7-methylthio-3,4-dihydropyrimido[4,5-d]pyrimidin-2(1H)-one (4.1 g, 12.8 mmol) in 50 mL of chloroform was cooled in ice and treated with 70% 3-chloroperbenzoic acid (9.8 g, 39.8 mmol). The mixture was stirred at room temperature for 2 hours, then treated twice with 100 mL of 10% aqueous sodium thiosulfate and left to stir for 30 minutes. The reaction was diluted with 400 mL dichloromethane and the phases were separated. The organic phase was washed with a saturated aqueous solution of sodium bicarbonate and then dried over magnesium sulfate and filtered. Concentration of the filtrate under reduced pressure gave a solid which was stirred with ethyl acetate, then filtered to give 2.6 g of 3-(2-chlorophenyl)-7-methylsulfonyl-3,4-dihydropyrimido[4,5-d]pyrimidin-2(1H)-one (sulfone 11.1) as a white solid. (MH$^+$= 364)

Example 67

Compound 4-19

This example illustrates the preparation of 3-(2-chlorophenyl)-7-(4-hydroxymethylcyclohexylamino)-3,4-dihydropyrimido[4,5-d]pyrimidin-2(1H)-one.

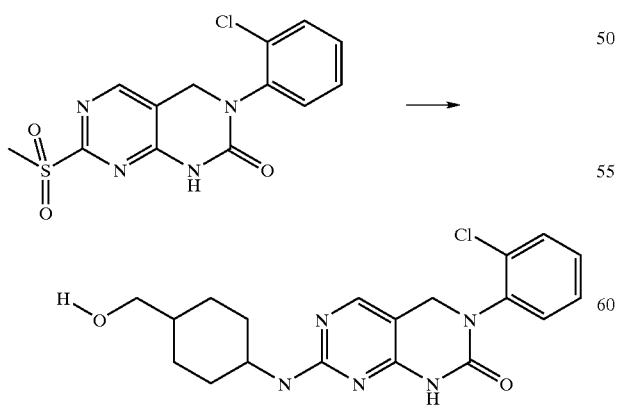

Sulfone 11.1 (350 mg, 104 mmol) was combined with 4-aminocyclohexylmethanol 1:1 cis/trans) (400 mg, 3.3 mmol) (prepared as described in *Chem.Ber.*; GE; 96; 1963; 2377–2386) with 0.3 mL of 1-methyl-2-pyrrolidinone. The mixture was heated at 1000 for 2 hours at which time it was cooled to room temperature. The reaction mixture was added to water and extracted with ethyl acetate, washed with water, dried, and concentrated in vacuo. The residue was purified by column chromatography on silica gel using 10:90 methanol/dichloromethane as eluant The column fractions containing the product were concentrated to a foam which was resuspended in methanol. Addition of hydrochloric acid (1.0M/Et$_2$O, 1.0 equivalent) gave a salt which was filtered to give the hydrochloride salt of 3-(2-chlorophenyl)-7-(4-hydroxymethylcyclohexylamino)-3,4-dihydropyrimido[4,5-d]pyrimidin-2(1H)-one.

Example 68

Compound 2-28

This example illustrates the preparation of 3-(2-chlorophenyl)-7-(1-ethoxycarbonylpiperidin-4-ylamino)-3,4-dihydropyrimido[4,5-d]pyrimidin-2(1H)-one.

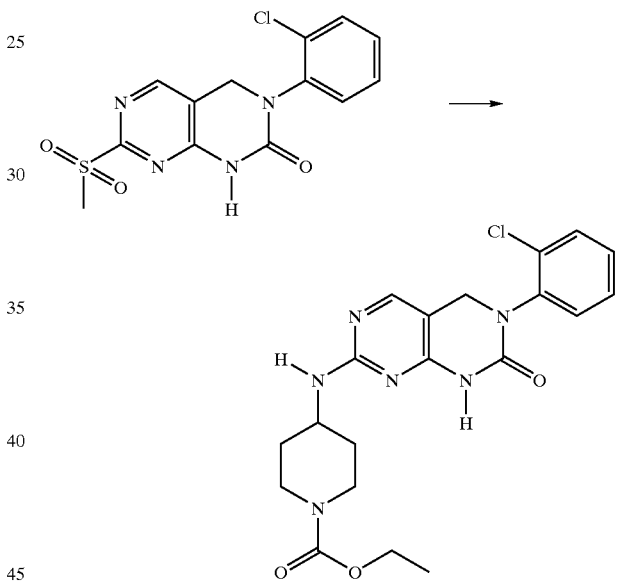

Sulfone 11.1 (1.3 g, 3.75 mmol) was taken up in ethyl 4-amino-1-piperidinecarboxylate (3.7 mL, 21 mmol) and heated to 120° C., at which temperature the initial suspension fully dissolved, then reprecipitated into suspension 10 minutes later. This secondary suspension was heated at 150° C. for 1 hour, then cooled to room temperature and poured into water to form a gummy mass. When stirred with 50 mL ether, the gum produced a small quantity of white solid, which was set aside. The remaining gum was treated with 10–15 mL methanol to form a white solid. The combined white solids totalled 0.685 g (1.59 mmol), of which 30 mg were submitted as the free base.

Example 69

Compound 4-25

This example illustrates the preparation of 7-(trans-4-aminocyclohexylamino)-3-(2-chlorophenyl)-3,4-dihydropyrimido[4,5-d]pyrimidin-2(1H)-one.

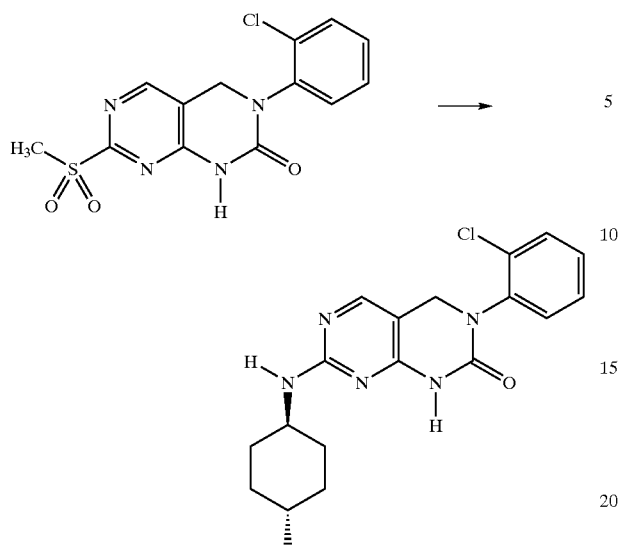

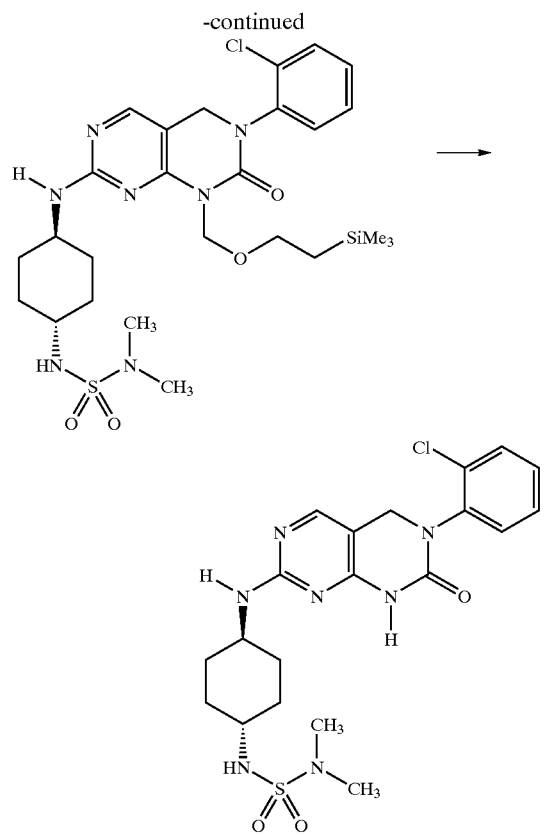

Sulfone 11.1 (196 mg, 0.579 mmol) and 0.36 g (3.2 mmol) of trans-1,4-diaminocyclohexane were dissolved in 5 mL of 1-methyl-2-pyrrolidinone. The reaction mixture was stirred at 80° C. for 3 hours, cooled, then 30 mL of ethyl acetate and 30 mL of water were added. The organic layer was separated and the aqueous layer was re-extracted with 30 mL of dichloromethane. The combined organic layers were concentrated in vacuo and the crude liquid formed a white precipitate upon standing. The solids were filtered and washed with ethyl acetate to give 28 mg (13%) of the title compound as a white powder, m.p. >30° C. The product was taken up in ethyl acetate and treated with HCl/Et$_2$O to form the hydrochloride salt of 7-(trans-4-aminocyclohexylamino)-3-(2-chlorophenyl)-3,4-dihydropyrimido[4,5-d]pyrimidin-2(1H)-one as a white powder.

Example 70

Compound 4-26

This example illustrates the preparation of 3-(2-chlorophenyl)-7-[trans-4-(N,N-dimethylsulfamoylamido) cyclohexylamino]-3,4-dihydropyrimido[4,5-d]pyrimidin-2(1H)-one.

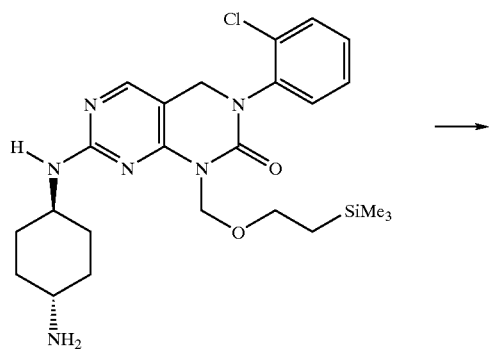

To a solution of 7-(trans-4-aminocyclohexylamino)-3-(2-chlorophenyl)-1-[2-(trimethylsilyl)ethoxymethyl]-3,4-dihydropyrimido[4,5-d]pyrimidin-2(1H)-one (318 mg, 0.632 mmol) (prepared as described in Example 87) in 20 mL of dichloromethane were added triethylamine (0.10 mL, 0.72 mmol) and a solution of dimethylsufamoyl chloride (0.12 g, 0.84 mmol) in 5 mL of dichloromethane. The reaction mixture was refluxed for 18 hours, cooled, then concentrated in vacuo. Purification by chromatography using 5% methanol/dichloromethane as eluant gave 271 mg (70%) of 3-(2-chlorophenyl)-7-[trans-4-(N,N-dimethylsulfamoylamido)cyclohexylamino]-1-[2-(trimethylsilyl) ethoxymethyl]-3,4-dihydropyrimido[4,5-d]pyrimidin-2 (1H)-one as a white foam. (MH+=610, m.p. 106.5–110.0° C.)

The 3-(2-chlorophenyl)-7-[trans-4-(N,N-dimethylsulfamoylamido)cyclohexylamino]-1-[2-(trimethylsilyl) ethoxymethyl]-3,4-dihydropyrimido[4,5-d]pyrimidin-2 (1H)-one (250 mg, 0.410 mmol) was dissolved in 10 mL of methanol and treated with 10 mL of 10% aqueous hydrochloric acid. The reaction mixture was stirred at 50° C. and monitored by TLC (5% methanol/dichloromethane). The reaction temperature was raised to 85° C. for 3 hours, and the reaction mixture was concentrated in vacuo. The resulting suspension was filtered to give a white solid, which was washed with ethyl acetate to give 125 mg (59%) of the hydrochloride salt of 3-(2-chlorophenyl)-7-[trans- 4-(NN-dimethylsulfamoylamido)cyclohexylamino]-3,4-dihydropyrimido[4,5-d]pyrimidin-2(1H)-one as a white powder.

Example 71

Compound 4-24

This example illustrates the preparation of 3-(2-chlorophenyl)-7-(1,4-dioxaspiro[4.5]dec-8-ylamino)-3,4- dihydropyrimido[4,5-d]pyrimidin-2(1H)-one.

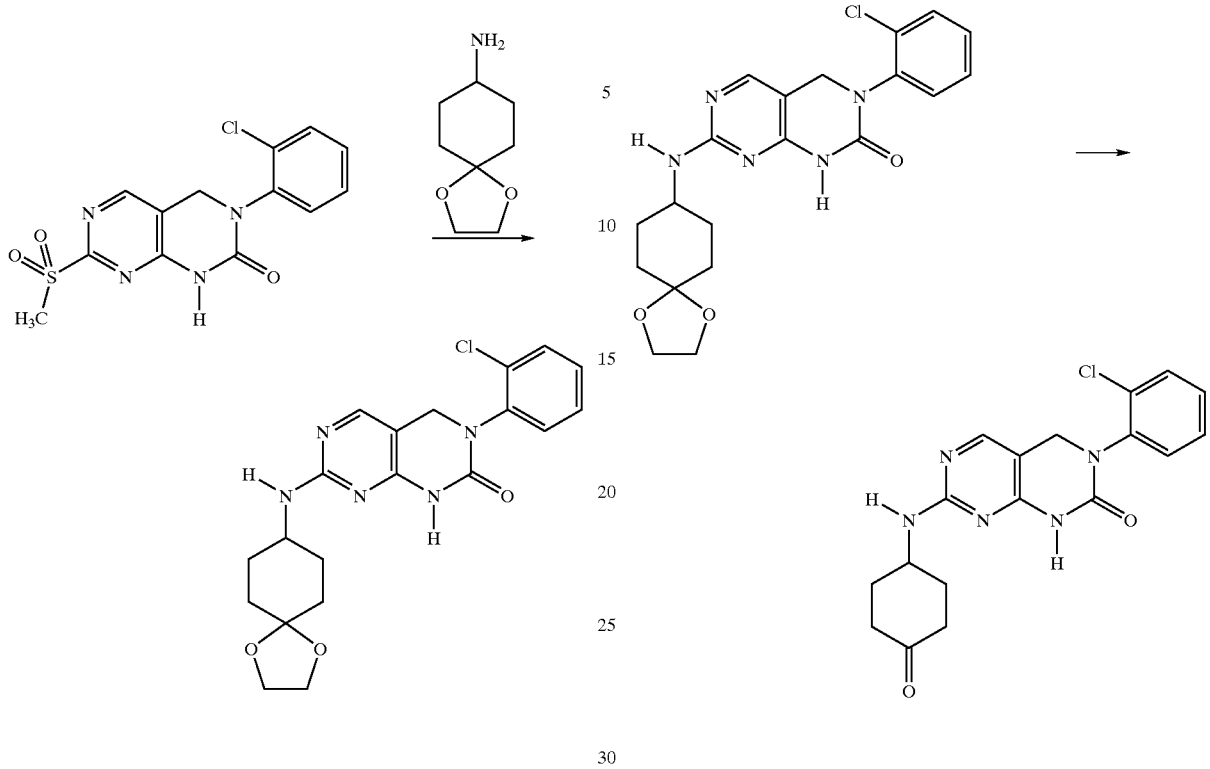

Sulfone 11.1 (4.6 g, 13 mmol) was combined with 1,4-dioxaspiro[4.5]dec-8-ylamine (4.2 g, 27 mmol) (prepared as described in Example 8) in 40 mL 1-methyl-2-pyrrolidinone. The reaction mixture was heated to 100° C. overnight, at which time it was cooled to room temperature, diluted with ethyl acetate and water, and filtered to give an off-white solid. 1M hydrochloric acid in diethyl ether was added to a slurry of the product (0.12 g, 0.29 mmol) in methanol, and the resulting solution was concentrated in vacuo. The residue was taken up in methanol/dichloromethane and purified by flash chromatography on silica gel using 2% methanol/dichloromethane as eluant to give the pure title compound as the free base. 1M Hydrochloric acid in diethyl ether was added to a slurry of the product in methanol. The resulting solution was concentrated under a stream of nitrogen, then pumped under reduced pressure to give 80 mg of the hydrochloride salt of the 3-(2-chlorophenyl)-7-(1,4-dioxaspiro[4.5]dec-8-ylamino)-3,4-dihydropyrimido[4,5-d]-pyrimidin-2(1H)-one as yellow solid.

Example 72

Compound 4-23

This example illustrates the preparation of 3-(2-chlorophenyl)-7-(4-oxo-cyclohexylamino)-3,4-dihydropyrimido[4,5-d]pyrimidin-2(1H)-one.

A mixture of 3-(2-chlorophenyl)-7-(1,4-dioxaspiro[4.5]dec-8-ylamino)-3,4-dihydropyrimido[4,5-d]pyrimidin-2 (1H)-one (0.17 g, 0.41 mmol) (prepared as described Example 71) in 1:1 tetrahydrofuran/3N aqueous hydrochloric acid was stirred at room temperature overnight. The reaction mixture was then diluted with ethyl acetate and treated with saturated aqueous sodium bicarbonate. The layers were separated, and the aqueous layer extracted with ethyl acetate. The organic layer was washed with brine, dried with sodium sulfate, and concentrated under reduced pressure. The residue was dissolved in methanol and purified by flash chromatography on silica gel using 2% ammonium hydroxide in 35% acetone/hexane as eluant. The fractions containing product were combined and concentrated under reduced pressure to a white solid which was suspended in methanol. Addition of 1M hydrochloric acid in diethyl ether gave the salt which was concentrated and pumped under reduced pressure to give 80 mg of the pure hydrochloride salt of 3-(2-chlorophenyl)-7-(4-oxo-cyclohexylamino)-3,4-dihydropyrimido[4,5-d]pyrimidin-2(1H)-one as a yellow foam.

Example 73

Compound 4-2

This example illustrates the alternative preparations of 3-(2-chlorophenyl)-7-(trans-4-hydroxycyclohexylamino)-3,4-dihydropyrimido[4,5-d]pyrimidin-2(1H)-one.

73.1 Preparation

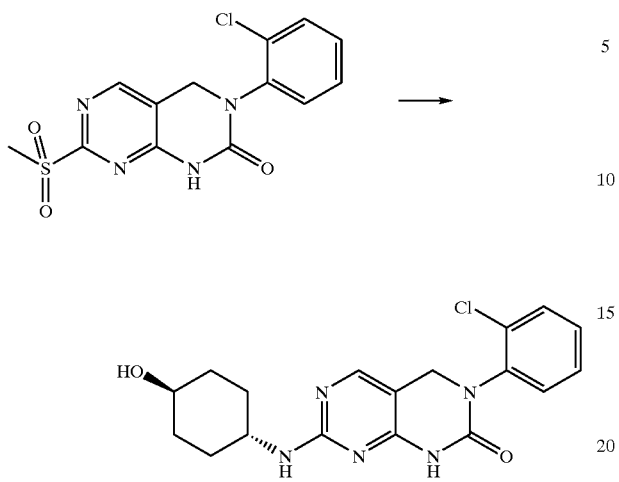

Sulfone 11.1 (0.400 g, 1.18 mmol) was combined with trans-4-aminocyclohexanol (0.272 g, 2.36 mmol) and 2-methoxyethyl ether (0.4 mL). The mixture was heated to 100–105° C. for 1 hour at which time it was cooled to room temperature and concentrated in vacuo. The residue was purified by column chromatography on silica gel using 9:1 dichloromethane/methanol. The column fractions containing product were combined and concentrated in vacuo to an oil which was re-dissolved in ethyl acetate and methanol. Addition of hydrochloric acid (1.0M/Et$_2$O, 1.0 equivalent) gave the salt which dissolved in the solvents. The solution was concentrated in vacuo to a solid which was triturated in ether, filtered and dried to give 0.220 g of 3-(2-chlorophenyl)-7-(trans-4-hydroxycyclohexylamino)-3,4-dihydropyrimido[4,5-d]pyrimidin-2(1H)-one.

73.2 Alternative Preparation

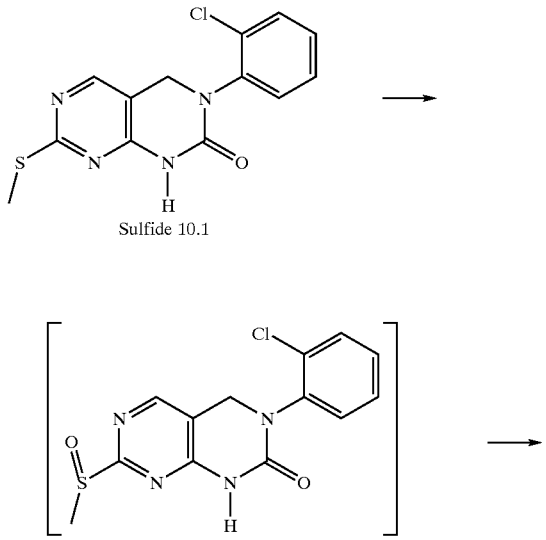

-continued

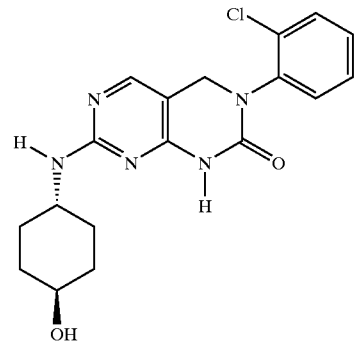

A solution of sulfide 10.1 (700 g) in 1-methyl-2-pyrrolidinone (3000 mL) was combined with N-chlorosuccinimide (350 g) in 500 mL 1-methyl-2-pyrrolidinone and 40 g water, and the mixture was stirred for 1.5 hours at 25° C. To this solution was added trans-4-aminocyclohexanol (865 g). The mixture was heated to 60° C. for 12–26 hours, cooled to 20–25° C. and treated with 10500 mL water. This mixture was cooled to 5–8° C. and stirred for 2 hours. The solid was collected by filtration, washed with water, hexanes and dried at 65° C. in a vacuum oven to provide 3-(2-chlorophenyl)-7-(trans-4-hydroxycyclohexlamino)- 3,4-dihydropyrimido[4,5-d] pyrimidin-2(1H)-one. The hydrochloride salt is formed by the action of ethanolic hydrochloric acid/water on the free base.

Example 74

Compound 4-5

This example illustrates an alternative preparation of 7-(trans-4-hydroxycyclohexylamino)-3-ortho-tolyl-3,4-dihydropyrimido[4,5-d]pyrimidin-2(1H)-one.

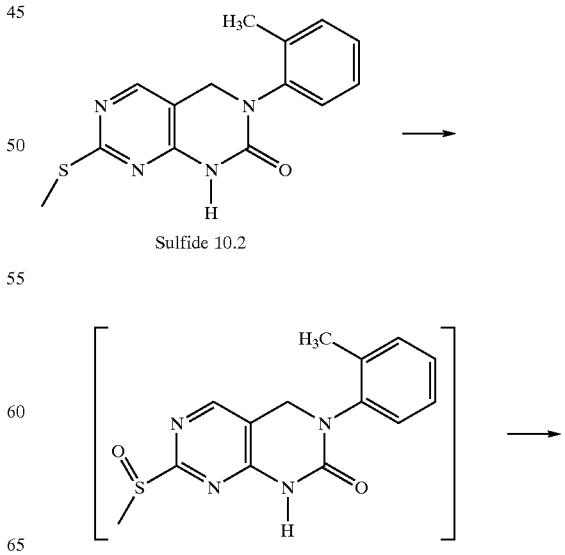

109
-continued

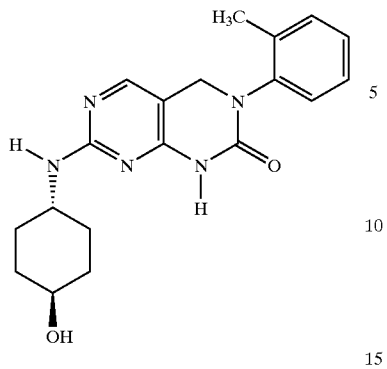

A solution of sulfide 10.2 (2 g) in 4 mL 1-methyl-2-pyrrolidinone was combined with N-chlorosuccinimide (1.03 g) in 4 mL 1-methyl-2-pyrrolidinone and 0.125 g water, and the mixture was stirred for 1.5 hours at 25° C. To this solution was added trans-4-aminocyclohexanol (2.65 g). The mixture was heated to 60° C. for 48 hours, cooled to 20–25° C. and treated with 10 mL water. This mixture was cooled to 5° C. and stirred for 2 hours. The solid was collected by filtration, washed with water, hexanes and dried in vacuo. The solid was purified by flash column chromatography using 95/5-90/10 dichloromethane/methanol as eluant to give 614 mg of 7-(trans-4-hydroxycyclohexylamino)-3-ortho-tolyl-3,4-dihydropyrimido[4,5-d]pyrimidin-2(1H)-one. The resulting solid was converted to the hydrochloride salt by the action of ethereal hydrochloric acid/ethyl acetate on the free base.

Example 75

Compound 4-15

This example illustrates the preparation of 3-(2-chlorophenyl)-7-(trans-4-formyloxycyclohexylamino)-3,4-dihydropyrimido[4,5-d]pyrimidin-2(1H)-one.

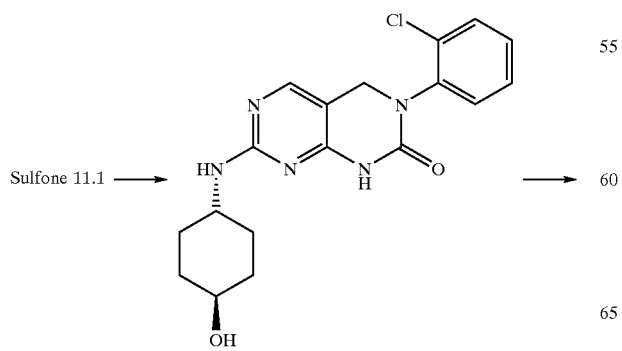

110
-continued

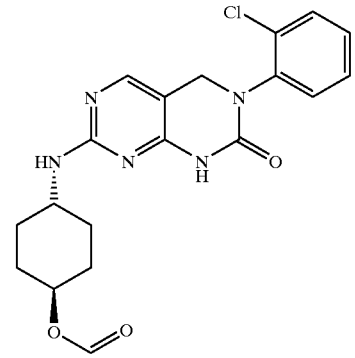

A mixture of 3-(2-chlorophenyl)-7-(trans-4-hydroxycyclohexylamino)-3,4-dihydropyrimido[4,5-d]pyrimidin-2 (1H)-one (300 mg, 0.8 mal) (prepared as described in Example 73) and 96% formic acid (2 mL) was stirred at 60° C. for 3 hours, then concentrated under reduced pressure. The residue was triturated in ether, filtered and dried to give 250 mg of 3-(2-chlorophenyl)-7-(trans-4-formyloxycyclohexylamino)-3,4-dihydropyrimido[4,5-d]pyrimidin-2(1H)-one.

Example 76

Compound 4-13

This example illustrates the preparation of 7-(trans-4-acetyloxycyclohexylamino)-3-(2-chlorophenyl)-3,4-dihydropyrimido[4,5-d]pyrimidin-2(1H)-one.

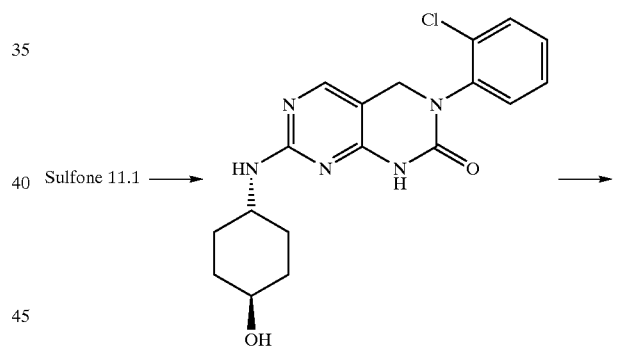

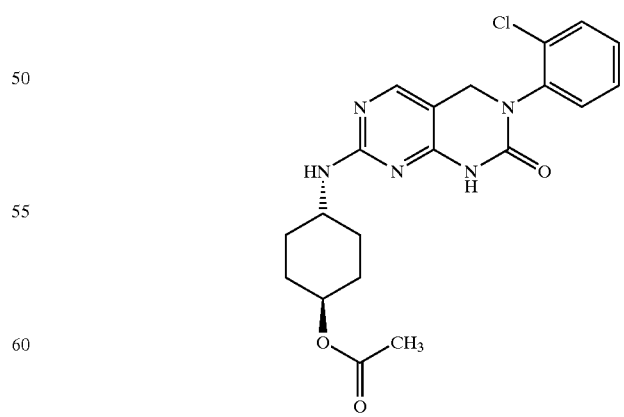

A suspension of 3-(2-chlorophenyl)-7-(trans-4-hydroxycyclohexylamino)-3,4-dihydropyrimido[4,5-d] pyrimidin-2(1H)-one (400 mg, 1.07 mmol) (prepared as described in Example 73), acetic anhydride (0.3 mL, 3.2 mmol) and pyridine (0.34 mL, 4.3 mmol) in 5 mL dichloromethane was stirred at 25° C. for 18 hours. The reaction mixture was filtered and the precipitate was washed with dichloromethane, dried and suspended in ethyl acetate. Addition of hydrochloric acid (1.0M/Et2O, 2.0 equivalent) gave the salt which was filtered and dried to give 200 mg of the hydrochloride salt of 7-(trans-4-acetyloxycyclohexylamino)-3-(2-chlorophenyl)-3,4-dihydropyrimido[4,5-d]pyrimidin-2(1H)-one.

Example 77

Compound 4-20

This example illustrates the preparation of 3-(2-chlorophenyl)-7-(trans-4-methoxycarbonyloxycyclohexylamino)-3,4-dihydropyrimido[4,5-d]pyrimidin-2(1H)-one.

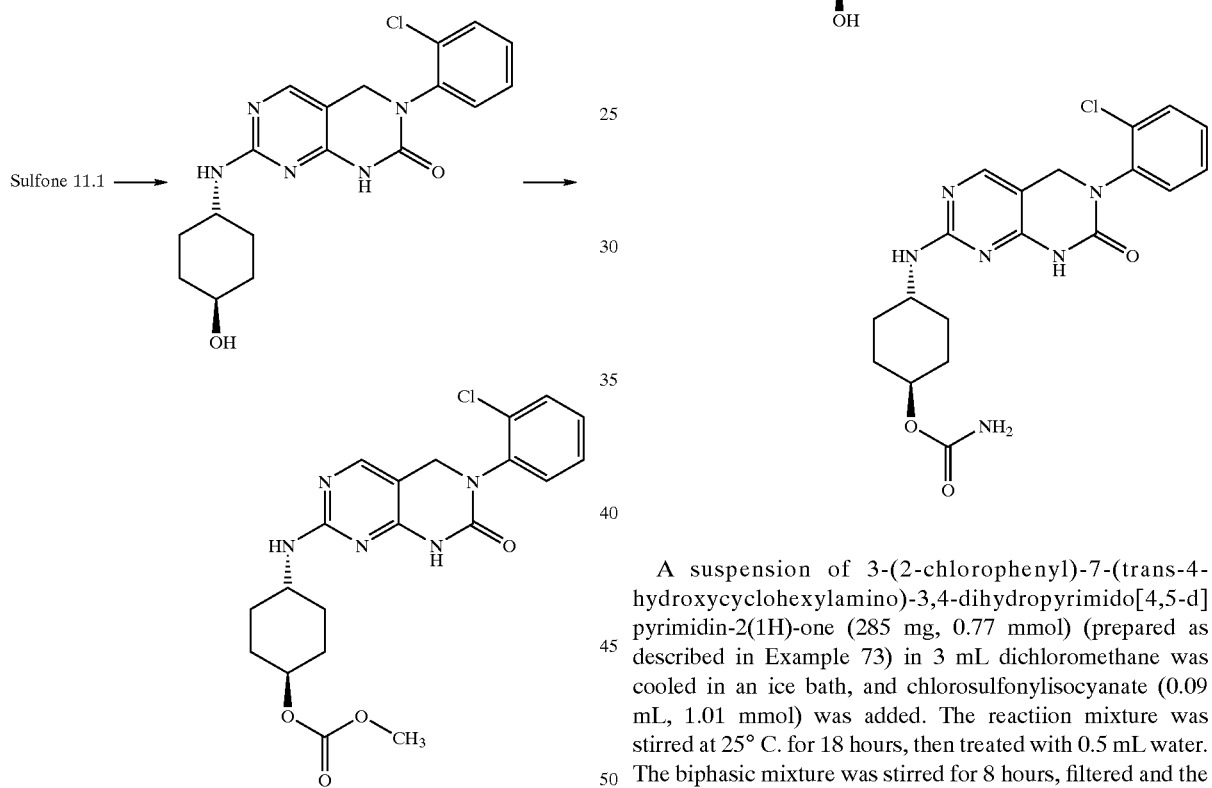

A suspension of 3-(2-chlorophenyl)-7-(trans-4-hydroxycyclohexylamino)-3,4-dihydropyrimido[4,5-d]pyrimidin-2(1H)-one (200 mg, 0.5 mmol) (prepared as described in Example 73), and 4-dimethylaminopyridine (6.5 mg, 0.05 mmol) in tetrahydrofuran was cooled in an ice bath. Dimethylpyrocarbonate (0.6 mL, 5.35 mmol) was added and the mixture was stirred at 25° C. for 18 hours. The reaction was filtered and the precipitate was purified by column chromatography on silica gel using 98:2 dichloromethane/methanol as eluant to obtain 30 mg of the title compound. Addition of hydrochloric acid (1.0M/Et₂O, 2.0 equivalent) gave the salt which was filtered and dried to give 34 mg of the hydrochloride salt of 3-(2-chlorophenyl)-7-(trans-4-methoxycarbonyloxycyclohexylamino)-3,4-dihydropyrimido[4,5-d]pyrimidin-2(1H)-one.

Example 78

Compound 4-21

This example illustrates the preparation of 7-(trans-4-carbamoyloxycyclohexylamino)-3-(2-chlorophenyl)-3,4-dihydropyrimido[4,5-d]pyrimidin-2(1H)-one.

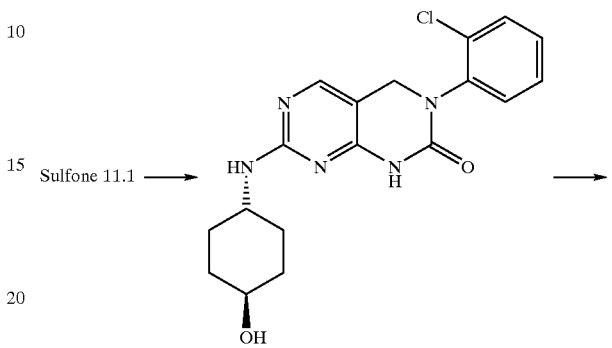

A suspension of 3-(2-chlorophenyl)-7-(trans-4-hydroxycyclohexylamino)-3,4-dihydropyrimido[4,5-d]pyrimidin-2(1H)-one (285 mg, 0.77 mmol) (prepared as described in Example 73) in 3 mL dichloromethane was cooled in an ice bath, and chlorosulfonylisocyanate (0.09 mL, 1.01 mmol) was added. The reactiion mixture was stirred at 25° C. for 18 hours, then treated with 0.5 mL water. The biphasic mixture was stirred for 8 hours, filtered and the precipitate was purified by column chromatography on silica gel using 97:3 dichloromethane/methanol to obtain 110 mg of the title compound. Addition of hydrochloric acid (1.0M/Et₂O, 2.0 equivalent) gave the salt which was filtered and dried to give 94 mg of the hydrochloride salt of 7-(trans-4-carbamoyloxycyclohexylamino)-3-(2-chlorophenyl)-3,4-dihydropyrimido[4,5-d]pyrimidin-2(1H)-one.

Example 79

Compound 4-22

This example illustrates the preparation of 3-(2-chlorophenyl)-7-(trans-4-methylaminocarbonyloxycyclohexylamino)-3,4-dihydropyrimido[4,5-d]pyrimidin-2(1H)-one.

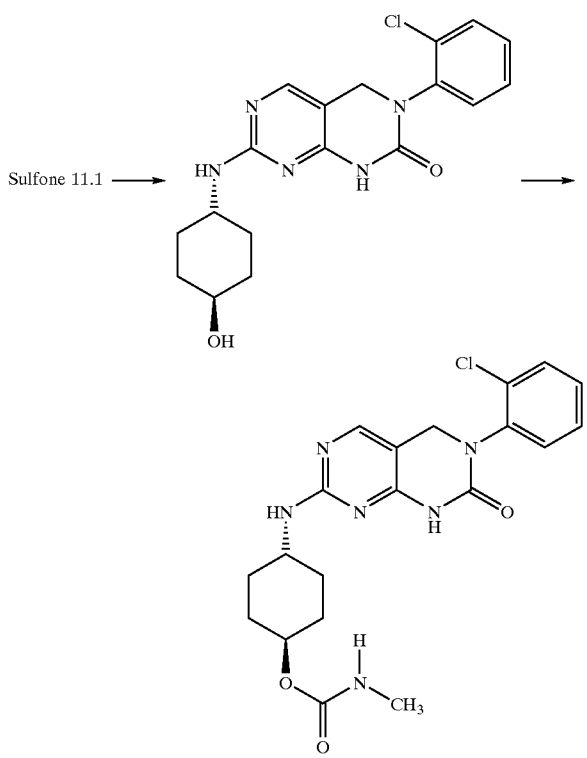

A suspension of 3-(2-chlorophenyl)-7-(trans-4-hydroxycyclohexylamino)-3,4-dihydropyrimido[4,5-d]pyrimidin-2(1H)-one (350 mg, 0.94 mmol) (prepared as described above in Example 73) in 3 mL dichloromethane was treated with 1 mL (excess) methyl isocyanate, and 1 mL triethylamine. The mixture was stirred under nitrogen atmosphere for one week. The reaction was filtered and the precipitate was washed with dichloromethane, dried and suspended in ethyl acetate. Addition of hydrochloric acid (1.0M/Et$_2$O, 2.0 equivalent) gave the salt which was filtered and dried to give 250 mg of the hydrochloride salt of 3-(2-chlorophenyl)-7-(trans-4-methylaminocarbonyloxy-cyclohexyl-amino)-3,4-dihydropyrimido[4,5-d]pyrimidin-2(1H)-one.

Example 80

Compound 4-3

This example illustrates the preparation of 7-(3-carboxy-isopropylamino)-3-(2-chlorophenyl)-3,4-dihydropyrimido[4,5-d]pyrimidin-2(1H)-one.

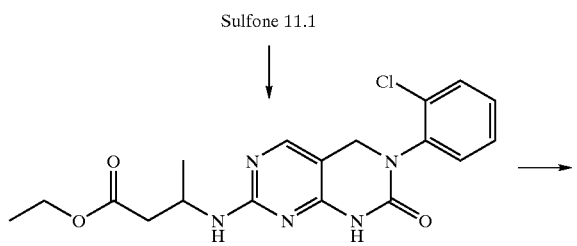

Sulfone 11.1 (1.0 g, 2.97 mmol) was combined with ethyl 3-aminobutyrate (0.87 mL, 5.94 mmol). The mixture was heated to 110–115° C. for 1 hour at which time it was cooled to room temperature. The residue was purified by column chromatography on silica gel using 10:1 dichloromethane/methanol. The column fractions containing product ester, 7-(3-carbethoxy-isopropylamino)-3-(2-chlorophenyl)-3,4-dihydropyrimido[4,5-d]pyrimidin-2(1H)-one were combined and concentrated in vacuo to a solid (1.10 g). The ester (0.500 g, 1.24 mmol) was dissolved in methanol. Addition of sodium hydroxide (0.05 g, 1.24 mmol) and water (1 mL) gave the sodium salt. The solution was concentrated in vacuo to a solid which was triturated in ethyl acetate for 1 hour, filtered and dried to give 0.41 g of 7-(3-carboxy-isopropylamino)-3-(2-chlorophenyl)-3,4-dihydropyrimido[4,5-d]pyrimidin-2(1H)-one. (MH$^+$=376, m.p. 170.0–185.5° C.)

Example 81

Compound 3-48

This example illustrates the preparation of 1-benzyl-3-(2-chlorophenyl)-7-(trans-4-hydroxycyclohexylamino)-3,4-dihydropyrimido[4,5-d]pyrimido-2(H)-one.

81.1 Preparation of 3-(2-chlorophenyl)-7-(trans-4-tert-butyldimethyl-silyloxy-cyclohexylamino)-3,4-dihydropyrimido[4,5-d]pyrimidin-2(1H)-one.

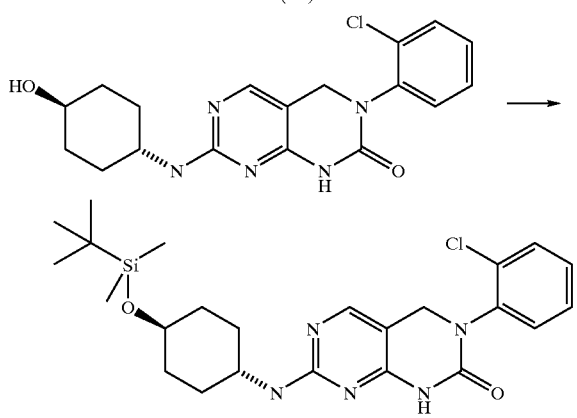

A suspension of 3-(2-chlorophenyl)-7-(trans-4-hydroxycyclohexylamino)-3,4-dihydropyrimido[4,5-d]pyrimidin-2(1H)-one (1.86 g, 5 mmol) (prepared as described in Example 73) was combined with tert-butyldimethylsilyl chloride (1.05 g, 7 mmol) and imidazole (0.75 g, 11 mmol) in dimethylformamide (35 mL). The reaction mixtur[0085] was heated at 50° C. for 24 hours, cooled to room temperature and added to water, stirred for 30 minutes, filtered and dried to give 1.88 g of 3-(2-chlorophenyl)-7-(trans-4-tert-butyl-dimethylsilyloxycy-clohexylamino)-3,4-dihydropyrimido[4,5-d]pyrimidin-2(1H)-one, m.p.289–294° C.

81.2 Preparation of 1-benzyl-3-(2-chlorophenyl)-7-(trans-4-tert-butyl-dimethylsilyloxycyclohexylamino)-3,4-dihydropyrimido[4,5-d]pyrimidin-2(1H)-one.

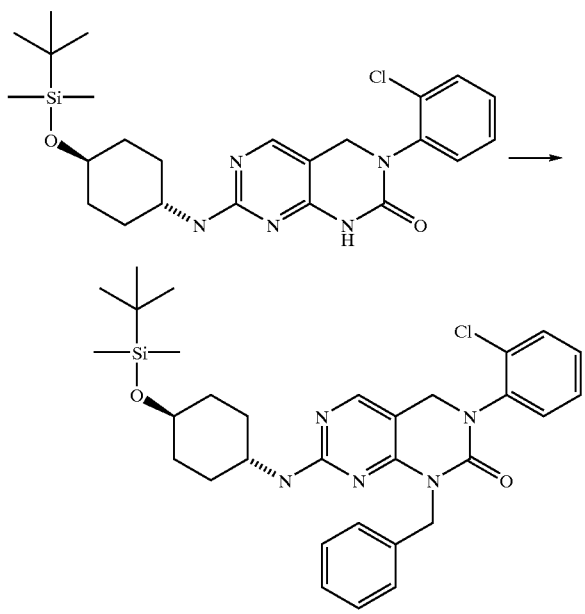

Sodium hydride (44 mg, 1.1 mmol (60% oil dispersion)) was added to a suspension of 3-(2-chlorophenyl)-7-(trans-4-tert-butyldimethylsilyloxycyclohexyl-amino)-3,4-dihydropyrimido[4,5-d]pyrimidin-2(1H)-one (486 mg, 1 mmol) in 1-methyl-2-pyrrolidinone, and was stirred at room temperature for 25 minutes. To this solution was added benzyl bromide (0.12 mL 1 mmol) and stirred at room temperature for 4 hours. The reaction mixture was added to water and extracted with ethyl acetate. The layers were separated, and the organic layer was washed with water, dried with magnesium sulfate, concentrated in vacuo. The residue was purified by column chromatography using 25:75 acetone/hexane as eluant to give 1-benzyl-3-(2-chlorophenyl)-7-(trans4-tert-butyldimethylsilyloxycyclohexylamino)-3,4-dihydropyrimido[4,5-d]pyrimidin-2 (1H)-one as an oil.

81.3 Preparation of 1-benzyl-3-(2-chlorophenyl)-7-(trans-4-hydroxycyclohexylamino)-3,4-dihydropyrimido[4,5-d]pyrimidin-2(1H)-one.

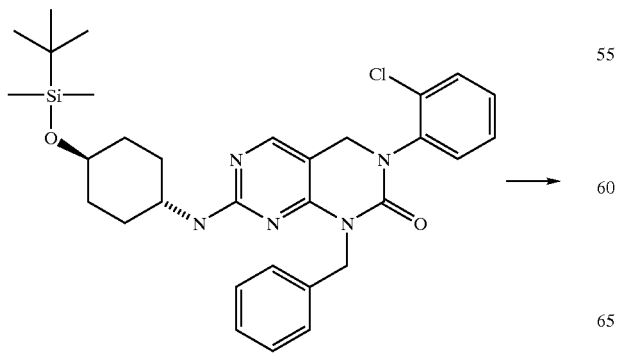

-continued

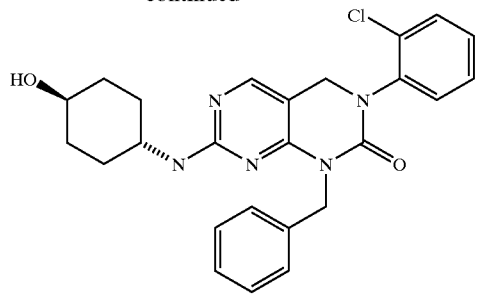

1-Benzyl-3-(2-chlorophenyl)-7-(trans-4-tert-butyldimethylsilyloxycyclohexylamino)-3,4-dihydropyrimido[4,5-d]pyrimidin-2(1H)-one was dissolved in tetrahydrofuran, and tetrabutylammonioum fluoride (1.0 M/tetrahydrofuran, 1.0 equivalent) was added. The reaction mixture was stirred at room temperature for 24 hours, was added to water, extracted with ethyl acetate, dried with magnesium sulfate, and concentrated in vacuo. The residue was purified by column chromatography on silica gel in 90:10 dichloromethane/methanol as eluant. The column fractions containing the product were combined and concentrated in vacuo to give the title compound. The product was suspended in methanol, and hydrochloric acid (1.0M/Et$_2$O, 1.0 equivalents) was added, stirred for 30 minutes and then evaporated to give a foam. The foam was stirred with methanol/diethyl ether, filtered and dried to give 130 mg of the hydrochloride salt of 1-benzyl-3-(2-chlorophenyl)-7-(trans-4-hydroxycyclohexylamino)-3,4-dihydropyrimido[4,5-d]pyrimidin-2(1H)-one.

Example 82

Compound 3-55

This example illustrates the preparation of 3-(2-chlorophenyl)-7-(trans-4-hydroxycyclohexylamino)-1-cyanomethyl-3,4-dihydropyrimido[4,5-d]-pyrimidin-2(1H)-one.

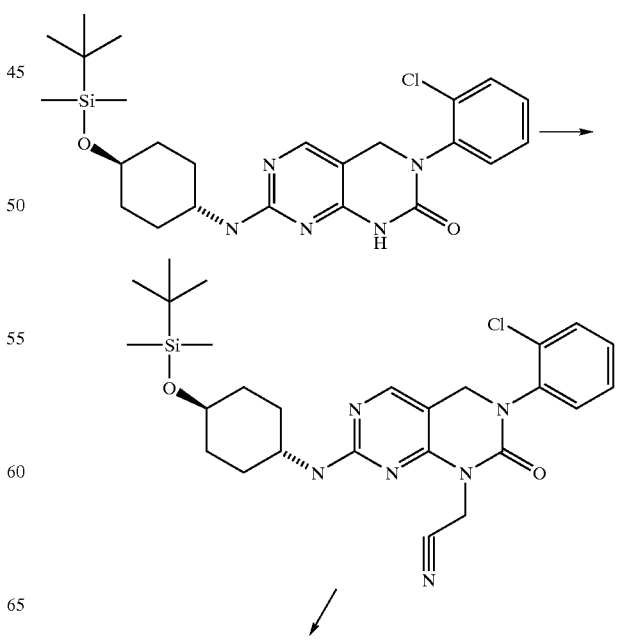

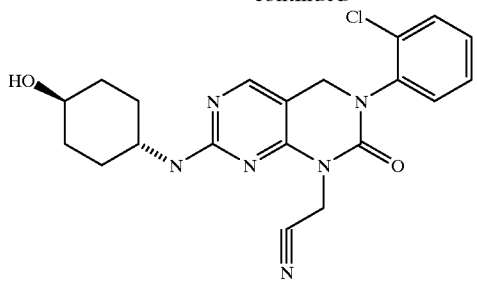

3-(2—Chlorophenyl)-7-(trans-4-tert-butyldimethylsilyl-oxycyclohexyl-amino)-3,4-dihydropyrimido[4,5-d]pyrimidin-2(1H)-one (486 mg, 1.0 mmol) (prepared as described in Example 81) was suspended in 1-methyl-2-pyrrolidinone (7 mL), and to this was added sodium hydride (44 mg, 1.1 mmol (60% oil dispersion)). The reaction mixture was stirred at room temperature for 25 minutes. To this solution was added iodoacetonitrile (0.167 mg, 1.0 mmol) and stirred at room temperature for 4 hours. The reaction mixture was added to water and extracted with ethyl acetate, washed with water, dried over magnesium sulfate, and evaporated under reduced pressure to give an oil. The oil was purified by column chromatography on silica gel using 25:75 acetone/hexane as eluant. The fractions containing the product were combined and evaporated under reduced pressure to give 510 mg of 3-(2-chlorophenyl)-7-(trans-4-tert-butyldimethyl-silyloxycyclohexylamino)-1-cyanomethyl-3,4-dihydropyrimido[4,5-d]pyrimidin-2(1H)-one as a white solid. $(M+H)^+527$, m.p. 100.2–148.7° C.

The 3-(2-chlorophenyl)-7-(trans-4-tert-butyldimethyl-silyloxycyclohexylamino)-1-cyanomethyl-3,4-dihydropyrimido[4,5-d]pyrimidin-2(1H)-one (510 mg, 0.97 mmol) was dissolved in tetrahydofuran, and tetrabutylammoniun fluoride (1.0M in THF, 1.0 equivalent) was added. The reaction mixture was stirred at room temperature for 12 hours, added to water, extracted with ethyl acetate, dried over magnesium sulfate, and evaporated under reduced pressure to give the title compound as an oil. This residue was purified by column chromatography on silica gel using 90:10 dichloromethane/methanol as eluant. The fractions containing the product were evaporated in vacuo to give 249 mg of 3-(2-chlorophenyl)-7-(trans-4-hydroxycyclohexyl-amino)-1-cyanomethyl-3,4-dihydropyrimido[4,5-d]-pyrimidin-2(1H)-one as a foam.

Example 83

Compound 3-49

This example illustrates the preparation of 3-(2-chlorophenyl)-7-(trans-4-hydroxycyclohexylamino)-1-methoxycarbonylmethyl-3,4-dihydropyrimido[4,5-d]pyrimidin-2(1H)-one.

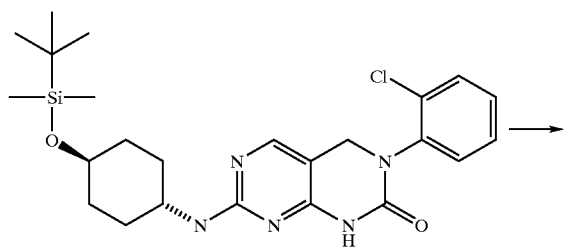

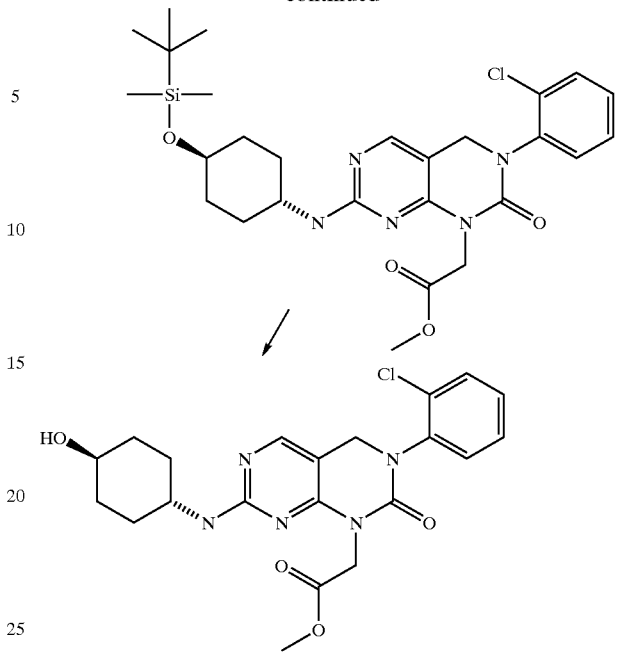

3-(Chlorophenyl)-7-(trans-4-tert-butyldimethylsilyl-oxycyclohexylamino)-3,4-dihydropyrimido[4,5-d]pyrimidin-2(1H)-one (972 mg, 2 mmol) (prepared as described in Example 81) was suspended in 1-methyl-2-pyrrolidinone (15 mL), and sodium hydride (88 mg, 2.2 mmol (60% oil dispersion)) was added. The reaction mixture was stirred at room temperature for 30 minutes, methyl bromoacetate (0.190 mL, 2 mmol) was added. The mixture was stirred for 6 hours. The reaction mixture was added to water and extracted with ethyl acetate, washed with water, dried over magnesium sulfate, and evaporated under reduced pressure. :The residue was purified by column chromatography on silica gel using 70:30 hexane/acetone as eluant. The fractions containing the product were combined and evaporated under reduced pressure to give 425 mg of 3-(2-chlorophenyl)-7-(trans-4-tert-butyldimethylsilyloxy-cyclohexylamino)-1-methoxycarbonylmethyl-3,4-dihydropyrimido-[4,5-d]pyrimidin-2(1H)-one as a white solid $((M+H)^+560$, m.p.165.7–167.4° C.

The 3-(2-chlorophenyl)-7-(trans-4-tert-butyldimethyl-silyloxycyclohexylamino)-1-methoxycarbonylmethyl-3,4-dihydropyrimido[4,5-d]pyrimidin-2(1H)-one was dissolved in tetrahydrofuran and tetrabutylammoniun fluoride(1.0M, 1.0 equivalents) was added, and stirred at room temperature for 12 hours. The reaction mixture was added to water, extracted with ethyl acetate, dried with magnesium sulfate, and evaporated under reduced pressure. The residue was purified by column chromatography on silica gel using 90:10 dichloromethane/methanol as eluant. The fractions containing the product were combined and evaporated under reduced pressure to give the title compound as a foam. This product was dissolved in methanol, and hydrochloric acid (1.0M, 1.0 equivalent) was added, stirred for 30 minutes and evaporated under reduced pressure. The residue was stirred with methanol/ethyl ether, for 4 hours, filtered and dried to give 294 mg of 3-(2-chlorophenyl)-7-(trans-4-hydroxycyclo- hexylamino)-1-methoxycarbonyl-methyl-3,4-dihydropyrimido[4,5-d]pyrimidin-2(1H)-one as a white solid.

Example 84

Compound 3-53

This example illustrates the preparation of 3-(2-chlorophenyl)-7-(trans-4-hydroxycyclohexylamino)-1- hydroxycarbonylmethyl-3,4-dihydropyrimido[4,5-d]pyrimidin-2(1H)-one.

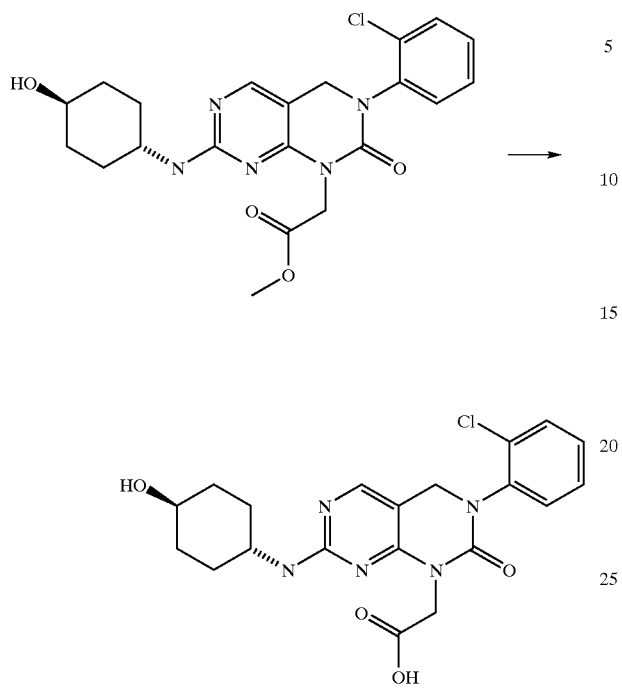

The 3-(2-chlorophenyl)-7-(trans-4-hydroxycyclohexyl-amino)-1-methoxycarbonyimethyl-3,4-dihydropyrimido[4,5-d]-pyrimidin-2(1H)-one (395 mg, 0.88 mmol) (prepared as described in Example 83) was suspended in ethanol (5 mL) and to this was added a solution of aqueous sodium hydroxide (0.85 mL 1.037N, 0.88 mmol). The reaction mixture was stirred at room temperature for 72 hours, then evaporated under reduced pressure to give the title compound as a foam. This residue was stirred in a mixture of methanol/diethyl ether for 2 hours, filtered, and dried to give 327 mg of 3-(2-chlorophenyl)-7-(trans-4-hydroxycyclohexylamino)-1-hydroxycarbonylmethyl-3,4-dihydropyrimido [4,5-d]pyrimidin-2(1H)-one as a white solid.

Example 85

Compound 3-56

This example illustrates the preparation of 3-(2-chlorophenyl)-7-(trans-4-hydroxycyclohexylamino)-1-(2-hydroxyethyl)-3,4-dihydropyrimido[4,5-d]pyrimidin-2(1H)-one.

85.1 Preparation of 1-(2-triisopropylsilyloxyethyl)-3-(2-chlorophenyl)-7-(trans-4-tert-butyldimethylsilyloxycyclohexylamino)-3,4-dihydropyrimido[4,5-d]pyrimidin-2(1H)-one.

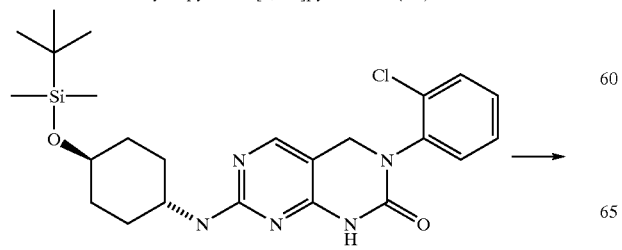

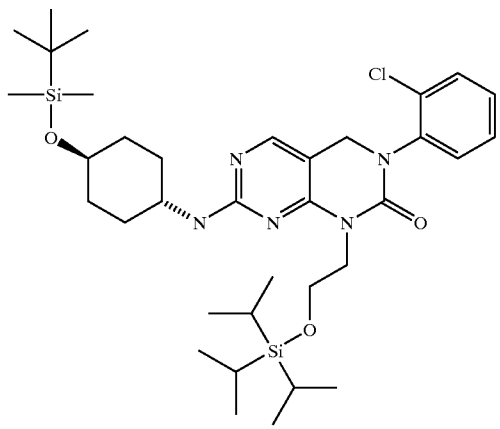

Sodium hydride (44 mg 1.1 mmol (60% oil dispersion)) was added to a suspension of 3-(2-chlorophenyl)-7-(trans-4-tert-butyldimethylsilyloxycyclohexyl-amino)-3,4-dihydropyrimido[4,5-d]pyrimidin-2(1H)-one (486 mg, 1.0 mmol) (prepared as described in Example 81) in 1-methyl-2-pyrrolidinone (7 mL), and stirred at room temperature for 25 minutes. 2-(Iodoethoxy) triisopropylsilane (328 mg, 1.0 mmol) was added, and the reaction mixture stirred at room temperature for 4 hours. The solution was added to water and extracted with ethyl acetate, washed with water, dried over magnesium sulfate and evaporated under reduced pressure to give the silyl proctected intermediate as an oil. The residue was purified by column chromatography on silica gel using 25:75 acetone/hexane as eluant and the fractions containing the product and evaporated under reduced pressure to give 604 mg of 1-(2-triisopropylsilyloxyethyl)-3-(2-chlorophenyl)-7-(trans-4-tert-butyldimethylsilyl-oxycyclohexylamino)-3,4-dihydropyrimido[4,5-d]pyrimidin-2(1H)-one as an oil, M+H)$^+$688

85.2 Preparation of 1-(2-hydroxyethyl)-3-(2-chlorophenyl)-7-(trans-4-tert-hydroxycyclohexylamino)-3,4-dihydropyrimido[4,5-d]pyrimidin-2(1H)-one.

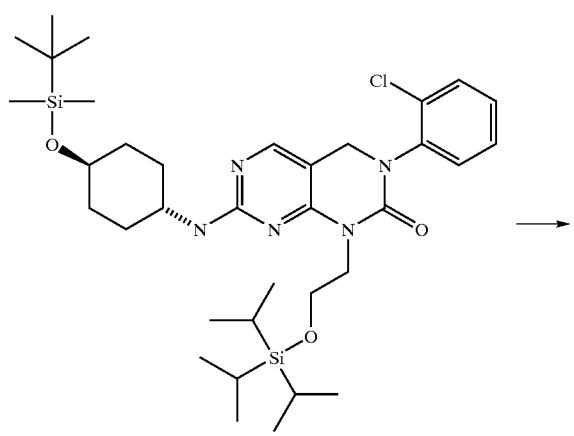

121
-continued

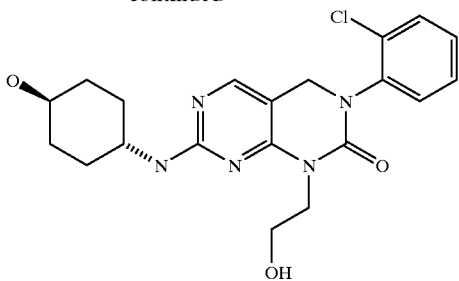

1-(2-Triisopropylsilyloxyethyl)-3-(2-chlorophenyl)-7-(trans-4-tert-butyldimethylsilyloxycyclohexylamino)-3,4-dihydropyrimido[4,5-d]pyrimidin-2(1H)-one (604 mg, 0.88 mmol) was dissolved in tetrahydrofuran. Tetrabutylammonium fluoride (1.0M in tetrahydrofuran) was added to the reaction mixture, and stirred at room temperature for 12 hours. The solution was added to water and extracted with ethyl acetate, dried over magnesium sulfate and evaporated under reduced pressure to give the title compound as an oil. The residue was purified by column chromatography on silica gel using 90:10 dichloromethane, and the fractions containing the product were concentrated in vacuo to give 145 mg of 1-(2-hydroxyethyl)-3-(2-chlorophenyl)-7-(trans-4-hydroxycyclohexylamino)-3,4-dihydropyrimido[4,5-d]pyrimidin-2(1H)-one as a foam.

Example 86

Compound 3-52

This example illustrates the preparation of 3-(2-chlorophenyl)-7-(trans-4-hydroxycyclohexylamino)-1-phenyl-3,4-dihydropyrimido[4,5-d]pyrimidin-2(1H)-one.

86.1 Preparation of ethyl 4-phenylamino-2-methylthiopyrimidine-5-carboxylate

A mixture of ethyl 4-chloro-2-methylthiopyrimidine-5-carboxylate (15 g, 64.5 mmol) and aniline (12 mL, 132 mmol) in 200 mL of acetonitrile was stirred at room temperature for 24 hours. The mixture was then evaporated and ethyl acetate and 2M aqueous hydrochloric acid were added to the residue. The phases were separated and the organic phase was washed with aqueous hydrochloric acid, dried over sodium sulfate, filtered and evaporated. The resulting solid was purified by trituration with 1:3 ether/hexanes to give 14.2 g (64%) of ethyl 4-phenylamino-2-methylthiopyrimidine-5-carboxylate as a white solid, mp 88.2–88.7° C.

86.2 Preparation of 4-phenylamino-2-methylthiopyrimidine-5-methanol

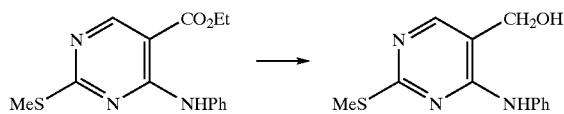

A solution of ethyl 4-phenylamino-2-methylthiopyrimidine-5-carboxylate (14.2 g, 49 mmol) in 100 mL of tetrahydrofuran was added dropwise to lithium aluminium hydride (1.9 g) in 50 mL of tetrahydrofuran at 0° C., at which time the mixture was stirred at room temperature for 9 hours. The mixture was then cooled in ice and cautiously treated dropwise with 3.3 mL of water, 3.3 mL of 2M aqueous sodium hydroxide, 4.4 mL of water and 500 mL of ethyl acetate. The resulting suspension was filtered through a filter aid, and the filtrate was concentrated. The product was filtered and washed with ether to give 7 g of 4-phenylamino-2-methylthiopyrimidine-5-methanol as a slightly colored solid, m.p. 142.2–143.2° C.

86.3 Preparation of 4-phenylamino-2-methylthiopyrimidine-5-carboxaldehyde

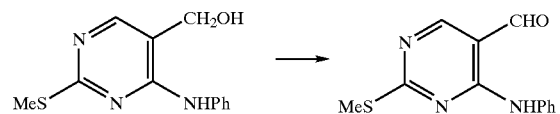

4-Phenylamino-2-methylthiopyrimidine-5-methanol (7 g, 28.3 mmol) of was stirred in 130 mL of dichloromethane and treated with manganese dioxide (25 g, 289 mmol). The suspension was stirred for 7 hours and then filtered, and the filtrate was evaporated. The residue was triturated with 1:3 ether/hexanes to give 6.4 g of 4-phenylamino-2-methylthiopyrimidine-5-carboxaldehyde as a white solid, m.p. 105.6–106.2° C.

86.4 Preparation of 5-(2-chlorophenyl)aminomethyl-4-phenylamino-2-methylthiopyrimidine

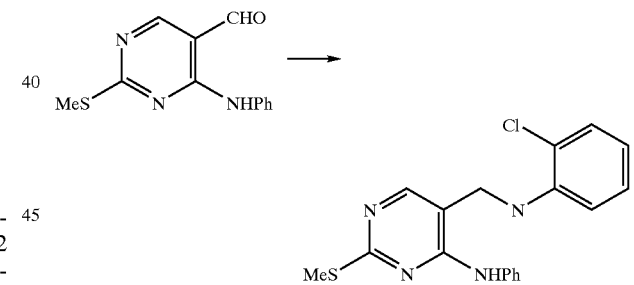

A mixture of 4-phenylamino-2-methylthiopyrimidine-5-carboxaldehyde(6.4 g, 26.5 mmol), 3 mL of 2-chloroaniline, and 4-toluenesulfonic acid (300 mg) in 150 mL of toluene was heated at reflux with the azeotropic removal of water for 2.5 hours. The mixture was cooled and filtered to give 6.6 g of solids. To this solid in 50 mL of tetrahydrofuran was added 20 mL of lithium aluminium hydride solution in 1M tetrahydrofuran. After stirring for 1.5 hours 1.2 mL of water, 1.2 mL of 15% sodium hydroxide and 3.8 mL of water were added to the mixture. The mixture was stirred for 15 minutes and filtered and washed with ethyl acetate. The filtrate was triturated with 1:1 ether/hexanes to give 6 g of 5-(2-chlorophenyl)aminomethyl-4-phenylamino-2-methylthiopyrimidine as a white solid., m.p. 131.1–131.5° C.

86.5 Preparation of 3-(2-chlorophenyl)-1-methyl-7-phenylthio-3,4-dihydro-pyrimido[4,5-d]pyrimidin-2(1H)-one

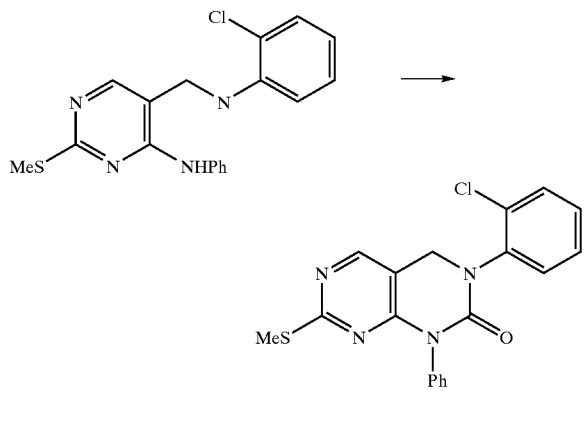

A cooled solution of 5-(2-chlorophenyl)aminomethyl-4-phenylamino-2-methylthiopyrimidine (6 g) and 5.2 mL of triethylamine in 75 mL of tetrahydrofuran was added dropwise 8.5 mL of phosgene (20% in toluene) in 35 mL of tetrahydrofuran. The mixture was stirred at room temperature overnight. Additional 3 mL phosgene (20% in toluene) was added to the mixture. After stirring for 15 minutes the mixture was treated with water and ethyl acetate. The phases were separated and the organic phase was washed with brine, dried over sodium sulfate, filtered and evaporated. The crude product was purified by column chromatography using 10:45 ethyl acetate/hexanes as eluant to give 2.1 g of 3-(2-chlorophenyl)-7-methylthio-1-phenyl-3,4-dihydropyrimido[4,5-d]-pyrimidin-2(1H)-one as a white solid, m.p. 79.5–82.4° C.

86.6 Preparation of 3-(2-chlorophenyl)-7-methanesulfonyl-1-phenyl-3,4-dihydropyrimido[4,5-d]pyrimidin-2(1H)-one

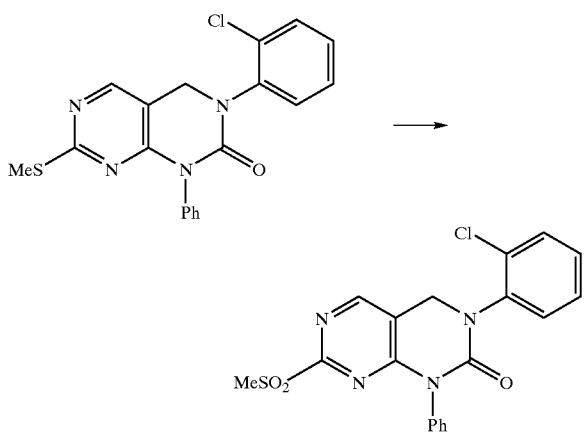

To 3-(2-chlorophenyl)-7-methylthio-1-phenyl-3,4-dihydropyrimido[4,5-d]pyrimidin-2(1H)-one (2 g) in 20 mL of tetrahydrofuran at 0° C. was added a solution of 8.1 g of Oxone® in 24 mL of water. The mixture was stirred for 5 hours at room temperature, diluted with ethyl acetate, washed with brine, dried over sodium sulfate, filtered, and evaporated to give 2 g of 3-(2-chlorophenyl)-7-methanesulfonyl-1-phenyl-3,4-dihydropyrimido[4,5-d]pyrimidin-2(1H)-one, m.p. 185.8–186.3° C.

86.7 Preparation of 3-(2-chlorophenyl)-7-methanesulfonyl-1-phenyl-3,4-dihydropyrimido[4,5-d]pyrimidin-2(1H)-one

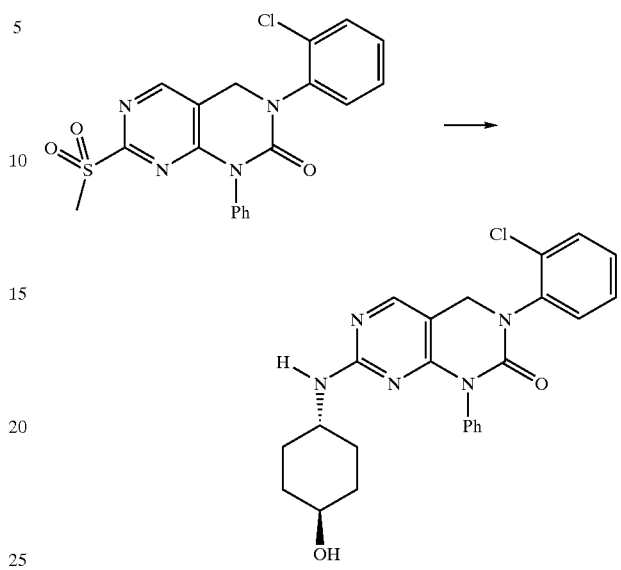

A suspension of 3-(2-chlorophenyl)-7-methanesulfonyl-1-phenyl-3,4-dihydropyrimido[4,5-d]pyrimidin-2(1H)-one (0.212 g) and 1-amino-4-cyclohexanol (0.19 g) in 0.3 mL of 1-methyl-2-pyrrolidinone was heated at 100° C. for 2 hours. The mixture was cooled, treated with 1:2 ether/hexanes, and filtered. The residue was purified using 10% methanol in dichloromethane to give 149 mg of the title compound, which was taken up in 10 mL of ethanol. Hydrogen chloride gas was bubbled through the solution for 5 minutes, concentrated, and treated with methanol and ether. The resulting solids were filtered and washed with ether to give 100 mg of the hydrochloride salt of 3-(2-chlorophenyl)-7-(trans-4-hydroxycyclohexylamino)-1-phenyl-3,4-dihydropyrimido[4,5-d]pyrimidin-2(1H)-one.

Example 87

Compound 4-28

This example illustrates the preparation of 3-(2-chlorophenyl)-7-[trans-4-(methanesulfonylamino)cyclohexylamino]-3,4-dihydropyrimido[4,5-d]pyrimidin-2(1H)-one.

87.1 Preparation 7-(trans-4-aminocyclohexylamino)-3-(2-chlorophenyl)-1-[2-(trimethylsilyl)ethoxymethyl]-3,4-dihydropyrimido[4,5-d]pyrimidin-2(1H)-one

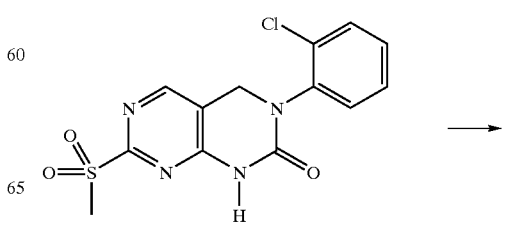

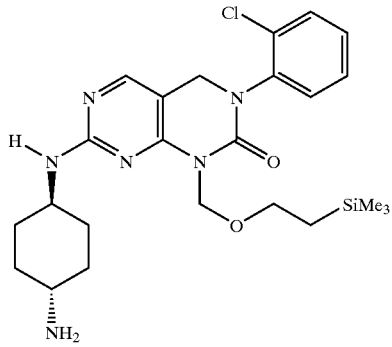

To a solution of sulfone 11.1 (3.0 g, 8.87 mmol) in 10 mL of 1-methyl-2-pyrrolidinone was added 60% sodium hydride (390 mg, 9.76 mmol, mineral oil). The reaction was stirred for 15 minutes at room temperature and then 2-(trimethylsilyl)ethoxymethyl chloride (1.57 mL, 8.87 mmol) was added. The reaction was stirred at room temperature for 4 hours. To this solution was then added 5.06 g of trans-1,4-diaminocyclohexane predissolved in 15 mL 1-methyl-2-pyrrolidinone. The reaction was then warmed to 60° C. for 24 hours. The reaction was poured into brine and the product extracted into ethyl acetate. The combined organic extracts were washed with saturated sodium bicarbonate and water, dried over magnesium sulfate, and concentrated in vacuo to give a light brown oil. Purification by chromatography using 2% methanol/dichloromethane to 5% methanol/dichloromethane as eluant gave 2.8 g of 7-(trans-4-aminocyclohexylamino)-3-(2-chlorophenyl)-1-[2-(trimethylsilyl)ethoxymethyl]-3,4-dihydropyrimido[4,5-d]pyrimidin-2(1H)-one as a pale yellow foam. (MH$^+$=502).

87.2 Preparation 3-(2-chlorophenyl)-7-[trans-4-(methanesulfonyl-amino)-cyclohexylamino]-1-[2-(trimethylsilyl)ethoxy-methyl]-3,4-dihydropyrimido[4,5-d]pyrimidin-2(1H)-one

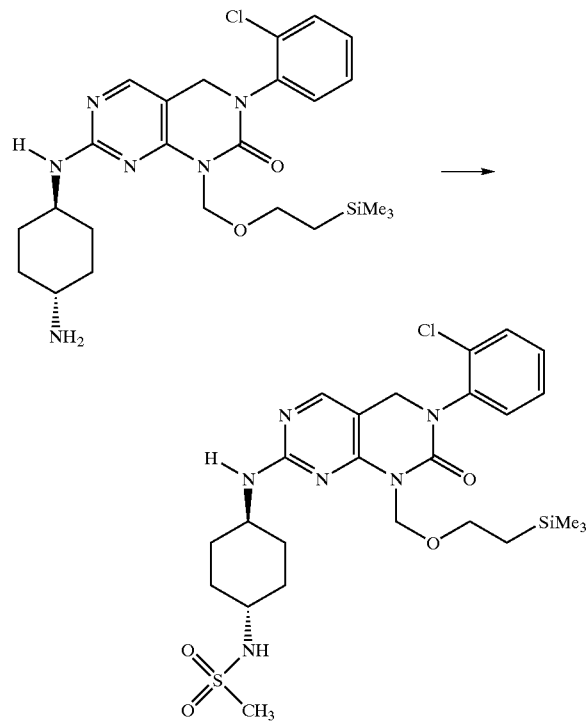

To a solution of 7-(trans-4-aminocyclohexylamino)-3-(2-chlorophenyl)-1-[2-(trimethylsilyl)ethoxymethyl]-3,4-dihydropyrimido[4,5-d]pyrimidin-2(1H)-one (500 mg, 1.04 mmol) in 5 mL of dicloromethane were added triethylamine (0.29 mL, 0.207 mmol) and a solution of methane sulfonic anhydride (0.2 g, 1.14 mmol) in 5 mL of dichloromethane. The reaction mixture was stirred at room temperature for 24 hours, diluted with ethyl acetate, and washed with aqueous 10% sodium bicarbonate. The organic extracts were concentrated in vacuo, and purified by chromatography using 2% methanol/dichloromethane to 3% methanol/dichloromethane as eluant to give 292 mg of 3-(2-chlorophenyl)-7-[trans-4-(methanesulfonylamino)cyclohexylamino]-1-[2-(trimethylsilyl)ethoxymethyl]-3,4-dihydropyrimido[4,5-d]pyrimidin-2(1H)-one as a white foam. (MH$^+$=581)

87.3 Preparation 3-(2-chlorophenyl)-7-[trans-4-(methanesulfonyl-amino)-cyclohexylamino]-3,4-dihydropyrimido[4,5-d]pyrimidin-2(1H)-one

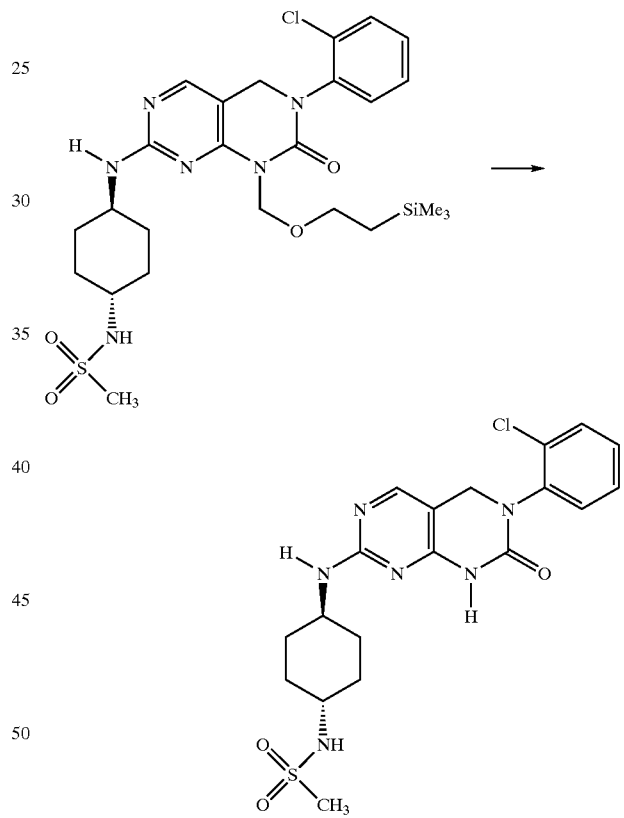

To a solution of the 3-(2-chlorophenyl)-7-[trans-4-(methanesulfonylamino)cyclohexylamino]-1-[2-(trimethylsilyl)ethoxymethyl]-3,4-dihydropyrimido[4,5-d]pyrimidin-2(1H)-one (290 mg, 0.5 mmol) in 5 mL methanol was added 4.0 mL of 10% aqueous hydrochloric acid. The reaction mixture was stirred at 40° C. for 24 hours, and was concentrated in vacuo. Repeated triturations of the colorless. oil with ethyl acetate gave 3-(2-chlorophenyl)-7-[trans-4-(methanesulfonylamino)cyclohexylamino]-3,4-dihydropyrimido[4,5-d]pyrimidin-2(1H)-one a white solid which was collected by vacuum filtration.

TABLE 1

7-Hydroxyalkylamino- and 7-Hydroxycycloalkylamino-substituted 1-methyl-3,4-dihydropyrimido[4,5-d]pyrimidin-2(1H)-one derivatives

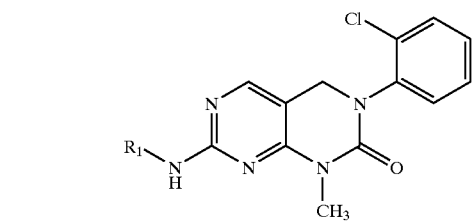

| Cpd | R¹ | mp (° C.) or MS (MH⁺) | Method of Preparation |
|---|---|---|---|
| 1-1 | HO−CH₂CH₂CH₂− | 334 | Example 2 |
| 1-2 | HO−CH₂−CH(CH₃)− | 348 | Example 4 |
| 1-3 | CH₃−CH(OH)−CH₂− | 348 | Example 5 |
| 1-4 | HO−CH₂−C*H(CH₃)− | 253.8–255.0° C. | Example 2 |
| 1-5 | (HOCH₂)₂CH− | 364 | Example 2 |
| 1-6 | HO−CH₂−CH(OH)−CH₂CH₂− | 364 | Example 2 |
| 1-7 | HO−CH₂−C(CH₃)₂− | 362 | Example 2 |
| 1-8 | HO−CH₂−CH(CH₂CH₃)− | 362 | Example 2 |
| 1-9 | CH₃−CH(OH)−CH₂CH₂CH₂− | 362 | Example 2 |

TABLE 1-continued

7-Hydroxyalkylamino- and 7-Hydroxycycloalkylamino-substituted 1-methyl-3,4-dihydropyrimido[4,5-d]pyrimidin-2(1H)-one derivatives

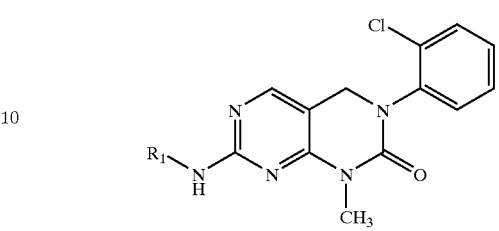

| Cpd | R¹ | mp (° C.) or MS (MH⁺) | Method of Preparation |
|---|---|---|---|
| 1-10 | CH₃CH₂−CH(OH)−CH₂− | 362 | Example 2 |
| 1-11 | (HOCH₂)₂C(CH₃)− | 378 | Example 2 |
| 1-12 | CH₃−CH(OH)−CH(CH₃)−CH(OH)−CH₂− (one isomer) | 108–130° C. | Example 3 |
| 1-13 | CH₃−CH(OH)−CH(−)−CH₂OH (stereo) | 199–204° C.; 378 | Example 3 |
| 1-14 | CH₃−CH(OH)−CH(−)−CH₂OH (stereo) | 378 | Example 3 |
| 1-15 | (CH₃)₂CH−CH(CH₂OH)− | 376 | Example 2 |
| 1-16 | CH₃CH₂CH₂−CH(CH₂OH)− | 376 | Example 2 |
| 1-17 | trans-4-hydroxycyclohexyl | 388 | Example 3 |

TABLE 1-continued

7-Hydroxyalkylamino- and 7-Hydroxycycloalkylamino-substituted
1-methyl-3,4-dihydropyrimido[4,5-d]pyrimidin-2(1H)-one derivatives

| Cpd | R¹ | mp (° C.) or MS (MH⁺) | Method of Preparation |
|---|---|---|---|
| 1-18 | 2-methylpentyloxymethyl group | 390 | Example 2 |
| 1-19 | trans-2-hydroxycyclohexyl | 388 | Example 3 |
| 1-20 | cis-2-hydroxycyclohexyl | 388 | Example 3 |
| 1-21 | (1-(hydroxymethyl)cyclopentyl) | 388 | Example 2 |
| 1-22 | 2-(hydroxymethyl)-4-methylpentyl | 390 | Example 2 |
| 1-23 | 2-(hydroxymethyl)-4-methylpentyl (stereoisomer) | 390 | Example 3 |

The $IC_{50}$'s of compounds 1-1 through 1-23 in the in vitro p38 assay were less than 10 $\mu$M.

TABLE 2

7-Heterocyclylamino- and 7-Heterocyclylalkylamino-substituted
3,4-dihydropyrimido[4,5-d]pyrimidin-2(1H)-one derivatives

| Cpd | R1 | R3 | R2 | R4 | mp (° C.) MS (MH⁺) | Example |
|---|---|---|---|---|---|---|
| 2-1 | 3-(piperidin-1-yl)propyl | CH₃ | 2-Cl | H | 401 | 2 |
| 2-2 | 4-(piperidin-1-yl)butyl | CH₃ | 2-Cl | H | 415 | 2 |

TABLE 2-continued
7-Heterocyclylamino- and 7-Heterocyclylalkylamino-substituted
3,4-dihydropyrimido[4,5-d]pyrimidin-2(1H)-one derivatives
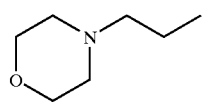
| Cpd | R1 | R3 | R2 | R4 | mp (° C.) MS (MH+) | Example |
|---|---|---|---|---|---|---|
| 2-3 | 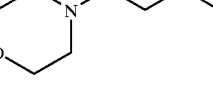 | CH₃ | 2-Cl | H | 402 | 2 |
| 2-4 | 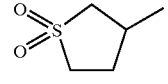 | CH₃ | 2-Cl | H | 417 | 2 |
| 2-5 | 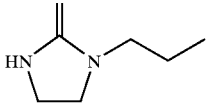 | CH₃ | 2-Cl | H | 408 | 2 |
| 2-6 | 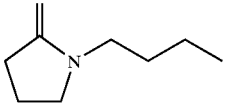 | CH₃ | 2-Cl | H | 402 | 2 |
| 2-7 | 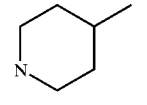 | CH₃ | 2-Cl | H | 415 | 2 |
| 2-8 | 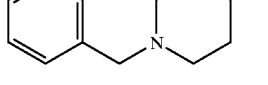 | CH₃ | 2-CH₃ | H | 212.6–218.9° C. | 25 |
| 2-9 | 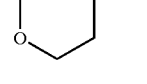 | CH₃ | 2-CH₃ | H | 253–253.9° C. 443 | 24 |
| 2-10 | 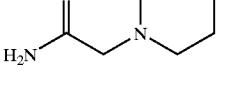 | H | 2-Cl | H | 360 | 47 |
| 2-11 | 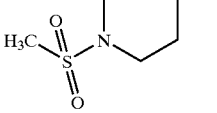 | CH₃ | 2-CH₃ | H | 410 | 52 |
| 2-12 |  | CH₃ | 2-CH₃ | H | 230.0–233.0° C. | 32 |

TABLE 2-continued

7-Heterocyclylamino- and 7-Heterocyclylalkylamino-substituted
3,4-dihydropyrimido[4,5-d]pyrimidin-2(1H)-one derivatives

| Cpd | R1 | R3 | R2 | R4 | mp (° C.)<br>MS (MH+) | Example |
|---|---|---|---|---|---|---|
| 2-13 | 4-methylpiperidin-1-yl-CH₂CH₂-OH | CH₃ | 2-CH₃ | H | 250–257° C.<br>397 | 27 |
| 2-14 | (S)-4-methylpiperidin-1-yl-CH₂-CH(OH)-CH₂OH | CH₃ | 2-CH₃ | H | 195–208° C.<br>427 | 26 |
| 2-15 | 4-methylpiperidin-1-yl-CH₂CH₂-CN | CH₃ | 2-CH₃ | H | 195–208.5° C.<br>406 | 28 |
| 2-16 | 4-methylpiperidin-1-yl-CH₂-CN | CH₃ | 2-CH₃ | H | 165–172° C.<br>410 | 29 |
| 2-17 | 4-methylpiperidin-1-yl-CH₂-CN | CH₃ | 2-Cl | H | 412 | 33 |
| 2-18 | 4-methylpiperidin-1-yl-CH₂-C(O)NH₂ | CH₃ | 2-CH₃ | H₃N-C(O)-CH₂CH₃ | 487 | 31 |
| 2-19 | 4-ethylpiperidin-1-yl-CH₂-C(O)N(CH₃)₂ | H | 2-Cl | H | 210.2–214.4° C.<br>458 | 57 |
| 2-20 | 4-ethylpiperidin-1-yl-CH₂CH₂-C(O)OCH₃ | CH₃ | 2-CH₃ | H | 241.6–242.1° C.<br>347 | 30 |

TABLE 2-continued

7-Heterocyclylamino- and 7-Heterocyclylalkylamino-substituted
3,4-dihydropyrimido[4,5-d]pyrimidin-2(1H)-one derivatives

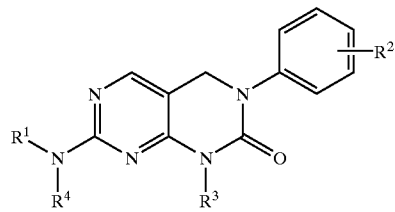

| Cpd | R1 | R3 | R2 | R4 | mp (° C.)<br>MS (MH+) | Example |
|---|---|---|---|---|---|---|
| 2-21 | (4-ethylpiperidinyl-CH2CF3) | H | 2-Cl | H | 260.6–261.5° C.<br>455 | 55 |
| 2-22 | (4-ethylpiperidinyl-CH2CN) | H | 2-Cl | H | 207.2–207.7° C.<br>412 | 56 |
| 2-23 | (4-ethylpiperidinyl-CH2C(O)NH2) | H | 2-Cl | H | 229.9–232.2° C.<br>430 | 58 |
| 2-24 | (4-ethylpiperidinyl-CH2COOH) | H | 2-Cl | H | 215–219° C.<br>431 | 59 |
| 2-25 | (4-methyl-1-methylpiperidinyl) | H | 2-Cl | CH3 | 243.2–243.7° C. | 50 |
| 2-26 | (4-methylpiperidinyl-CH2C(O)NH2) | H | 2-Cl | H | 416 | 52 |
| 2-27 | (4-methylpiperidinyl-CH2CF3) | H | 2-Cl | H | 441 | 53 |
| 2-28 | (4-methylpiperidinyl-C(O)OEt) | H | 2-Cl | H | 431 | 68 |

The IC$_{50}$'s of compounds 2-1 through 2-11, 2-13 through 2-24, and 2-28 in the in vitro p38 assay were less than 10 μM.

TABLE 3

7-Heteroalkylamino- and 7-Heterosubstitutedcycloalkylamino-substituted
3,4-dihydropyrimido[4,5-d]pyrimidin-2(1H)-one derivatives

| Cpd | R1 | R3 Other than H | R2 | R4 | mp (° C.) MS (MH+) | Example |
|---|---|---|---|---|---|---|
| 3-1 | H₃N–CH₂–C(CH₃)(CH₃)–CH₂CH₃ | CH₃ | 2-Cl | H | 183–235 375 | 2 |
| 3-2 | H₃N–CH₂–C(CH₃)(CH₃)–CH₂CH₃ | CH₃ | 2-Cl | H | 375 | 2 |
| 3-3 | H₃N–CH₂–C(CH₃)(CH₃)–CH₂CH₃ | CH₃ | 2-CH₃ | H | 355 | 2 |
| 3-4 | (CH₃)₂N–CH₂CH₂CH₃ | CH₃ | 2-Cl | H | 361 | 2 |
| 3-5 | H₃C–C(=O)–NH–CH₂CH₂CH₃ | CH₃ | 2-Cl | H | 375 | 3 |
| 3-6 | 4-methylcyclohexylamine | CH₃ | 2-Cl | H | 387 | 2 |
| 3-7 | H₃C–CH₂CH₂–CH(CH₃)–CH₂OH | CH₃ | 3-Cl | H | 390 | 2 |
| 3-8 | H₃N–CH₂–CH(OH)–CH₂CH₃ | CH₃ | 2-Cl | H | 363 | 2 |
| 3-9 | trans-4-aminocyclohexan-1-ol | CH₃ | 2-CH₃ | H | 368 | 21 |
| 3-10 | trans-4-aminocyclohexan-1-ol | CH₃ | 2-F | H | 371 | 3 |
| 3-11 | HO–CH₂–C(CH₃)(CH₃)–CH₂– | CH₃ | 3-Cl | H | 362 | 2 |

TABLE 3-continued

7-Heteroalkylamino- and 7-Heterosubstitutedcycloalkylamino-substituted
3,4-dihydropyrimido[4,5-d]pyrimidin-2(1H)-one derivatives

| Cpd | R1 | R3 Other than H | R2 | R4 | mp (° C.) MS (MH+) | Example |
|---|---|---|---|---|---|---|
| 3-12 | HOCH2C(CH3)2CH2- | CH3 | 2-CH3 | H | 342 | 2 |
| 3-13 | HOCH2C(CH3)2CH2- | CH3 | 3-CH3 | H | | 2 |
| 3-14 | (CH3)2CHCH(CH3)CH2OH | CH3 | 3-Cl | H | 376 | 2 |
| 3-15 | (CH3)2CHCH(CH3)CH2OH | CH3 | 2-CH3 | H | 356 | 2 |
| 3-16 | trans-2-methylcyclohexan-1-ol | CH3 | 2-F | H | 372 | 3 |
| 3-17 | trans-2-methylcyclohexan-1-ol | CH3 | 2-CH3 | H | 368 | 3 |
| 3-18 | cis-2-methylcyclohexan-1-ol | CH3 | 2-F | H | 372 | 3 |
| 3-19 | cis-2-methylcyclohexan-1-ol | CH3 | 2-CH3 | H | 368 | 3 |
| 3-20 | 1-(hydroxymethyl)-1-methylcyclopentane | CH3 | 2-Cl | H | 388 | 3 |
| 3-21 | (S)-HOCH2CH(CH3)- | CH3CH2OCH2CH(CH3)CH2OCH2CH3 | 2-Cl | H | 169.7–175.1° C. 464 | 41 |

TABLE 3-continued

7-Heteroalkylamino- and 7-Heterosubstitutedcycloalkylamino-substituted
3,4-dihydropyrimido[4,5-d]pyrimidin-2(1H)-one derivatives

| Cpd | R1 | R3 Other than H | R2 | R4 | mp (° C.) MS (MH+) | Example |
|---|---|---|---|---|---|---|
| 3-22 | (S)-2-methyl-3-hydroxypropyl | 4-methylpiperidinyl | 2-Cl | H | 244–248° C. 417 | 40 |
| 3-23 | 2,3-dihydroxy-3-methylbutyl | CH$_3$ | 2-CH$_3$ | H | 119.8–121.8° C. 358 | 22 |
| 3-24 | trans-2-methylcyclohexylamino | CH$_3$ | 2-Cl | H | 387 | 3 |
| 3-25 | cis-2-methylcyclohexylamino | CH$_3$ | 2-Cl | H | 387 | 3 |
| 3-26 | trans-4-hydroxycyclohexyl | pyrrolidinylpropyl | 2-Cl | H | 471 | 37 |
| 3-27 | trans-4-hydroxycyclohexyl | N,N-diethylaminopropyl | 2-Cl | H | 473 | 38 |
| 3-28 | 2,2-dimethyl-3-hydroxy-3-hydroxymethylpropyl | CH$_3$ | 2-Cl | H | 203.1–204.1° C. 392 | 6 |
| 3-29 | trans-4-hydroxycyclohexyl | methylthiopropyl | 2-Cl | H | 448 | 60 |

TABLE 3-continued

7-Heteroalkylamino- and 7-Heterosubstitutedcycloalkylamino-substituted
3,4-dihydropyrimido[4,5-d]pyrimidin-2(1H)-one derivatives

| Cpd | R1 | R3 Other than H | R2 | R4 | mp (° C.) MS (MH+) | Example |
|---|---|---|---|---|---|---|
| 3-30 | trans-4-hydroxycyclohexyl | $CH_3$-$N(CH_3)$-propyl (dimethylaminopropyl) | 2-Cl | H | 445 | 39 |
| 3-31 | trans-4-hydroxycyclohexyl | $(CH_3)_2N$-$CH_2$-$C(CH_3)_2$-$CH_2CH_3$ | 2-Cl | H | 487 | 61 |
| 3-32 | trans-4-hydroxycyclohexyl | $CH_3$-$N(CH_3)$-C(O)-$CH_2CH_3$ | 2-Cl | H | 459 | 43 |
| 3-33 | $HOCH_2$-$CH(OH)$-$C(CH_3)_2$-$CH_3$ | $CH_3$ | 2-$CH_3$ | H | 372 | 23 |
| 3-34 | $CH_3$-$CH(OH)$-$CH(CH_3)$-$CH_2OH$ | $CH_3$ | 2-Cl | H | — | 3 |
| 3-35 | trans-4-hydroxycyclohexyl | 1-methyl-3-piperidinyl | 2-Cl | H | 471 | 62 |
| 3-36 | trans-4-hydroxycyclohexyl | 1-methyl-4-piperidinyl | 2-Cl | H | 417 | 62 |
| 3-37 | trans-4-hydroxycyclohexyl | $H_2N$-C(O)-$CH_2CH_3$ | 2-Cl | H | 431 | 43 |

TABLE 3-continued

7-Heteroalkylamino- and 7-Heterosubstitutedcycloalkylamino-substituted 3,4-dihydropyrimido[4,5-d]pyrimidin-2(1H)-one derivatives

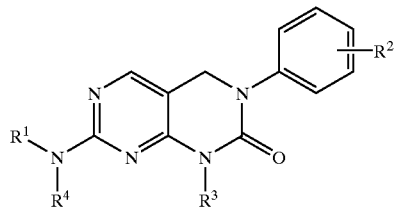

| Cpd | R1 | R3 Other than H | R2 | R4 | mp (° C.) MS (MH+) | Example |
|---|---|---|---|---|---|---|
| 3-38 | 4-methoxycyclohexyl | CH₃ | 2-Cl | CH₃ | 416 | 14 |
| 3-39 | 4-methoxycyclohexyl | CH₃ | 2-Cl | H | 402 | 14 |
| 3-40 | 4-(2-methoxyethoxy)cyclohexyl | CH₃ | 2-Cl | H | 446 | 15 |
| 3-41 | 4-acetoxycyclohexyl | CH₃ | 2-Cl | H | 430 | 16 |
| 3-42 | 4-allyloxycyclohexyl | CH₃ | 2-Cl | H | 428 | 13 |
| 3-43 | 1-(hydroxymethyl)cyclohexyl | CH₃ | 2-Cl | H | 203.7–207.8° C. 402 | 7 |
| 3-44 | 4-(2,3-dihydroxypropoxy)cyclohexyl | CH₃ | 2-Cl | H | 462 | 17 |
| 3-45 | 1,4-dioxaspiro[4.5]dec-8-yl | CH₃ | 2-Cl | H | 164.1–168.1° C. 430 | 8 |
| 3-46 | 4-oxocyclohexyl | CH₃ | 2-Cl | H | 233.4–236.3° C. 386 | 10 |

TABLE 3-continued
7-Heteroalkylamino- and 7-Heterosubstitutedcycloalkylamino-substituted
3,4-dihydropyrimido[4,5-d]pyrimidin-2(1H)-one derivatives
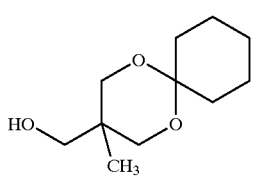
| Cpd | R1 | R3 Other than H | R2 | R4 | mp (° C.) MS (MH+) | Example |
|---|---|---|---|---|---|---|
| 3-47 | 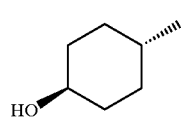 | CH₃ | 2-Cl | H | 148.3–263.7° C. 488 | 9 |
| 3-48 | 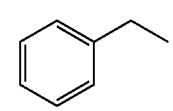 | 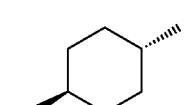 | 2-Cl | H | 218.5–221° C. 464 | 81 |
| 3-49 | 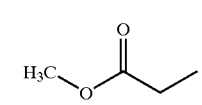 | 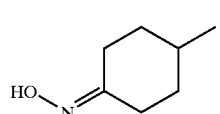 | 2-Cl | H | 212–215° C. 446 | 83 |
| 3-50 | 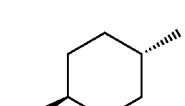 | CH₃ | 2-Cl | H | 181.0–225.0° C. 401 | 11 |
| 3-52 | 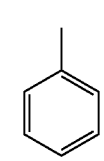 | 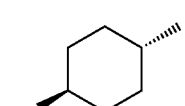 | 2-Cl | H | 277.6–279.1° C. | 86 |
| 3-53 | 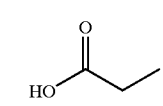 | 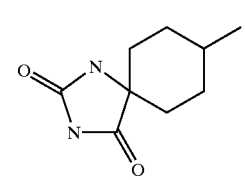 | 2-Cl | H | 230–240° C. 432 | 84 |
| 3-54 | 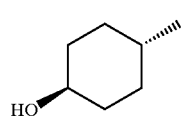 | CH₃ | 2-Cl | H | >300.° C. 456 | 12 |
| 3-55 | 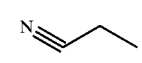 | 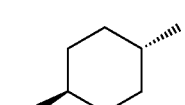 | 2-Cl | H | 130.8° C. 413 | 82 |
| 3-56 | 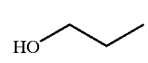 | 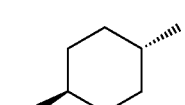 | 2-Cl | H | 96.6–122.8° C. 418 | 85 |

TABLE 3-continued

7-Heteroalkylamino- and 7-Heterosubstitutedcycloalkylamino-substituted
3,4-dihydropyrimido[4,5-d]pyrimidin-2(1H)-one derivatives

| Cpd | R1 | R3 Other than H | R2 | R4 | mp (° C.) MS (MH+) | Example |
|---|---|---|---|---|---|---|
| 3-57 | H3C-S(O)2-NH-cyclohexyl-CH3 | CH3 | 2-Cl | H | 263.3–264.4° C. | 19 |
| 3-58 | (H3C)2N-S(O)2-NH-cyclohexyl-CH3 | CH3 | 2-Cl | H | 221.8–225° C. | 20 |
| 3-59 | H3N-cyclohexyl-CH3 | CH3 | 2-Cl | H | 247–255° C. | 18 |
| 3-60 | HO-cyclohexyl- | CF3-CH2-CH2- (with F substituents) | 2-Cl | H | 130–133.5° C. 456 | 42 |

The IC$_{50}$'s of compounds 3-1, 3-3, 3-5 through 3–10, 3-12, 3–14 through 3-23, 3-27 through 3-36, 3-38, 3-39, 3-41 through 3–58, and 3-60 in the in vitro p38 assay were less than 10 μM.

TABLE 4

7-Heteroalkylamino- and 7-Heterosubstitutedcycloalkylamino-substituted
3,4-dihydropyrimido[4,5-d]pyrimidin-2(1H)-one derivatives

| Cpd | R1 | R2 | R4 | mp (° C.) MS (MH+) | Example |
|---|---|---|---|---|---|
| 4-1 | HO-CH2-C(CH3)(CH2OH)- | 2-Cl | H | | 44 |

TABLE 4-continued

7-Heteroalkylamino- and 7-Heterosubstitutedcycloalkylamino-substituted
3,4-dihydropyrimido[4,5-d]pyrimidin-2(1H)-one derivatives

| Cpd | R1 | R2 | R4 | mp (° C.) MS (MH+) | Example |
|---|---|---|---|---|---|
| 4-2 | trans-4-methyl-4-hydroxycyclohexyl | 2-Cl | H | 193.7–194.5° C. 375 | 73 |
| 4-3 | HO₂C-CH(CH₃)- | 2-Cl | H | 170–185.5° C. | 80 |
| 4-4 | HOCH₂-CH(OH)-CH(CH₃)- | 2-CH₃ | H | 161–172° C. 344 | 63 |
| 4-5 | trans-4-methyl-4-hydroxycyclohexyl | 2-CH₃ | H | 214.0–217.5° C. | 74 |
| 4-6 | HOCH₂-CH(OH)-CH(CH₃)- | 2-Cl | H | 123–129° C. 364 | 45 |
| 4-7 | HOCH₂-C(CH₃)₂- | 2-Cl | H | 348 | 4 |
| 4-8 | cis-4-methyl-4-hydroxycyclohexyl | 2-Cl | H | 167–178.5° C. 373 | 46 |
| 4-9 | HOCH₂-CH(Ph)(CH₃)- | 2-Cl | H | 396 | 3 |
| 4-10 | HOCH₂-CH(CH₃)- | 2-Cl | H | 334 | 4 |
| 4-11 | CH₃CH₂O-CH₂-CH(CH₃)-CH₂-OCH₂CH₃ | 2-Cl | H | — | 3 |

TABLE 4-continued

7-Heteroalkylamino- and 7-Heterosubstitutedcycloalkylamino-substituted
3,4-dihydropyrimido[4,5-d]pyrimidin-2(1H)-one derivatives

| Cpd | R1 | R2 | R4 | mp (° C.) MS (MH+) | Example |
|---|---|---|---|---|---|
| 4-12 | H₃C–CH(CH₃)–CH₂OH | 2-Cl | H | 177.4–184.5° C. | 3 |
| 4-13 | trans-4-methylcyclohexyl acetate | 2-Cl | H | >300° C. 416 | 76 |
| 4-14 | 1-methylcyclopentyl-CH₂OH | 2-Cl | H | 249.9–250.1° C. 374 | 48 |
| 4-15 | trans-4-methylcyclohexyl formate | 2-Cl | H | >300° C. 402 | 75 |
| 4-16 | 1-methylcyclohexyl-CH₂OH | 2-Cl | H | 241.8–242.4° C. 387 | 49 |
| 4-17 | 4-ethyl-cyclohexan-1-ol | 2-Cl | H | 208.3–217.9° C. 388 | 54 |
| 4-18 | trans-4-methylcyclohexan-1-ol | 2-Cl | H | 271.1–272° C. | 51 |
| 4-19 | 4-methyl-(hydroxymethyl)cyclohexyl | 2-Cl | H | shrinks 171° C. bubbles 181° C. 388 | 67 |
| 4-20 | trans-4-methylcyclohexyl methyl carbonate | 2-Cl | H | >260° C. 432 | 77 |
| 4-21 | trans-4-methylcyclohexyl carbamate | 2-Cl | H | 267–267.6° C. 417 | 78 |

TABLE 4-continued

7-Heteroalkylamino- and 7-Heterosubstitutedcycloalkylamino-substituted
3,4-dihydropyrimido[4,5-d]pyrimidin-2(1H)-one derivatives

| Cpd | R1 | R2 | R4 | mp (° C.) MS (MH+) | Example |
|---|---|---|---|---|---|
| 4-22 | methylcarbamate-O-cyclohexyl (trans) | 2-Cl | H | 269–271° C. 431 | 79 |
| 4-23 | 4-methylcyclohexanone | 2-Cl | H | 204.0–210.0° C. 372 | 72 |
| 4-24 | 8-methyl-1,4-dioxaspiro[4.5]decane | 2-Cl | H | 173.6–189.7° C. 416 | 71 |
| 4-25 | 4-amino-methylcyclohexyl | 2-Cl | H | >300° C. 373 | 69 |
| 4-26 | N,N-dimethylsulfamoylamino-methylcyclohexyl | 2-Cl | H | 235.5–237° C. 373 | 70 |
| 4-27 | (S)-2-hydroxy-1-methylethyl | 2-Cl | H | 334 | 4 |
| 4-28 | methanesulfonylamino-methylcyclohexyl | 2-Cl | H | 292.8–293.2° C. 451 | 87 |

The IC$_{50}$'s of compounds 4-1 through 4-8, 4-10 through 4-28 in the in vitro p38 assay were less than 10 μM.

Example 88

In Vitro p38 MAP Kinase Inhibition Assay

This example illustrates a p38 (MAP) kinase in vitro assay useful for evaluating the compounds of the present invention.

The p38 MAP kinase inhibitory activity of compounds of this invention in vitro was determined by measuring the transfer of the γ-phosphate from γ-$^{33}$P-ATP by p38 kinase to Myelin Basic Protein (MBP), using a minor modification of the method described in Ahn, et al., *J. Biol. Chem.* 266:4220–4227 (1991).

The phosphorylated form of the recombinant p38 MAP kinase was co-expressed with SEK-1 and MEKK in *E. Coli* (see, Khokhlatchev, et al., *J. Biol. Chem.* 272:11057–11062 (1997)) and then purified by affinity chromatography using a Nickel column.

The phosphorylated p38 MAP kinase was diluted in kinase buffer (20 mM 3-(N-morpholino)propanesulfonic acid, pH 7.2, 25 mM β-glycerol phosphate, 5 mM ethylene glycol-bis(beta-aminoethyl ether)-N,N,N',N'-tetraacetic acid, 1 mM sodium ortho-vanadate, 1 mM dithiothreitol, 40 mM magnesium chloride). Test compound dissolved in DMSO or only DMSO (control) was added and the samples were incubated for 10 minutes at 30° C. The kinase reaction was initiated by the addition of a substrate cocktail containing MBP and γ-$^{33}$P-ATP. After incubating for an additional 20 minutes at 300° C., the reaction was terminated by adding 0.75% phosphoric acid. The phosphorylated MBP was then separated from the residual γ-$^{33}$P-ATP using a phosphocellulose membrane (Millipore, Bedfrod, Mass.) and quantitated using a scintillation counter (Packard, Meriden, Conn.).

Example 89

In Vitro TNF-α Inhibition Assay

This example illustrates an in vitro assay to evaluate the inhibition of LPS-induced TNF-α production in THP1 cells.

The ability of the compounds of this invention to inhibit the TNF-α release was determined using a minor modification of the methods described in Blifeld, et al. *Transplantation*, 51:498–503 (1991).

(a) Induction of TNF Biosynthesis:

THP-1 cells were suspended in culture medium {RPMI (Gibco-BRL, Gailthersburg, Md.) containing 15% fetal bovine serum, 0.02 mM 2-mercaptoethanol}, at a concentration of 2.5×10$^6$ cells/mL and then plated in 96 well plate (0.2 mL aliquots in each well). Test compounds were dissolved in DMSO and then diluted with the culture medium such that the final DMSO concentration was 5%. Twenty five μL aliquots of test solution or only medium with DMSO (control) were added to each well. The cells were incubated for 30 minutes at 37° C. LPS (Sigma, St. Louis, Mo.) was added to the wells at a final concentration of 0.5 μg/ml, and cells were incubated for an additional 2 hours. At the end of the incubation period, culture supernatants were collected and the amount of TNF-α present was determined using an ELISA assay as described below.

(b) ELISA Assay:

The amount of human TNF-α present was determined by a specific trapping ELISA assay using two anti-TNF-α antibodies (2TNF-H12 and 2TNF-H34) described in Reimund, J. M., et al. *GUT*. Vol. 39(5), 684–689 (1996).

Polystyrene 96-well plates were coated with 50 μl per well of antibody 2TNF-H12 in PBS (10 μg/mL) and incubated in a humidified chamber at 4° C. overnight. The plates were washed with PBS and then blocked with 5% nonfat-dry milk in PBS for 1 hour at room temperature and washed with 0.1% BSA (bovine serum albumin) in PBS.

TNF standards were prepared from a stock solution of human recombinant TNF-α (R&D Systems, Minneapolis, Minn.). The concentration of the standards in the assay began at 10 ng/mL followed by 6 half log serial dilutions.

Twenty five μL aliquots of the above culture supernatants or TNF standards or only medium (control) were mixed with 25 μL aliquots of biotinylated monoclonal antibody 2TNF-H34 (2 μg/mL in PBS containing 0.1% BSA) and then added to each well. The samples were incubated for 2 hours at room temperature with gentle shaking and then washed 3 times with 0.1% BSA in PBS. 50 μL of peroxidase-streptavidin (Zymed, South San Francisco, Calif.) solution containing 0.416 μg/mL of peroxidase-streptavidin and 0.1% BSA in PBS was added to each well. The samples were incubated for an additional 1 hour at room temperature and then washed 4 times with 0.1% BSA in PBS. Fifty μL of O-phenylenediamine solution (1 μg/mL O-phenylenediamine and 0.03% hydrogen peroxide in 0.2M citrate buffer pH 4.5) was added to each well and the samples were incubated in the dark for 30 minutes, at room temperature. Optical density of the sample and the reference were read at 450 nm and 650 nm, respectively. TNF-α levels were determined from a graph relating the optical density at 450 nm to the concentration used.

The IC$_{50}$ value was-defined as the concentration of the test compound corresponding to half-maximal reduction in 450 nm absorbance.

Example 90

This example illustrates an in vivo assay to evaluate the inhibition of LPS-induced TNF-α production in mice (or rats).

The ability of the compounds of this invention to inhibit the TNF-α release, in vivo, was determined using a minor modification of the methods described in described in Zanetti, et. al., *J. Immunol.*, 148:1890 (1992) and Sekut, et. al., *J. Lab. Clin. Med.*, 124:813 (1994).

Female BALB/c mice weighing 18–21 grams (Charles River, Hollister, Calif.) were acclimated for one week. Groups containing 8 mice each were dosed orally either with the test compounds suspended or dissolved in an aqueous vehicle containing 0.9% sodium chloride, 0.5% sodium carboxymethyl-cellulose, 0.4% polysorbate 80, 0.9% benzyl alcohol (CMC vehicle) or only vehicle (control group). After 30 minutes, the mice were injected intraperitoneally with 20 μg of LPS (Sigma, St. Louis, Mo.). After 1.5 hours, the mice were sacrificed by CO$_2$ inhalation and blood was harvested by cardiocentesis. Blood was clarified by centrifugation at 15,600×g for 5 minutes, and sera were transferred to clean tubes and frozen at −20° C. until analyzed for TNF-α by ELISA assay (Biosource International, Camarillo, Calif.) following the manufacturer's protocol.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound selected from the group of compounds represented by formula I:

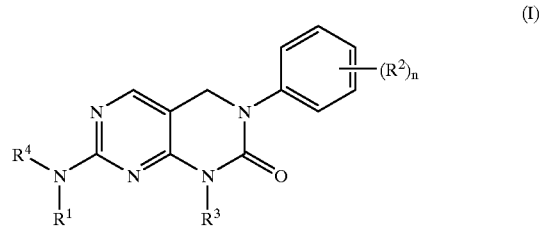

wherein the subscript n is an integer of from 0 to 3;

R$^1$ is acyl, heteroalkyl, arylheteroalkyl, heteroalkenyl, heteroalkynyl, heteroalkylcarbonyl, heterosubstituted cycloalkyl, heterosubstituted cycloalkylalkyl, heterosubstituted cycloalkylalkenyl, heterosubstituted cycloalkylalkynyl, heteroalkylsubstituted cycloalkyl, heterocyclyl, heterocyclylalkyl, heterocyclyl spiro cycloalkyl, -(alkylene)—C(O)—R$^{11}$, or -(heteroalkylene)—C(O)—R$^{11}$;

wherein:

R$^{11}$ is alkyl, haloalkyl, amino, monosubstituted amino, disubstituted amino, cycloalkyl, cycloalkylalkyl, aryl, aralkyl, heteroaryl, heteroaralkyl, hydroxy, or alkoxy;

R$^2$ is independently in each occurrence alkyl, halo, heteroalkyl, or vinyl;

R$^3$ is hydrogen, alkyl, heteroalkyl, aryl, aralkyl, heteroaryl, heteroaralkyl, cycloalkyl, cycloalkenyl, cycloalkylalkyl, haloalkyl, cyanoalkyl, heterosubstituted cycloalkyl, heterosubstituted cycloalkylalkyl, heteroalkylsubstituted cycloalkyl, heterocyclyl, heterocyclylalkyl, -(alkylene)—C(O)R$^{31}$, or -(heteroalkylene)—C(O)R$^{31}$; and R$^4$ is hydrogen, alkyl, or -(alkylene)—C(O)R$^{31}$;

wherein:

R$^{31}$ is alkyl, haloalkyl, hydroxy, alkoxy, amino, monsubstituted amino, disubstituted amino, cycloalkyl, cycloalkylalkyl, aryl, aralkyl, heteroaryl, or heteroaralkyl;

or an individual isomer, a racemic or nonracemic mixture of isomers, or a pharmaceutically acceptable salt thereof.

2. A compound in accordance with claim 1, wherein n is an integer of from 1 to 2, and each R$^2$ is independently halo or alkyl.

3. A compound in accordance with claim 2, wherein n is an integer of from 1 to 2, and each R$^2$ is independently halo.

4. A compound in accordance with claim 3, wherein —(R$^2$)$_n$ represents 2-halo or 2,6-dihalo.

5. A compound in accordance with claim 2, wherein n is an integer of from 1 to 2, and each R$^2$ is independently alkyl.

6. A compound in accordance with claim 5, wherein —(R$^2$)$_n$ represents 2-methyl.

7. A compound in accordance with claim 1, wherein R$^3$ is hydrogen, alkyl, haloalkyl, or heteroalkyl.

8. A compound in accordance with claim 7, wherein R$^3$ is hydrogen.

9. A compound in accordance with claim 7, wherein R$^3$ is methyl.

10. A compound in accordance with claim 7, wherein R$^3$ is 2,2,2-trifluoroethyl.

11. A compound in accordance with claim 7, wherein R$^3$ is heteroalkyl.

12. A compound in accordance with claim 1, wherein R$^1$ is hydrogen or alkyl.

13. A compound in accordance with claim 12, wherein R$^4$ is hydrogen.

14. A compound in accordance with claim 12, wherein R$^4$ is methyl.

15. A compound in accordance with claim 1, wherein R$^1$ is heteroalkyl, arylheteroalkyl, heterosubstituted cycloalkyl, heterosubstituted cycloalkylalkyl, heteroalkylsubstituted cycloalkyl, heterocyclyl, or heterocyclylalkyl.

16. A compound in accordance with claim 15, wherein R$^1$ is heteroalkyl.

17. A compound in accordance with claim 16, wherein R$^1$ is hydroxyalkyl.

18. A compound in accordance with claim 1, wherein R$^1$ is heteroalkyl, R$^2$ is halo or methyl, R$^3$ is methyl, R$^4$ is hydrogen, and n is 1 or 2.

19. A compound in accordance with claim 1, wherein R$^1$ is hydroxyalkyl, R$^2$ is halo or methyl, R$^3$ is methyl, R$^4$ is hydrogen, and n is 1 or 2.

20. A compound in accordance with claim 15, wherein R$^1$ is heterosubstituted cycloalkyl.

21. A compound in accordance with claim 20, wherein R$^1$ is 4-hydroxycycloalkyl, cis-4-hydroxycycloalkyl, trans-4-hydroxycycloalkyl, 4-oxo-cycloalkyl, or 4-methoxycycloalkyl.

22. A compound in accordance with claim 1, wherein R$^1$ is heterosubstituted cycloalkyl, R$^2$ is halo, R$^3$ is hydrogen or methyl, R$^4$ is hydrogen or methyl, and n is 1 or 2.

23. A compound in accordance with claim 1, wherein R$^1$ is 4-hydroxycycloalkyl, 4-oxocycloalkyl, or 4-methoxycycloalkyl, R$^2$ is halo, R$^3$ is hydrogen or methyl, R$^4$ is hydrogen or methyl, and n is 1 or 2.

24. A compound in accordance with claim 15, wherein R$^1$ is heterocyclyl or heterocyclylalkyl.

25. A compound in accordance with claim 1, wherein R$^1$ is heterocyclyl or heterocyclylalkyl, R$^2$ is halo or methyl, R$^3$ is methyl or hydrogen, R$^4$ is hydrogen or methyl, and n is 1 or 2.

26. A method for the preparation of a compound of claim 1, said method comprising:

(a) treating a compound of Formula II

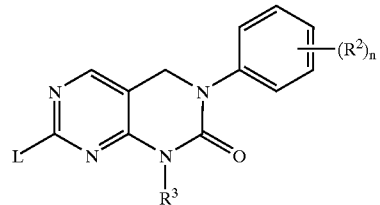

wherein n, R$^2$ and R$^3$ have the meanings provided in claim 1, any interfering reactive group present is in protected form, and L is a leaving group, with an amine of Formula III

R$^1$R$^4$—NH     (III)

wherein R$^1$ and R$^4$ have the meaning provided in claim 1, any interfering reactive group present is in protected form, and deprotecting any protected group present in the reaction product.

27. A method for the preparation of a compound of claim 1, said method comprising:

(a) treating a compound of formula IV

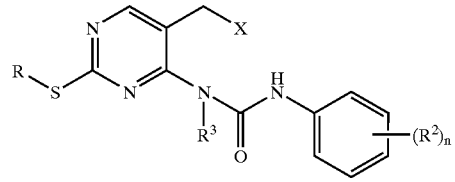

wherein X is halo, R is alkyl, and R$^2$ and R$^3$ have the meaning provided in claim 1, in the presence of a base to afford a compound of formula V

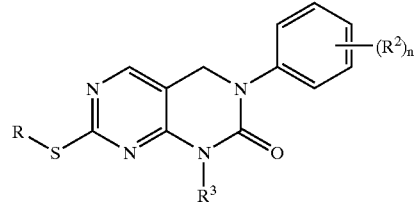

(b) treating a compound of formula V with an oxidizing agent followed by an amine of the formula R$^1$R$^4$NH, wherein and R$^1$ and R$^4$ have the meaning provided in claim 1, to afford a compound of claim 1.

28. A method in accordance with claim 27, wherein the base is hexamethyldisilazane.

29. A pharmaceutical composition comprising a therapeutically effective amount of at least one compound of claim 1, or an isomer, racemic or non-racemic mixture of isomers, or a pharmaceutically acceptable salt thereof, in admixture with at least one pharmaceutically acceptable carrier.

30. A method of treating a p38 mediated disorder comprising administering to a subject in need of such treatment, an effective amount of at least one compound of claim 1.

31. A method in accordance with claim 30, wherein the p38 mediated disorder is arthritis, Crohn's disease, irritable bowel syndrome, adult respiratory distress syndrome, chronic obstructive pulmonary disease, osteoporosis, or Alzheimer's disease.

* * * * *

UNITED STATES PATENT AND TRADEMARK OFFICE
CERTIFICATE OF CORRECTION

PATENT NO. : 6,451,804 B1
DATED : September 17, 2002
INVENTOR(S) : James Patrick Dunn et al.

It is certified that error appears in the above-identified patent and that said Letters Patent is hereby corrected as shown below:

Column 159,
Line 32, the variable "$R^1$" should read -- $R^4$ --.

Signed and Sealed this

Second Day of September, 2003

JAMES E. ROGAN
*Director of the United States Patent and Trademark Office*